US007674503B2

(12) United States Patent
Sasaki

(10) Patent No.: US 7,674,503 B2
(45) Date of Patent: Mar. 9, 2010

(54) OXIME DERIVATIVE, PHOTOPOLYMERIZABLE COMPOSITION, COLOR FILTER, AND PROCESS FOR PRODUCING THE SAME

(75) Inventor: Tomoya Sasaki, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 346 days.

(21) Appl. No.: 11/709,864

(22) Filed: Feb. 23, 2007

(65) Prior Publication Data

US 2007/0203255 A1 Aug. 30, 2007

(30) Foreign Application Priority Data

Feb. 24, 2006 (JP) ............................ 2006-049359
Mar. 10, 2006 (JP) ............................ 2006-066783

(51) Int. Cl.
*G03F 7/00* (2006.01)
*G02B 5/20* (2006.01)

(52) U.S. Cl. ........................ 427/510; 522/39; 564/254; 564/255; 430/7

(58) Field of Classification Search .................. 522/26, 522/39; 430/7, 281.1–288.1; 564/254, 255; 427/510
See application file for complete search history.

(56) References Cited

U.S. PATENT DOCUMENTS

| | | | | |
|---|---|---|---|---|
| 4,590,145 A * | 5/1986 | Itoh et al. | ................ | 430/281.1 |
| 5,019,482 A * | 5/1991 | Ai et al. | ................... | 430/283.1 |
| 6,485,885 B1 * | 11/2002 | Oka et al. | ................ | 430/270.1 |
| 6,512,020 B1 * | 1/2003 | Asakura et al. | ............... | 522/57 |
| 6,596,445 B1 * | 7/2003 | Matsumoto et al. | ............ | 430/7 |
| 6,949,678 B2 * | 9/2005 | Kunimoto et al. | ........... | 564/255 |
| 7,381,842 B2 * | 6/2008 | Kunimoto et al. | ........... | 564/255 |
| 2001/0012596 A1 * | 8/2001 | Kunimoto et al. | ........... | 430/138 |
| 2004/0002007 A1 * | 1/2004 | Hitoshi et al. | .................. | 430/1 |
| 2004/0170924 A1 * | 9/2004 | Kunimoto et al. | ........ | 430/281.1 |
| 2005/0191567 A1 * | 9/2005 | Kunimoto et al. | .............. | 430/7 |
| 2006/0166114 A1 * | 7/2006 | Lee | .............................. | 430/7 |

FOREIGN PATENT DOCUMENTS

| | | | |
|---|---|---|---|
| JP | 6-184482 | A | 7/1994 |
| JP | 7-140654 | A | 6/1995 |
| JP | 2000-80068 | A | 3/2000 |
| JP | 2004-534797 | A | 11/2004 |
| JP | 2005-99488 | A | 4/2005 |

* cited by examiner

*Primary Examiner*—Susan W Berman
(74) *Attorney, Agent, or Firm*—Sughrue Mion, PLLC

(57) ABSTRACT

There are provided a compound represented by the following formula (I), a photopolymerizable composition containing (A) a photopolymerization initiator represented by the formula (I) and (B) a radical polymerizable monomer, a color filter produced by using the photopolymerizable composition, and a process for producing the color filter:

Formula (I)

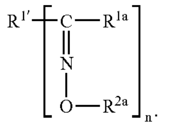

7 Claims, No Drawings

OXIME DERIVATIVE, PHOTOPOLYMERIZABLE COMPOSITION, COLOR FILTER, AND PROCESS FOR PRODUCING THE SAME

CROSS-REFERENCE TO RELATED APPLICATION

This application claims priority under 35 USC 119 from Japanese patent Application Nos. 2006-049359 and 2006-066783, the disclosures of which are incorporated by reference herein.

BACKGROUND OF THE INVENTION

1. Field of the Invention

The present invention relates to a new oxime derivative; a photopolymerizable composition which comprises a photopolymerization initiator having a specific structure and is preferably used in UV ink or UV inkjet, or in a color filter, a black matrix or the like that is used in a liquid crystal display element or a solid-state imaging element; a color filter; and a process for producing the color filter.

2. Description of the Related Art

Oxime derivatives are widely used as medicines, agricultural chemicals, antibacterial agents, synthesis intermediates, or photosensitive compounds. Examples of the photosensitive compounds include photopolymerization initiators, photo-acid agents, and photo-base agents.

Photopolymerization technique is used as a technique for producing an adhesive, a printing plate, a semiconductor, a liquid crystal, a color filter for a solid-state imaging element, and so forth.

As photopolymerization initiators therein, various oxime derivatives are disclosed in U.S. Pat. Nos. 3,558,309 and 4,255,513, Japanese Patent Application Laid-Open (JP-A) Nos. 61-24558, 2000-80068, 2001-233842, and 2002-323762, Japanese Patent Application National Publication (Laid-Open) Nos. 2002-519732, and 2004-534797, and WO 04/050653 and WO 05/080337.

However, in photopolymerization technique, a photopolymerization initiator is desired which has higher sensitivity, thermal stability and storage stability with precipitation after application to the substrate being reduced.

Photopolymerization technique is a useful technique applicable to various uses. Examples of compositions in which photopolymerization technique can be used include:

compositions for producing a colorant-containing or colorant-non-containing paint or vanish, a powdery coating material, a printing ink, an inkjet ink, a UV ink, a printing surface, an adhesive, a composition for dental surgery, a gel coat, or photoresists for electronic engineering, such as an electroplating resist, an etching resist, wet and dry thin films, and a soldering resist; compositions for producing a color filter for various display devices; compositions for forming a structure in a process for producing a plasma display panel, an electroluminescent display device, or an LCD; composite compositions; compositions for sealing a resist (including a photoresist), a color filter, a black matrix, or electrical or electronic parts; compositions for producing a magnetic recording material, fine mechanical parts, a waveguide, an optical switch, a plating mask, an etching mask, a color test agent, a glass fiber cable coat, or a screen-printing stencil; compositions for producing a three-dimensional object by stereo-lithography; an image recording material, in particular an image recording material for holographic recording; compositions for or a fine electronic circuit; compositions as discoloring materials for image recording materials in which microcapsules are used; and compositions for forming dielectric layers for successive laminations of printed circuit boards.

JP-A Nos. 2000-80068 and 2001-233842, Japanese Patent Application National Publication (Laid-Open) No. 2004-534797, and pamphlets of WO 04/050653 and WO 05/080337 disclose a photopolymerizable composition in which a specific oxime compound is used as a photopolymerization initiator.

Out of the above-mentioned applications, a color filter which is used in a liquid crystal display element (LCD) or a solid liquid crystal display element (such as a CCD, or a CMOS) is described below.

Known methods for producing a color filter which is used in a liquid crystal display element (LCD) or a solid liquid crystal display element (such as a CCD, or a CMOS) include the dye method, the printing method, the electrodepositing method, and the pigment dispersing method.

Out of these methods, the pigment dispersing method is a method of using a colored radiation-sensitive composition wherein a pigment is dispersed in any one of various photosensitive compositions to produce a color filter by photolithography, and has an advantage that the color filter has stability against light, heat and so on since the pigment is used. This method is widely used as a method suitable for producing a color filter for a large-screen and high definition color display having a high position precision since the patterning is performed by photolithography.

When a color filter is produced by the pigment dispersing method, a radiation-sensitive composition is applied onto a glass substrate with a spin coater, a roll coater or the like and then dried to form a coating layer and subsequently this coating layer is subjected to patterning-exposure to light and development, thereby forming colored pixels. This operation is repeated for the respective colors in accordance with the number of desired hues, so as to yield a color filter. As this pigment dispersing method, disclosed are examples using a negative photosensitive composition wherein an alkali-soluble resin is used together with a photopolymerizable monomer and a photopolymerization initiator (see, for example, JP-A Nos. 2-199403, 4-76062, 5-273411, 6-184482, and 7-140654).

In the meantime, in recent years, there is desire for higher definition of color filters for solid-state imaging elements. A technique has been suggested, the technique using a dye that is soluble in organic solvent, which may be referred to merely as a "dye" hereinafter, instead of the pigment (see, for example, JP-A No. 2005-99488).

SUMMARY OF THE INVENTION

Regarding such compositions using photopolymerization, further improvement in sensitivity and reduction of solid precipitation after the production of the composition are needed in order to improve the productivity of the color filter.

In particular, when such a composition is used to form a color filter or a black matrix used in a liquid crystal display element (LCD) or a solid liquid crystal display element (such as a CCD or a CMOS), there are strong needs for further improvement in sensitivity in both of the method using a pigment and the method using a dye. This is because a negative curable composition containing a colorant has a lower sensitivity than other negative curable compositions. It is presumed that the reason for the lower sensitivity is caused by lower absorption efficiency of the photosensitive component due to large optical absorption of the colorant. Furthermore, improvement in the resistance of the composition against developer after photopolymerization of the composition is also requested.

The present invention has been made in view of the above circumstances, and provides an oxime derivative, a photopolymerizable composition, a color filter, and a process for producing the same.

According to an aspect of the invention, a compound represented by the following formula (I) is provided:

Formula (I)

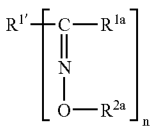

In the formula (I), $R^{1'}$ represents a substituent containing an aromatic ring or heteroaromatic ring; $R^{1a}$ is an alkyl group having at least one substituent selected from the following group A, $R^{2a}$ represents an alkanoyl group, an alkenoyl group, an aryloyl group, an alkoxycarbonyl group, an aryloxycarbonyl group, a heterocyclic oxycarbonyl group, a heteroaryloxycarbonyl group, an alkylthiocarbonyl group, an arylthiocarbonyl group, a heterocyclic thiocarbonyl group, a heteroarylthiocarbonyl group, or —CO—CO-Rd wherein Rd represents an aromatic or heteroaromatic group which may have a substituent; and n represents an integer of 1 to 6.

Group (A): a cyano group, an alkenyl group, an alkynyl group, —NArAr', —SAr, —COOH, —CONRaRb, —NRa—CO—Rb, —O—CO—NRaRb, —NRa—CO—ORb, —NRa—CO—NRaRb, —SO-Rc, —$SO_2$-Rc, —O—$SO_2$-Rc, —$SO_2$—NRaRb, —NRa—$SO_2$—Ra, —CO—NRa—CORb, —CO—NRa—$SO_2$—Rb, —$SO_2$—NRa—CO—Rb, —$SO_2$—NRa—$SO_2$-Rc, —Si(Ra)$_l$(ORb)$_m$, and a heterocyclic group In group (A), Ar and Ar' each independently represent an aromatic ring or heteroaromatic ring which may have a substituent, Ra and Rb each independently represent a hydrogen atom, or an alkyl, aromatic or heteroaromatic group which may have a substituent, Rc represents an alkyl, aromatic or heteroaromatic group which may have a substituent, and l and m each independently represents an integer of 0 to 3 provided that l and m satisfy the relationship: l+m=3.

According to another aspect of the invention, a photopolymerizable composition comprises (A) a photopolymerization initiator represented by the formula (I) and (B) a radical polymerizable monomer.

According to another aspect of the invention, a photopolymerization method is provided. The photopolymerization method includes irradiating the above composition including the radical polymerizable monomer with electromagnetic radiation having a wavelength in the range of 150 to 600 nm, electron beams, or X-rays to photopolymerize the composition.

According to another aspect of the invention, a color filter is provided. In the color filter the above photopolymerizable composition is used.

According to another aspect of the invention, a process for producing a color filter is provided. The method includes applying the above photopolymerizable composition onto a support, exposing the composition to radiation through a mask, and developing the composition to form a pattern.

DESCRIPTION OF THE PRESENT INVENTION

The oxime derivative, the photopolymerizable composition, the color filter, and the process for producing the color filter according to the invention will be described in detail hereinafter. The oxime derivative according to the invention has the following structure:

Formula (I)

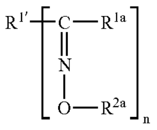

In the formula (I), $R^{1'}$ represents a substituent containing an aromatic ring or heteroaromatic ring.

The aromatic ring (the aromatic ring in the invention) may be a single ring or condensed ring structure. Specific examples thereof include benzene, naphthalene, anthracene, phenanthrene, and pyrene rings. Preferable ones include benzene, naphthalene, and anthracene ring, and more preferable ones include benzene and naphthalene rings.

The heteroaromatic ring (the heteroaromatic ring in the invention) may be a single ring or condensed ring structure. Specific examples thereof include furan, pyrrole, thiophene, pyridine, oxazole, imidazole, indole, and acridine rings. Preferable ones include pyrrole, thiophene, indole, and acridine rings, and more preferable ones include pyrrole, thiophene, and acridine rings. Even more preferable ones include thiophene, indole, and acridine rings.

The aromatic ring or heteroaromatic ring may have a group that will be described later as a "substituent". Of those substituents, preferable ones include halogens, and alkoxy, hydroxyl, alkyl, alkanoyl, aryloyl, and heterocyclic groups, and heterocyclic carbonyl groups. More preferable ones include halogens, and the alkoxy, hydroxyl, alkanoyl and aryloyl groups, and even more preferable ones include alkoxy, hydroxyl, alkanoyl and aryloyl groups. These substituents may be bonded to a carbon atom in the aromatic ring or heteroaromatic ring to form a condensed ring structure.

The "substituent containing an aromatic ring or heteroaromatic ring" as $R^{1'}$ may be the above-mentioned aromatic ring and/or heteroaromatic ring itself, or any combination of the above-mentioned aromatic ring and/or heteroaromatic ring with a partial structure selected from a group (B) in the item "Substituent" described later. The aromatic ring or heteroaromatic ring is as described above.

When the "substituent containing an aromatic ring or heteroaromatic ring" as $R^{1'}$ is any combination of the above-mentioned aromatic ring and/or heteroaromatic ring with a partial structure selected from the group (B) in the item "Substituent" described later, the partial structure selected from the group (B) is preferably a carbonyl, sulfinyl, sulfonyl, or phosphine oxide group, more preferably a carbonyl, sulfonyl, or phosphine oxide group, and even more preferably a carbonyl or phosphine oxide group.

$R^{1'}$ is an n-valent group. Thus, n groups containing the oxime derivative are substituted at arbitrary positions of the structure of $R^{1'}$. n is from 1 to 6, preferably from 1 to 5, more preferably from 1 to 3.

When n is, for example, 1, $R^{1'}$ is preferably a phenyl group which may have a substituent, or a benzoyl group which may have a substituent, more preferably an unsubstituted phenyl or benzoyl group, or a phenyl or benzoyl group substituted with an alkoxy, aryloxy, alkylthio or arylthio group.

When n is 2 or more, $R^{1'}$ may be a structure wherein any one of the structures exemplified for the case of n=1 is converted into a bivalent or higher-valent structure by acquiring valence at arbitrary positions.

$R^{1a}$ is an alkyl group having at least one substituent selected from the following group (A).

Group A:

A cyano group, an alkenyl group, an alkynyl group, —NArAr', —SAr, —COOH, —CONRaRb, —NRa—CO—Rb, —O—CO—NRaRb, —NRa—CO—ORb, —NRa—CO—NRaRb, —SO-Rc, —$SO_2$-Rc, —O—$SO_2$-Rc, —$SO_2$—NRaRb, —NRa—$SO_2$—Ra, —CO—NRa—CORb, —CO—NRa—$SO_2$—Rb, —$SO_2$—NRa—CO—Rb, —$SO_2$—NRa—$SO_2$-Rc, —$Si(Ra)_l(ORb)_m$, and a heterocyclic group.

In the above, Ar and Ar' each independently represent an aromatic or heteroaromatic group which may have a substituent, Ra and Rb each independently represent a hydrogen atom, or an alkyl, aromatic or heteroaromatic group which may have a substituent, Rc represents an alkyl, aromatic or heteroaromatic group which may have a substituent, and l and m each independently represent an integer of 0 to 3 provided that l and m satisfy the relationship: l+m=3

The aromatic or heteroaromatic rings as Ar, Ar', Ra, Rb, and Rc each independently represent a group that is within the scope of the definition of $R^{1'}$, and preferable examples thereof are also the same as those exemplified for $R^{1'}$.

The substituents that the aromatic or heteroaromatic groups as Ar, Ar', Ra, Rb and Rc have may be each independently a halogen, or an alkoxy, hydroxyl, alkyl, alkanoyl, aryloyl or heterocyclic group, or a heterocyclic carbonyl group. Preferable ones include a halogen, or an alkoxy, hydroxyl, alkanoyl, aryloyl or heterocyclic group, or a heterocyclic carbonyl group, and more preferable ones include a halogen, or an alkoxy, alkanoyl, aryloyl or heterocyclic group, or a heterocyclic carbonyl group, and still more preferable ones include a halogen, an alkoxy, alkanoyl or aryloyl group, or a heterocyclic carbonyl group.

The alkyl groups represented by Ra, Rb and Rc each independently represent an alkyl group which will be described below in the invention.

The alkyl group in the invention may be linear, branched or cyclic. When the alkyl group is cyclic, the group may be monocyclic or polycyclic and may partially contain an unsaturated bond.

The linear alkyl group has preferably 1 to 30 carbon atoms, more preferably 1 to 20 carbon atoms, even more preferably 1 to 15 carbon atoms, and particularly preferably 1 to 12 carbon atoms. In the explanation, the branched alkyl group is assumed as a linear alkyl group having a substituent.

The cyclic alkyl group has preferably 3 to 20 carbon atoms, more preferably 4 to 17 carbon atoms, even more preferably 5 to 15 carbon atoms, and particularly preferably 6 to 12 carbon atoms.

Specific examples of the alkyl group in the invention include methyl, ethyl, n-propyl, i-propyl, n-butyl, cyclopentyl, cyclohexyl, norbornyl, adamantly, and 2-ethylhexyl groups. Preferable ones include methyl, ethyl, and n-propyl groups.

The alkyl group may further have, at any position thereof, a substituent. The substituent may be selected from the above-mentioned alkyl groups themselves and any of the groups described as the after-mentioned "substituent". Among the substituents, preferable ones include halogens, and alkoxy, alkoxycarbonyl, aryl, aryloxy, hydroxyl, and aromatic groups, and more preferable ones include halogens, and alkoxy, alkoxycarbonyl, aryl, aryloxy, and aromatic groups. Even more preferable ones include halogens, and alkoxy, alkoxycarbonyl, aryl and aryloxy groups.

In the case of a cyclic alkyl group, a partial structure selected from the group (B), which will be described later, may be inserted in any of the carbon-carbon bonds constituting the ring.

The alkenyl group in the invention may be linear, branched or cyclic, and may further have, at any position thereof, a substituent. The substituent may be selected from the groups described as the after-mentioned "substituent".

In the case of the cyclic alkenyl group, a partial structure selected from the group (B), which will be described later, may be inserted in any of the carbon-carbon bonds constituting the ring.

Specific examples of the alkenyl group include vinyl, allyl, 1-methylvinyl, 3-butene-1-yl, cyclopentane-2-ene-1-yl, cyclohexane-2-ene-1-yl, and cyclohexane-1-ene-1-yl. Preferable ones include vinyl, allyl, 1-methylvinyl, 3-butene-1-yl, cyclopentane-2-ene-1-yl, and cyclohexane-2-ene-1-yl groups. More preferable ones include vinyl, allyl, 1-methylvinyl, and 3-butene-1-yl groups. Even more preferable ones include vinyl, allyl, and 1-methylvinyl groups.

The alkynyl group in the invention is an ethynyl group, and any hydrogen atom in this ethynyl group may be replaced by a substituent. The substituent may be selected from the groups described as the after-mentioned "substituent". Preferable ones include ethynyl, 2-methylethynyl, 2-ethylethynyl, and 2-phenylethynyl groups, and more preferable ones include ethynyl, 2-methylethynyl, and 2-ethylethynyl groups. Even more preferable ones include ethynyl and 2-methylethynyl groups.

The heterocyclic group in the invention is a cyclic group having therein one or more heteroatoms (such as a nitrogen, sulfur, or oxygen atom), and may be a saturated cyclic group or unsaturated cyclic group. The heterocyclic group may be monocyclic, or condensed cyclic. However, the heterocyclic group is differentiated from heteroaromatic groups (=heteroaryl groups).

Examples of the heterocyclic group include tetrahydrofuranyl, dihydrofuranyl, tetrahydropyranyl, dihydropyranyl, oxocanyl, dioxanyl, tetrahydrothiophenyl, dithianyl, pyrrolidinyl, pyrrolinyl, tetrahydropyridinyl, piperazinyl, homopiperazinyl, and piperidinyl groups. The heterocyclic group may further have, at any position thereof, a substituent. The substituent may be selected from the groups described as the after-mentioned "substituent".

<Re: Substituent>

The scope of "substituent" in the invention includes a halogen atom (e.g., a fluorine, chlorine, bromine, or iodine atom), or a hydroxyl, cyano, nitro, carbonic acid, sulfonic acid, sulfinic acid, alkyl (which may be linear, branched or cyclic), alkenyl (which may be linear, branched or cyclic), alkynyl, aromatic, heteroaromatic, heterocyclic or formyl group, or a combination of one partial structure selected from the following group (B) with one partial structure selected from alkyl, alkenyl, alkynyl, heterocyclic, aromatic and heteroaromatic groups.

Group (B):

Ether, amino, thioether, carbonyl, ester, amide, urethane (—O—CO—N(R)—), urea (—N(R)—CO—N(R)—), sulfinyl (—SO—), sulfonyl (—$SO_2$—), sulfonic ester (—$SO_2$—O—), sulfonamide (—$SO_2$—N(R)—), imide (—CO—N(R)—CO—), sulfonylamide (—$SO_2$—N(R)—CO—), disulfonylimide ($-SO_2-N(R)-SO_2-$), and phosphine oxide groups, this phosphine oxide group having a structure represented by the following:

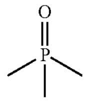

In the formula (I), n represents an integer of 1 to 6, preferably 1 to 4, more preferably 1 or 2.

The word "aryl" has the same meaning as the above-mentioned word "aromatic", and the word "heteroaryl" has the same meaning as the above-mentioned word "heteroaromatic".

Rd, which is described in the above, is preferably an alkyl, aryl or heteroaryl group, and is more preferably an alkyl or aryl group.

$R^{1a}$ in the formula (I) preferably represents an alkyl group having at least one substituent selected from a cyano group, an alkenyl group, —SAr, —COOH, —CONRaRb, —NRa—CO—Rb, —NRa—CO—NRaRb, $-SO_2$-Rc, $-SO_2-$NRaRb, —NRa—$SO_2$—Ra, —CO—NRa—$SO_2$—Rb, $-SO_2-$NRa—CO—Rb, —Si(Ra)$_l$(ORb)$_m$, or a heterocyclic group, more preferably represents an alkyl group having at least one substituent selected from a cyano group, an alkenyl group, —SAr, —COOH, —CONRaRb, —NRa—CO—Rb, $-SO_2$-Rc, $-SO_2-$NRaRb, —NRa—$SO_2$—Ra, —CO—NRa—$SO_2$—Rb, $-SO_2-$NRa—CO—Rb, or a heterocyclic group, still more preferably an alkyl group having at least one substituent selected from an alkenyl group or —SAr, further more preferably an alkyl group having at least one —SAr as a substituent. When $R^{1a}$ represents an alkyl group substituted by at least one —SAr, the Ar moiety preferably has at least one substituent other than hydrogen.

$R^{2a}$ in the formula (I) represents an alkanoyl, alkenoyl, aryloyl, alkoxycarbonyl, aryloxycarbonyl, heterocyclic oxycarbonyl, heteroaryloxycarbonyl, alkylthiocarbonyl, arylthiocarbonyl, heterocyclic thiocarbonyl, heteroarylthiocarbonyl, or —CO—CO-Rd wherein Rd represents an alkyl, aromatic or heteroaromatic group which may have a substituent.

$R^{2a}$ is preferably an alkanoyl, aryloyl, alkylthiocarbonyl, arylthiocarbonyl, or heteroarylthiocarbonyl group, and is more preferably an alkanoyl, or aryloyl group.

The alkanoyl group represented by $R^{2a}$ may or may not have a substituent, and has preferably 1 to 20 carbon atoms, more preferably 1 to 15 carbon atoms, even more preferably 1 to 12 carbon atoms. The substituent may be the above-mentioned "substituent", and is preferably a halogen, or a hydroxyl, alkoxy, or amino group, more preferably a halogen, alkoxy, or amino group.

Specific examples thereof are preferably acetyl, ethylcarbonyl, and dimethylaminomethyl groups.

The aryloyl group represented by $R^{2a}$ may or may not have a substituent, and has preferably 6 to 25 carbon atoms, more preferably 6 to 17 carbon atoms, even more preferably 6 to 12 carbon atoms. The substituent may be the above-mentioned "substituent", and is preferably a halogen, or an alkoxy, aryloxy or alkoxycarbonyl group, more preferably a halogen, or an alkoxy, or aryloxy group.

Specific examples thereof are preferably benzoyl and 4-chlorobenzoyl groups. A benzoyl group is more preferable.

The alkoxycarbonyl group represented by $R^{2a}$ may or may not have a substituent, and has preferably 2 to 20 carbon atoms, more preferably 2 to 15 carbon atoms, even more preferably 2 to 12 carbon atoms. The substituent may be the above-mentioned "substituent", and is preferably a halogen or an alkoxy group, more preferably a halogen.

Specific examples thereof are preferably methoxycarbonyl and ethoxycarbonyl groups. A methoxycarbonyl group is more preferable.

The aryloxycarbonyl group represented by $R^{2a}$ may or may not have a substituent, and has preferably 6 to 20 carbon atoms, more preferably 6 to 15 carbon atoms, even more preferably 6 to 12 carbon atoms. The substituent may be the above-mentioned "substituent", and is preferably a halogen, or an alkoxy or aryloxy group, more preferably a halogen or an alkoxy group.

Specific examples thereof are preferably phenyloxycarbonyl and naphthaleneoxycarbonyl groups. A phenyloxycarbonyl group is more preferable.

The heterocyclic oxycarbonyl group represented by $R^{2a}$ may or may not have a substituent, and has preferably 5 to 20 carbon atoms, more preferably 5 to 15 carbon atoms, even more preferably 5 to 12 carbon atoms. The substituent may be the above-mentioned "substituent", and is preferably a halogen, or an alkoxy or alkyl group, more preferably a halogen or an alkoxy group.

Specific examples thereof are preferably tetrahydrofurfuryloxycarbonyl and 2-morpholinoxycarbonyl groups. A tetrahydrofurfuryloxycarbonyl group is more preferable.

The heteroaryloxycarbonyl group represented by $R^{2a}$ may or may not have a substituent, and has preferably 5 to 20 carbon atoms, more preferably 5 to 15 carbon atoms, even more preferably 5 to 12 carbon atoms. The substituent may be the above-mentioned "substituent", and is preferably a halogen, or an alkyl or alkoxy group, more preferably a halogen, or an alkoxy group.

Specific examples thereof are preferably 4-pyridineoxycarbonyl and 2-thiopheneoxycarbonyl groups. A 2-thiopheneoxycarbonyl group is more preferable.

The alkylthiocarbonyl group represented by $R^{2a}$ may or may not have a substituent, and has preferably 1 to 20 carbon atoms, more preferably 1 to 15 carbon atoms, even more preferably 1 to 12 carbon atoms. The substituent may be the above-mentioned "substituent", and is preferably a halogen, or an alkoxy, hydroxyl or alkyl group, more preferably a halogen, or an alkoxy or alkyl group.

Specific examples thereof are preferably methylthiocarbonyl, ethylthiocarbonyl, and propylthiocarbonyl groups. A methylthiocarbonyl and ethylthiocarbonyl groups are more preferable.

The arylthiocarbonyl group represented by $R^{2a}$ may or may not have a substituent, and has preferably 6 to 20 carbon atoms, more preferably 6 to 15 carbon atoms, even more preferably 6 to 12 carbon atoms. The substituent may be the above-mentioned "substituent", and is preferably a halogen, or an alkoxy, hydroxyl or alkyl group, more preferably a halogen, or an alkoxy or alkyl group.

Specific examples thereof are preferably phenylthiocarbonyl and 4-methylphenylthiocarbonyl groups. A phenylthiocarbonyl group is more preferable.

The heterocyclic thiocarbonyl group represented by $R^{2a}$ may or may not have a substituent, and has preferably 5 to 20 carbon atoms, more preferably 5 to 15 carbon atoms, even more preferably 5 to 12 carbon atoms. The substituent may be the above-mentioned "substituent", and is preferably a halogen, or an alkoxy, hydroxyl or alkyl group, more preferably a halogen, or an alkoxy or alkyl group.

Specific examples thereof are preferably tetrahydrofuran 2-thiocarbonyl and 2-morpholinothiocarbonyl groups. A tetrahydrofuran 2-thiocarbonyl group is more preferable.

The heteroarylthiocarbonyl group represented by $R^{2a}$ may or may not have a substituent, and has preferably 5 to 20 carbon atoms, more preferably 5 to 15 carbon atoms, even more preferably 5 to 12 carbon atoms. The substituent may be the above-mentioned "substituent", and is preferably a halogen, or an alkoxy, hydroxyl or alkyl group, more preferably a halogen, or an alkoxy or alkyl group.

Specific examples thereof are preferably thiophene-2-thiocarbonyl and furan-2-thiocarbonyl groups. A thiophene-2-thiocarbonyl group is more preferable.

In the —CO—CO-Rd represented by $R^{2a}$, Rd represents an alkyl, aromatic or heteroaromatic group which may have a substituent.

The alkyl group represented by Rd has the same scope as that of the "alkyl group in the invention" described above, and preferable examples thereof are also the same.

The aromatic or heteroaromatic group represented by Rd have the same scope as that of the aromatic or heteroaromatic groups in $R^{1'}$, respectively, and preferable examples thereof are also the same.

R bonded to any one of the N atoms in the group (B) is any one selected from a hydrogen atom, an alkyl group, an alkenyl group, an aromatic group, a heteroaromatic group or a heterocyclic group. Preferable ones include a hydrogen atom and alkyl, alkenyl, aromatic, heteroaromatic and heterocyclic groups, and more preferable ones include a hydrogen atom and alkyl, alkenyl, aromatic, heteroaromatic and heterocyclic groups.

The alkyl group represented by R is the "alkyl group in the invention" described above, and is preferably a methyl, ethyl or n-propyl group, more preferably a methyl or ethyl group.

The alkenyl group represented by R is the "alkenyl group in the invention" described above, and is preferably a vinyl, allyl or 2-ethylvinyl group, more preferably a vinyl or allyl group.

The aromatic group represented by R is the "aromatic group in the invention" described above, and is preferably a phenyl, tolyl, naphthyl, or anthryl group, more preferably a phenyl, tolyl, or naphthyl group.

The heteroaromatic group represented by R is the "heteroaromatic group in the invention" described above, and is preferably a furyl, thienyl, pyrrolyl, or indolyl group, more preferably a thienyl, pyrrolyl, or indolyl group.

The heterocyclic group represented by R is the "heterocyclic group in the invention" described above, and is preferably a tetrahydrofuryl or morpholyl group, more preferably a morpholyl group.

The oxime derivative according to the invention has the following isomers (A) and (B) in terms of its chemical structure. The oxime derivative may be present as a mixture of the isomers.

(A)

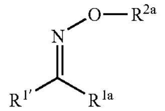

(B)

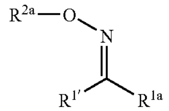

Specific examples of the oxime derivative represented by the formula (I) are illustrated below. As described above, any one of the examples may be present as a mixture of isomers thereof. It should be noted that the compound according to the invention is not limited to these examples.

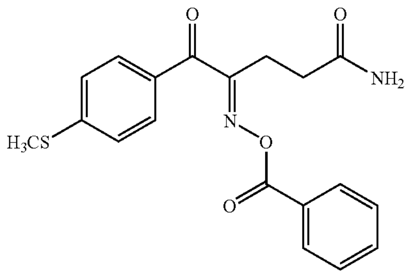

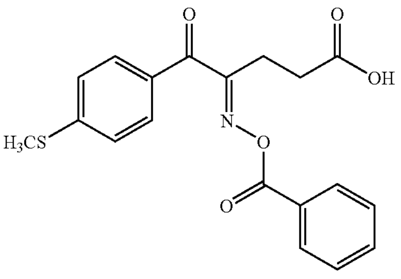

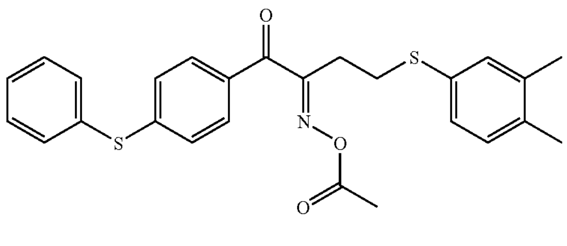

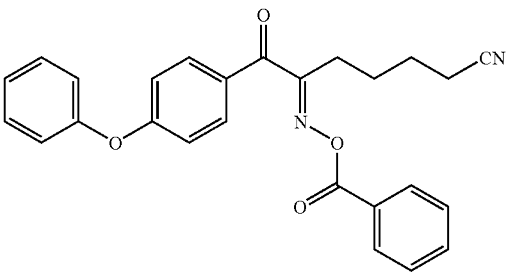

-continued
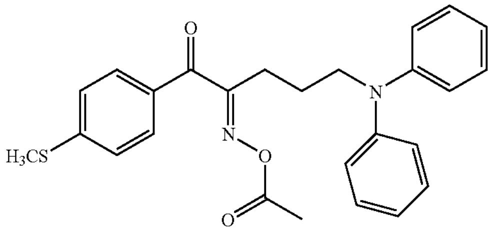
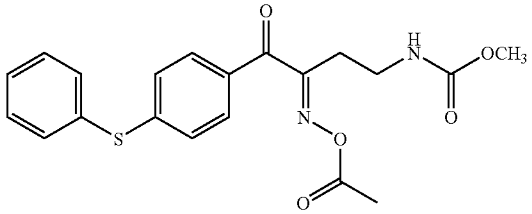
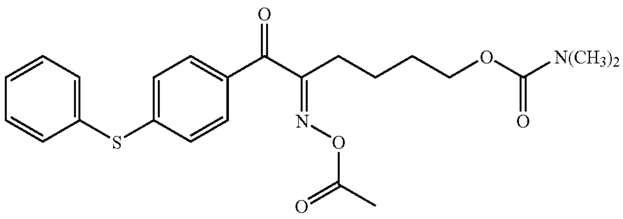
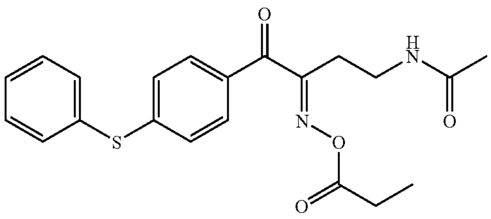
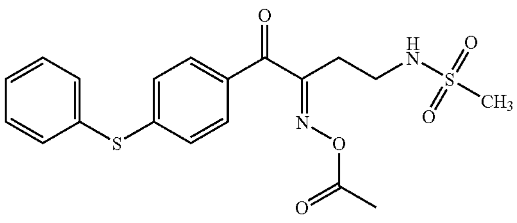
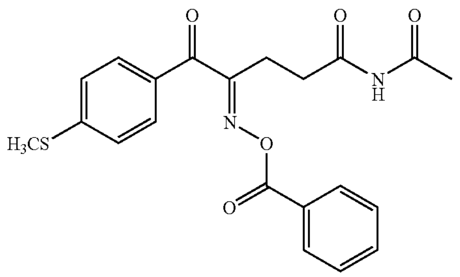
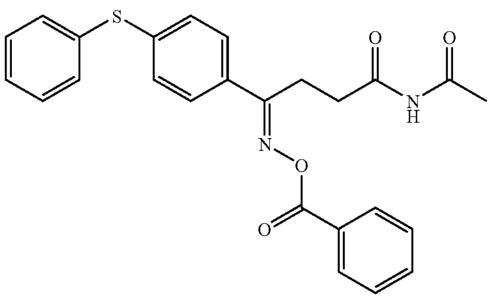
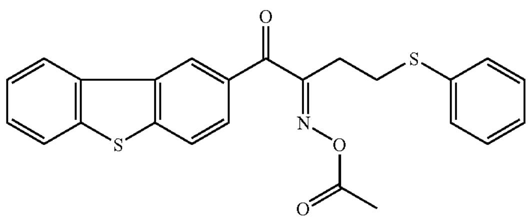
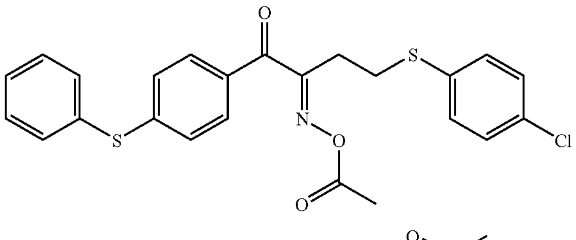
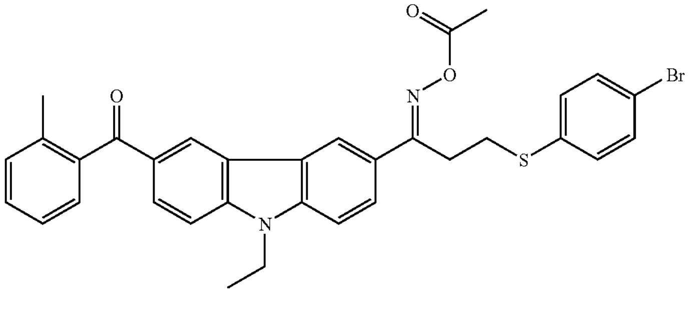

-continued
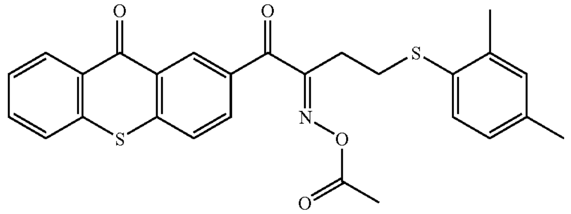
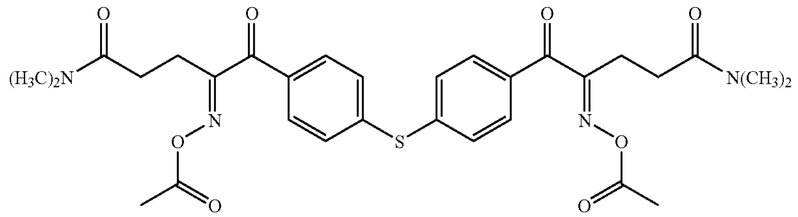
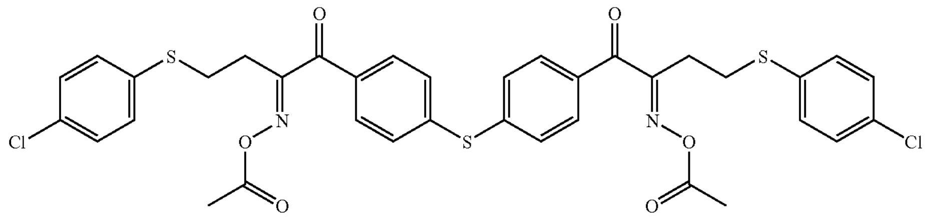
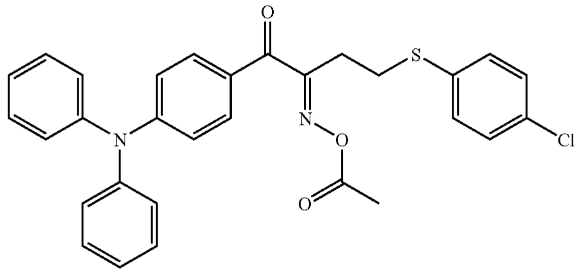
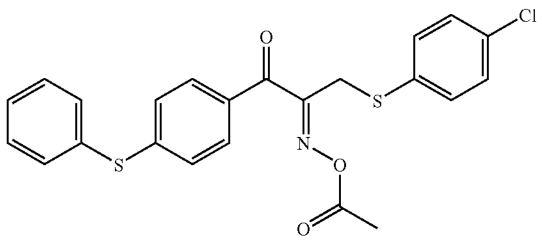
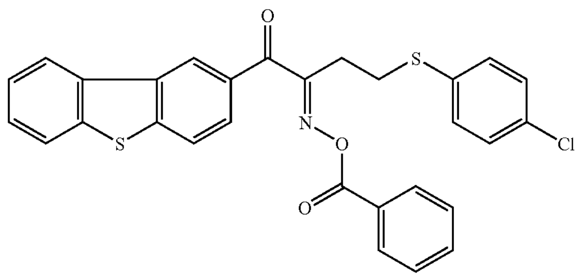
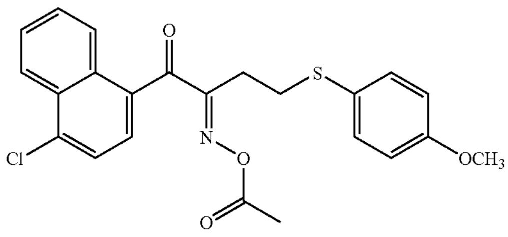
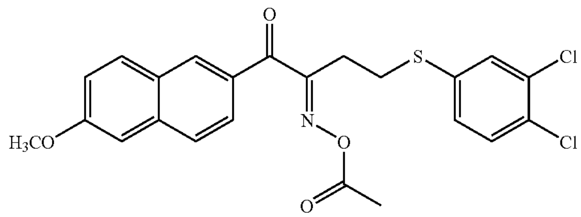
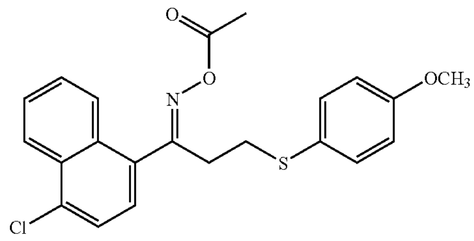
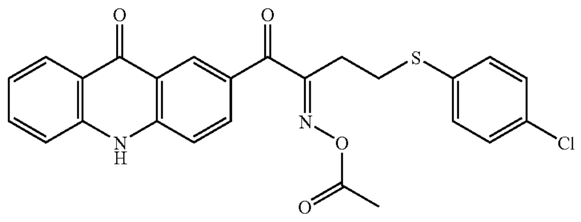

-continued
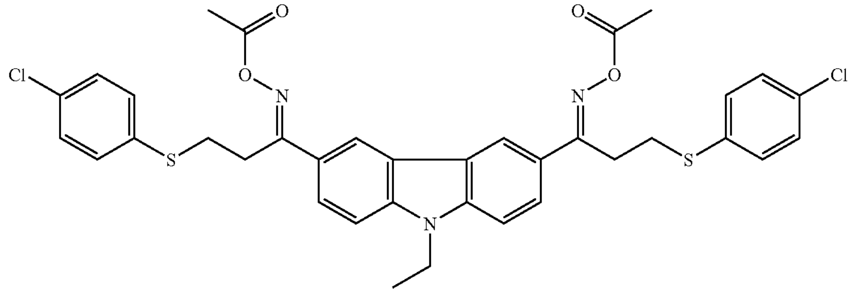
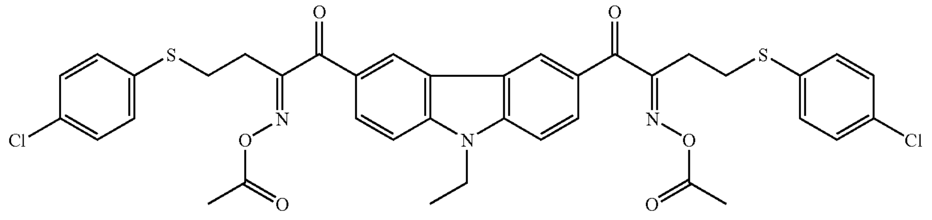
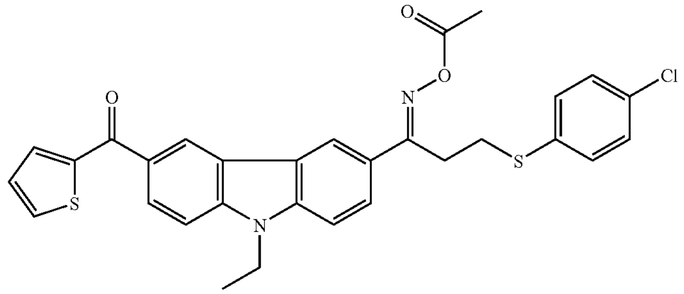
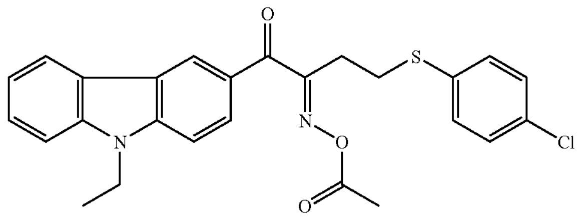
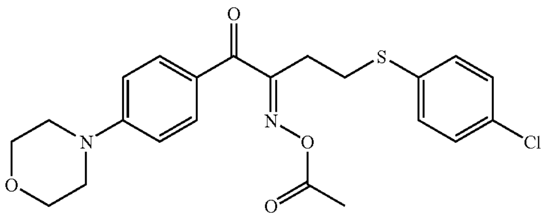
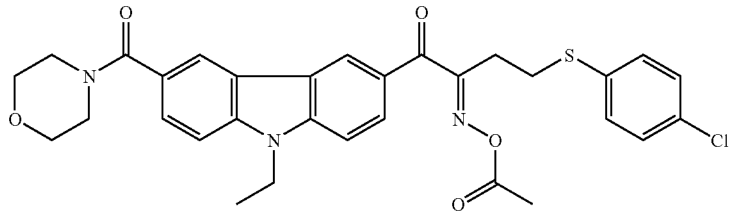
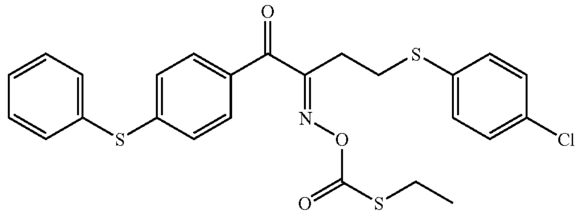
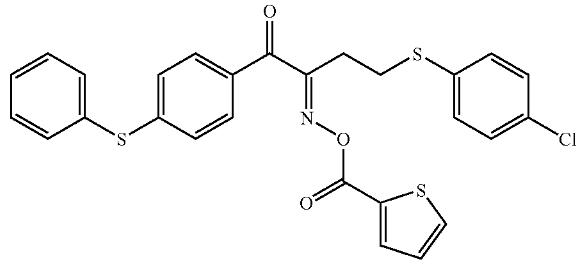

-continued

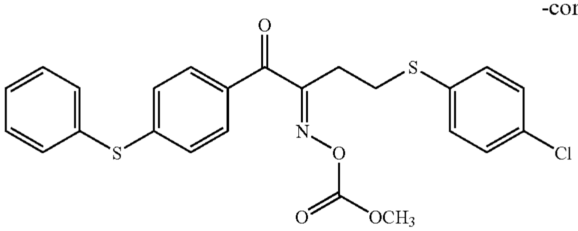

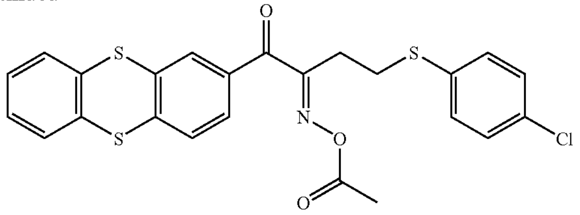

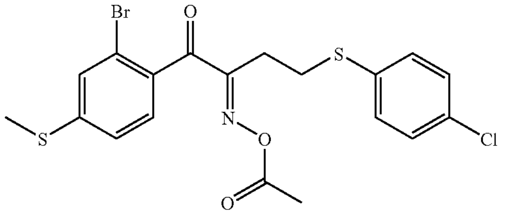

When the oxime derivative according to the invention is used as a photopolymerization initiator, the photopolymerizing properties thereof, such as the sensitivity and curing rate thereof, can be improved or promoted by combining the derivative with various sensitizers. Examples of the sensitizers include compounds described in JP-A No. 2000-80068, paragraphs (0112) to (0118).

The oxime derivative according to the invention is useful as a medicine, an agricultural chemical, an antibacterial agent, a synthesis intermediate, or a photopolymerization initiator used at the time of producing an adhesive, a printing plate, a semiconductor, a liquid crystal, a color filter for a solid-state imaging element, or the like, and is in particular useful as a constituent component of an photocurable composition used in the production of a color filter.

The oxime derivative according to the invention can be synthesized by a known synthesis process, which is not particularly limited.

<Process for Synthesizing the Oxime Derivative>

A scheme of the process for synthesizing the oxime derivative according to the invention is illustrated below. The process for synthesizing the oxime derivative according to the invention is not limited to this process. In the scheme shown below, each of X and Y is the same group as $R^{1a}$ in the formula (I) or a group that is a precursor of $R^{1a}$ in the formula (I).

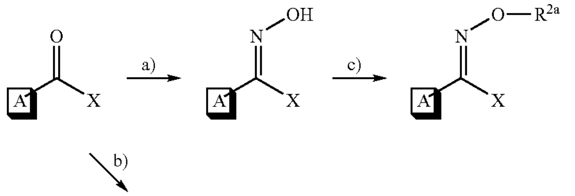

-continued

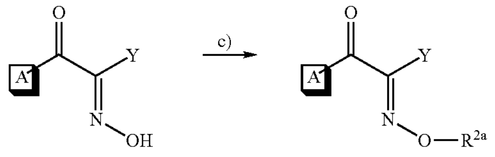

a) hydroxylamine or hydrochloride thereof b) NaOMe/nitrous ester c) halogenated NaOH/$R^{2a}$ or halogenated pyridine/$R^{2a}$ wherein $R^{2a}$ has the same meaning as $R^{2a}$ in the formula (I).

Conditions preferable for this synthesizing process may be conditions described in JP-A No. 2000-80068, paragraph (0067).

<<Photopolymerizable Composition>>

The photopolymerizable composition according to the invention, which may be referred to as the composition according to the invention hereinafter, comprises (A) a photopolymerization initiator represented by the formula (I), and (B) a radical polymerizable monomer.

If necessary, (E) other components, such as a crosslinking agent, a photosensitizing agent, a sensitizer or a surfactant, can be used.

(A) Photopolymerization Initiator Represented by the Formula (I)

The photopolymerization initiator represented by the formula (I) is as described above.

Specific examples of the oxime derivative represented by the formula (I) are illustrated below. As described above, the oxime derivative may be present as a mixture of isomers thereof. It should be noted that the compound according to the invention is not limited to these examples.

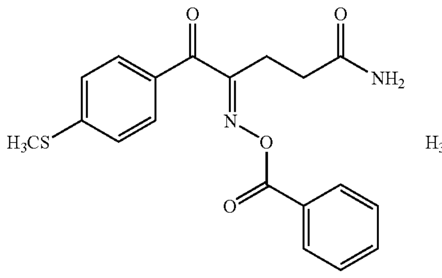

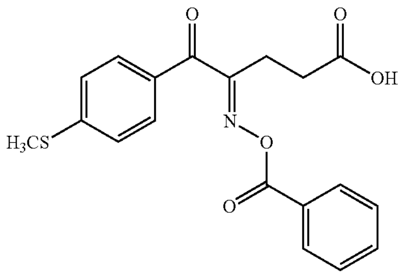

-continued
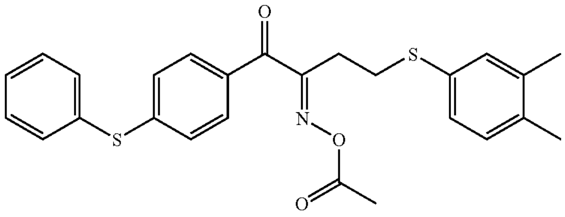
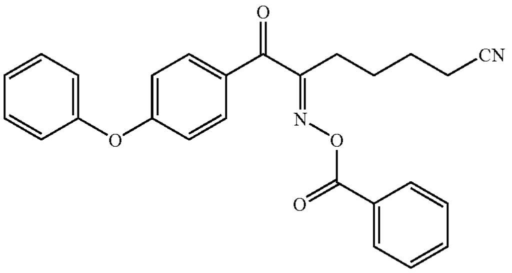
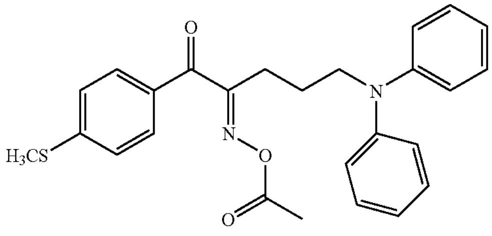
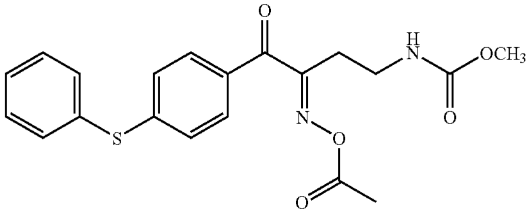
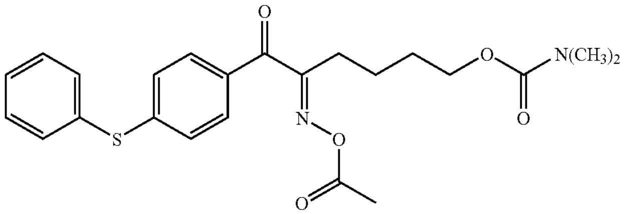
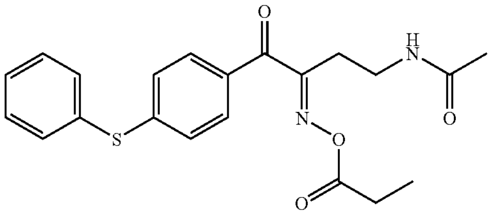
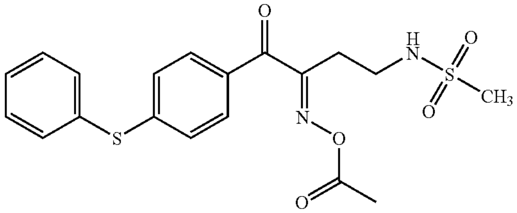
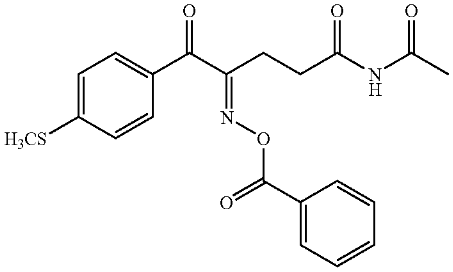
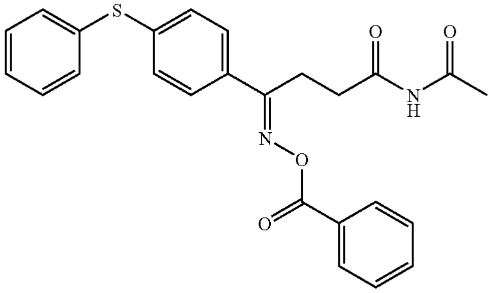
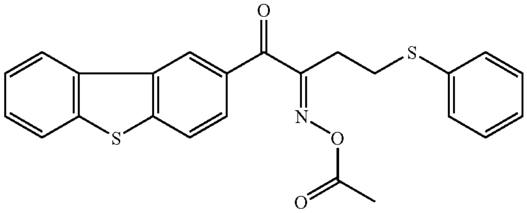
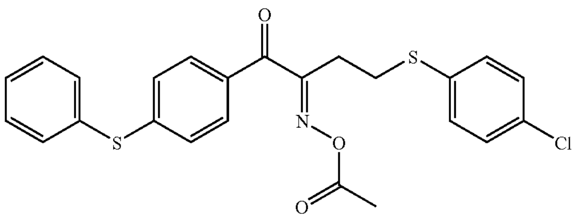

-continued
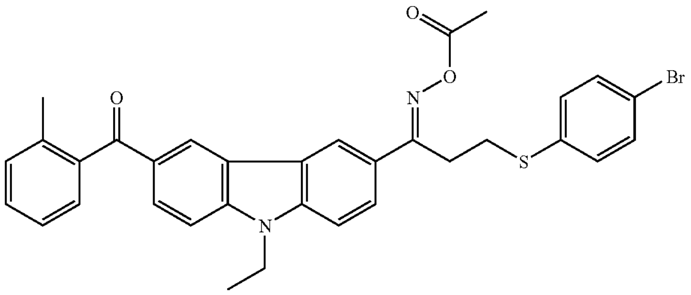
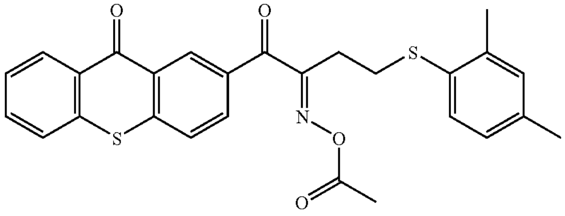
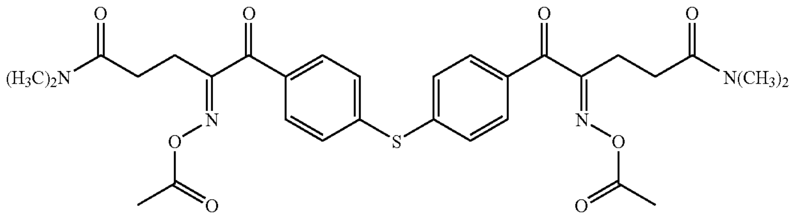
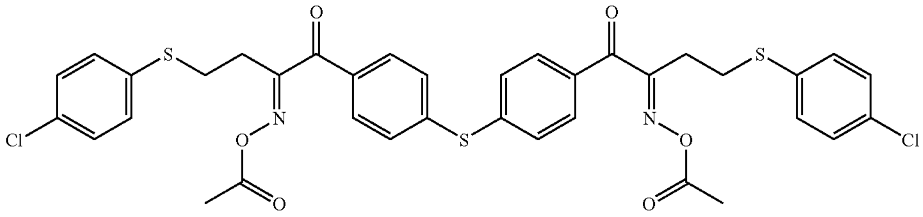
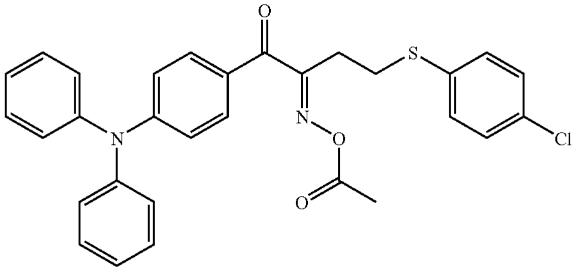
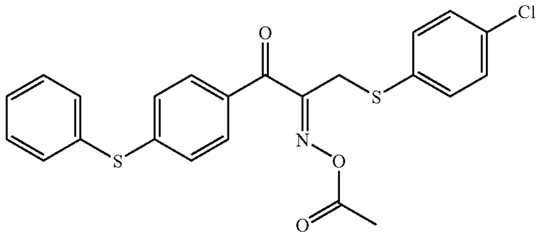
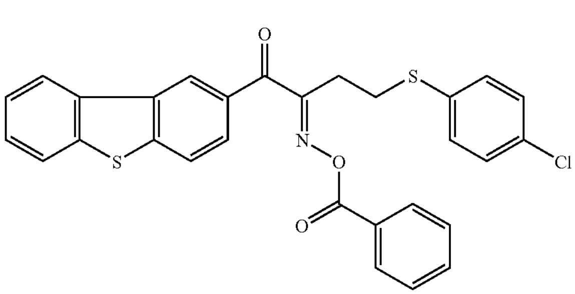
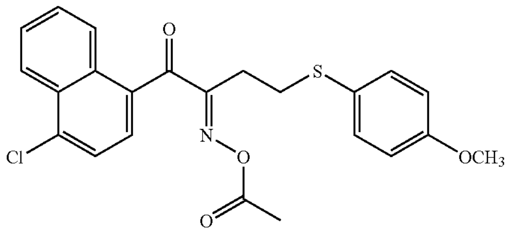

-continued
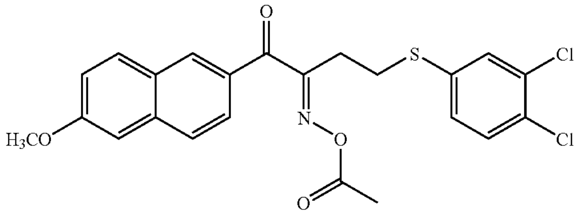
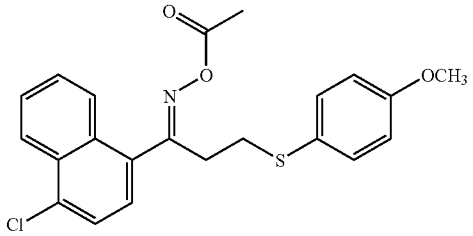
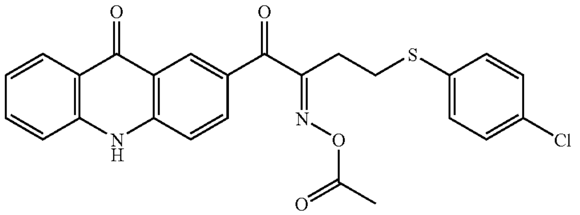
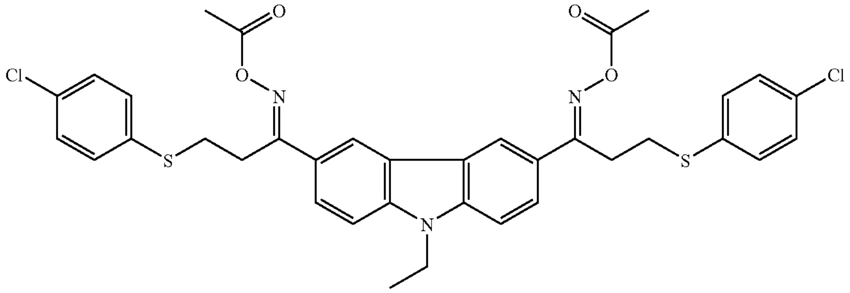
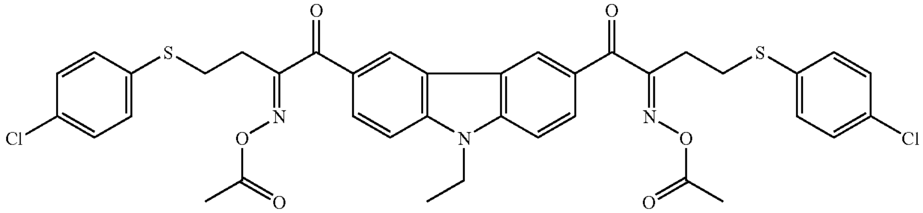
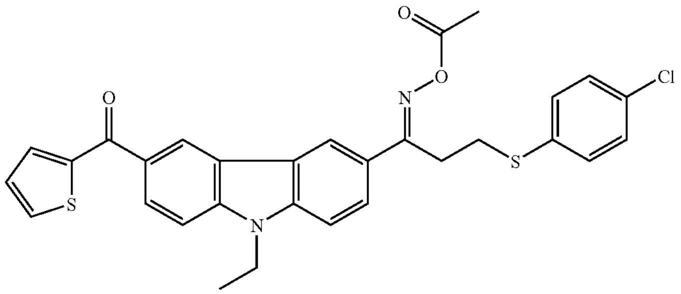
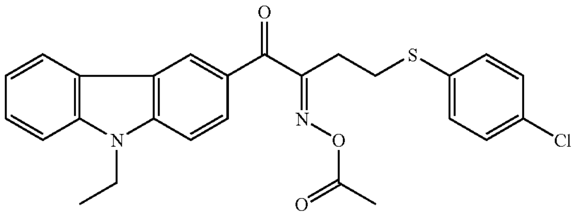
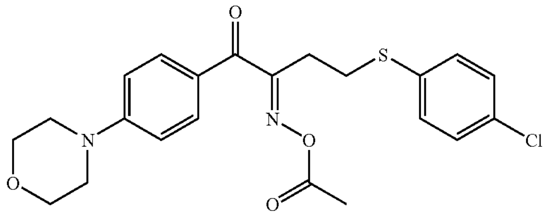
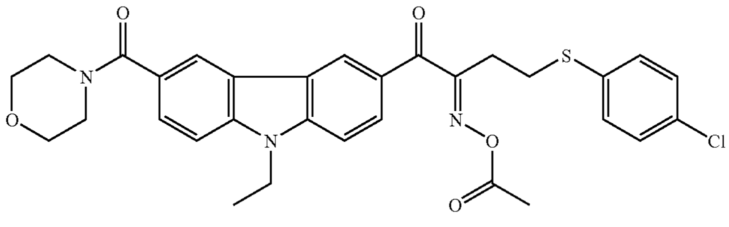

-continued

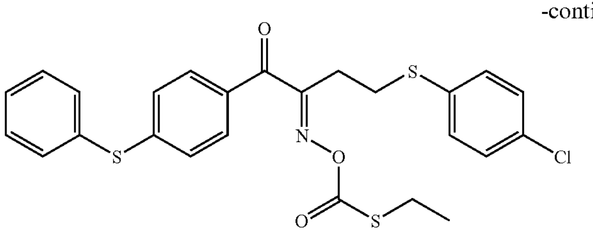

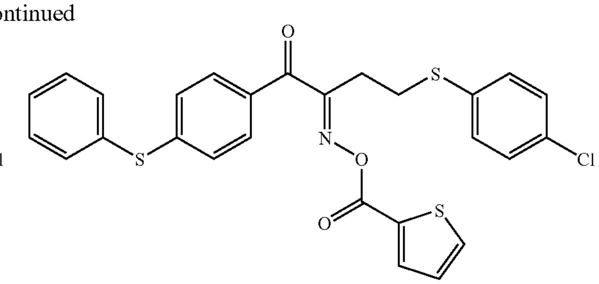

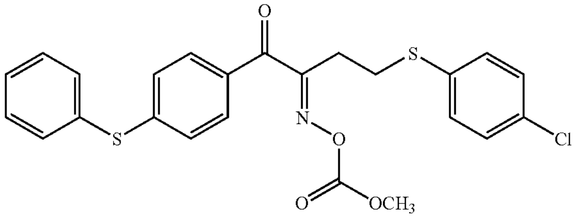

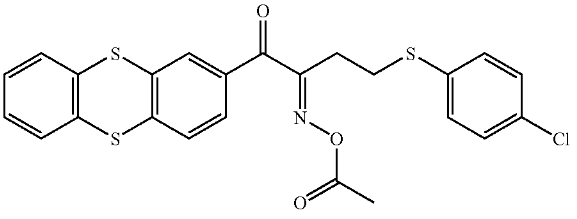

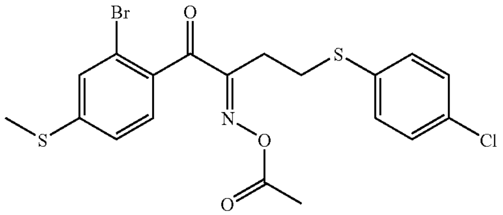

The oxime derivative according to the invention has a high photopolymerization sensitivity when the derivative is used in a photopolymerizable composition. When the photopolymerizable composition is made or the photopolymerizable composition is applied to a substrate, the precipitation of a solid is decreased.

The oxime derivative according to the invention can be synthesized by a known synthesis process, which is not particularly limited.

<Process for Synthesizing the Oxime Derivative>

A scheme of the process for synthesizing the oxime derivative is illustrated below. The process for synthesizing the oxime derivative is not limited to this process. In the scheme shown below, each of X and Y is the same group as $R^{1a}$ in the formula (I) or a group that is a precursor of $R^{1a}$ in the formula (I).

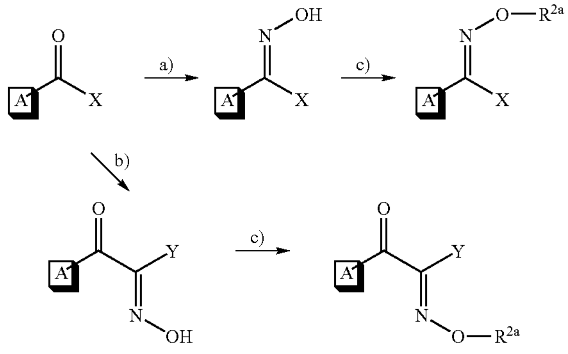

a) hydroxylamine or a salt thereof b) a base such as NaOMe/nitrous ester c) a base such as NaOH/a halogenated product of $R^{2a}$ or an anhydride of $R^{2a}$, or an amine (such as pyridine)/a halogenated product of $R^{2a}$ or an anhydride of $R^{2a}$ wherein $R^{2a}$ has the same meaning as $R^{2a}$ in the formula (I).

Conditions preferable for this synthesizing process may be conditions described in JP-A No. 2000-80068, paragraph (0067).

The photopolymerizing properties, such as the sensitivity and curing rate, of the oxime derivative according to the invention as a photopolymerization initiator are can be improved by being combined with various sensitizers. Examples of the sensitizers include compounds described in JP-A No. 2000-80068, paragraphs (0112) to (0118).

With respect to the content by percentage of the photopolymerization initiator represented by the formula (I) in the invention, the concentration thereof in the solids of the composition according to the invention is preferably from 0.5 to 35% by mass, more preferably from 1 to 25% by mass, even more preferably from 2 to 20% by mass.

If the concentration of the photopolymerization initiator represented by the formula (I) is less than 0.5% by mass, the photopolymerizing properties such as the sensitivity and the curing rate may be insufficient. If the concentration is more than 35% by mass, light does not reach the deep part of the composition so that the sensitivity may fall or the strength or developer resistance of the photopolymerized portion may fall.

In the invention, two or more kinds of the photopolymerization initiator represented by the formula (I) may be used.

A known photopolymerization initiator other than the compound of the formula (I) may be incorporated into the composition according to the invention.

The known photopolymerization initiator is not particularly limited as long as the initiator can initiate the polymerization of the radical polymerizable monomer (B), which will be detailed later. The photopolymerization initiator is preferably selected from the viewpoint of the property, initiation efficiency, absorption wavelength, availability, costs and other factors.

A photopolymerization initiator which can be used as the known photopolymerization initiator may be, for example: at least one active halogen compound selected from halomethyloxadiazole compounds and halomethyl-s-triazine compounds; a 3-aryl-substituted coumalin compound or a lophine dimer; a benzophenone compound; an acetophenone compound or a derivative thereof; a cyclopentadiene-benzene-iron complex or a salt thereof; an oxime compound other than those represented by the formula (I); or an acylphosphine (oxide) compound.

Examples of the halomethyloxadiazole compound as an active halogen compound include 2-halomethyl-5-vinyl-1,3,4-oxadiazole compounds described in Japanese Patent Application Publication (JP-B) No. 57-6096, 2-trichloromethyl-5-styryl-1,3,4-oxadiazole, 2-trichloromethyl-5-(p-cyanostyryl)-1,3,4-oxadiazole, and 2-trichloromethyl-5-(p-methoxystyryl)-1,3,4-oxadiazole.

Examples of the halomethyl-s-triazine compound as an active halogen compound include vinyl-halomethyl-s-triazine compounds described in JP-B No. 59-1281, and 2-(naphtho-1-yl)-4,6-bis-halomethyl-s-triazine compounds and 4-(p-aminophenyl)-2,6-di-halomethyl-s-triazine compounds described in JP-A No. 53-133428.

Specific examples thereof include 2,4-bis(trichloromethyl)-6-p-methoxystyryl-s-triazine, 2,6-bis(trichloromethyl)-4-(3,4-methylenedioxyphenyl)-1,3,5-triazine, 2,6-bis(trichloromethyl)-4-(4-methoxyphenyl)-1,3,5-triazine, 2,4-bis(trichloromethyl)-6-(1-p-dimethylaminophenyl-1,3-butadienyl)-s-triazine, 2-trichloromethyl-4-amino-6-p-methoxystyryl-s-triazine, 2-(naphtho-1-yl)-4,6-bis-trichloromethyl-s-triazine, 2-(4-methoxy-naphtho-1-yl)-4,6-bis(trichloromethyl-s-triazine), 2-(4-ethoxy-naphtho-1-yl)-4,6-bis-trichloromethyl-s-triazine, 2-(4-butoxy-naphtho-1-yl)-4,6-bis-trichloromethyl-s-triazine, 2-[4-(2-methoxyethyl)-naphtho-1-yl]-4,6-bis-trichloromethyl-s-triazine, 2-[4-(2-ethoxyethyl)-naphtho-1-yl]-4,6-bis-trichloromethyl-s-triazine, 2-[4-(2-butoxyethyl)-naphtho-1-yl]-4,6-bis-trichloromethyl-s-triazine, 2-(2-methoxy-naphtho-1-yl)-4,6-bis-trichloromethyl-s-triazine, 2-(6-methoxy-5-methyl-naphtho-2-yl)-4,6-bis-trichloromethyl-s-triazine, 2-(6-methoxy-naphtho-1-yl)-4,6-bis-trichloromethyl-s-triazine, 2-(5-methoxy-naphtho-1-yl)-4,6-bis-trichloromethyl-s-triazine, 2-(4,7-dimethoxy-naphtho-1-yl)-4,6-bis-trichloromethyl-s-triazine, 2-(6-ethoxy-naphtho-2-yl)-4,6-bis-trichloromethyl-s-triazine, 2-(4,5-dimethoxy-naphtho-1-yl)-4,6-bis-trichloromethyl-s-triazine, 4-[p-N,N-di(ethoxycarbonylmethyl)aminophenyl]-2,6-di(trichloromethyl)-s-triazine, 4-[o-methyl-p-N,N-di(ethoxycarbonylmethyl)aminophenyl]-2,6-di(trichloromethyl)-s-triazine, 4-[p-N,N-di(chloroethyl)aminophenyl]-2,6-di(trichloromethyl)-s-triazine, 4-[o-methyl-p-N,N-di(chloroethyl)aminophenyl]-2,6-di(trichloromethyl)-s-triazine, 4-(p-N-chloroethylaminophenyl)-2,6-di(trichloromethyl)-s-triazine, 4-(p-N-ethoxycarbonylmethylaminophenyl)-2,6-di(trichloromethyl)-s-triazine, 4-[p-N,N-di(phenyl)aminophenyl]-2,6-di(trichloromethyl)-s-triazine, 4-(p-N-chloroethylcarbonylaminophenyl)-2,6-di(trichloromethyl)-s-triazine, 4-[p-N-(p-methoxyphenyl)carbonylaminophenyl]-2,6-di(trichloromethyl)-s-triazine, 4-[m-N,N-di(ethoxycarbonylmethyl)aminophenyl]-2,6-di(trichloromethyl)-s-triazine, 4-[m-bromo-p-N,N-di(ethoxycarbonylmethyl)aminophenyl]-2,6-di(trichloromethyl)-s-triazine, 4-[m-chloro-p-N,N-di(ethoxycarbonylmethyl)aminophenyl]-2,6-di(trichloromethyl)-s-triazine, 4-[m-fluoro-p-N,N-di(ethoxycarbonylmethyl)aminophenyl]-2,6-di(trichloromethyl)-s-triazine, 4-[o-bromo-p-N,N-di(ethoxycarbonylmethyl)aminophenyl]-2,6-di(trichloromethyl)-s-triazine, 4-[o-chloro-p-N,N-di(ethoxycarbonylmethyl)aminophenyl]-2,6-di(trichloromethyl)-s-triazine, 4-[o-fluoro-p-N,N-di(ethoxycarbonylmethyl)aminophenyl]-2,6-di(trichloromethyl)-s-triazine, 4-[o-bromo-p-N,N-di(chloroethyl)aminophenyl]-2,6-di(trichloromethyl)-s-triazine, 4-[o-chloro-p-N,N-di(chloroethyl)aminophenyl]-2,6-di(trichloromethyl)-s-triazine, 4-[o-fluoro-p-N,N-di(chloroethyl)aminophenyl]-2,6-di(trichloromethyl)-s-triazine, 4-[m-bromo-p-N,N-di(chloroethyl)aminophenyl]-2,6-di(trichloromethyl)-s-triazine, 4-[m-chloro-p-N,N-di(chloroethyl)aminophenyl]-2,6-di(trichloromethyl)-s-triazine, 4-[m-fluoro-p-N,N-di(chloroethyl)aminophenyl]-2,6-di(trichloromethyl)-s-triazine, 4-(m-bromo-p-N-ethoxycarbonylmethylaminophenyl)-2,6-di(trichloromethyl)-s-triazine, 4-(m-chloro-p-N-ethoxycarbonylmethylaminophenyl)-2,6-di(trichloromethyl)-s-triazine, 4-(m-fluoro-p-N-ethoxycarbonylmethylaminophenyl)-2,6-di(trichloromethyl)-s-triazine, 4-(o-bromo-p-N-ethoxycarbonylmethylaminophenyl)-2,6-di(trichloromethyl)-s-triazine, 4-(o-chloro-p-N-ethoxycarbonylmethylaminophenyl)-2,6-di(trichloromethyl)-s-triazine, 4-(o-fluoro-p-N-ethoxycarbonylmethylaminophenyl)-2,6-di(trichloromethyl)-s-triazine, 4-(m-bromo-p-N-chloroethylaminophenyl)-2,6-di(trichloromethyl)-s-triazine, 4-(m-chloro-p-N-chloroethylaminophenyl)-2,6-di(trichloromethyl)-s-triazine, 4-(m-fluoro-p-N-chloroethylaminophenyl)-2,6-di(trichloromethyl)-s-triazine, 4-(o-bromo-p-N-chloroethylaminophenyl)-2,6-di(trichloromethyl)-s-triazine, 4-(o-chloro-p-N-chloroethylaminophenyl)-2,6-di(trichloromethyl)-s-triazine, and 4-(o-fluoro-p-N-chloroethylaminophenyl)-2,6-di(trichloromethyl)-s-triazine.

Other examples include TAZ series (e.g., TAZ-107, TAZ-110, TAZ-104, TAZ-109, TAZ-140, TAZ-204, TAZ-113, and TAZ-123) manufactured by Midori Kagaku Co., Ltd., T series (e.g., T-OMS, T-BMP, T-R, and T-B) manufactured by Panchim Co., IRGACURE series (e.g., IRGACURE 907, IRGACURE 369, IRGACURE 379, IRGACURE 651, IRGACURE 184, IRGACURE 500, IRGACURE 1000, IRGACURE 149, and IRGACURE 261) and DALOCURE series (e.g., DALOCURE 1173) manufactured by Ciba Specialty Chemicals. Ltd., 4,4'-bis(diethylamino)-benzophenone, 2-benzyl-2-dimethylamino-4-morpholinobutyrophenone, 2,2-dimethoxy-2-phenylacetophenone, 2-methyl-1-phenyl-2-morpholinopropane-1-one, 2-methyl-1'-[4-(hexyl)phenyl]-2-morpholinopropane-1'-one, and 2-ethyl-2-dimethylamino-1-(4-morpholinophenyl)-butanone-1.

The acylphospine(oxide) compound is not particularly limited, and examples thereof include IRGACURE 819, DALOCURE 4265, and DALOCURE TPO manufactured by Ciba Specialty Chemicals. Ltd.

The following are also preferable: a 2-(o-chlorophenyl)-4,5-diphenylimidazolyl dimer, a 2-(o-fluorophenyl)-4,5-diphenylimidazolyl dimer, a 2-(o-methoxyphenyl)-4,5-diphenylimidazolyl dimer, a 2-(p-methoxyphenyl)-4,5-diphenylimidazolyl dimer, a 2-(p-dimethoxyphenyl)-4,5-diphenylimidazolyl dimer, a 2-(2,4-dimethoxyphenyl)-4,5-diphenylimidazolyl dimer, a 2-(p-methylmercaptophenyl)-4,5-diphenylimidazolyl dimer, and benzoin isopropyl ether.

As an oxime photopolymerization initiator made of an oxime compound, for example, oxime initiators described in JP-A Nos. 2000-80068 and 2001-233842, and WO 02/100903A1 are known.

Examples of the oxime compound include 2-(O-benzoyloxime)-1-[4-(phenylthio)phenyl]-1,2-butanedione, 2-(O-benzoyloxime)-1-[4-(phenylthio)phenyl]-1,2-pentanedione, 2-(O-benzoyloxime)-1-[4-(phenylthio)phenyl]-1,2-hexanedione, 2-(O-benzoyloxime)-1-[4-(phenylthio)phenyl]-1,2-heptanedione, 2-(O-benzoyloxime)-1-[4-(phenylthio)phenyl]-1,2-octanedione, 2-(O-benzoyloxime)-1-[4-(methylphenylthio)phenyl]-1,2-butanedione, 2-(O-benzoyloxime)-1-[4-(ethylphenylthio)phenyl]-1,2-butanedione, 2-(O-benzoyloxime)-1-[4-(butylphenylthio)phenyl]-1,2-butanedione, 1-(O-acetyloxime)-1-[9-ethyl-6-(2-methylbenzoyl)-9H-carbazole-3-yl]ethanone, 1-(O-acetyloxime)-1-[9-methyl-6-(2-methylbenzoyl)-9H-carbazole-3-yl]ethanone, 1-(O-acetyloxime)-1-[9-propyl-6-(2-methylbenzoyl)-9H-carbazole-3-yl]ethanone, 1-(O-acetyloxime)-1-[9-ethyl-6-(2-methylbenzoyl)-9H-carbazole-3-yl]ethanone, and 1-(O-acetyloxime)-1-[9-ethyl-6-(2-butylbenzoyl)-9H-carbazole-3-yl]ethanone. However, the oxime compound is not limited to these examples.

In an embodiment, only one of these photopolymerization initiators is added to the compound represented by the formula (I). In another embodiment, a combination of two or more of these photopolymerization initiators are added to the compound represented by the formula (I).

When known photopolymerization initiators are used, the total content thereof is preferably within the aforementioned range for the content of the compound represented by the formula (I).

(C) Colorant

The photopolymerizable composition according to the invention may contain a colorant in accordance with the use.

The colorant is not particularly limited, and may be selected from dyes, pigments and others.

Of the dyes, a dye soluble in an organic solvent is preferable.

This organic solvent soluble organic dye may be appropriately selected from known dyes that can be used for conventional color filters, for example, dyes disclosed in JP-A Nos. 64-90403, 64-91102, 1-94301, 6-11614, 5-333207, 6-35183, 6-51115, and 6-194828, Japanese Patent No. 2592207, U.S. Pat. Nos. 4,808,501, 5,667,920, and 5,059,500.

From the viewpoint of chemical structure, the following dyes can be used: triphenylmethane dyes, azo dyes (such as pyrazole azo dyes, anilino azo dyes, pyrazolo triazole azo dyes, and pyridone azo dyes), anthrapyridone dyes, anthraquinone dyes, benzylidene dyes, oxonol dyes, cyanine dyes, phenothiazine dyes, azomethine dyes (such as pyrrolopyrazole azomethine dyes), xanthene dyes, phthalocyanine dyes, benzopyran dyes, and indigo dyes.

When the composition according to the invention is used in a resist which is developed with water or an alkali, the colorant is preferably an acidic dye and/or a derivative thereof from the viewpoint of removing the binder and/or dye completely by development. Besides, the following are also useful: a direct dye, a basic dye, a mordant dye, an acidic mordant dye, an azoic dye, a disperse dye, an oil soluble dye, a food dye, and derivatives thereof.

The following will describe the acidic dye and the derivatives thereof.

—Acidic Dye and Derivatives Thereof—

The acidic dye is not particularly limited as long as the dye is a colorant having an acidic group such as a sulfonic acid group, a carboxylic acid group or a phenolic hydroxyl group. The acidic dye is selected, considering all of the required performances such as solubility in the organic solvent described later or in the developer to be used at the time of development, capability of forming a salt with a basic compound, light absorbance, interaction with other components in the photopolymerizable composition, light resistance, and heat resistance.

Specific examples of the acidic dye are listed up below. In the invention, the acidic dye is not limited thereto.

Acid Alizarin violet N;

Acid Black 1, 2, 24, and 48;

Acid Blue 1, 7, 9, 15, 18, 23, 25, 27, 29, 40, 42, 45, 51, 62, 70, 74, 80, 83, 86, 87, 90, 92, 96, 103, 108, 112, 113, 120, 129, 138, 147, 150, 158, 171, 182, 192, 210, 242, 243, 249, 256, 259, 267, 278, 280, 285, 290, 296, 315, 324:1, 335, and 340;

Acid Chrome Violet K;

Acid Fuchsin;

Acid Green 1, 3, 5, 9, 16, 25, 27, 50, 58, 63, 65, 80, 104, 105, 106, and 109;

Acid Orange 6, 7, 8, 10, 12, 26, 50, 51, 52, 56, 62, 63, 64, 74, 75, 94, 95, 107, 108, 169, and 173;

Acid Red 1, 4, 8, 14, 17, 18, 26, 27, 29, 31, 34, 35, 37, 42, 44, 50, 51, 52, 57, 66, 73, 80, 87, 88, 91, 92, 94, 97, 103, 111, 114, 129, 133, 134, 138, 143, 145, 150, 151, 158, 176, 182, 183, 198, 206, 211, 215, 216, 217, 227, 228, 249, 252, 257, 258, 260, 261, 266, 268, 270, 274, 277, 280, 281, 308, 312, 315, 316, 339, 341, 345, 346, 349, 382, 383, 394, 401, 412, 417, 418, 422, and 426;

Acid Violet 6B, 7, 9, 17, 19, and 49;

Acid Yellow 1, 3, 7, 9, 11, 17, 23, 25, 29, 34, 36, 38, 40, 42, 54, 65, 72, 73, 76, 79, 98, 99, 111, 112, 113 114, 116, 119, 123, 128, 134, 135, 138, 139, 140, 144, 150, 155, 157, 160, 161, 163, 168, 169, 172, 177, 178, 179, 184, 190, 193, 196, 197, 199, 202, 203, 204, 205, 207, 212, 214, 220, 221, 228, 230, 232, 235, 238, 240, 242, 243, and 251;

Direct Yellow 2, 33, 34, 35, 38, 39, 43, 47, 50, 54, 58, 68, 69, 70, 71, 86, 93, 94, 95, 98, 102, 108, 109, 129, 136, 138, and 141;

Direct Orange 34, 39, 41, 46, 50, 52, 56, 57, 61, 64, 65, 68, 70, 96, 97, 106, and 107;

Direct Red 79, 82, 83, 84, 91, 92, 96, 97, 98, 99, 105, 106, 107, 172, 173, 176, 177, 179, 181, 182, 184, 204, 207, 211, 213, 218, 220, 221, 222, 232, 233, 234, 241, 243, 246, and 250;

Direct Violet 47, 52, 54, 59, 60, 65, 66, 79, 80, 81, 82, 84, 89, 90, 93, 95, 96, 103, and 104;

Direct Blue 57, 77, 80, 81, 84, 85, 86, 90, 93, 94, 95, 97, 98, 99, 100, 101, 106, 107, 108, 109, 113, 114, 115, 117, 119, 137, 149, 150, 153, 155, 156, 158, 159, 160, 161, 162, 163, 164, 166, 167, 170, 171, 172, 173, 188, 189, 190, 192, 193, 194, 196, 198, 199, 200, 207, 209, 210, 212, 213, 214, 222, 228, 229, 237, 238, 242, 243, 244, 245, 247, 248, 250, 251, 252, 256, 257, 259, 260, 268, 274, 275, and 293;

Direct Green 25, 27, 31, 32, 34, 37, 63, 65, 66, 67, 68, 69, 72, 77, 79, and 82;

Mordant Yellow 5, 8, 10, 16, 20, 26, 30, 31, 33, 42, 43, 45, 56, 61, 62, and 65;

Mordant Orange 3, 4, 5, 8, 12, 13, 14, 20, 21, 23, 24, 28, 29, 32, 34, 35, 36, 37, 42, 43, 47, and 48;

Mordant Red 1, 2, 3, 4, 9, 11, 12, 14, 17, 18, 19, 22, 23, 24, 25, 26, 30, 32, 33, 36, 37, 38, 39, 41, 43, 45, 46, 48, 53, 56, 63, 71, 74, 85, 86, 88, 90, 94, and 95;

Mordant Violet 1, 2, 4, 5, 7, 14, 22, 24, 30, 31, 32, 37, 40, 41, 44, 45, 47, 48, 53, and 58;

Mordant Blue 1, 2, 3, 7, 8, 9, 12, 13, 15, 16, 19, 20, 21, 22, 23, 24, 26, 30, 31, 32, 39, 40, 41, 43, 44, 48, 49, 53, 61, 74, 77, 83, and 84;

Mordant Green 1, 3, 4, 5, 10, 15, 19, 26, 29, 33, 34, 35, 41, 43, and 53;

Food Yellow 3;

Solvent Yellow 14, 82, 94, and 162;

Solvent Orange 2, 7, 11, 15, 26, and 56;

Solvent Blue 25, 35, 37, 38, 55, 59, and 67;

Solvent Red 49; and derivatives of these dyes.

Preferable ones also include azo, xanthene and phthalocyanine acidic dyes other than the above dyes. Moreover, preferable ones also include acidic dyes such as C.I. Solvent Blue 44 and 38, C.I. Solvent Orange 45, Rhodamine B, Rhodamine 110, and 3-[(5-chloro-2-phenoxyphenyl)hydrazono]-3,4-dihydro-4-oxo-5-[(phenylsulfonyl)amino]-2,7-naphthalene-disulfonic acid; and derivatives of these dyes.

Examples of the derivatives of the acidic dyes include inorganic salts of an acidic dye having an acidic group derived from sulfonic acid, carboxylic acid or the like, salts of an acidic dye and a nitrogen-containing compound, and sulfonamides of an acid dye. The derivatives of the acidic dyes are not particularly limited, and are desirably dissolvable when the composition according to the invention is prepared into a solution form. The derivative to be used is selected considering all of the required performances, such as solubility in the organic solvent or the developer used at development, light absorbance, interaction with other components in the photopolymerizable composition according to the invention, light resistance, and heat resistance.

The above-mentioned "salts of an acidic dye and a nitrogen-containing compound" are described below. The salts may be effective in improving the solubility of the acidic dye (or providing the dye with solubility in organic solvent) or in improving the heat resistance or light resistance of the dye.

The above-mentioned "nitrogen-containing compound" to be used to form a salt with an acidic dye, or the "nitrogen-containing compound" that forms an amide bond in the above-mentioned "sulfonamides of any acidic dye" is selected in consideration of all of the required performances, such as solubility of the salt or amide compound in the organic solvent or the developer, salt-formability, the light absorbance or the chromatic valence (color number) of the acidic dye derivative, interaction with other components in the photopolymerizable composition, heat resistance and light resistance required for the colorant. When the nitrogen-containing compound is selected only from the viewpoint of the light absorbance or the chromatic valence, the molecular weight of the nitrogen-containing compound is preferably as low as possible. The molecular weight is preferably 300 or less, more preferably 280 or less, even more preferably 250 or less.

Specific examples of the nitrogen-containing compound are listed up below. However, in the invention, the nitrogen-containing compound is not limited to these examples. In the following nitrogen-containing compounds, compounds having no —NH— group are not within the scope of nitrogen-containing compounds that form an amide bond.

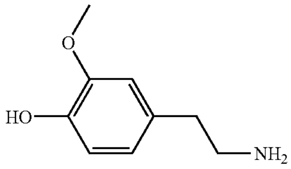
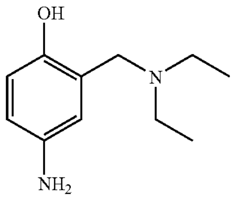
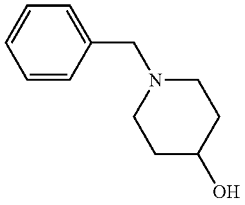
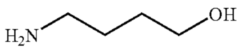

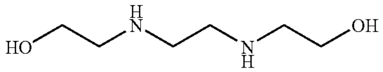
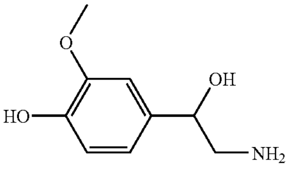
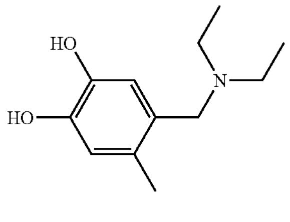

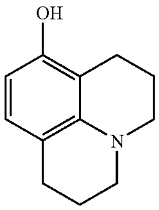
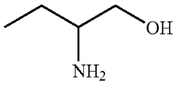
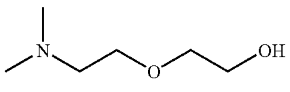
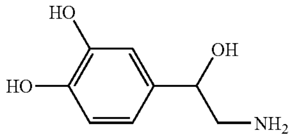

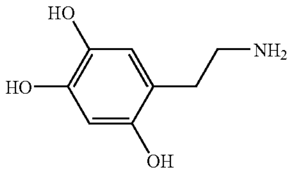
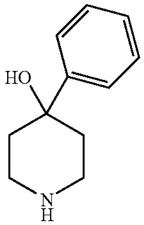
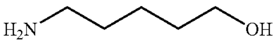
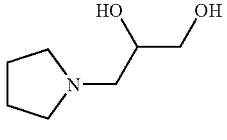

-continued
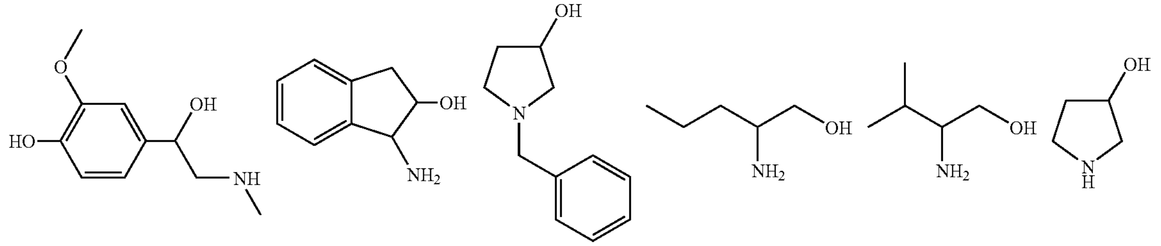
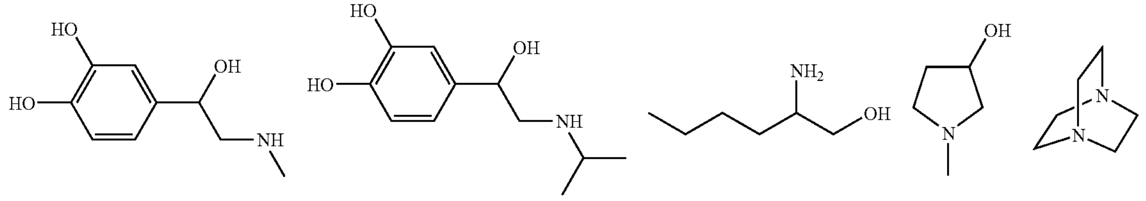
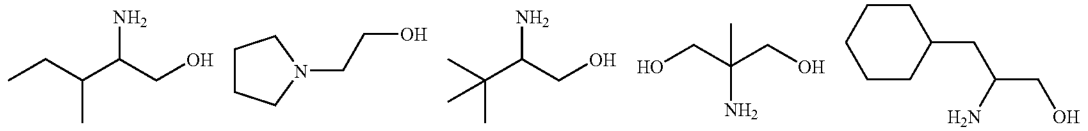
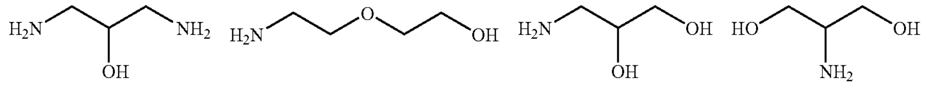
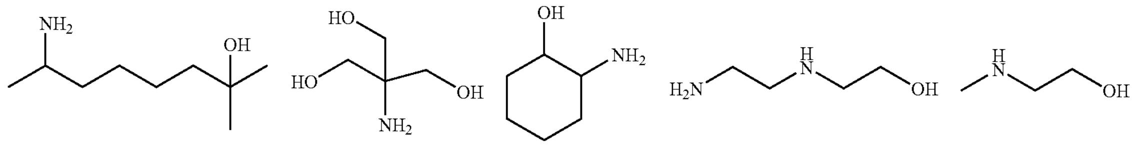
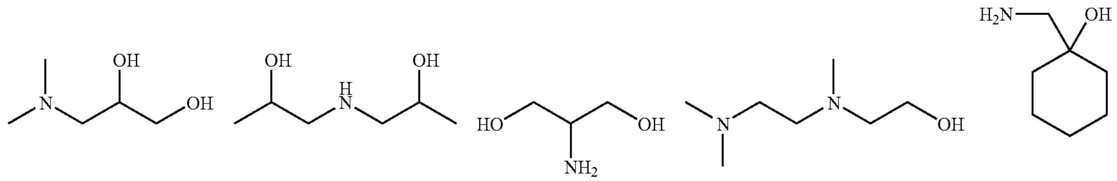
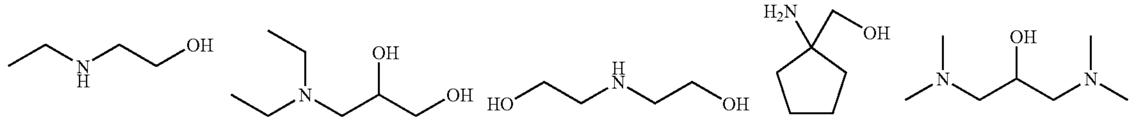
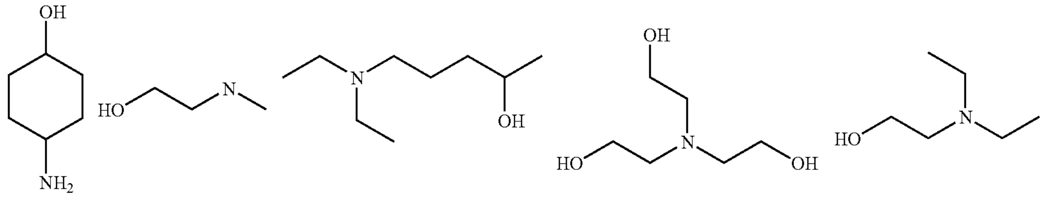
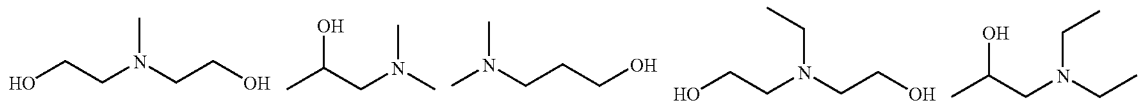
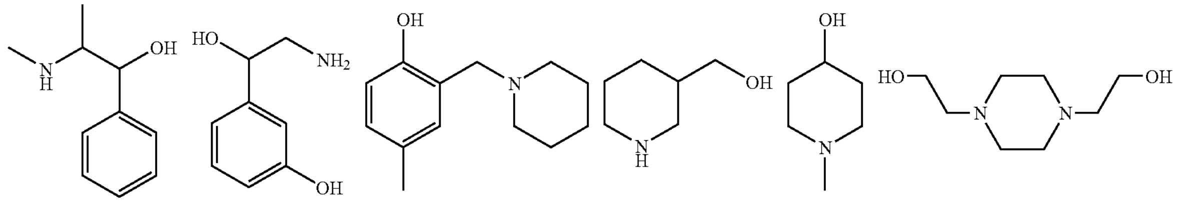

-continued
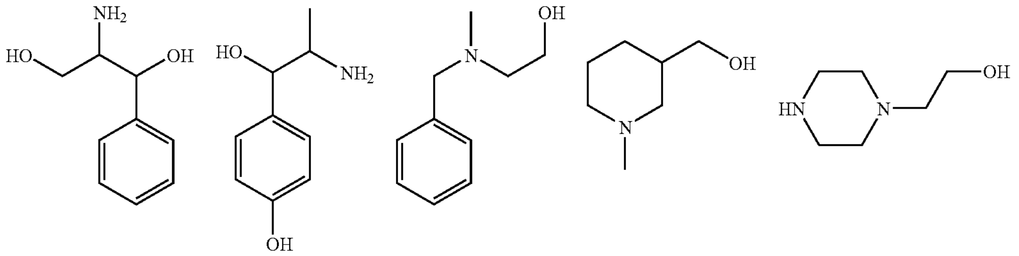
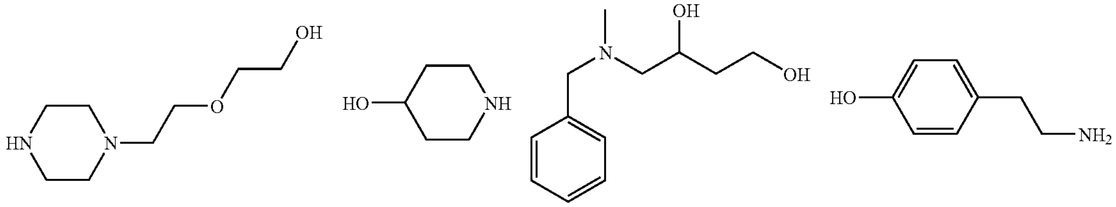
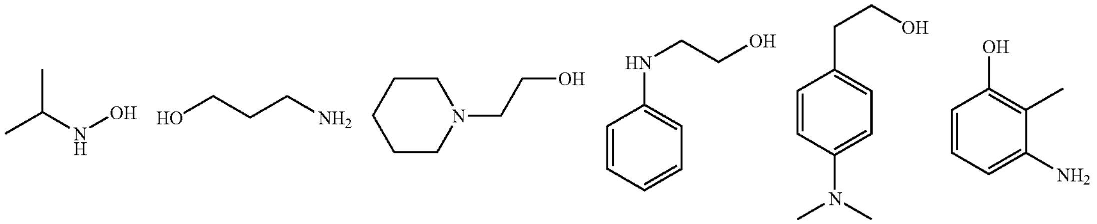
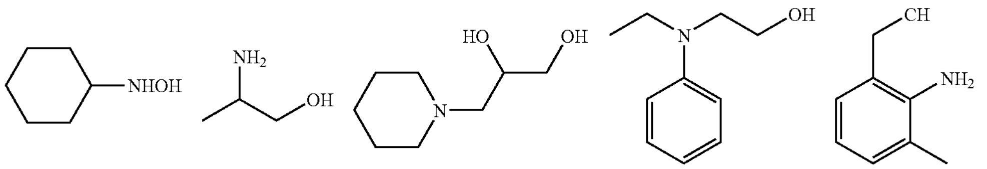
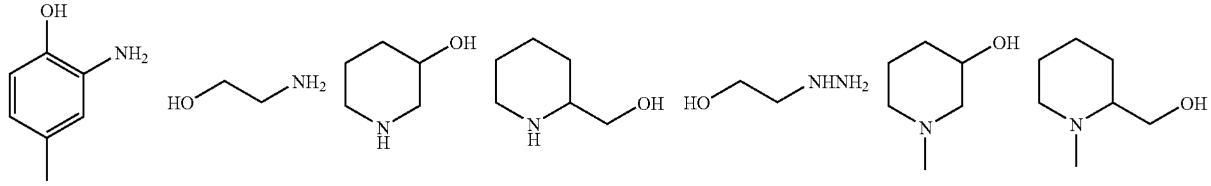
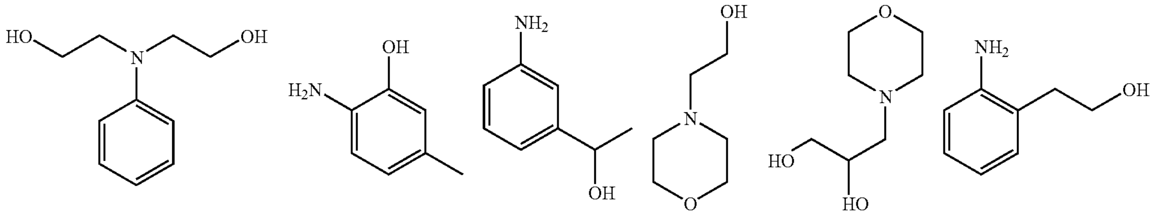
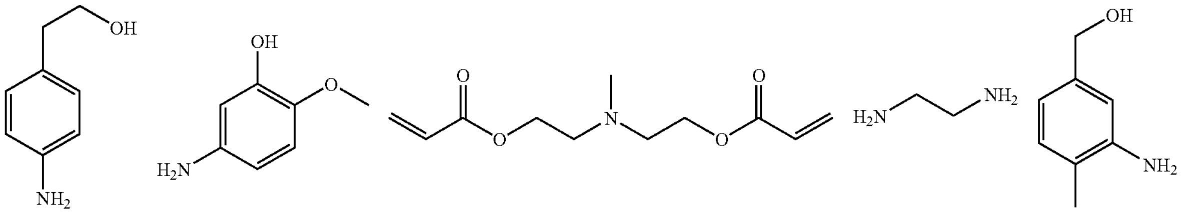
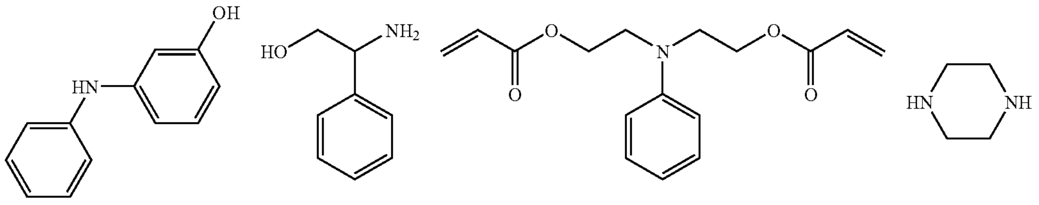

-continued

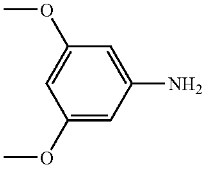
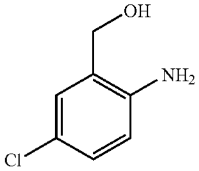
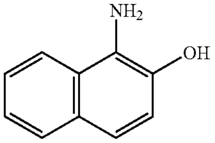
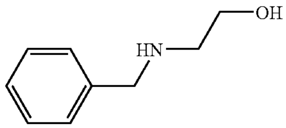
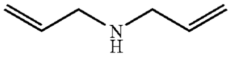

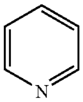
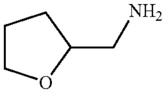
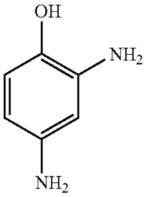
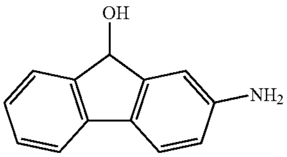
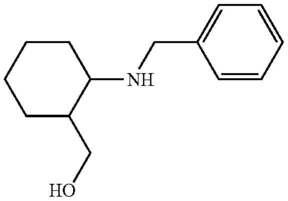

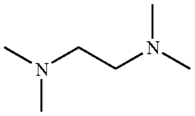
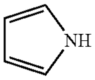
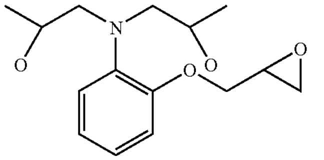
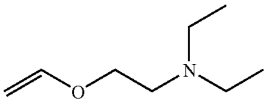
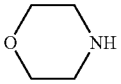

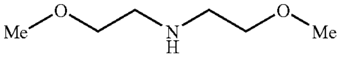
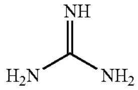
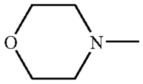
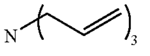
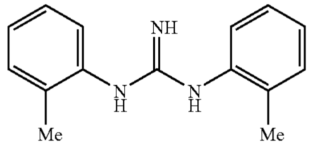

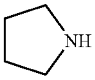
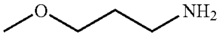

In the salt of the acidic dye and the nitrogen-containing compound, the mole ratio (n) of the nitrogen-containing compound to the acidic functional groups of the acidic dye is a value that determines the mole ratio between the acidic dye molecule and the amine compound as the counter ion, and can be selected at will in accordance with conditions for forming a salt of the acidic dye and the amine compound. Specifically, the mole ratio (n) is, in practice, often in the range of $0<n\leqq5$, and is selected in consideration of all of the required performances such as solubility in the organic solvent or the developer to be used for development, salt-formability, light absorbance, interaction with other components in the composition, light resistance, and heat resistance. When the mole ratio (n) is selected only from the viewpoint of the light absorbance, the range of $0<n\leqq4.5$ is preferable, the range of $0<n\leqq4$ is more preferable, and the range of $0<n\leqq3.5$ is still more preferable.

Out of the above-mentioned dyes, preferable ones include azo dyes (typical examples of which include pyridone azo dyes, pyrimidine azo dyes, pyrazole azo dyes, anilino azo dyes and pyrazolo triazole dyes), phthalocyanine dyes and azomethine dyes.

Specific examples of the azo dyes are listed up below [exemplary compounds (1) to (72)]. In the invention, however, the azo dyes are not limited to these examples. Tautomers of the specific examples are also preferable.

(1)

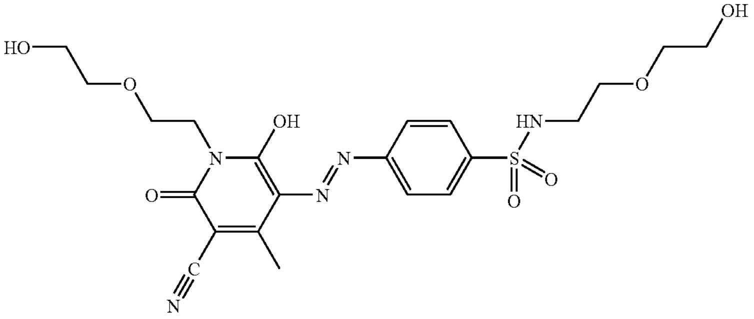

-continued
(2)
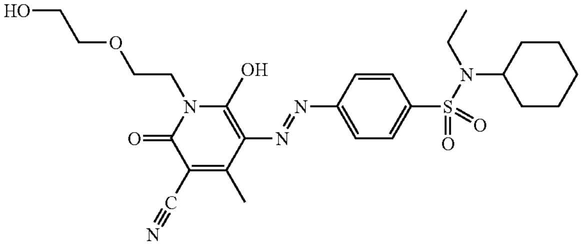
(3)
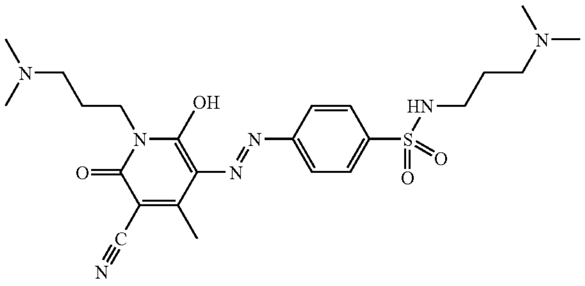
(4)
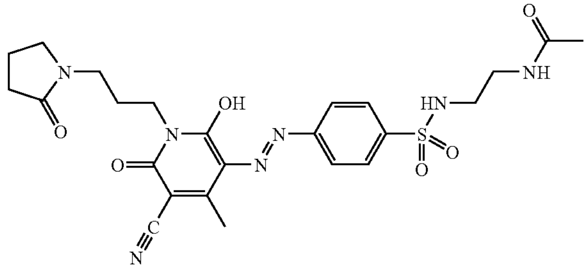
(5)
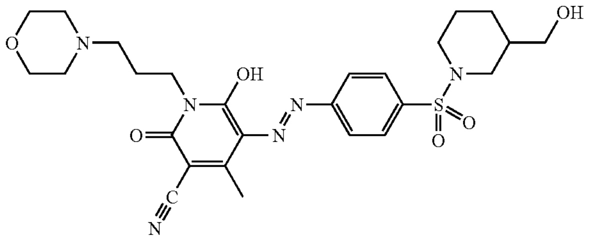
(6)
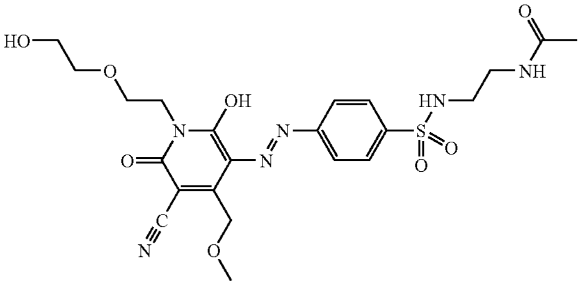
(7)
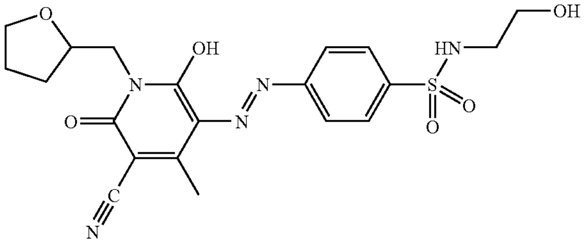
(8)
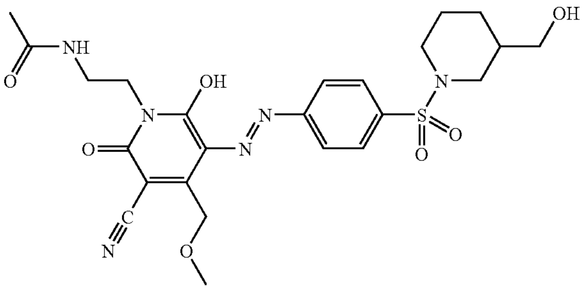
(9)
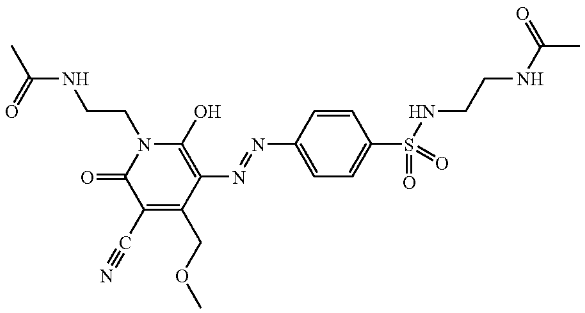
(10)
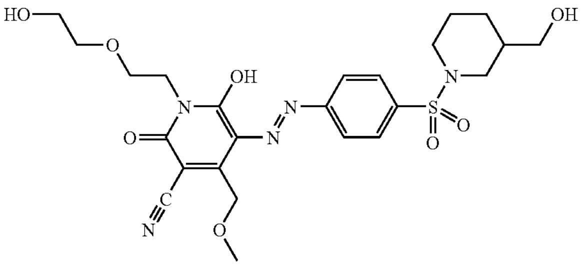
(11)
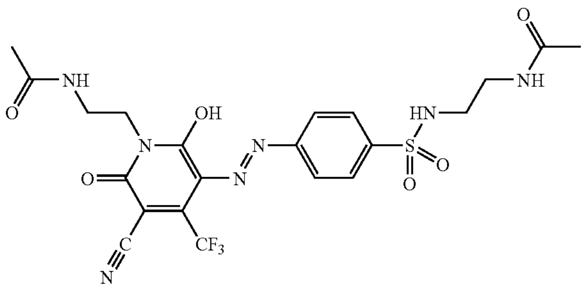

-continued
(12)
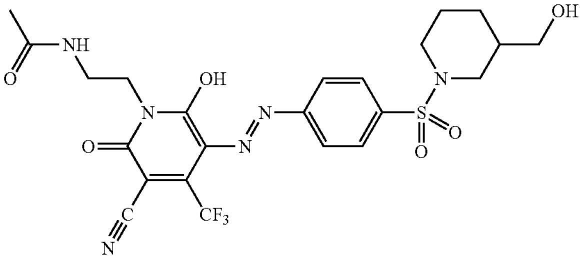
(13)
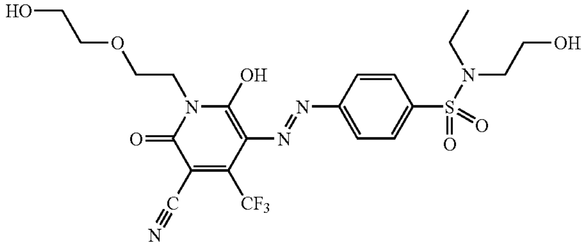
(14)
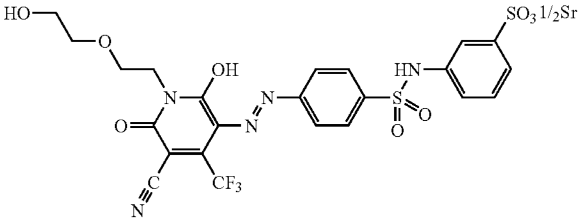
(15)
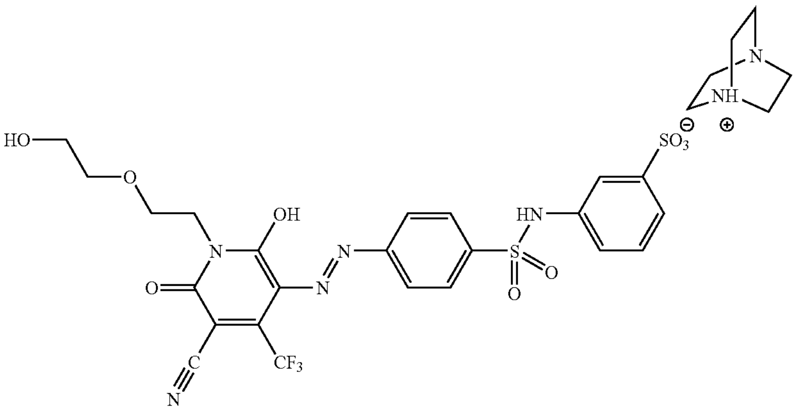
(16)
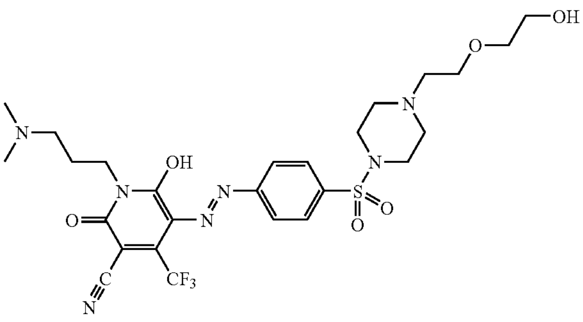
(17)
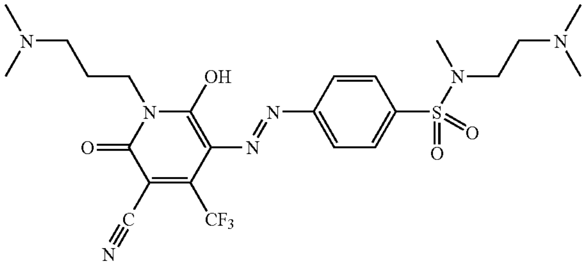
(17)
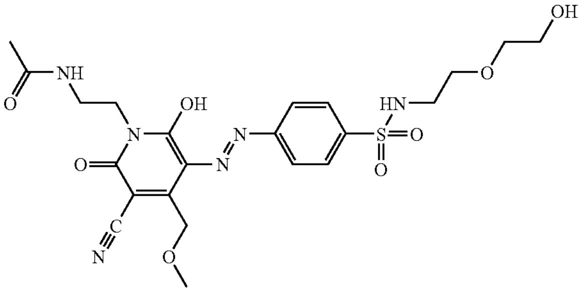
(18)
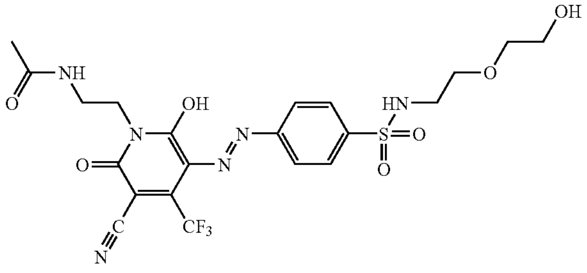

-continued
(19)
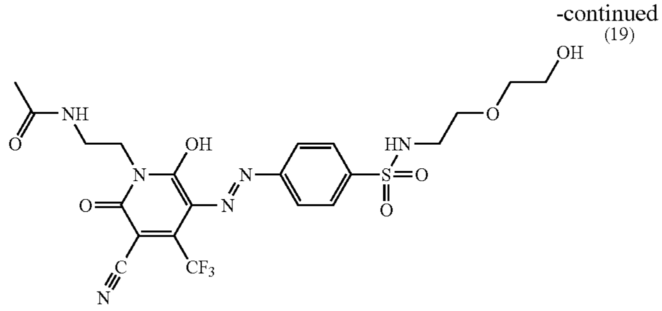
(20)
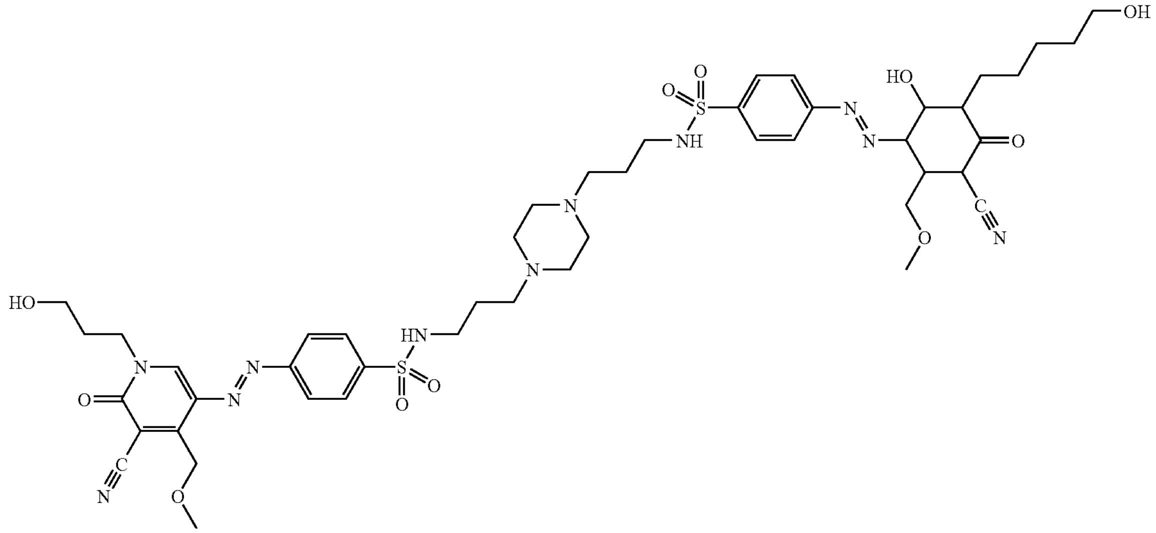
(21)
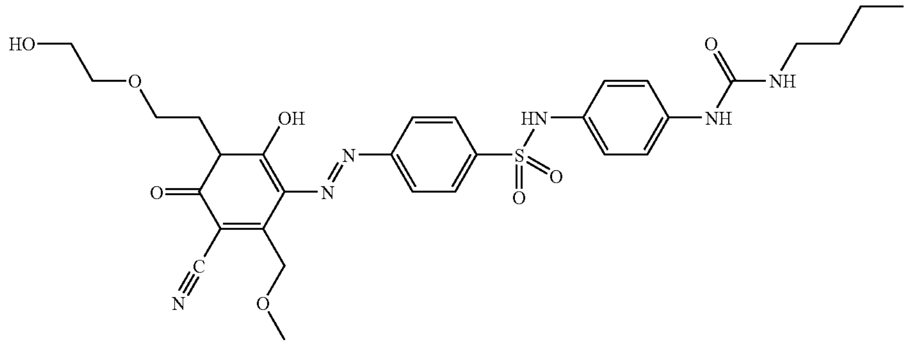
(22)
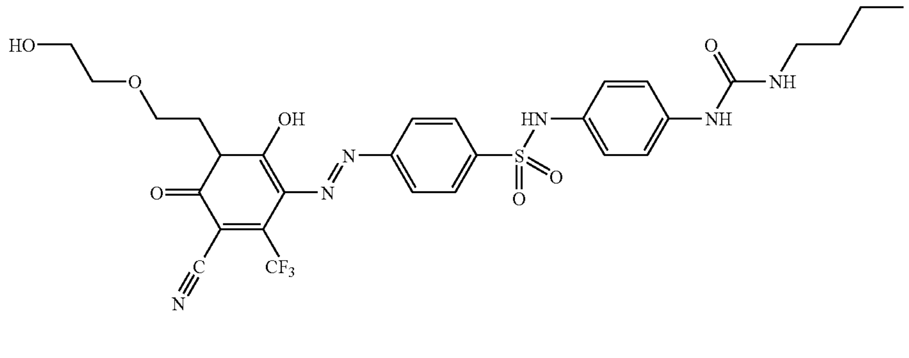

-continued
(23)
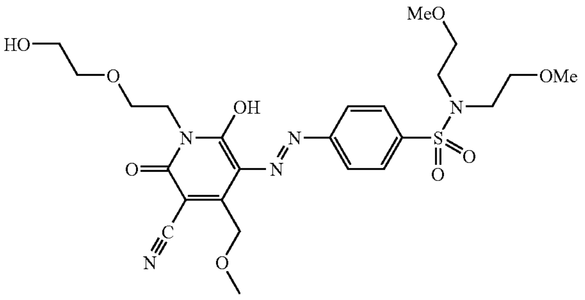
(24)
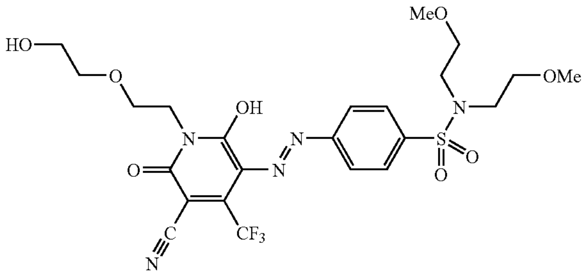
(25)
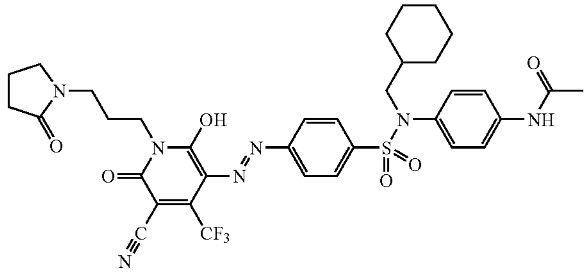
(26
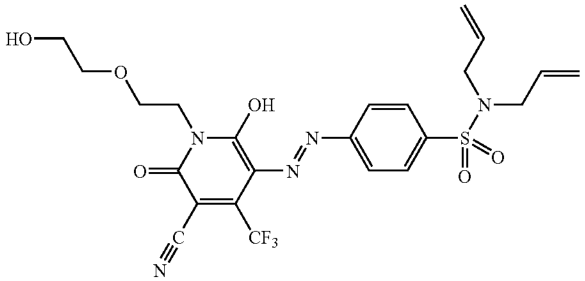
(27)
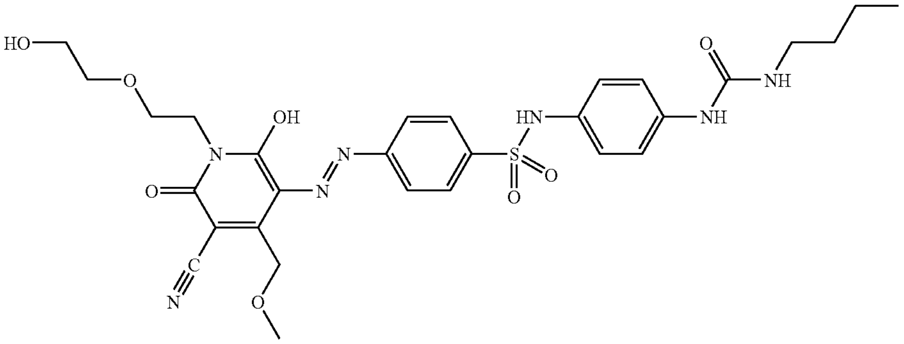
(28)
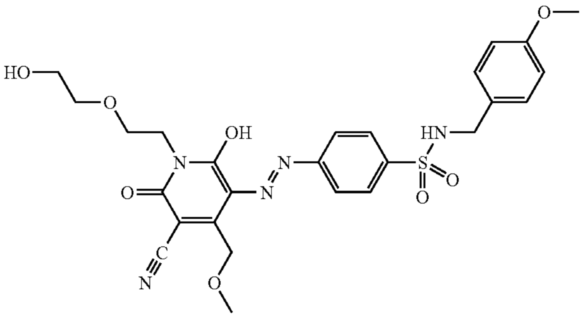
(29)
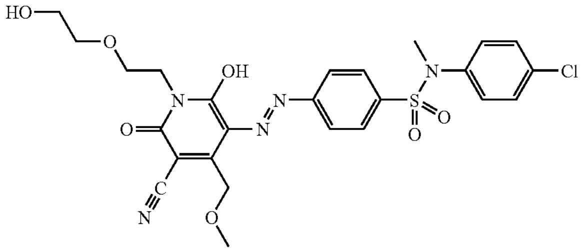

-continued
(30)
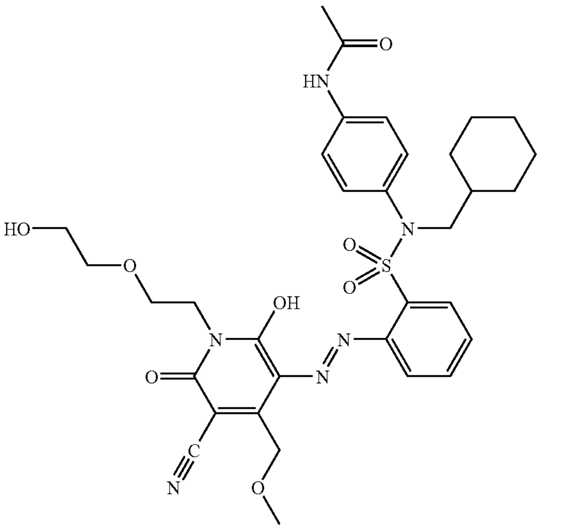
(31)
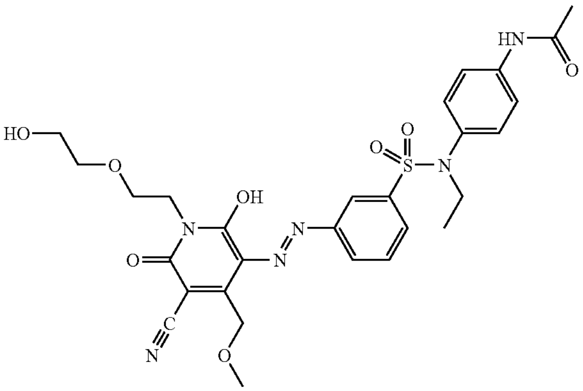
(32)
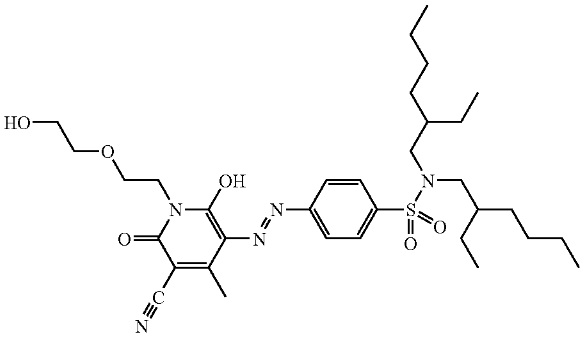
(33)
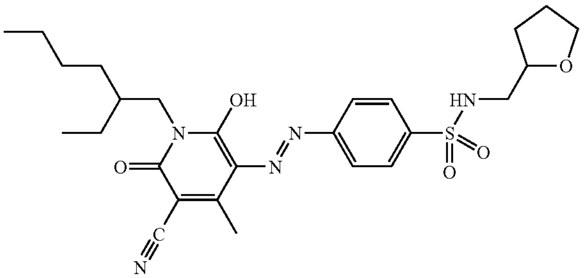
(34)
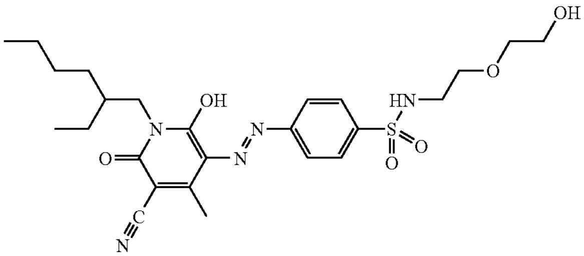
(35)
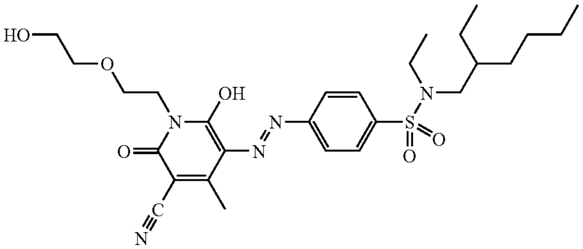
(36)
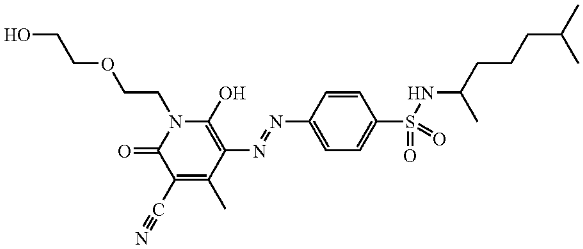
(37)
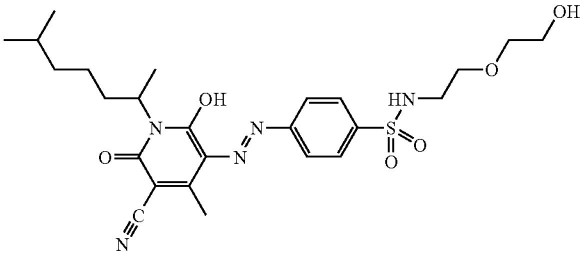

-continued
(38)
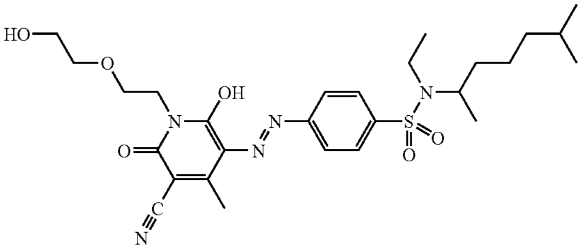
(39)
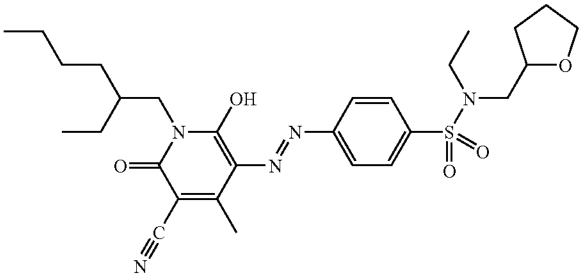
(40)
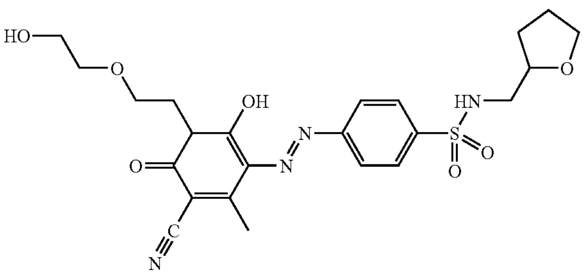
(41)
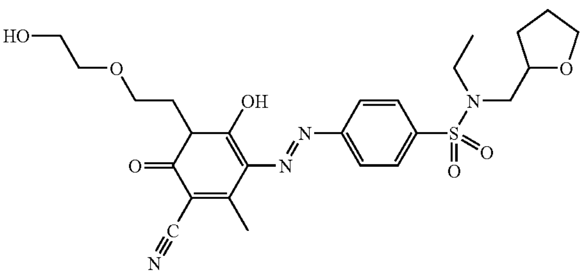
(42)
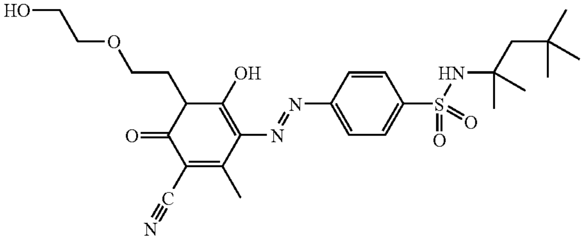
(43)
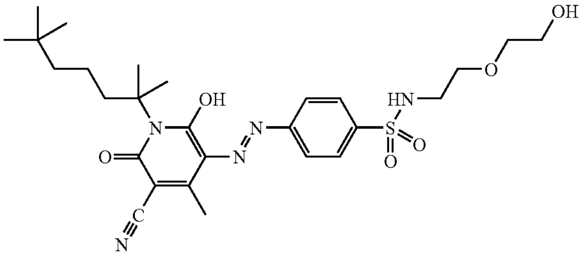
(44)
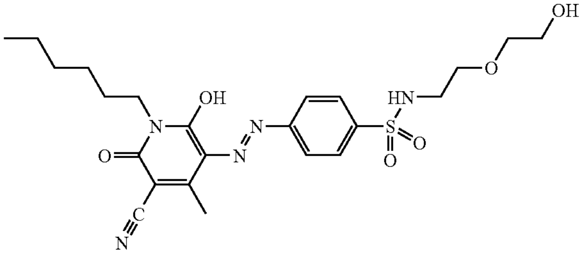
(45)
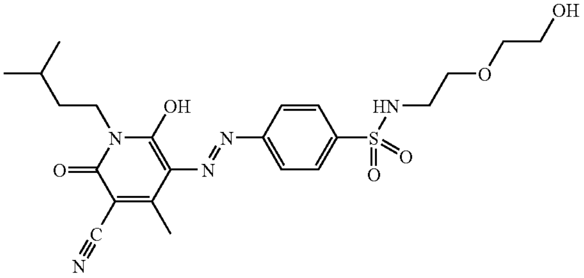

-continued
(46)
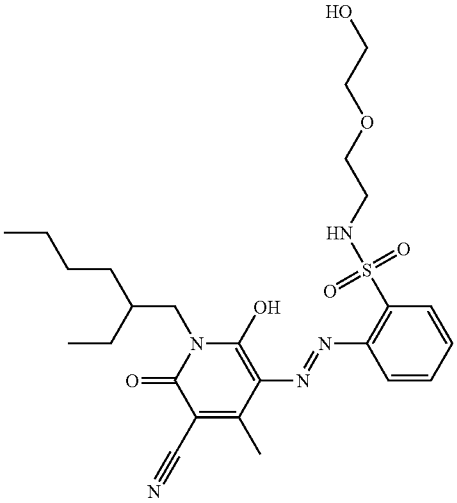
(47)
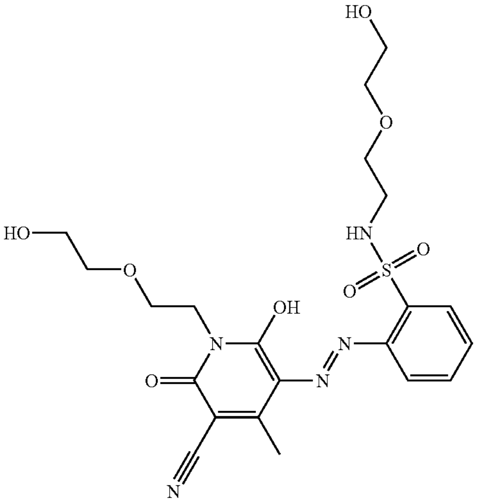
(48)
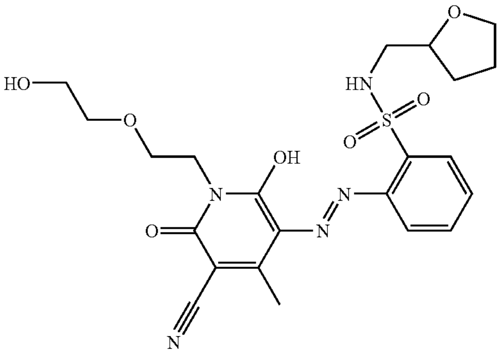
(49)
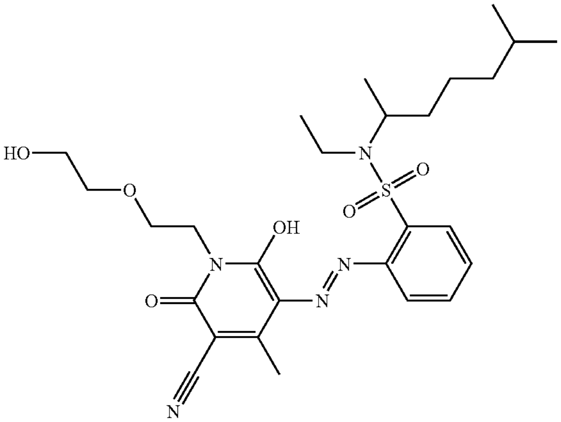
(50)
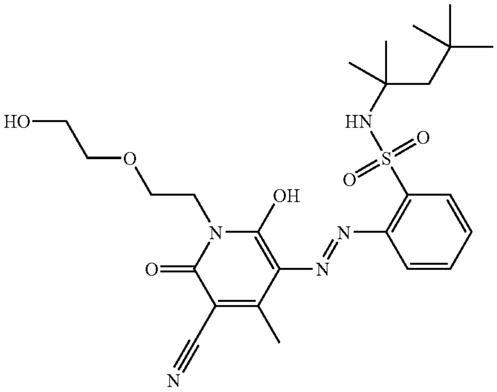
(51)
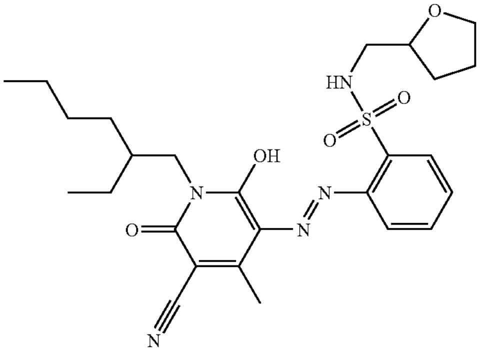

-continued
(52)
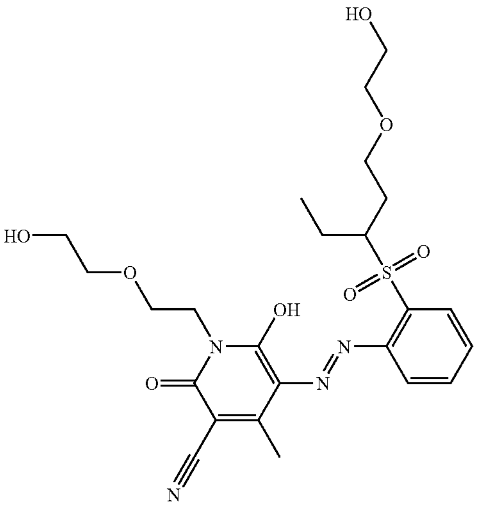
(53)
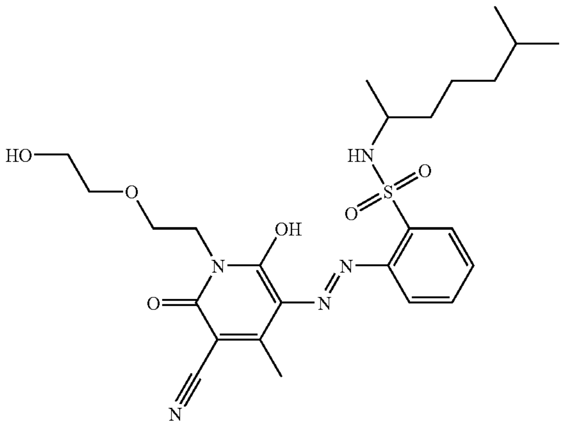
(54)
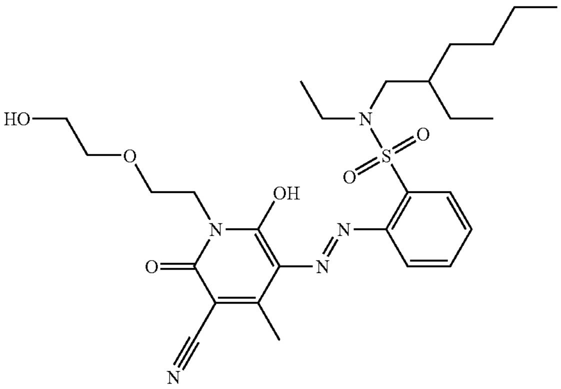
(55)
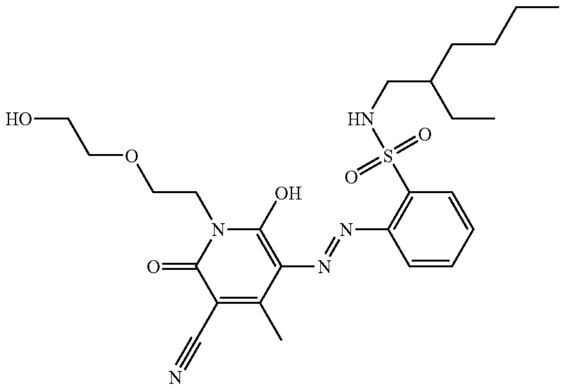
(56)
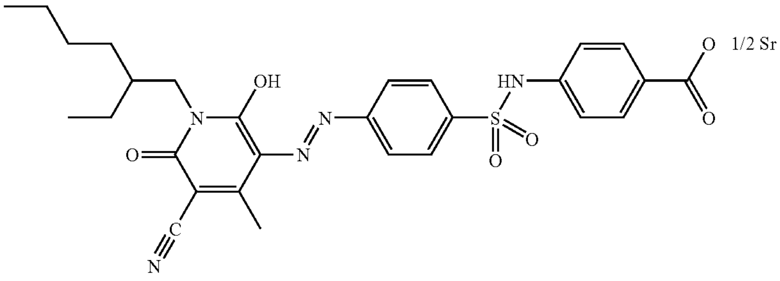
(57)
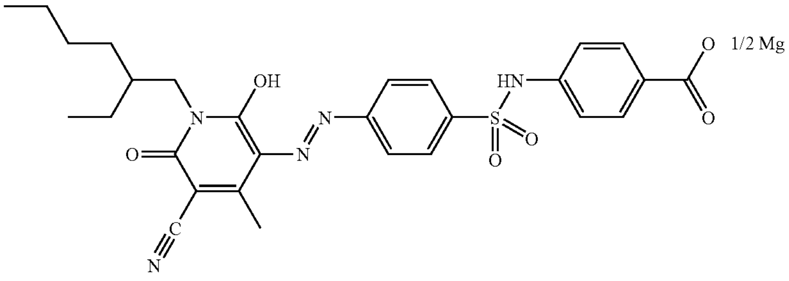

-continued
(58)
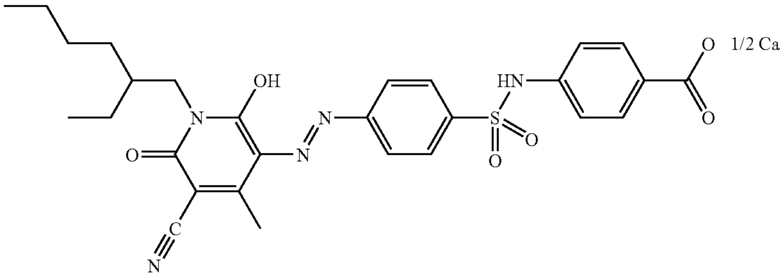
(59_
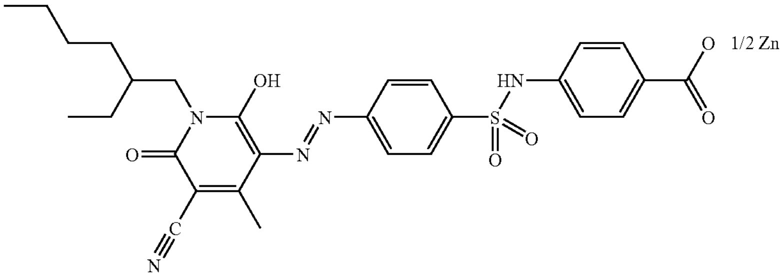
(60)
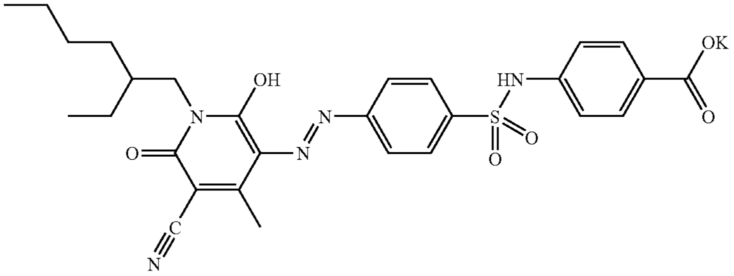
(61)
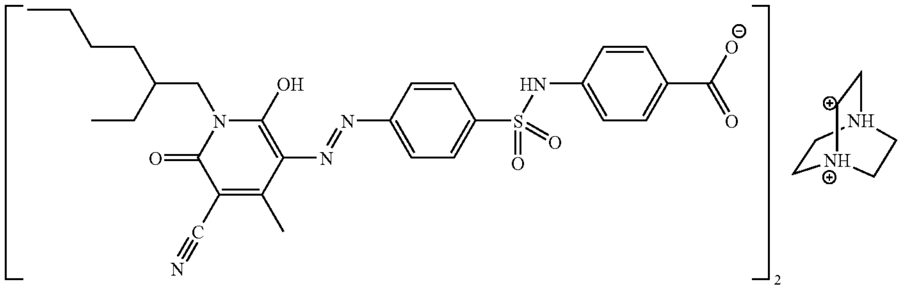
(61)
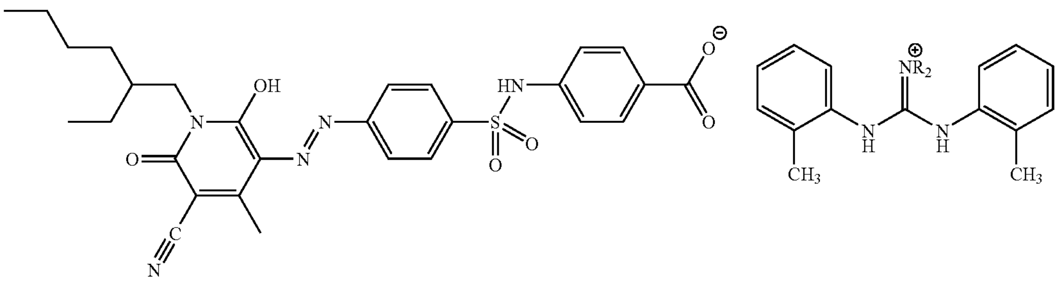

-continued
(62)
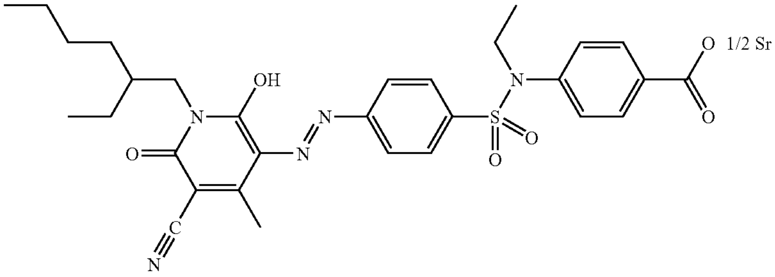
(63)
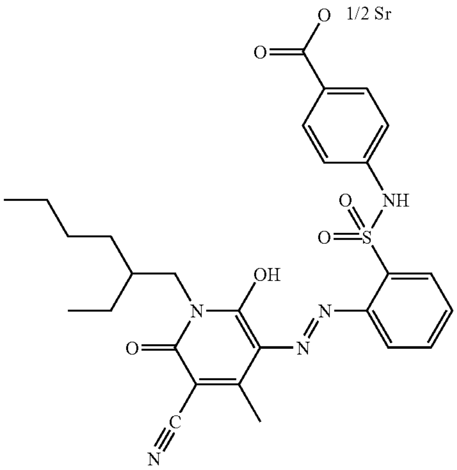
(64)
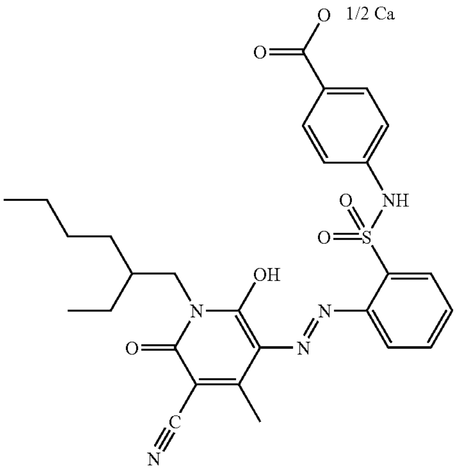
(65)
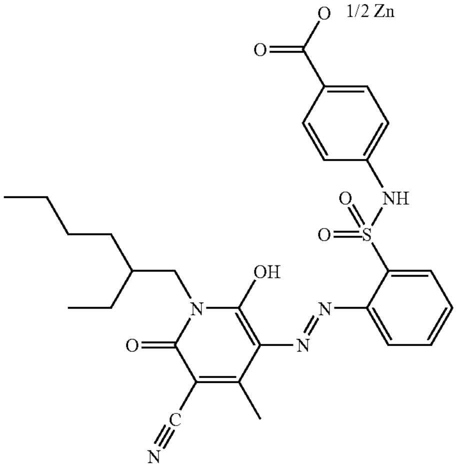
(66)
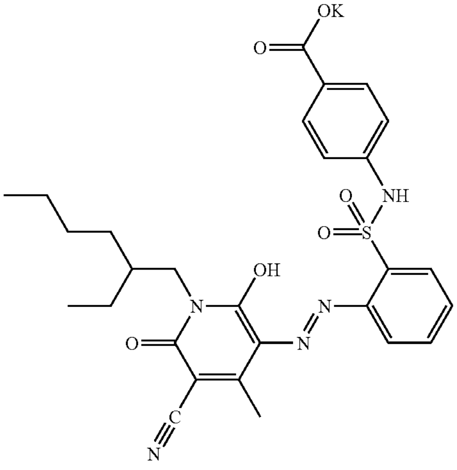

-continued
(68)
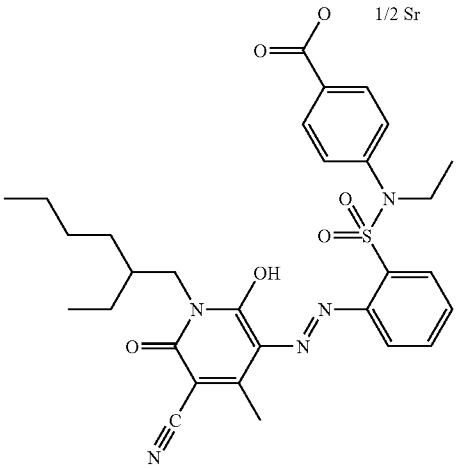
(69)
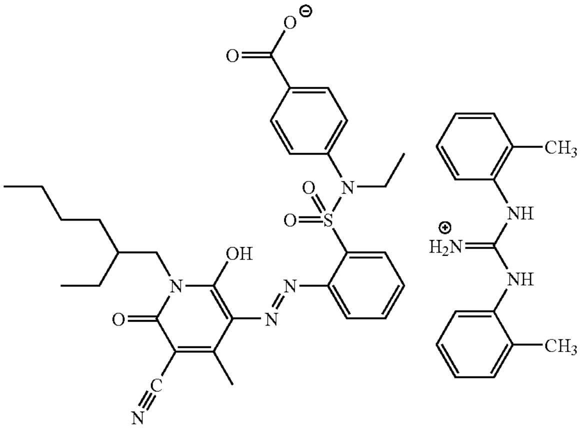
(70)
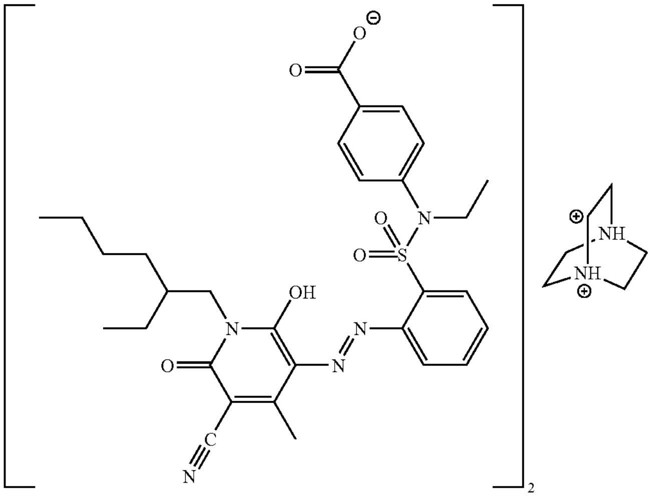
(71)
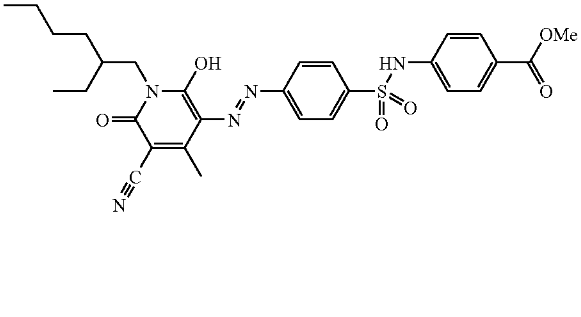
(72)
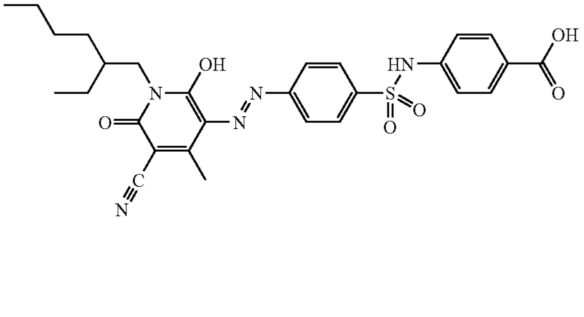

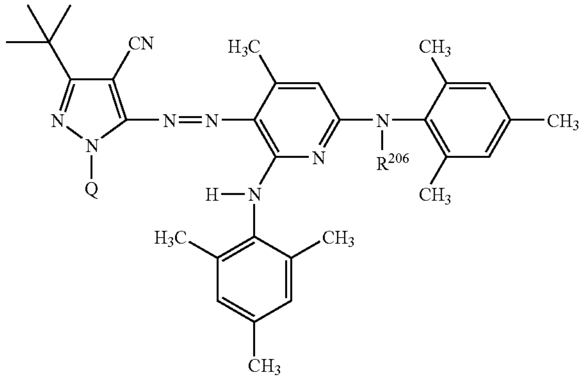
| Dye | Q | $R^{206}$ |
|---|---|---|
| ma-1 | 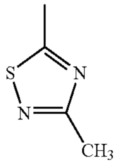 | $-CH_2CH_2CH_2OH$ |
| ma-2 | 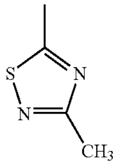 | 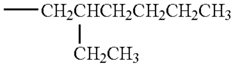 |
| ma-3 | 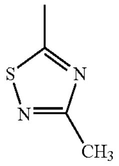 | $-COCH_2CH_2CH_2OH$ |
| ma-4 | 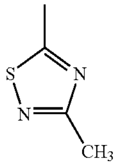 | $-CH_2CH_2CH_2COOH$ |
| ma-5 | 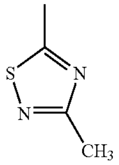 | 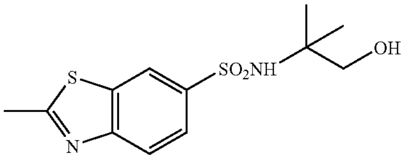 |
| ma-6 | 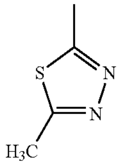 | $-CH_2CH_2CH_2OH$ |

-continued
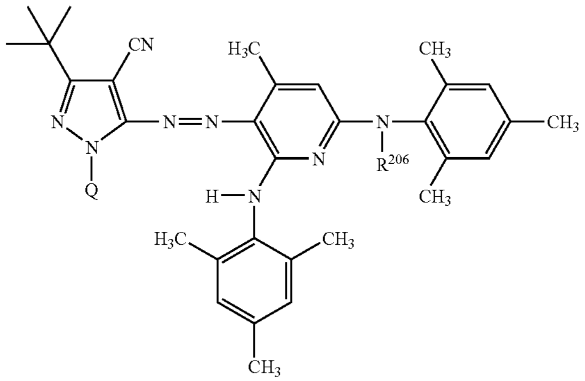
| Dye | Q | $R^{206}$ |
| --- | --- | --- |
| ma-7 | 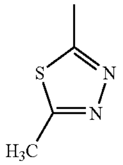 | 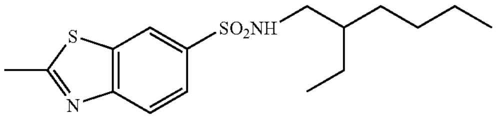 |
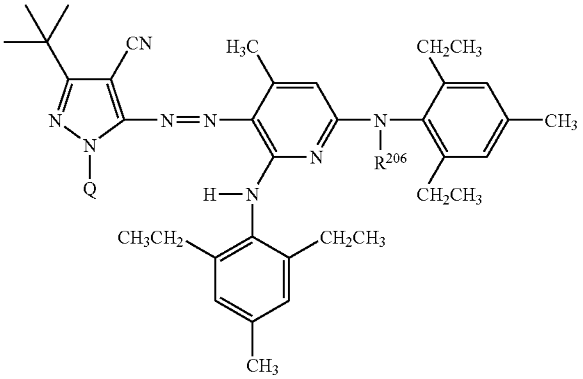
| Dye | Q | $R^{206}$ |
| --- | --- | --- |
| mb-1 | 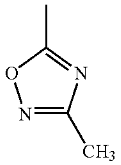 | $—CH_2CH_2OH$ |
| mb-2 | 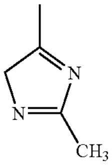 | $—CH_2CHCH_2CH_2CH_2CH_3$<br>$CH_2CH_3$ |

-continued
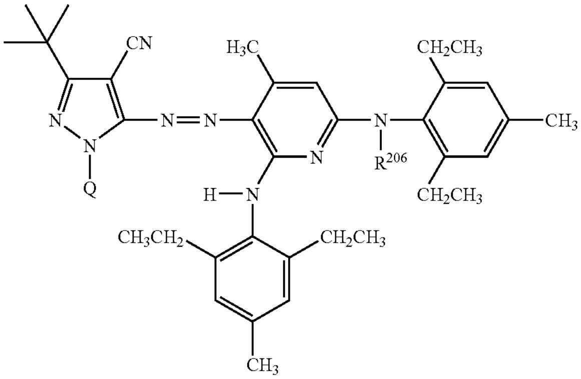
| Dye | Q | $R^{206}$ |
| --- | --- | --- |
| mb-3 | 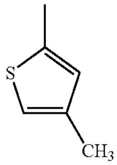 | $—COCH_2CH_2CH_2OH$ |
| mb-4 | 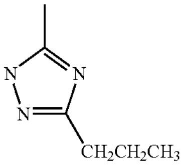 | $—CH_2CH_2CH_2COOH$ |
| mb-5 | 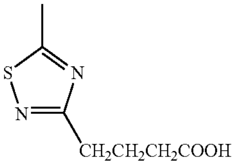 | 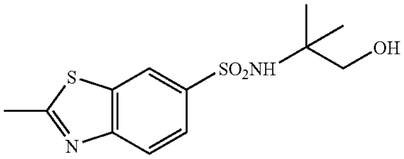 |
| mb-6 | 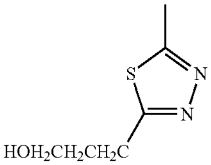 | $—CH_2CH_2CH_2OH$ |
| mb-7 | 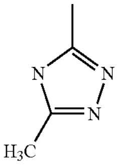 | 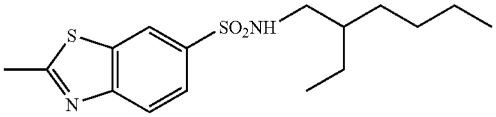 |

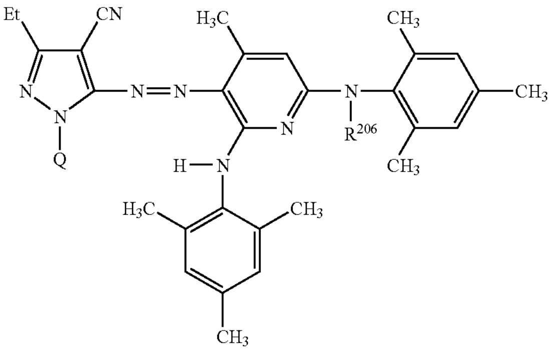
| Dye | Q | $R^{206}$ |
| --- | --- | --- |
| mc-1 | 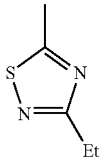 | $—CH_2CH_2OH$ |
| mc-2 | 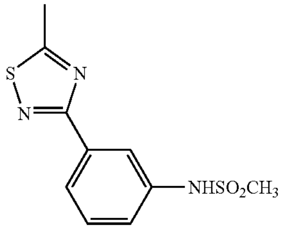 | $—CH_2CHCH_2CH_2CH_2CH_3$<br>$CH_2CH_3$ |
| mc-3 | 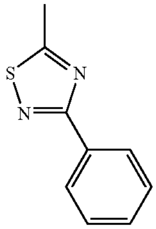 | $—COCH_2CH_2CH_2OH$ |
| mc-4 | 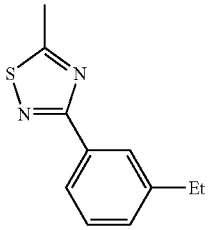 | $—CH_2CH_2CH_2COOH$ |
| mc-5 | 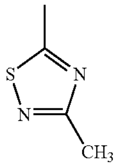 | 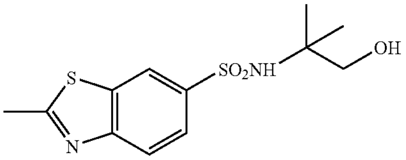 |

-continued
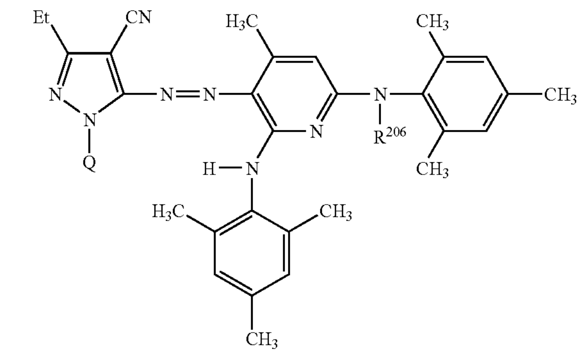
| Dye | Q | $R^{206}$ |
| --- | --- | --- |
| mc-6 | 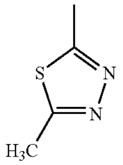 | $—CH_2CH_2CH_2OH$ |
| mc-7 | 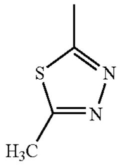 | 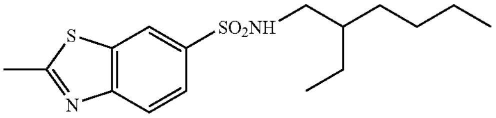 |
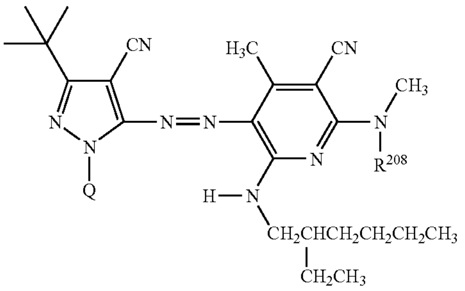
| Dye | Q | $R^{206}$ |
| --- | --- | --- |
| md-1 | 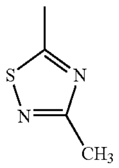 | $—CH_2CH_2CH_2OH$ |
| md-2 | 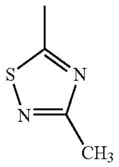 | 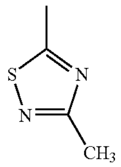 |

-continued
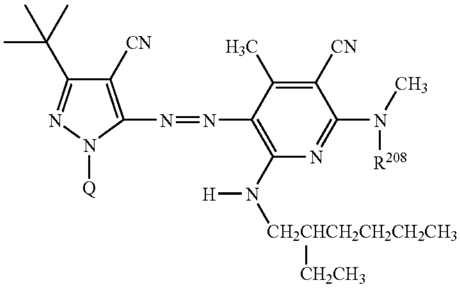
| Dye | Q | $R^{206}$ |
|---|---|---|
| md-3 | 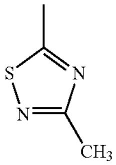 | —H |
| md-4 | 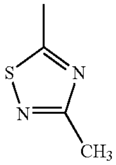 | $—CH_2CH_2CH_2COOH$ |
| md-5 | 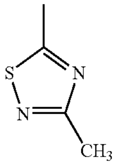 | 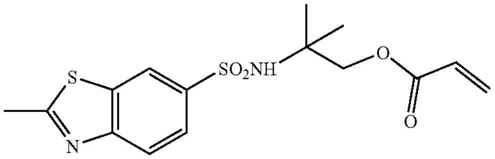 |
| md-6 | 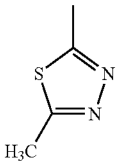 | $—CH_2CH_2CH_2OH$ |
| md-7 | 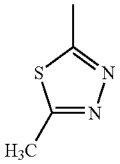 | 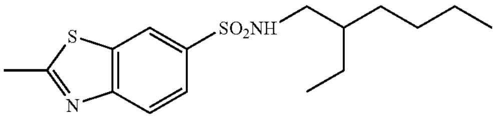 |

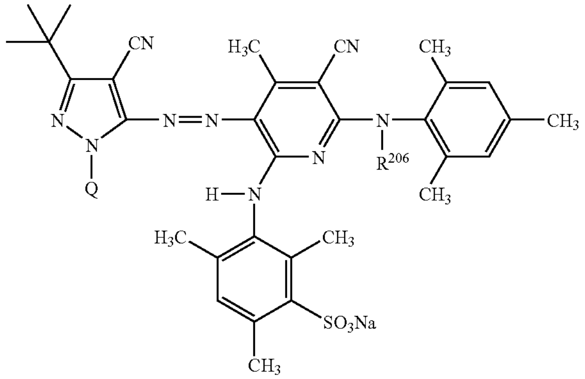
| Dye | Q | $R^{206}$ |
|---|---|---|
| me-1 | 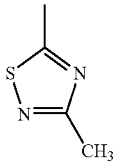 | $—CH_2CH_2CH_3$ |
| me-2 | 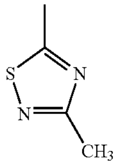 | 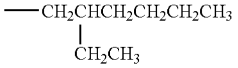 |
| me-3 | 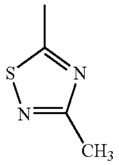 | $—COCH_3$ |
| me-4 | 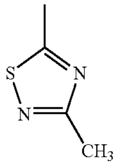 | —H |
| me-5 | 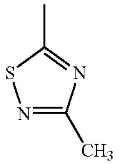 | 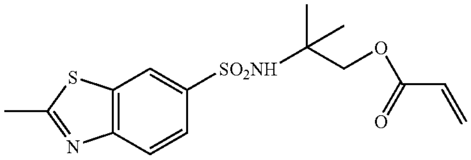 |
| me-6 | 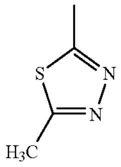 | 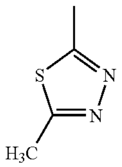 |

-continued
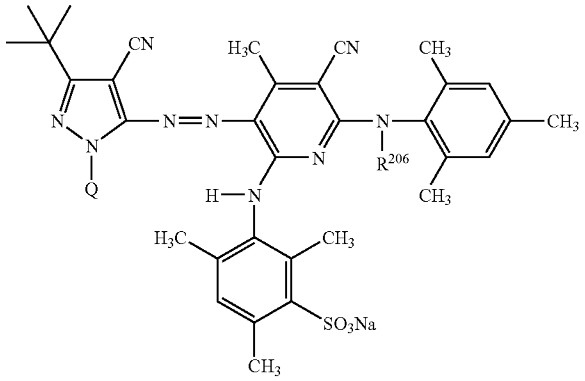
| Dye | Q | $R^{206}$ |
|---|---|---|
| me-7 | 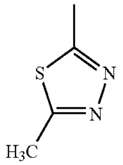 | 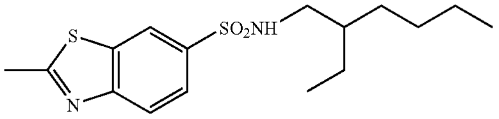 |
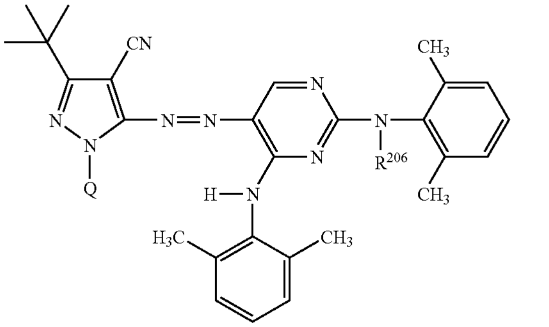
| Dye | Q | $R^{206}$ |
|---|---|---|
| mf-1 | 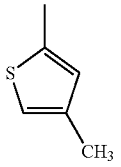 | $—CH_2CH_2CH_2OH$ |
| mf-2 | 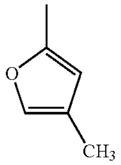 | 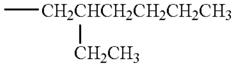 |
| mf-3 | 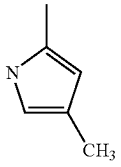 | $—COCH_2CH_2CH_2OH$ |

-continued
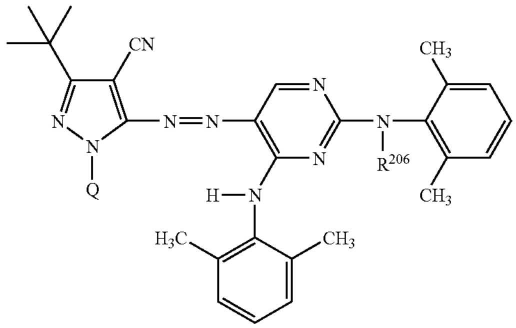
| Dye | Q | $R^{206}$ |
|---|---|---|
| mf-4 | 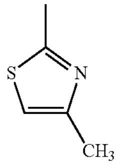 | $—CH_2CH_2NHSO_2CH_3$ |
| mf-5 | 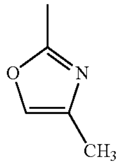 | 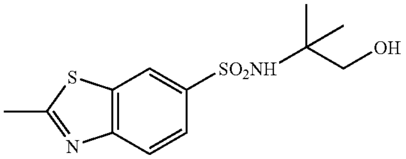 |
| mf-6 | 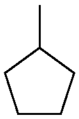 | $—CH_2CH_2CH_2OH$ |
| mf-7 | 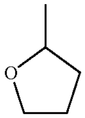 | 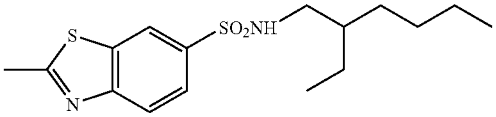 |
mx-1
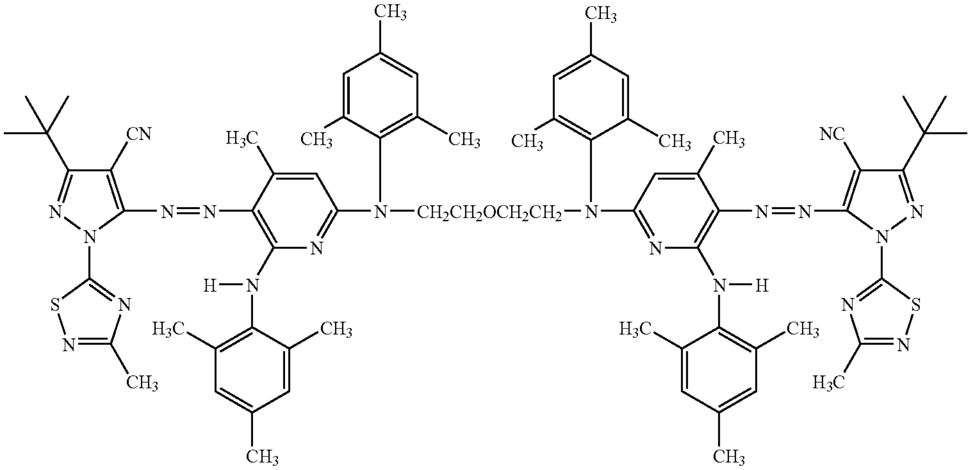

-continued
mx-2
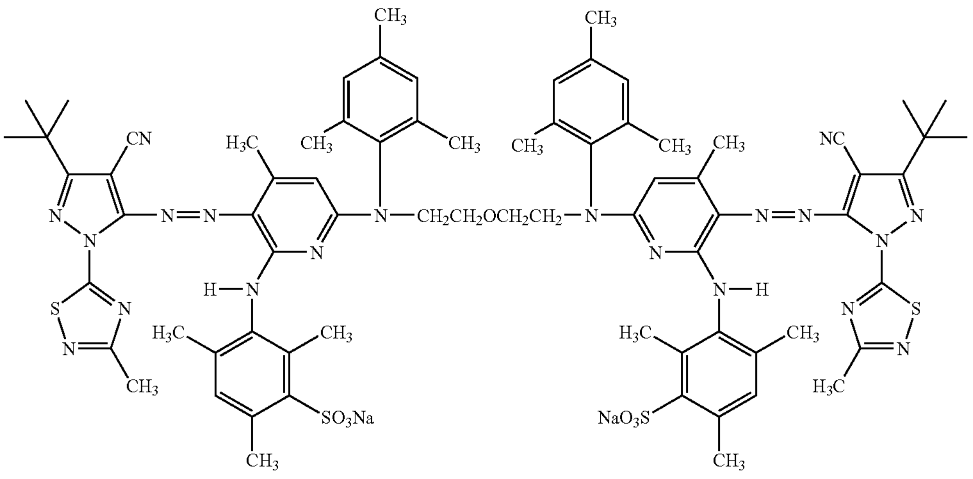
mx-3
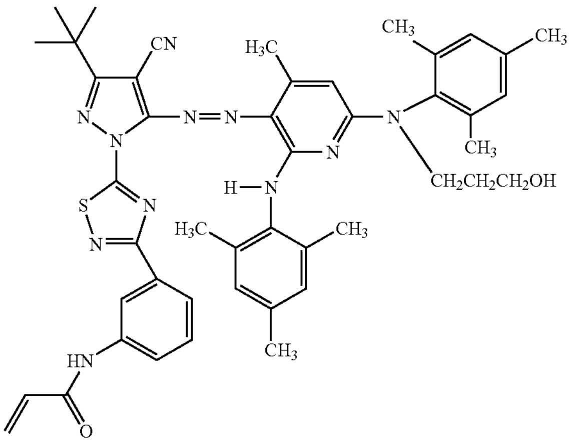
mx-4
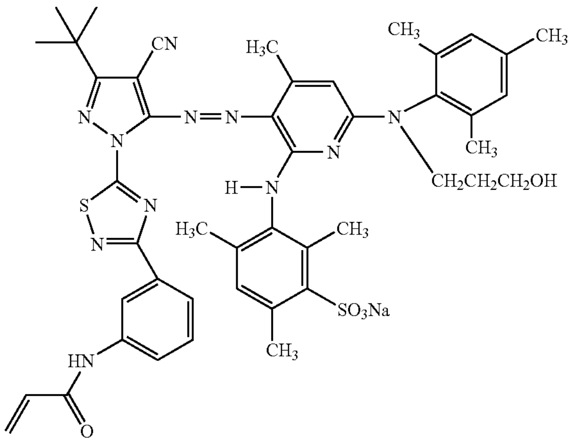
mx-5
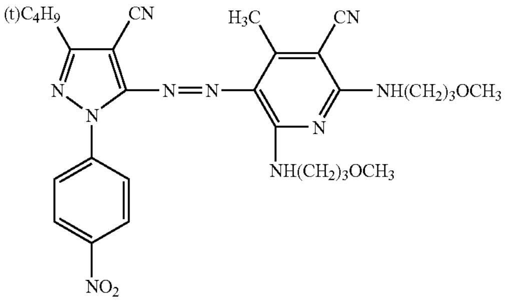
mx-6
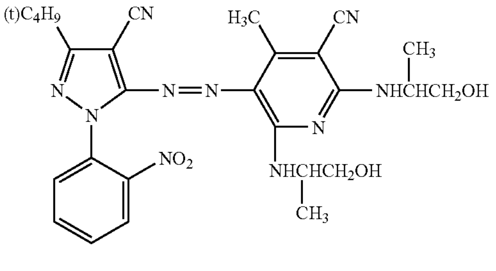

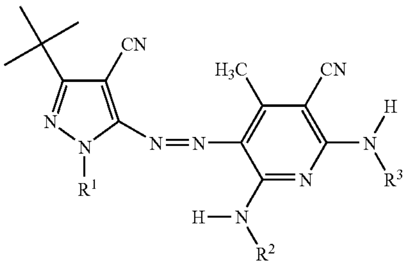
| Dye | $R^1$ | $R^2$ | $R^3$ |
|---|---|---|---|
| a-1 | 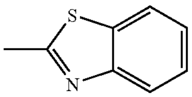 | 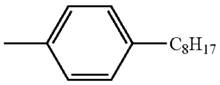 | 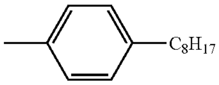 |
| a-2 | 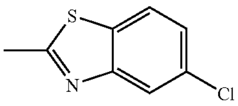 | 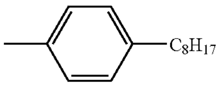 | 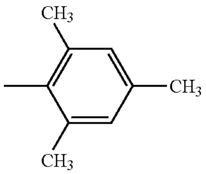 |
| a-3 | 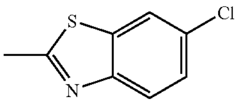 | 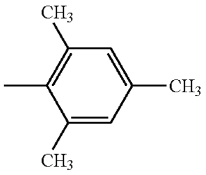 | 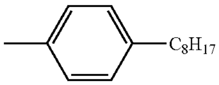 |
| a-4 | 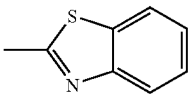 | 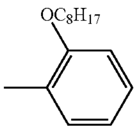 | 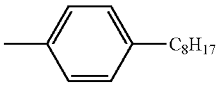 |
| a-5 | 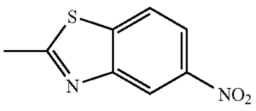 | 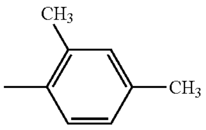 | 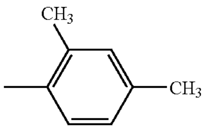 |

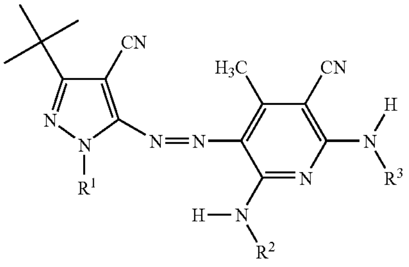
| Dye | $R^1$ | $R^2$ | $R^3$ |
|---|---|---|---|
| a-6 | 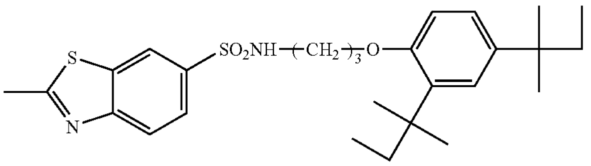 | 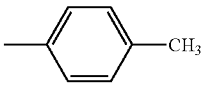 | 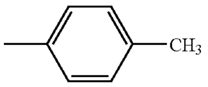 |
| a-7 | 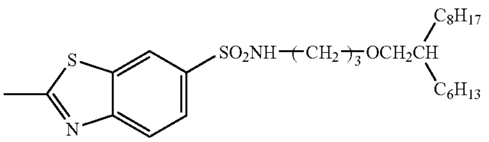 | 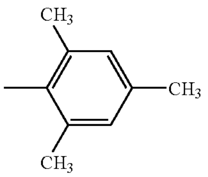 | 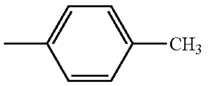 |
| a-8 | 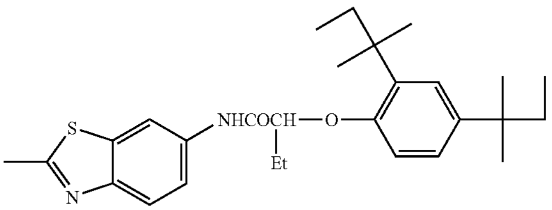 | 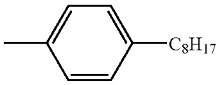 | 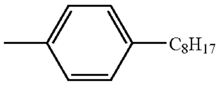 |
| a-9 | 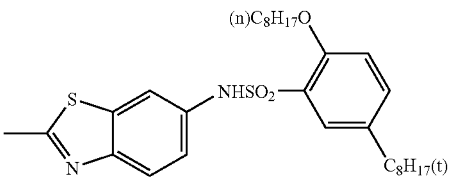 | 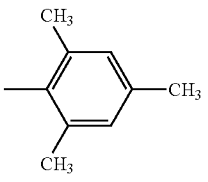 | $C_8H_{17}$(t) |
| a-10 | 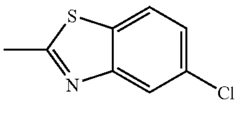 | 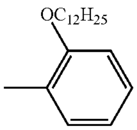 | 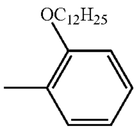 |

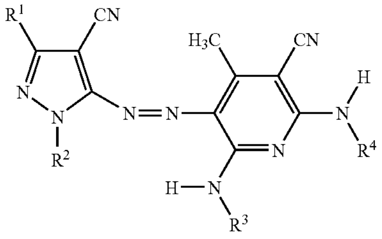
| Dye | $R^1$ | $R^2$ | $R^3$ | $R^4$ |
|---|---|---|---|---|
| a-11 | 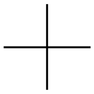 | 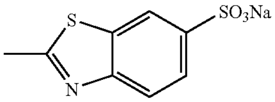 | 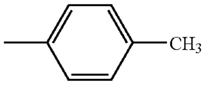 | 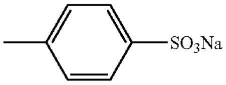 |
| a-12 | 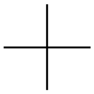 | 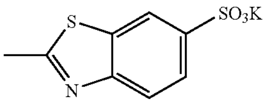 | 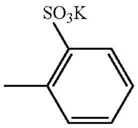 | 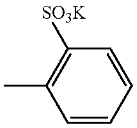 |
| a-13 | 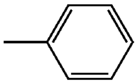 | 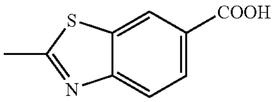 | 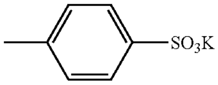 | 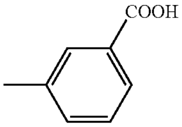 |
| a-14 | 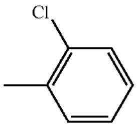 | 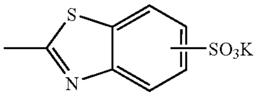 (4,5-mix) | 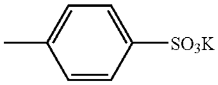 | 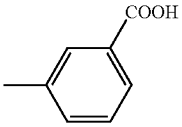 |
| a-15 | 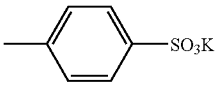 | 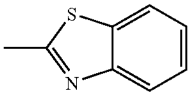 | 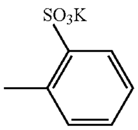 | 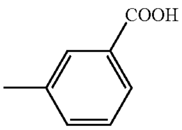 |

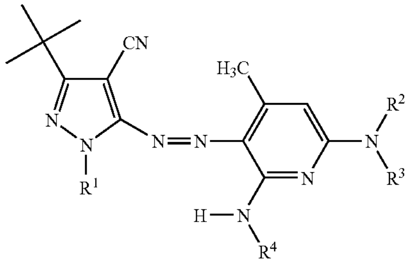
| Dye | $R^1$ | $R^2$ | $R^3$ | $R^4$ |
|---|---|---|---|---|
| a-16 | 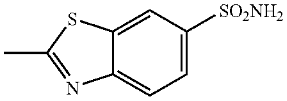 | 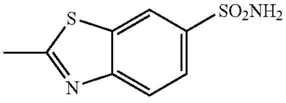 | 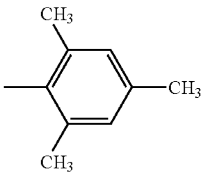 | 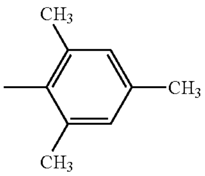 |
| a-17 | 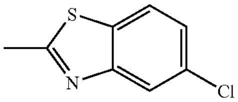 | $—SO_2CH_3$ | 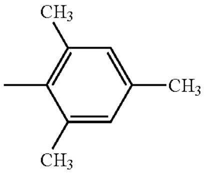 | 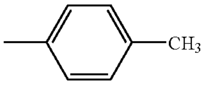 |
| a-18 | 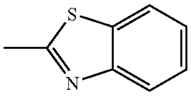 | $—COCH_3$ | $C_8H_{17}(t)$ | $C_8H_{17}(t)$ |
| a-19 | 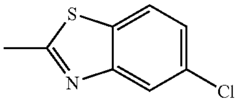 | 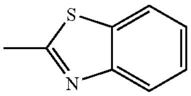 | 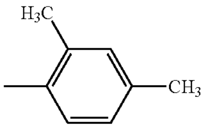 | 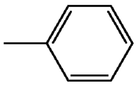 |
| a-20 | 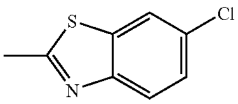 | $—SO_2CH_3$ | 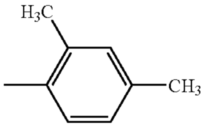 | $C_8H_{17}(t)$ |

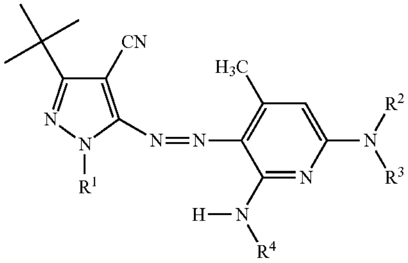
| Dye | $R^1$ | $R^2$ | $R^3$ | $R^4$ |
|---|---|---|---|---|
| a-21 | 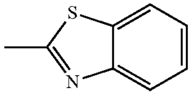 | 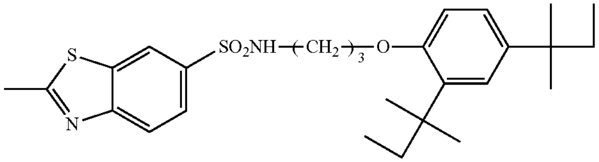 | 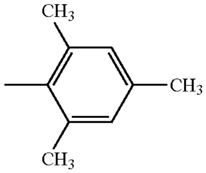 | 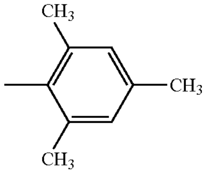 |
| a-22 | 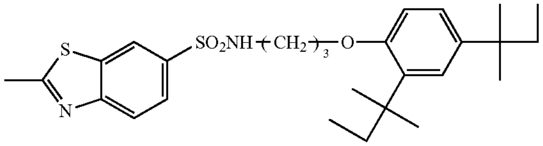 | 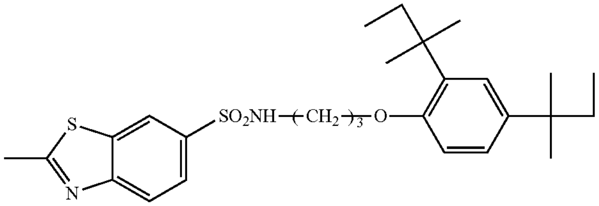 | 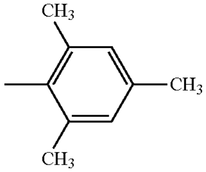 | 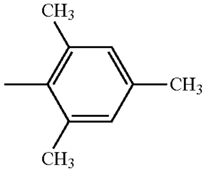 |
| a-23 | 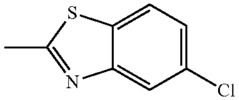 | 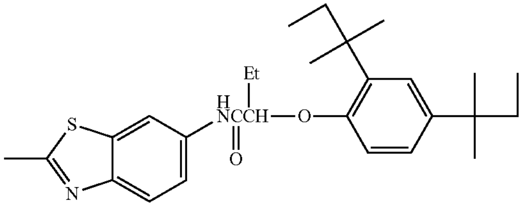 | 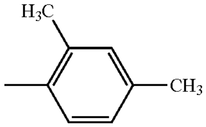 | 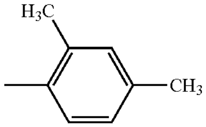 |

-continued
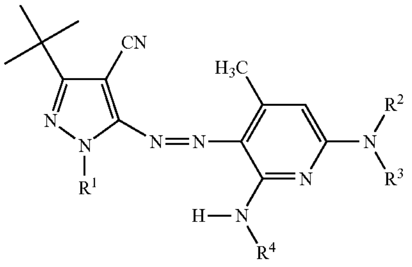
| Dye | $R^1$ | $R^2$ | $R^3$ | $R^4$ |
|---|---|---|---|---|
| a-24 | 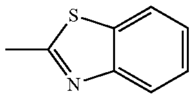 | 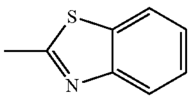 | 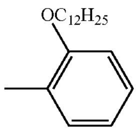 | 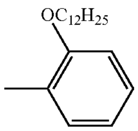 |
| a-25 | 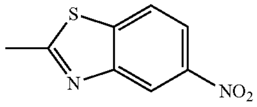 | 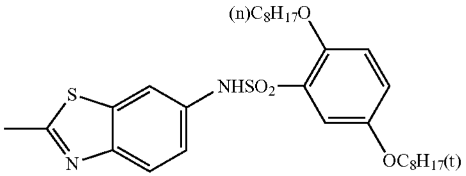 | 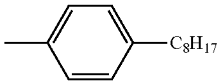 | $C_8H_{17}(t)$ |

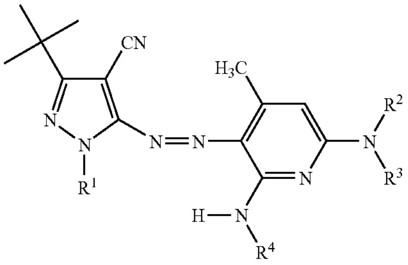
| Dye | $R^1$ | $R^2$ |
|---|---|---|
| a-26 | 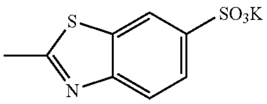 | 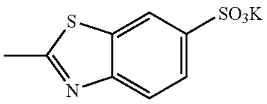 |
| a-27 | 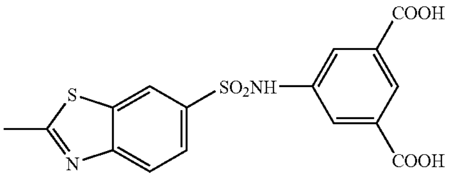 | 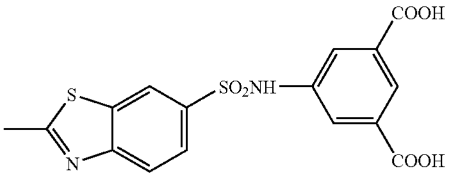 |
| a-28 | 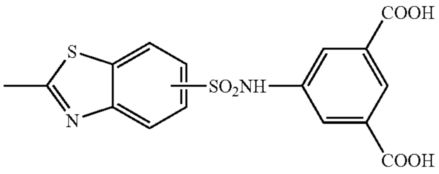 (5,6-mix) | 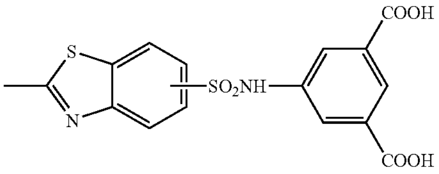 (5,6-mix) |
| a-29 | 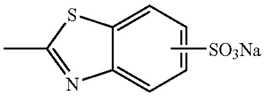 (5,6-mix) | 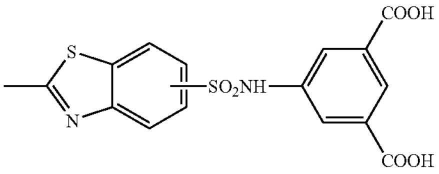 (5,6-mix) |
| Dye | $R^3$ | $R^4$ |
|---|---|---|
| a-26 | 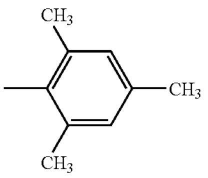 | 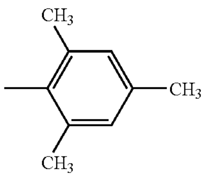 |
| a-27 | 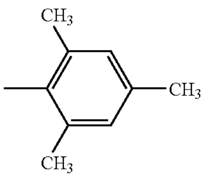 | 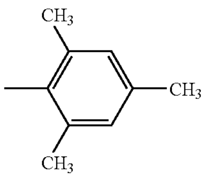 |

-continued
| | | |
|---|---|---|
| a-28 | 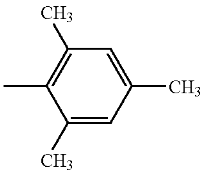 | 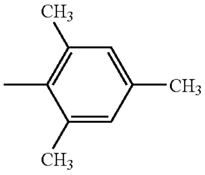 |
| a-29 | 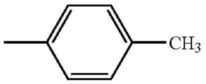 | 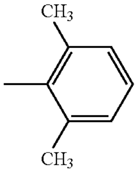 |
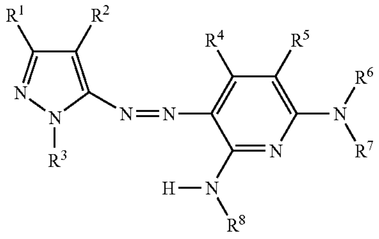
| Dye | $R^1$ | $R^2$ | $R^3$ | $R^4$ | $R^5$ | $R^6$ |
|---|---|---|---|---|---|---|
| a-30 | 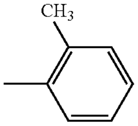 | CN | 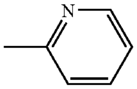 | H | $CONH_2$ | $SO_2CH_3$ |
| a-31 | 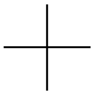 | Br | 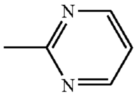 | COOEt | H | 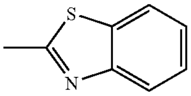 |
| a-32 | 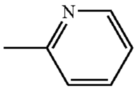 | $SO_2CH_3$ | 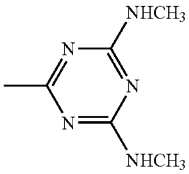 | $CONH_2$ | H | 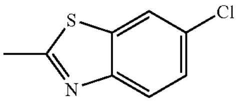 |
| a-33 | 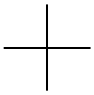 | CN | 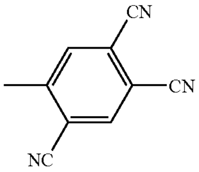 | H | H | 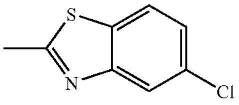 |
| Dye | $R^7$ | $R^8$ |
|---|---|---|
| a-30 | 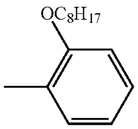 | 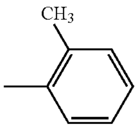 |
| a-31 | $C_8H_{17}(t)$ | $COCH_3$ |

-continued
| | | |
|---|---|---|
| a-32 | 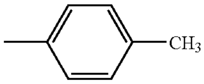 | 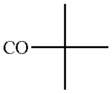 |
| a-33 | 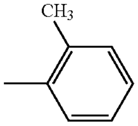 | $SO_2CH_3$ |
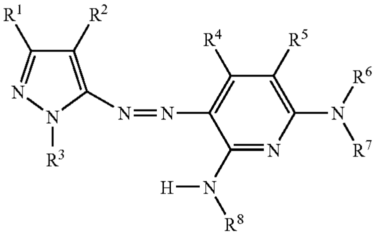
| Dye | $R^1$ | $R^2$ | $R^3$ | $R^4$ | $R^5$ | $R^6$ | $R^7$ | $R^8$ |
|---|---|---|---|---|---|---|---|---|
| a-34 | 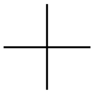 | Br | 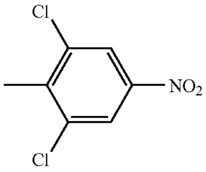 | H | $CONH_2$ | 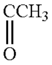 | 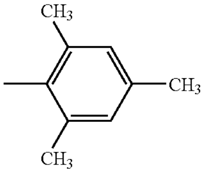 | 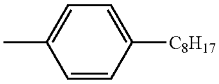 |
| a-35 | 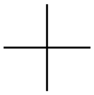 | CN | 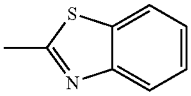 | $CH_3$ | H | 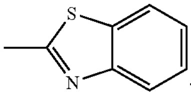 | 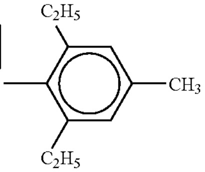 | 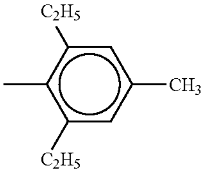 |
| a-36 | 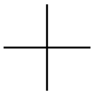 | CN | 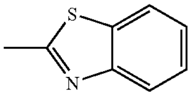 | $CH_3$ | CN | H | 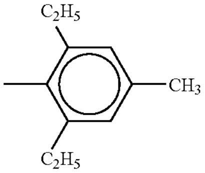 | 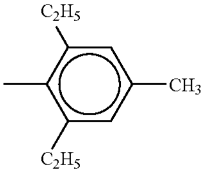 |

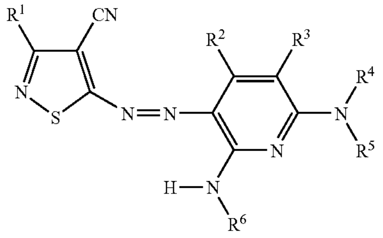
| Dye | $R^1$ | $R^2$ | $R^3$ | $R^4$ | $R^5$ | $R^6$ |
|---|---|---|---|---|---|---|
| b-1 | $CH_3$ | $CH_3$ | CN | H | 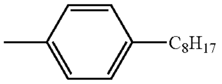 | 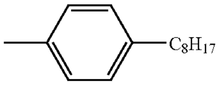 |
| b-2 | t-Bu | $CH_3$ | CN | H | 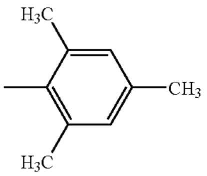 | 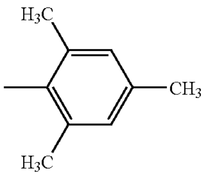 |
| b-3 | $CH_3$ | $CH_3$ | $CONH_2$ | H | 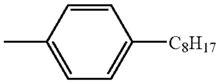 | 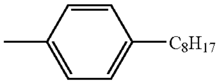 |
| b-4 | $CH_3$ | $CH_3$ | H | H | 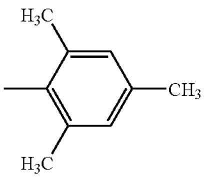 | 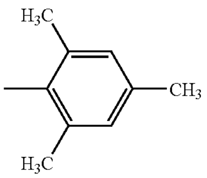 |
| b-5 | $CH_3$ | H | CN | H | 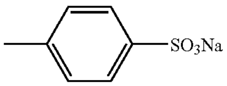 | 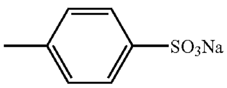 |
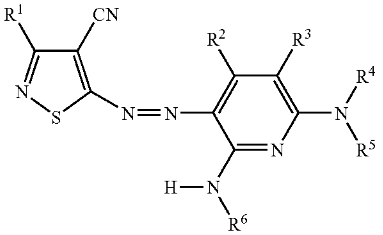
| Dye | $R^1$ | $R^2$ | $R^3$ | $R^4$ | $R^5$ | $R^6$ |
|---|---|---|---|---|---|---|
| b-6 | $CH_3$ | $CH_3$ | H | 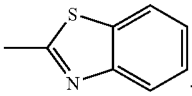 | 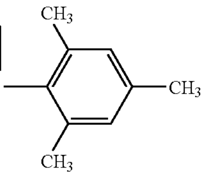 | 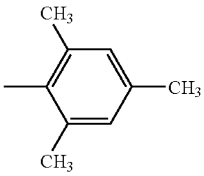 |

-continued
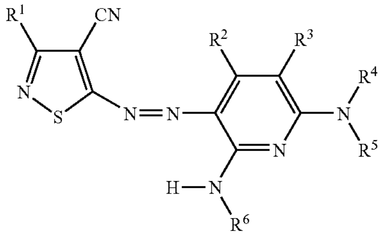
| Dye | $R^1$ | $R^2$ | $R^3$ | $R^4$ | $R^5$ | $R^6$ |
| --- | --- | --- | --- | --- | --- | --- |
| b-7 | $CH_3$ | $CH_3$ | H | 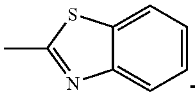 | 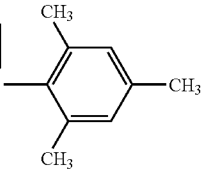 | 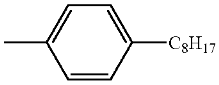 |
| b-8 | $CH_3$ | H | H | $SO_2CH_3$ | 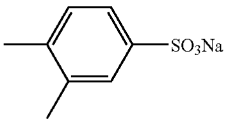 | 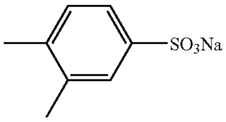 |
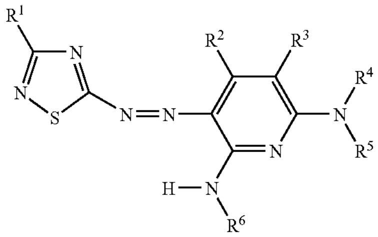
| Dye | $R^1$ | $R^2$ | $R^3$ | $R^4$ |
| --- | --- | --- | --- | --- |
| c-1 | $—SCH_3$ | $CH_3$ | CN | H |
| c-2 | 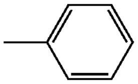 | H | $CONH_2$ | H |
| c-3 | 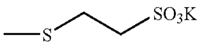 | $CH_3$ | H | 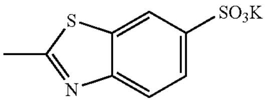 |
| c-4 | $—CH_3$ | $CH_3$ | H | 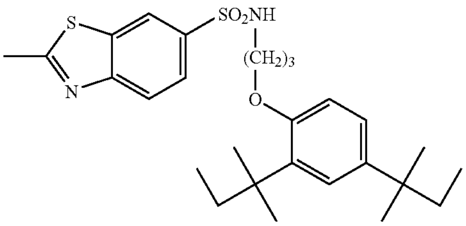 |

-continued
| | | | | |
|---|---|---|---|---|
| c-5 | 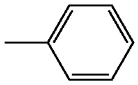 | H | H | 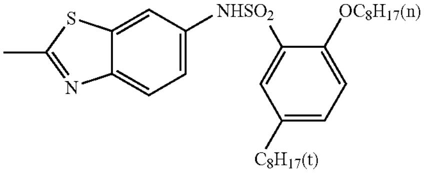 |
| Dye | $R^5$ | $R^6$ |
|---|---|---|
| c-1 | $C_8H_{17}$(t) | 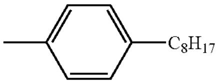 |
| c-2 | 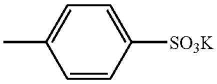 | 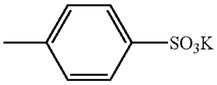 |
| c-3 | 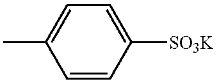 | 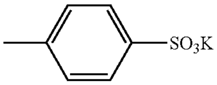 |
| c-4 | 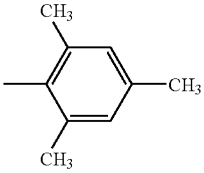 | 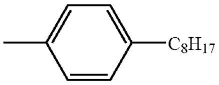 |
| c-5 | 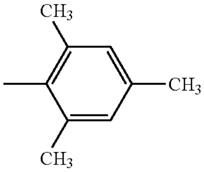 | $C_8H_{17}$(t) |
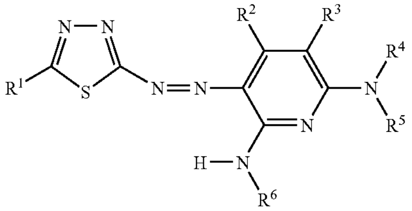
| Dye | $R^1$ | $R^2$ | $R^3$ | $R^4$ | $R^5$ | $R^6$ |
|---|---|---|---|---|---|---|
| d-1 | Me | $CH_3$ | CN | H | 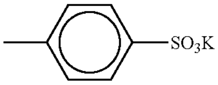 | 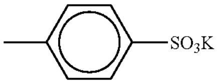 |
| d-2 | Me | $CH_3$ | CN | H | 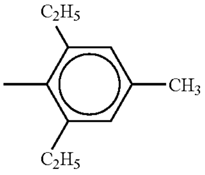 | 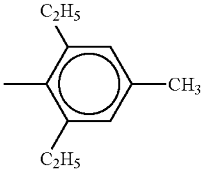 |

-continued
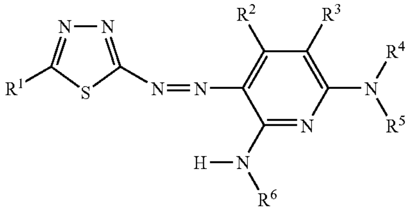
| Dye | $R^1$ | $R^2$ | $R^3$ | $R^4$ | $R^5$ | $R^6$ |
|---|---|---|---|---|---|---|
| d-3 | Me | H | H | 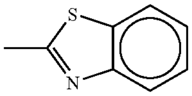 | 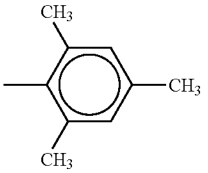 | 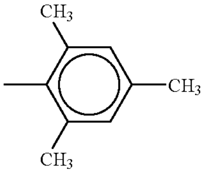 |
| d-4 | Ph | $CH_3$ | $CONH_2$ | H | 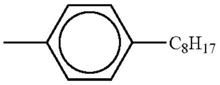 | 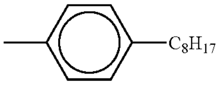 |
| d-5 | Ph | $CH_3$ | H | 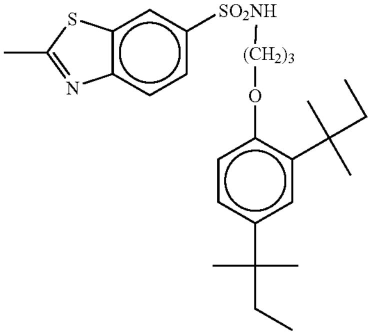 | 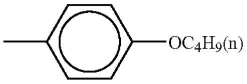 | 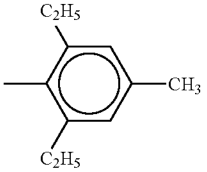 |
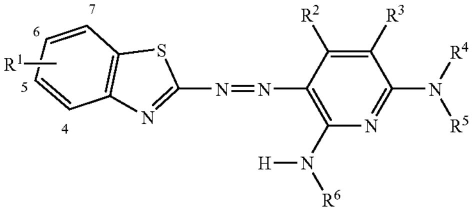
| Dye | $R^1$ | $R^2$ | $R^3$ | $R^4$ | $R^5$ | $R^6$ |
|---|---|---|---|---|---|---|
| e-1 | 5-Cl | $CH_3$ | $CONH_2$ | H | $C_8H_{17}$(t) | $C_8H_{17}$(t) |
| e-2 | 5,6-diCl | H | H | 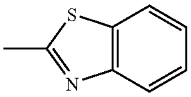 | 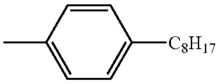 | 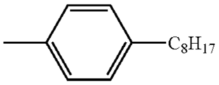 |
| e-3 | 5,6-diCl | $CH_3$ | H | 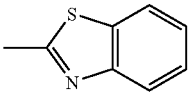 | 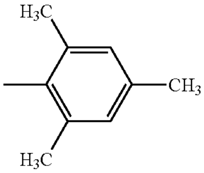 | 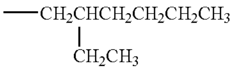 |

-continued
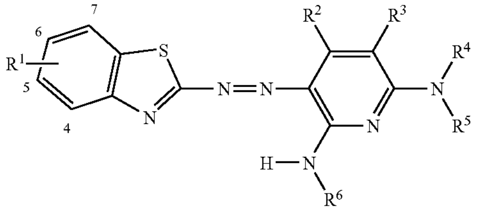
| Dye | $R^1$ | $R^2$ | $R^3$ | $R^4$ | $R^5$ | $R^6$ |
|---|---|---|---|---|---|---|
| e-4 | 5-Cl | H | CN | H | 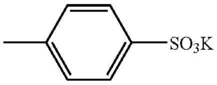 | 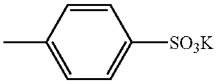 |
| e-5 | 5-Cl | $CH_3$ | H | H | 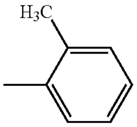 | 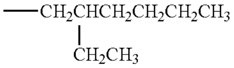 |
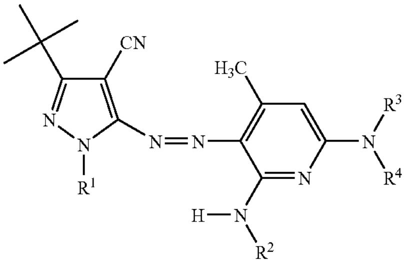
| Dye | $R^1$ | $R^2$ | $R^3$ | $R^4$ |
|---|---|---|---|---|
| f-1 | 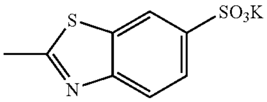 | 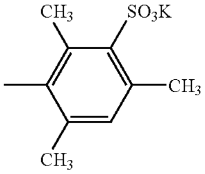 | 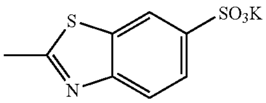 | 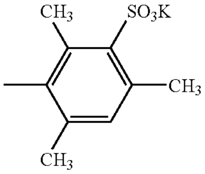 |
| f-2 | 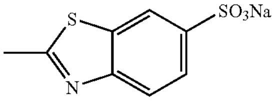 | 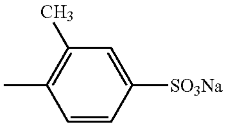 | 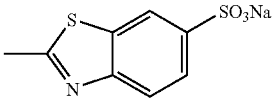 | 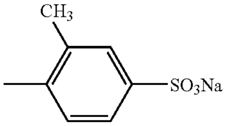 |
| f-3 | 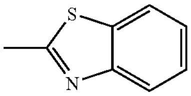 | 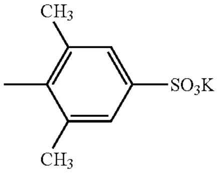 | 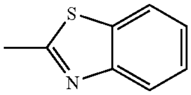 | 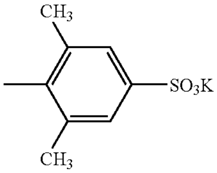 |
| f-4 | 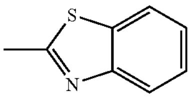 | 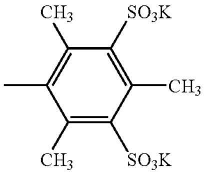 | 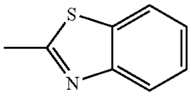 | 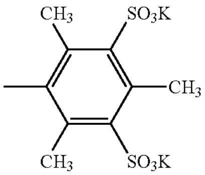 |

-continued
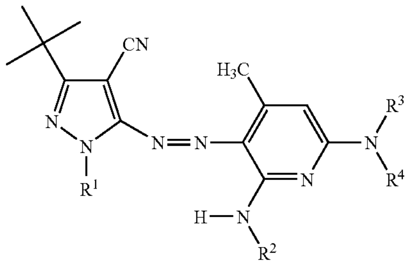
| Dye | $R^1$ | $R^2$ | $R^3$ | $R^4$ |
|---|---|---|---|---|
| f-5 | 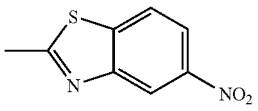 | 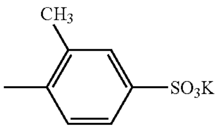 | 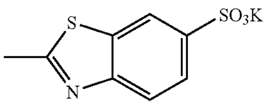 | 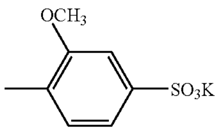 |
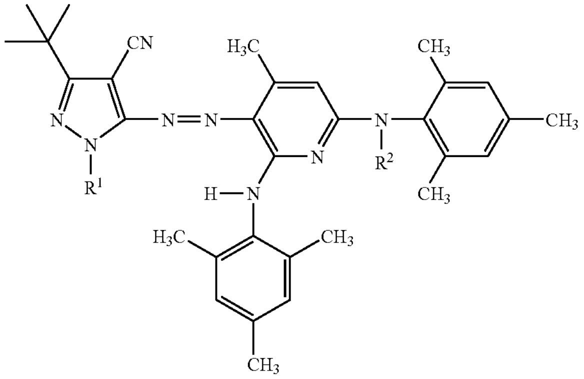
| Dye | $R^1$ | $R^2$ |
|---|---|---|
| f-6 | 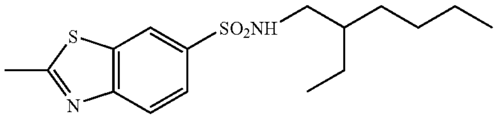 | H |
| f-7 | 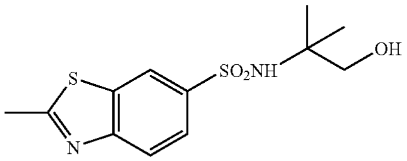 | H |
| f-8 | 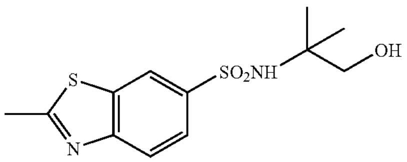 | 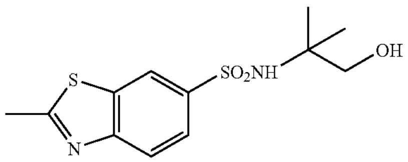 |

-continued
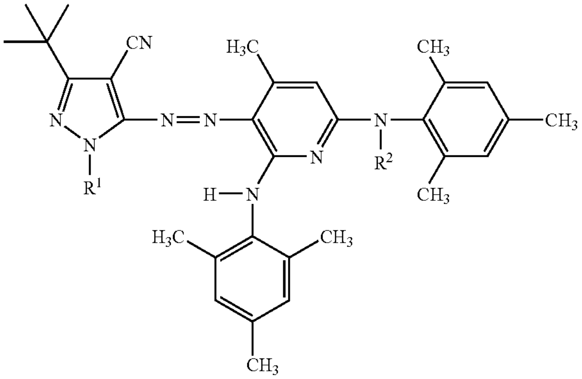
| Dye | $R^1$ | $R^2$ |
|---|---|---|
| f-9 | 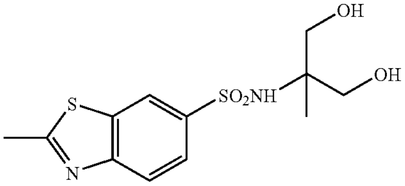 | 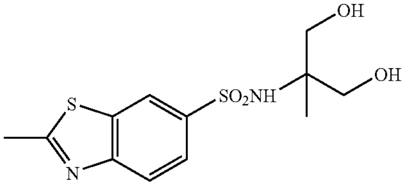 |
| f-10 | 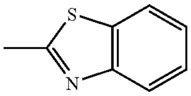 | 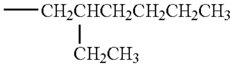 |
| f-11 | 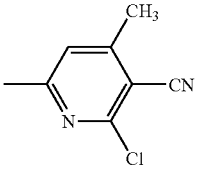 | 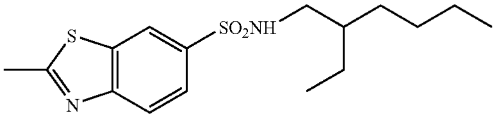 |
| f-12 | 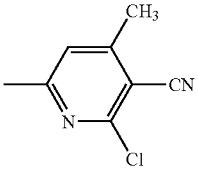 | 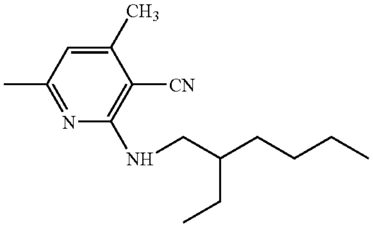 |
| f-13 | 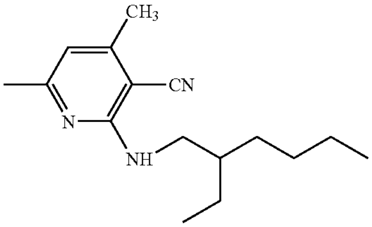 | 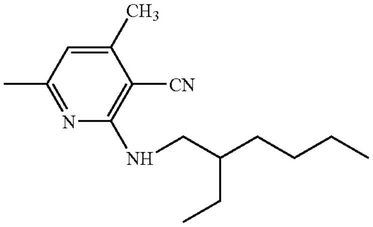 |

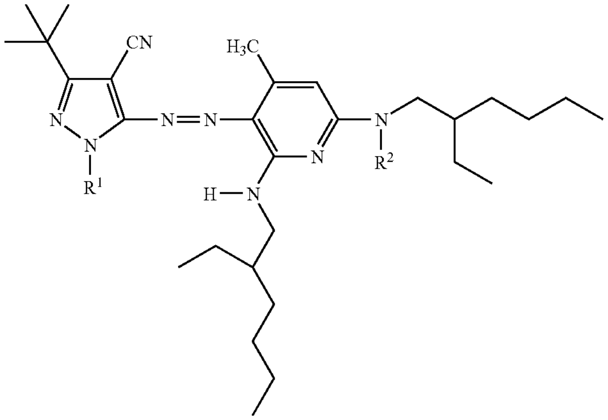
| Dye | $R^1$ | $R^2$ |
|---|---|---|
| f-14 | 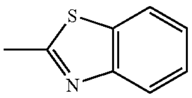 | H |
| f-15 | 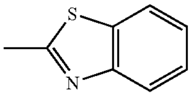 | $-CH_2CH_2CH_3$ |
| f-16 | 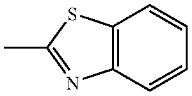 | $-CH_2CHCH_2CH_2CH_2CH_3$<br>$\quad\quad\ \ \vert$<br>$\quad\quad CH_2CH_3$ |
| f-17 | 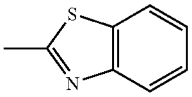 | 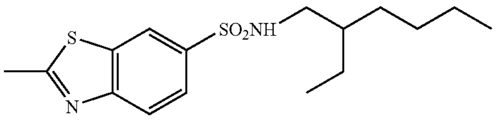 |
| f-18 | 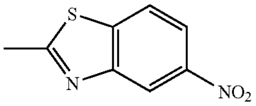 | 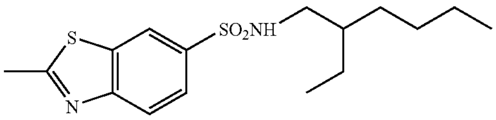 |
| f-19 | 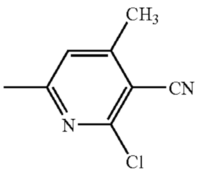 | 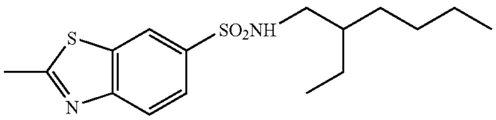 |
| f-20 | 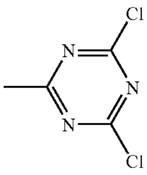 | 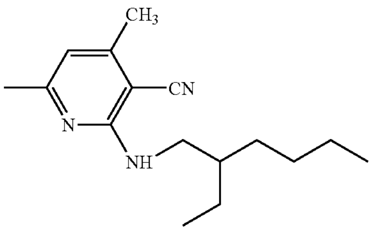 |

-continued
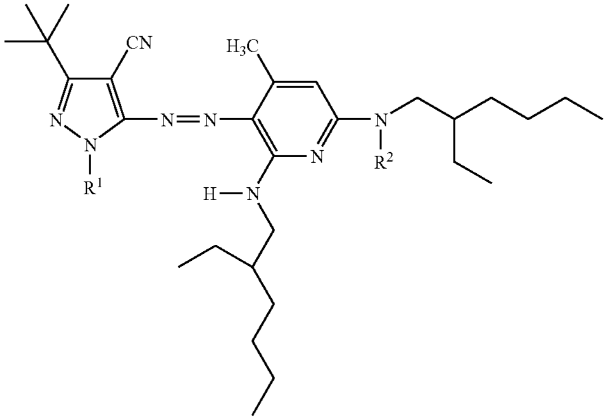
| Dye | $R^1$ | $R^2$ |
| --- | --- | --- |
| f-21 | 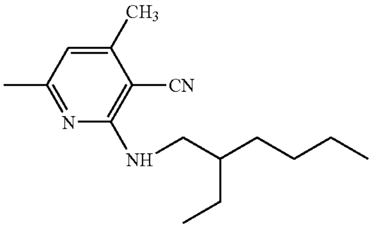 | 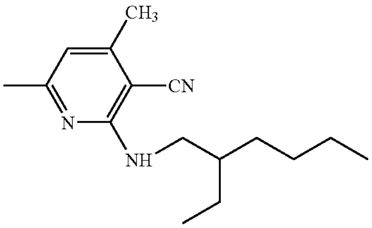 |
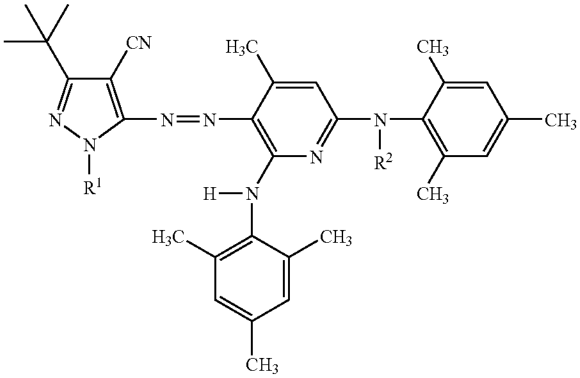
| Dye | $R^1$ | $R^2$ |
| --- | --- | --- |
| f-22 | 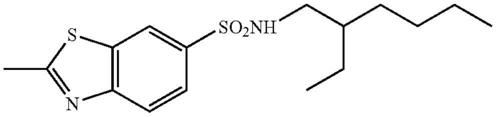 | H |
| f-23 | 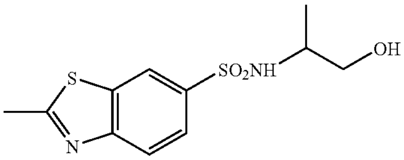 | 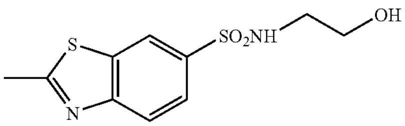 |

-continued
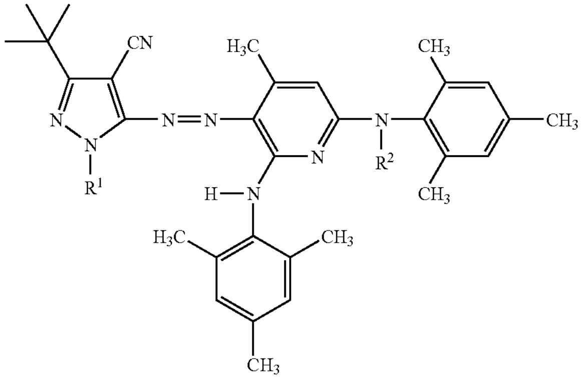
| Dye | $R^1$ | $R^2$ |
|---|---|---|
| f-24 | 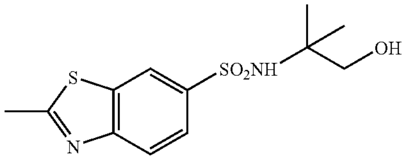 | 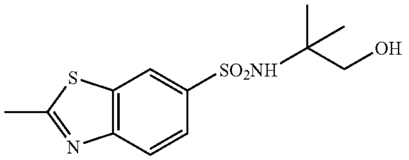 |
| f-25 | 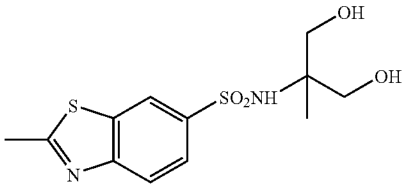 | 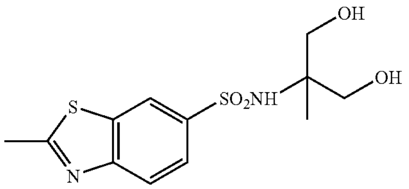 |
| f-26 | 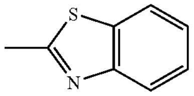 | 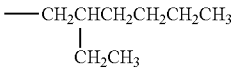 |
| f-27 | 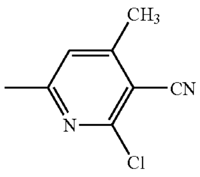 | 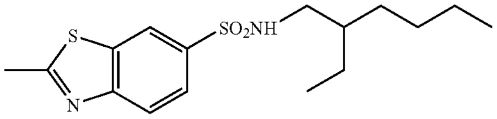 |
| f-28 | 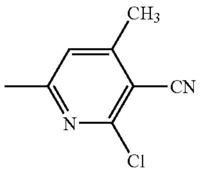 | 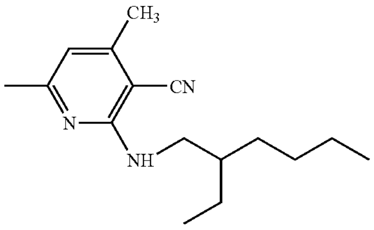 |
| f-29 | 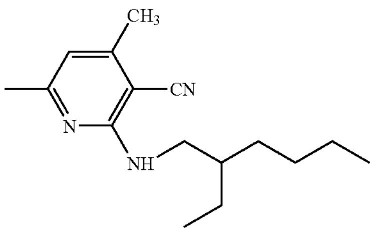 | 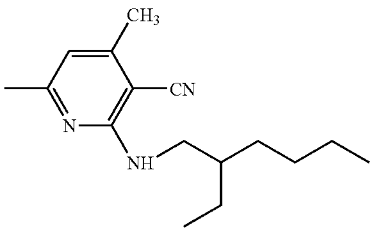 |

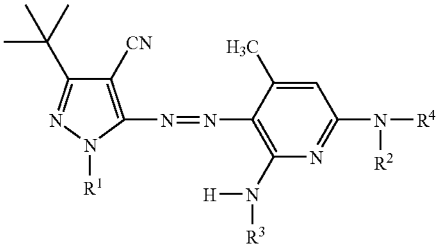
| Dye | $R^1$ | $R^2$ | $R^3$ | $R^4$ |
|---|---|---|---|---|
| f-30 | 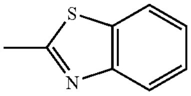 | H | 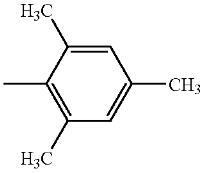 | 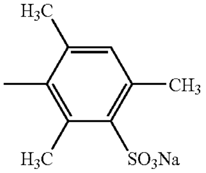 |
| f-31 | 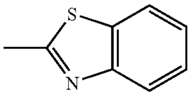 | 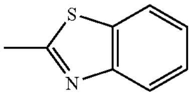 | 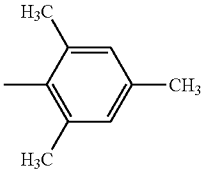 | 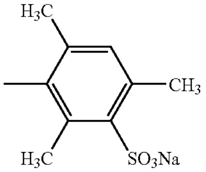 |
| f-32 | 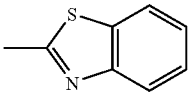 | 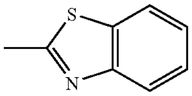 | 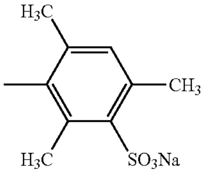 | 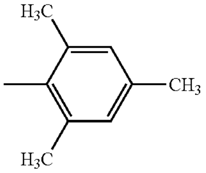 |
| f-33 | 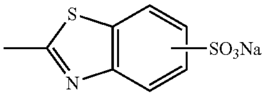 | 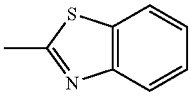 | 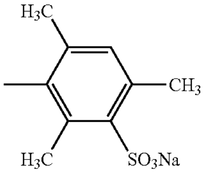 | 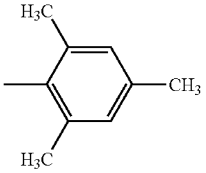 |
(1)
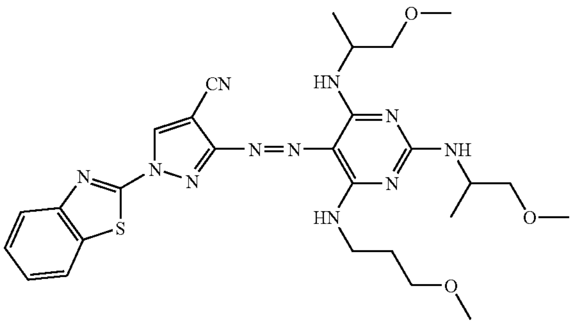
(2)
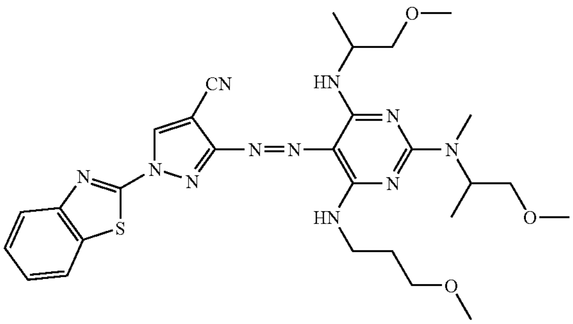

-continued
(3)
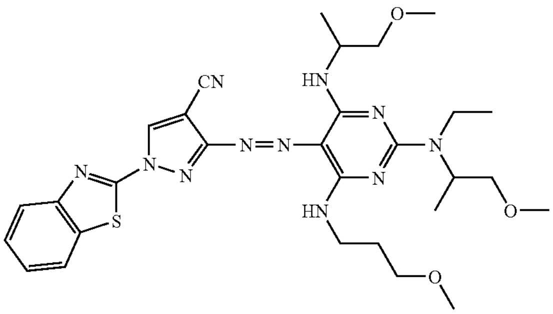
(4)
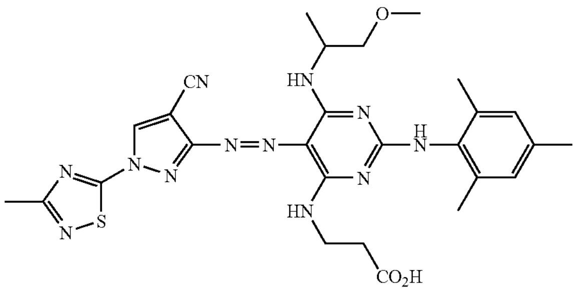
(5)
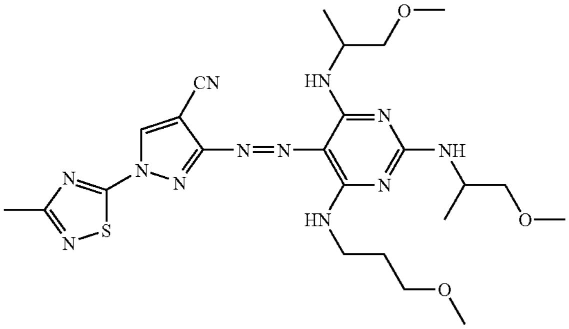
(6)
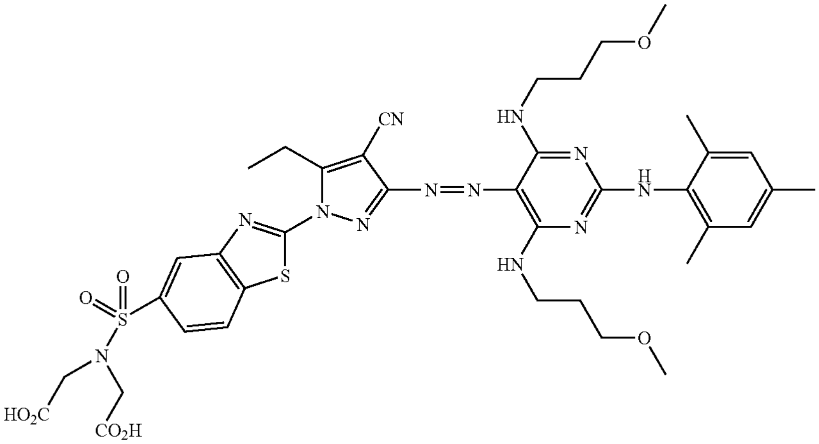
(7)
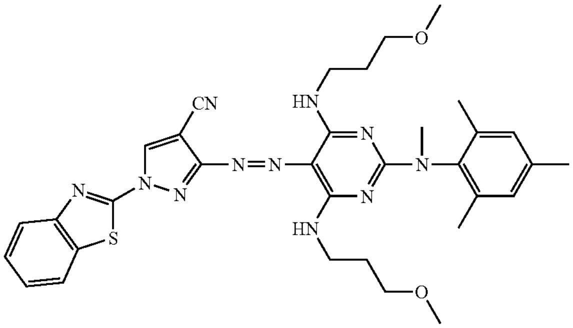

-continued
(8)
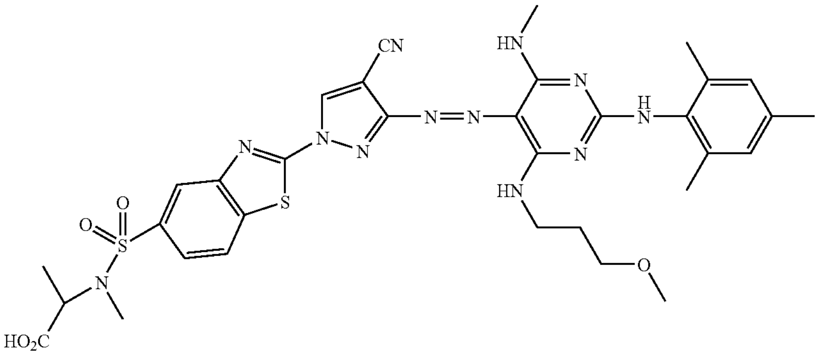
(9)
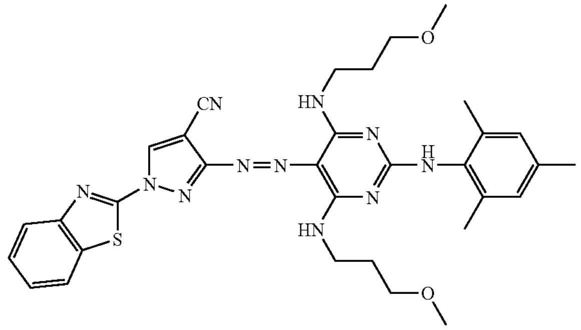
(10)
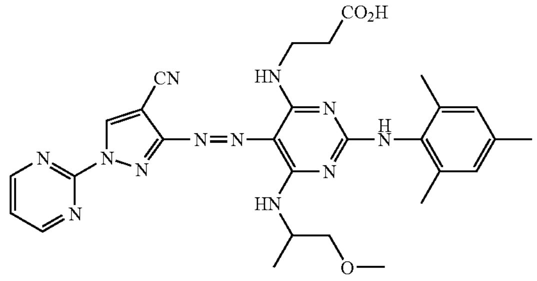
(11)
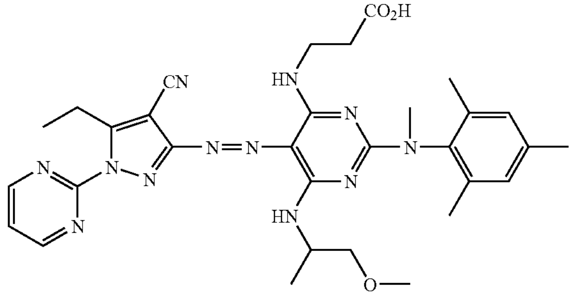
(12)
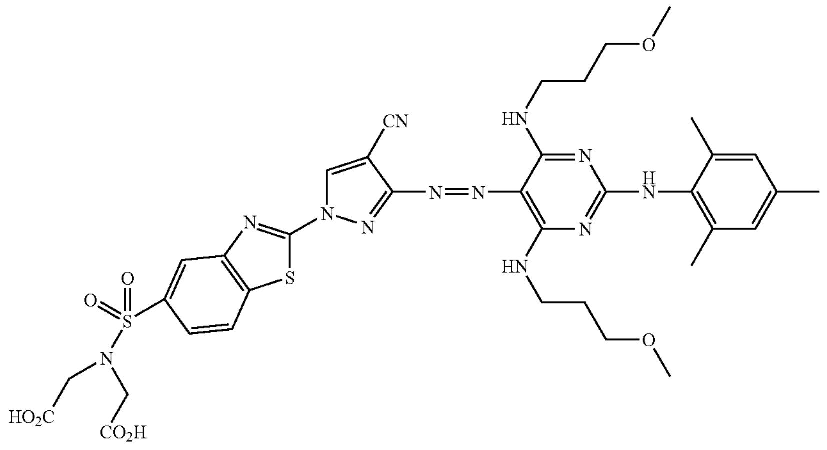

-continued
(13)
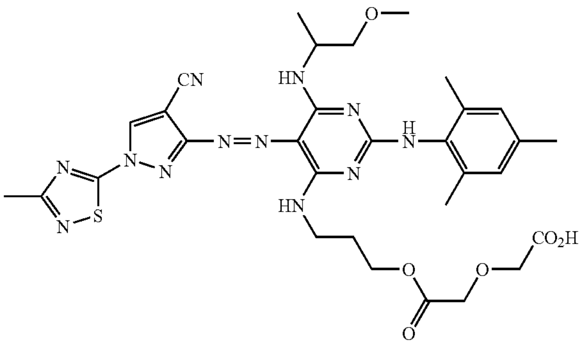
(14)
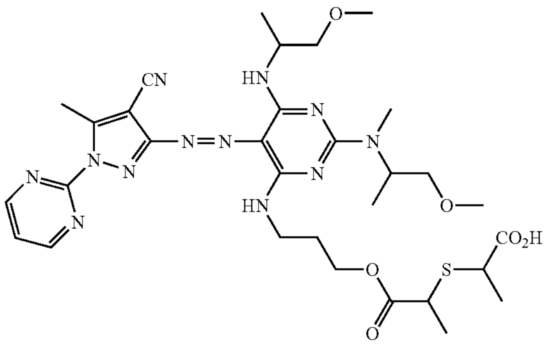
(15)
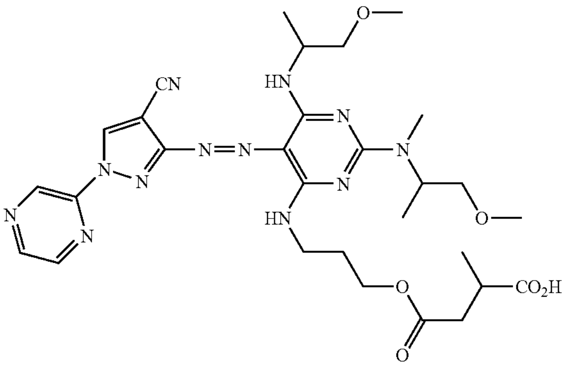
(16)
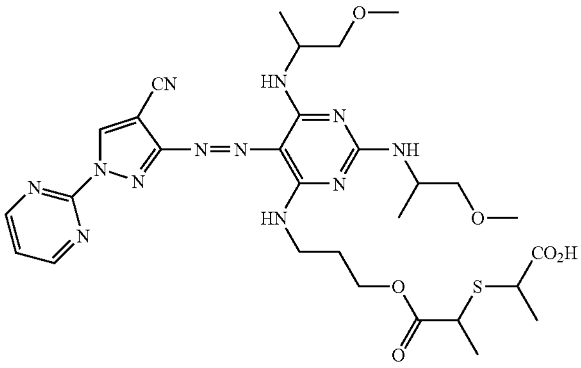
(17)
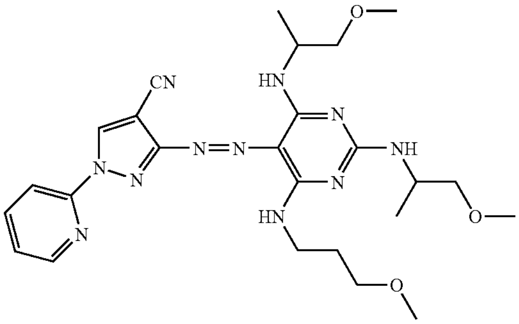
(18)
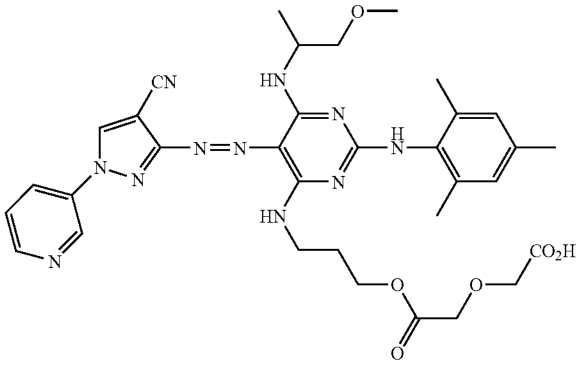
(19)
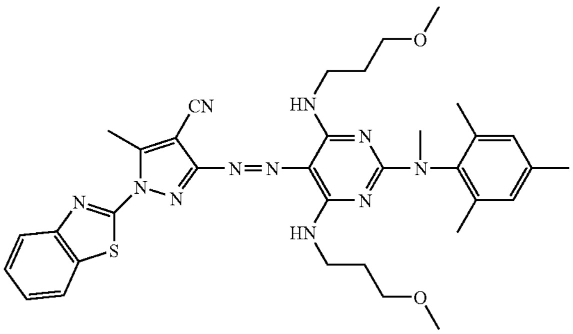

-continued
(20)
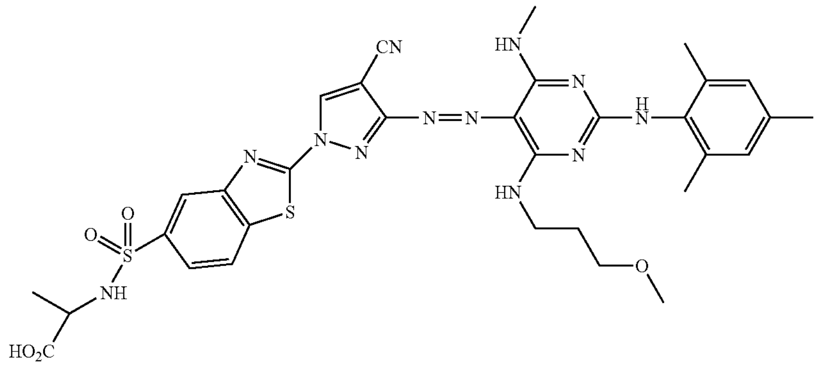
(21)
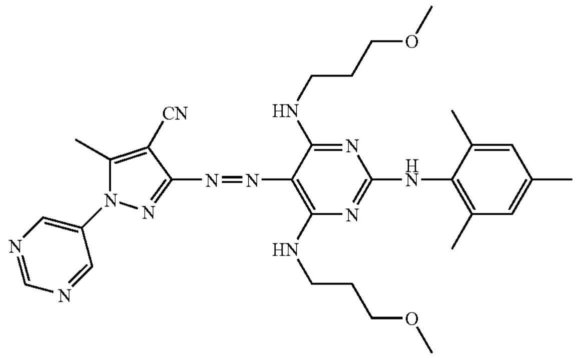
(22)
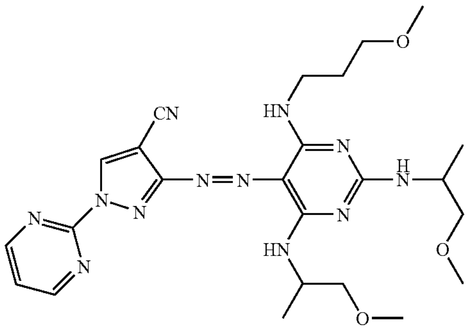
(23)
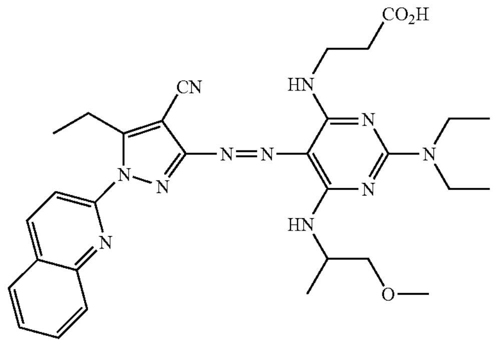
(24)
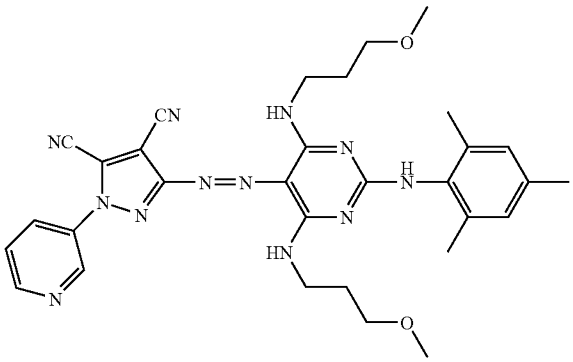
(25)
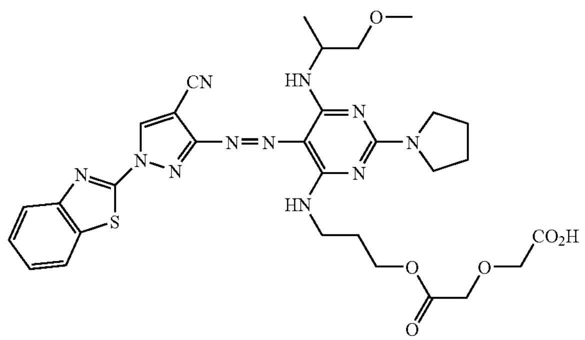
(26)
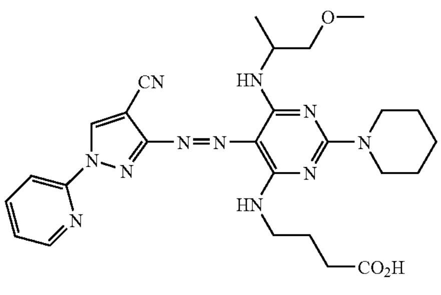

-continued
(27)
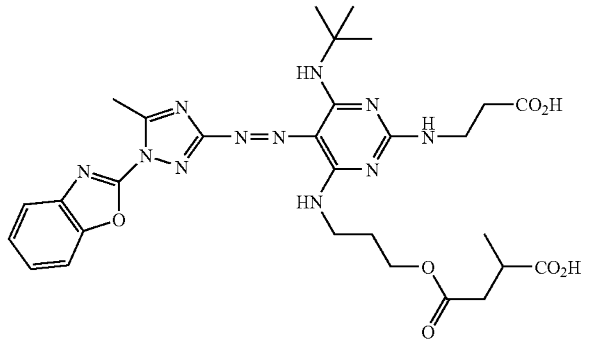
(28)
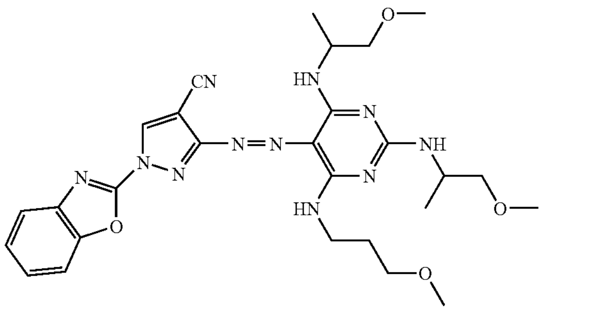
(29)
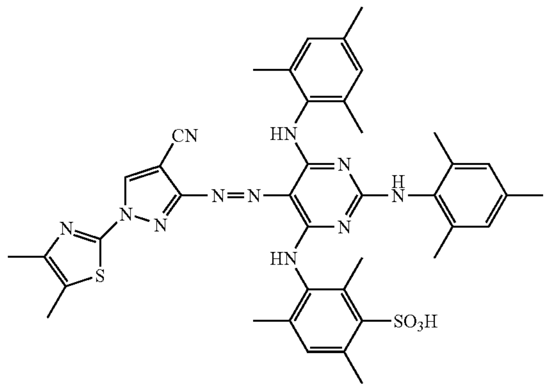
(30)
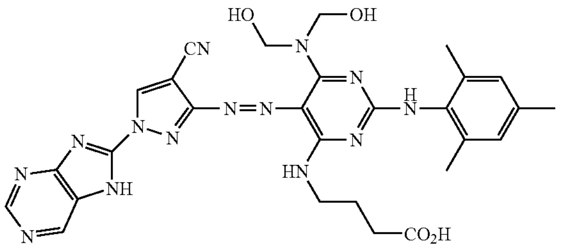
(31)
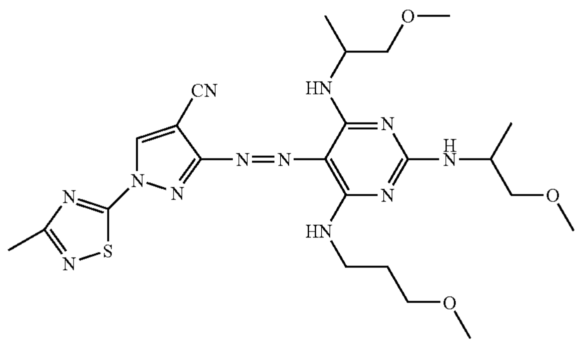
(32)
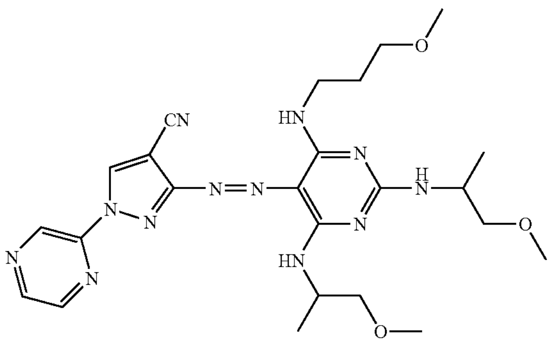
(33)
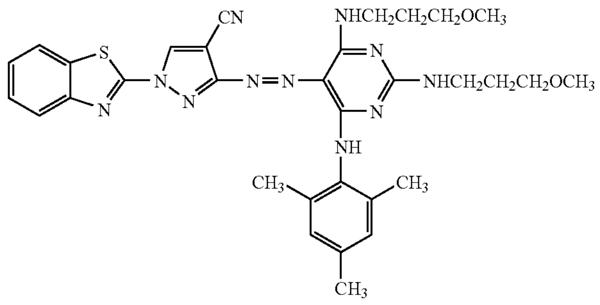
(34)
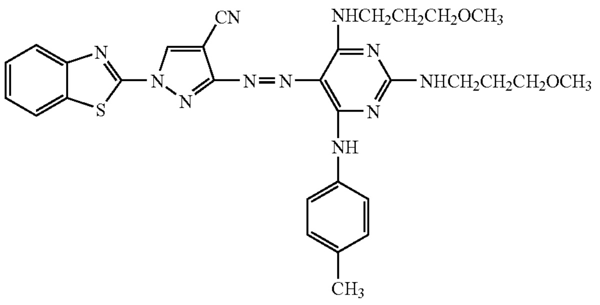

-continued
(35)
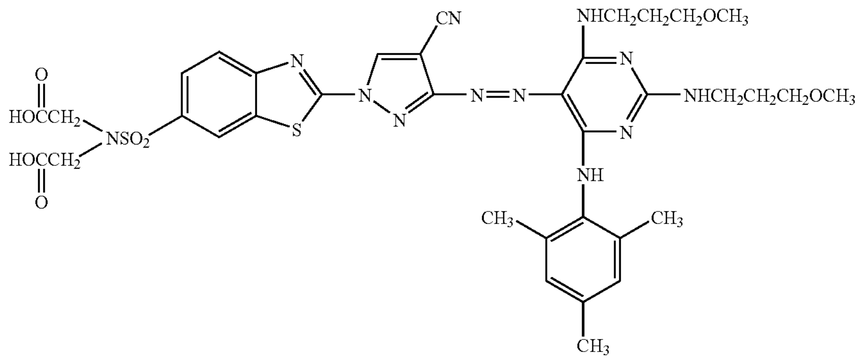
(36)
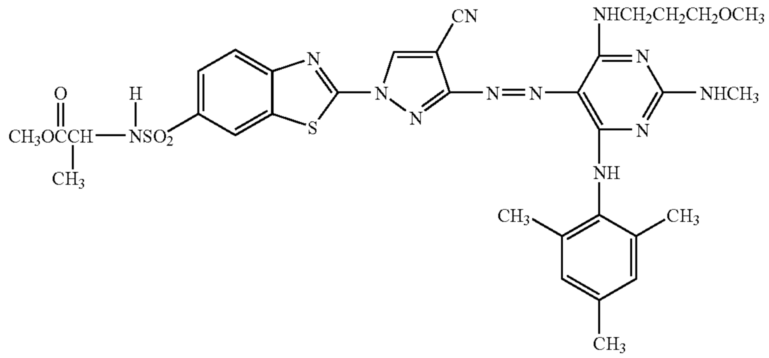
(37)
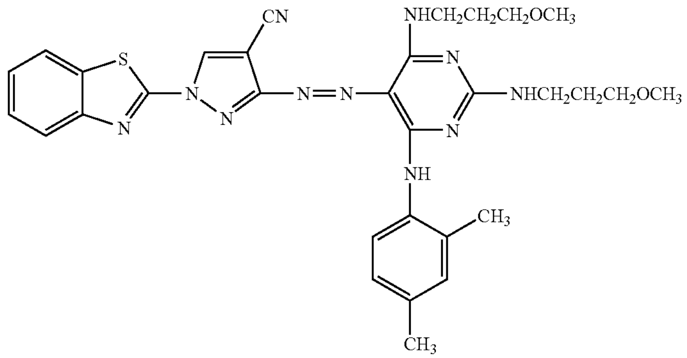
(38)
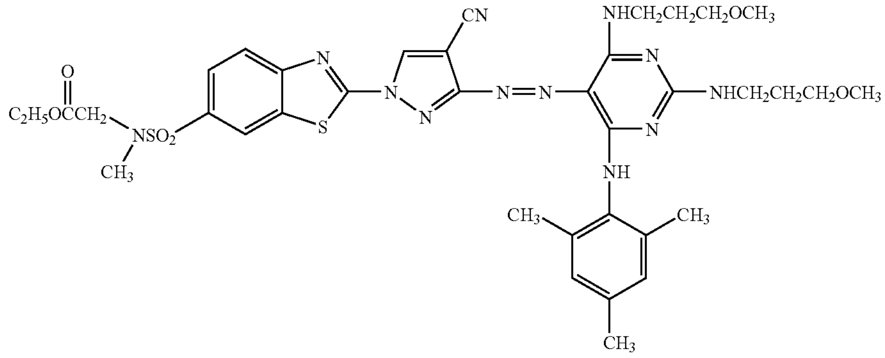

-continued
(39)
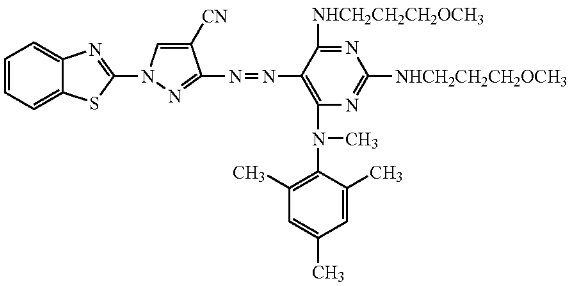
(40)
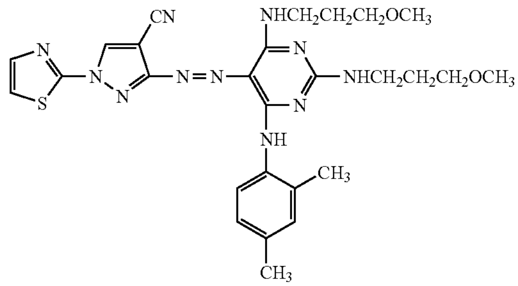
(41)
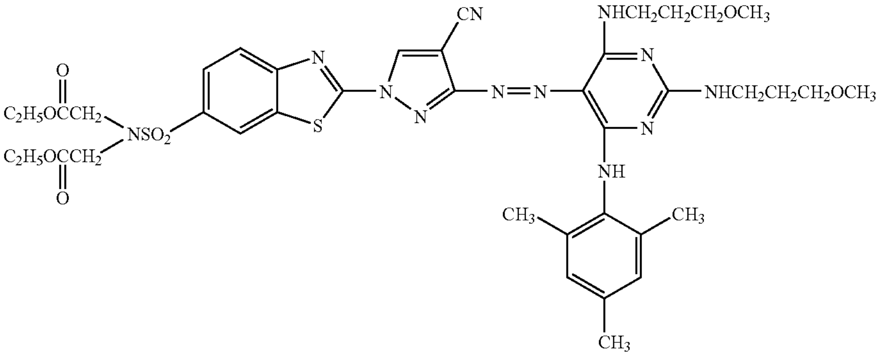
(42)
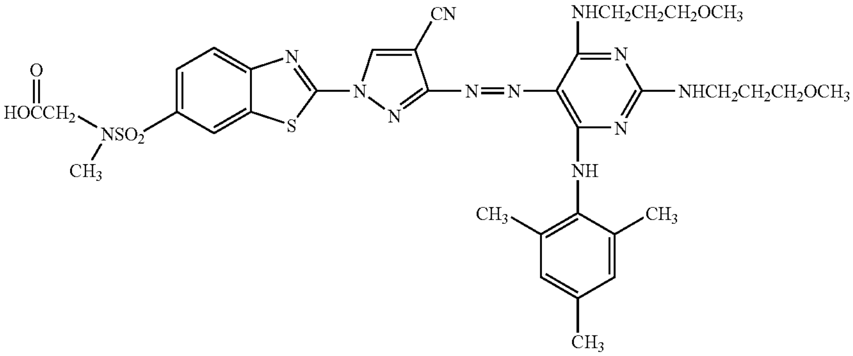
(43)
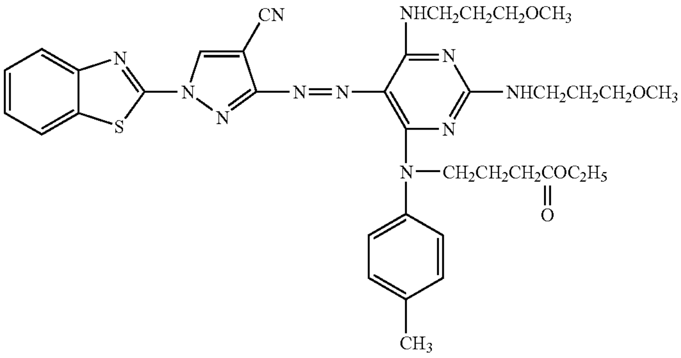

-continued
(44)
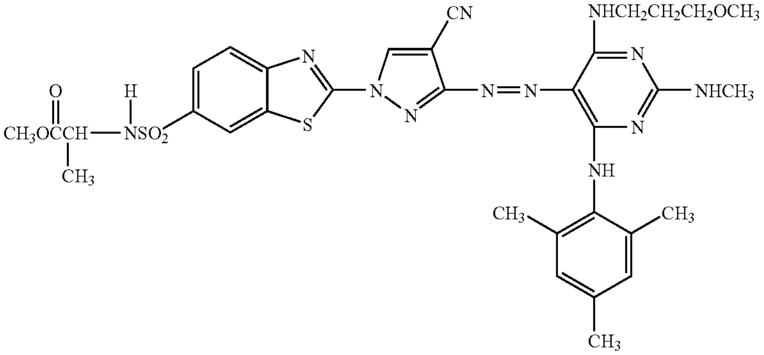
(45)
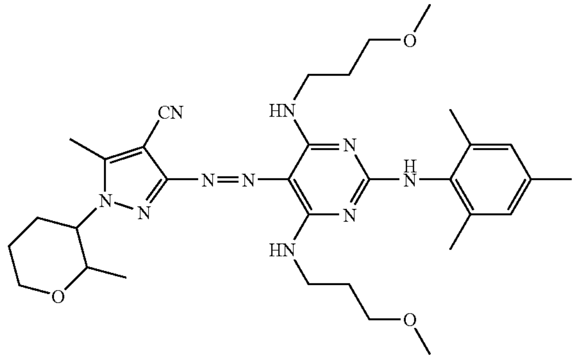
(46)
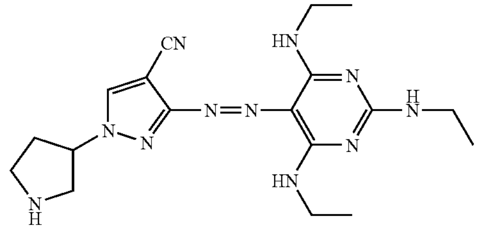
(47)
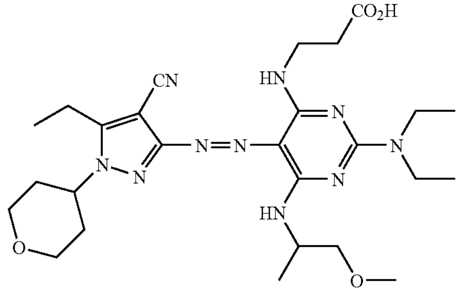
(48)
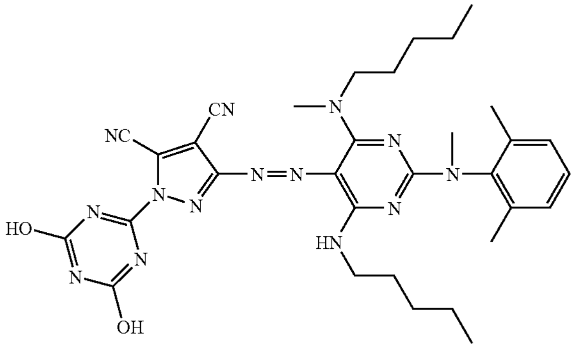
(49)
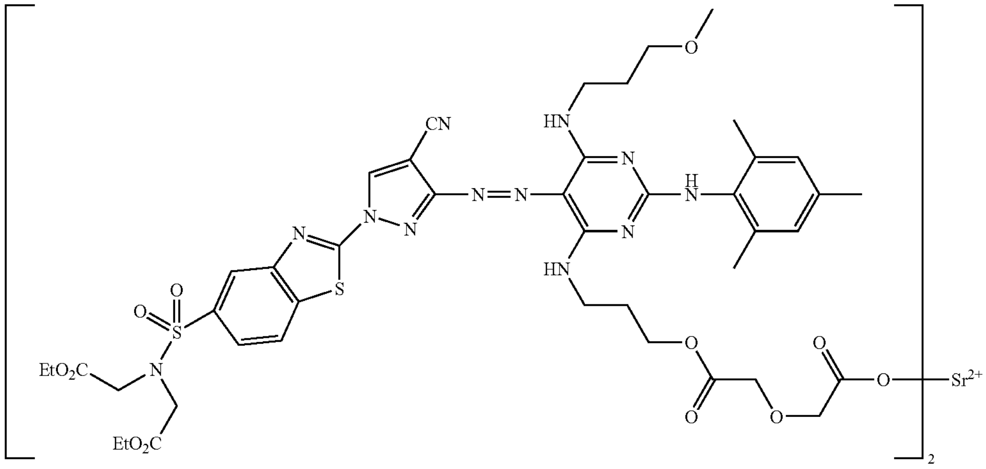

-continued
(50)
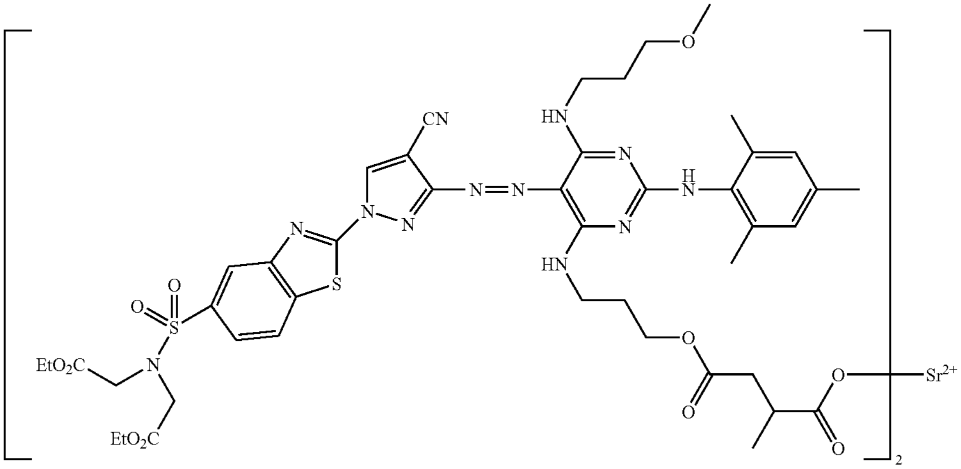
(51)
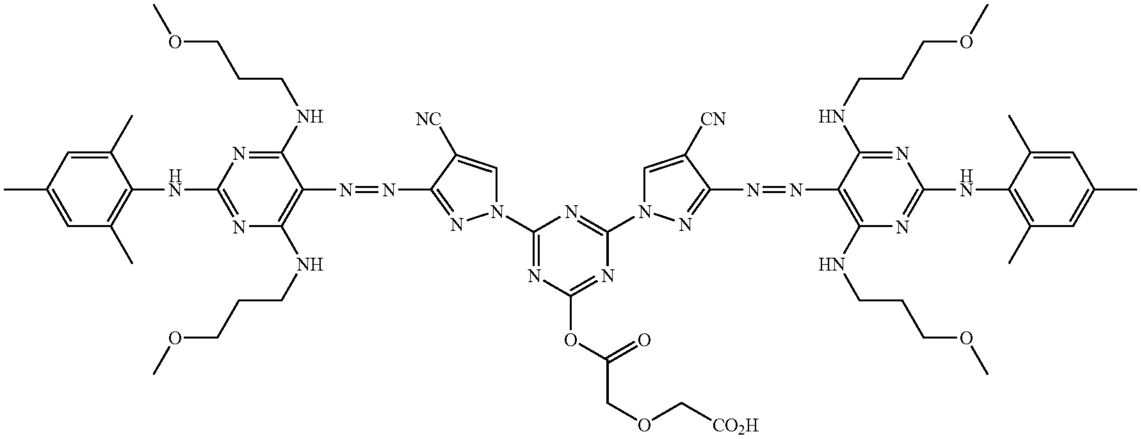
(52)
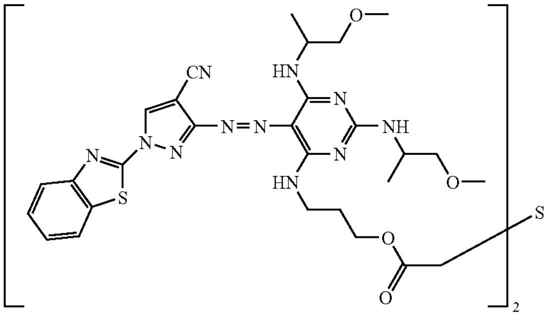
(53)
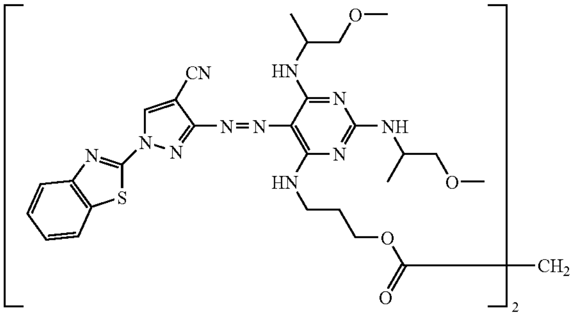
(54)
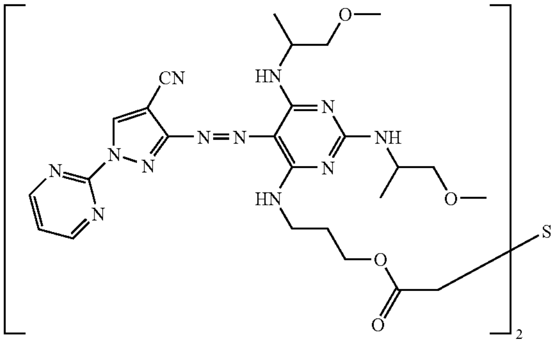
(55)
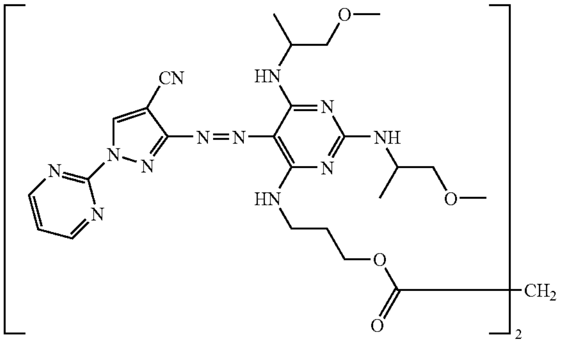

-continued
(56)
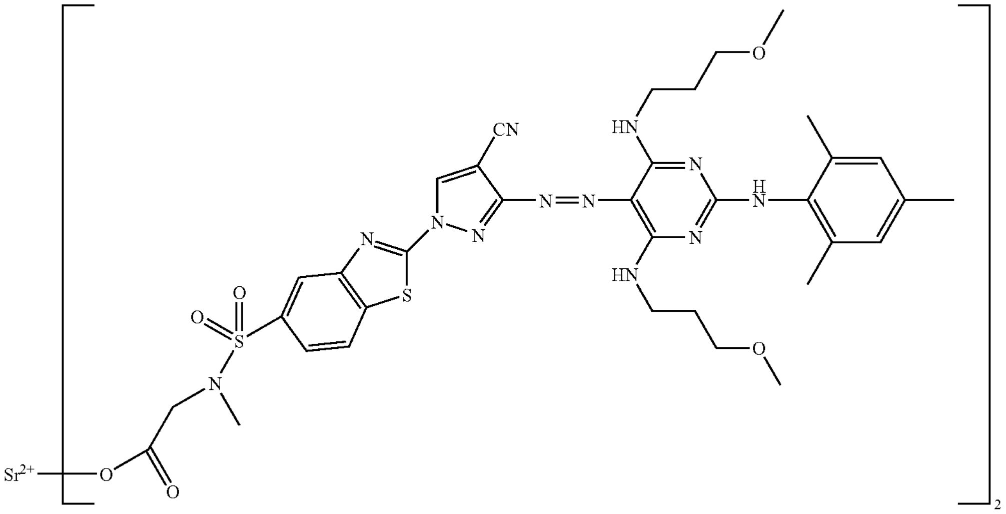
(57)
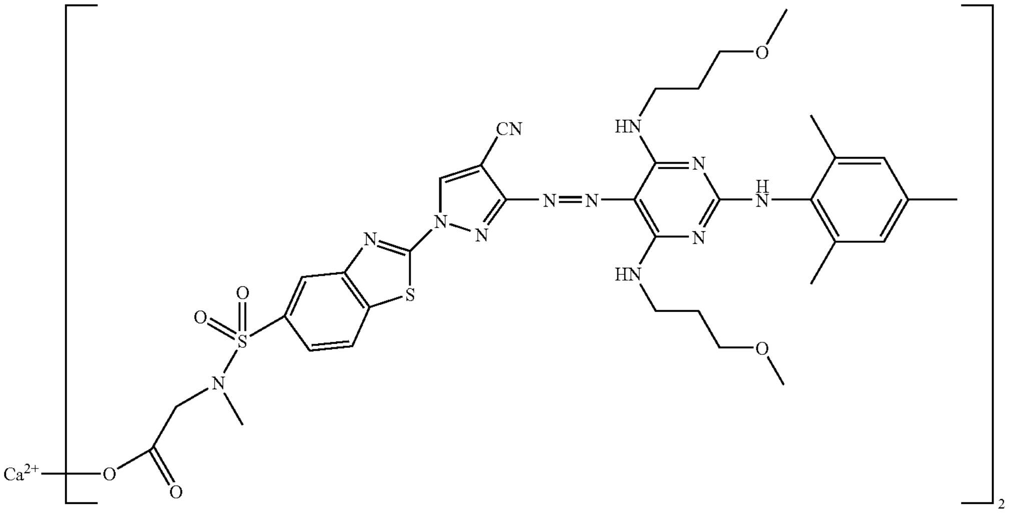
(58)
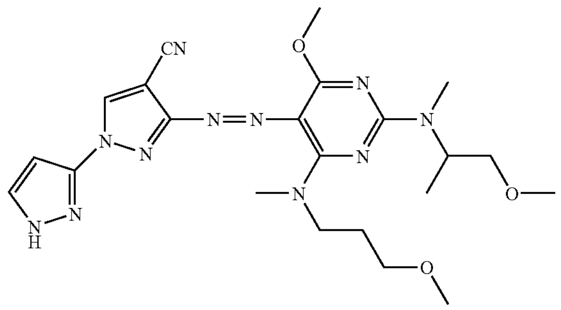
(59)
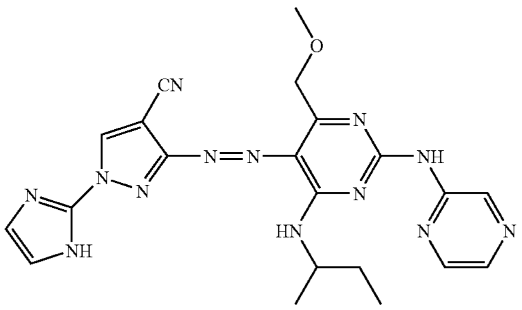

-continued
(60)
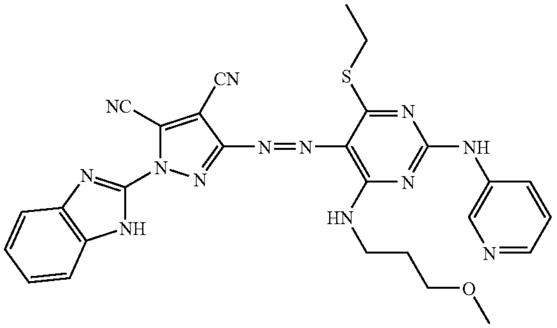
(61)
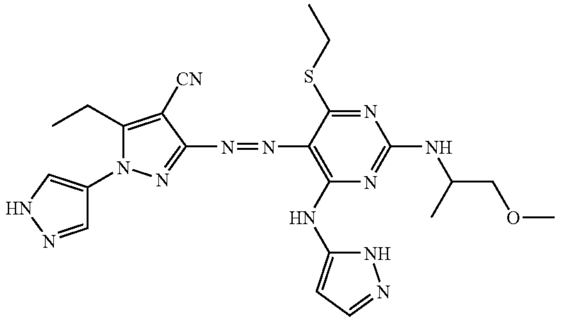
(62)
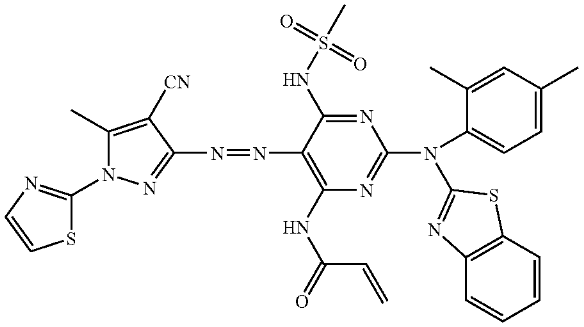
(63)
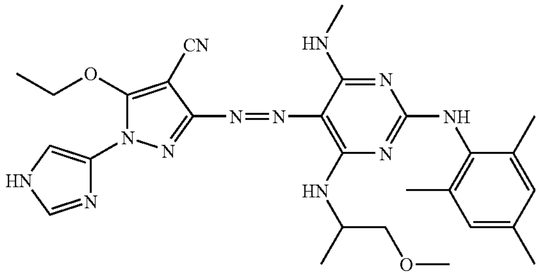
(64)
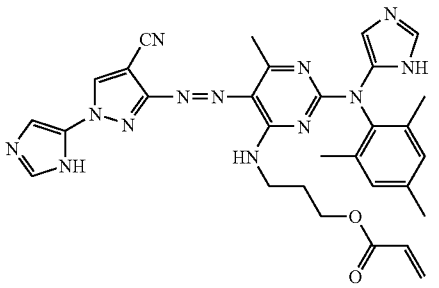
(65)
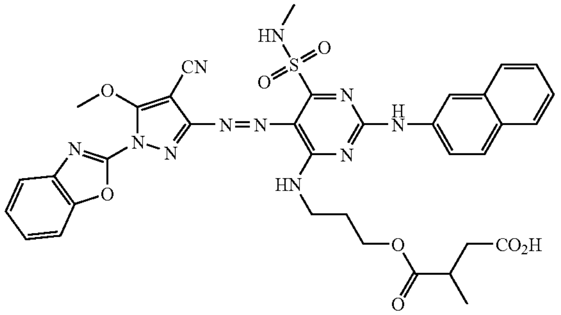
(66)
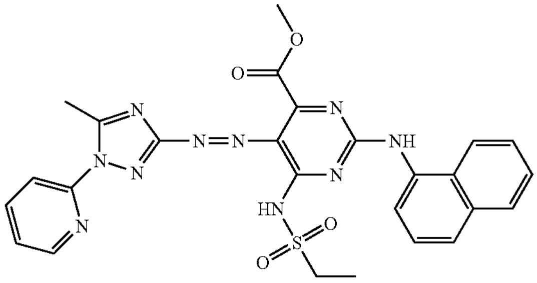
(67)
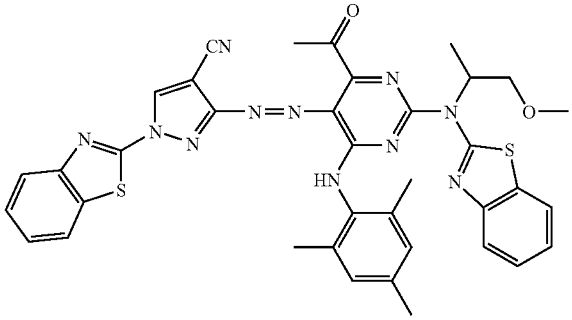

-continued
(68)
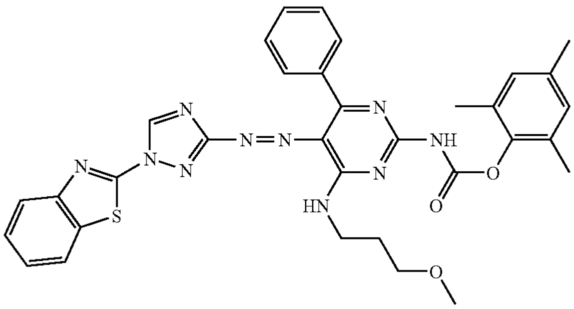
(69)
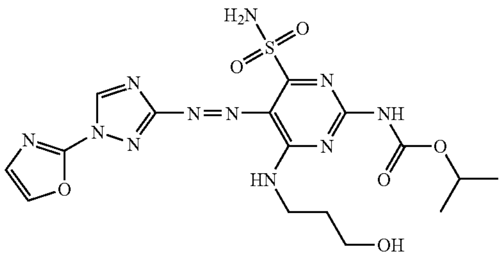
(70)
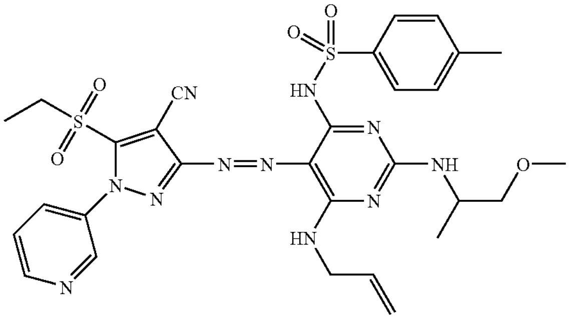
(71)
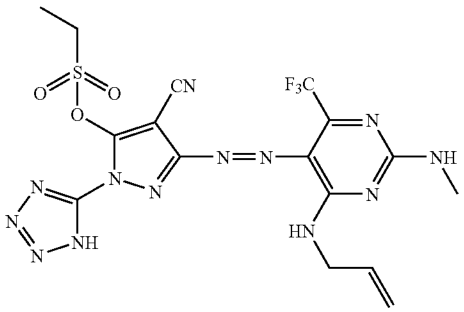
(72)
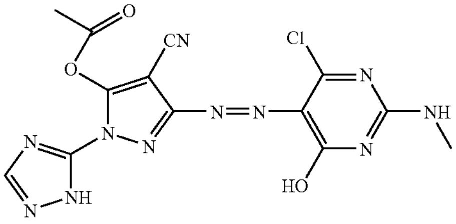
(73)
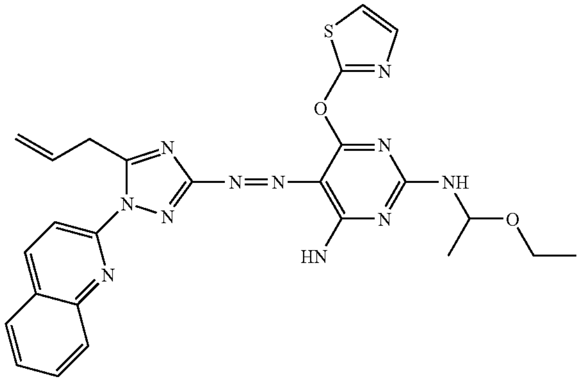
(74)
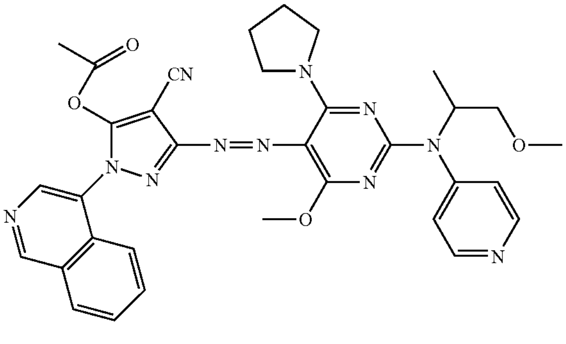
(75)
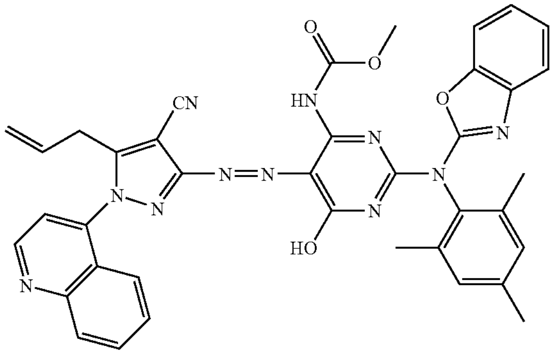

-continued
(76)
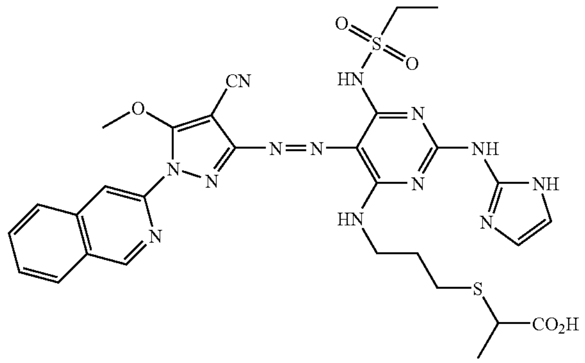
(77)
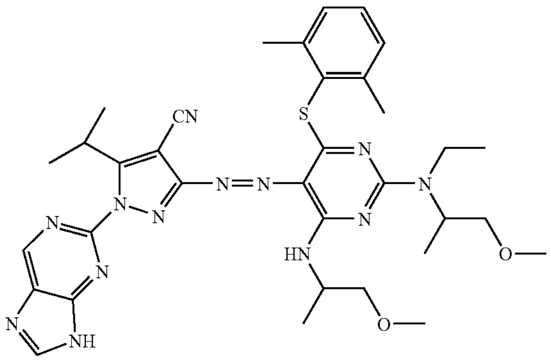
(78)
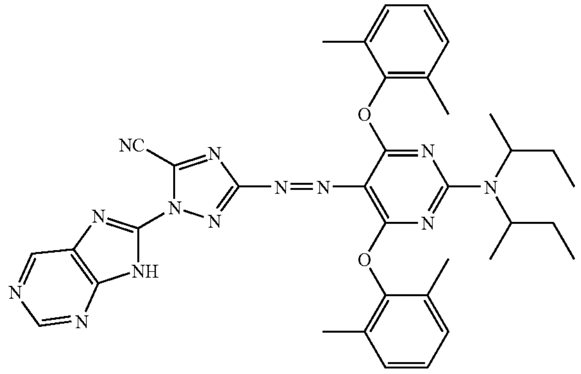
(79)
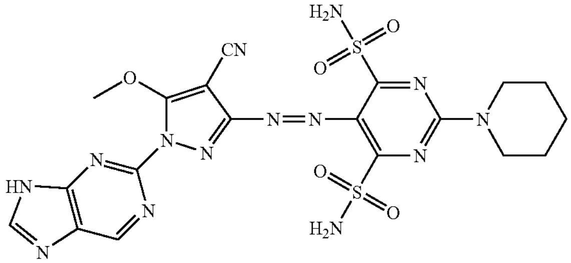
(80)
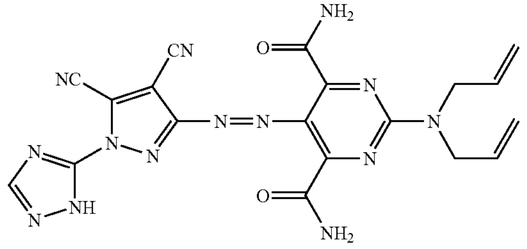
(81)
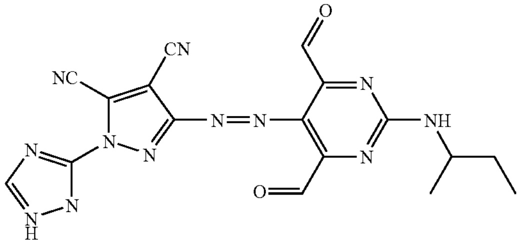
(82)
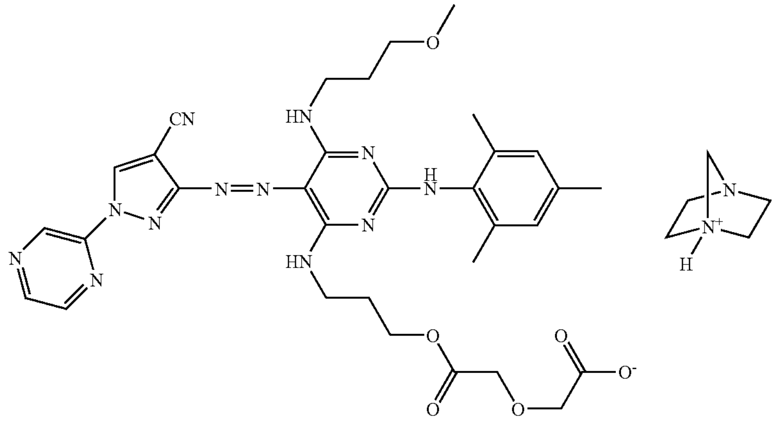

-continued
(83)
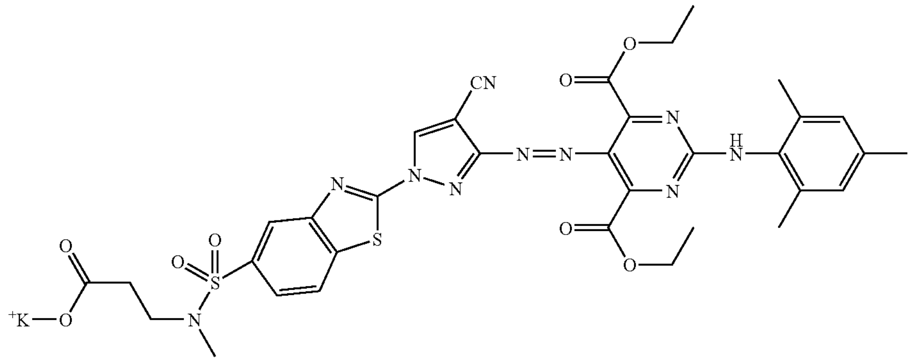
(84)
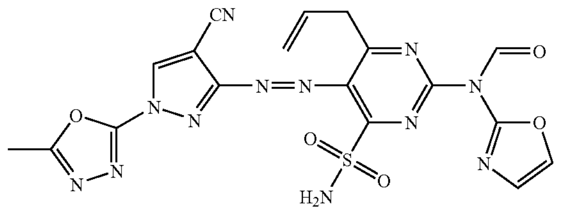
(85)
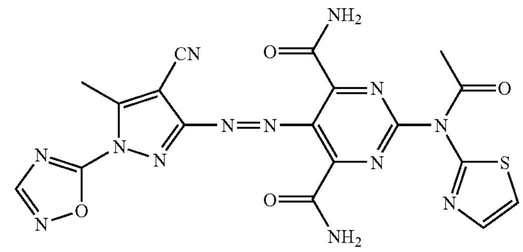
(86)
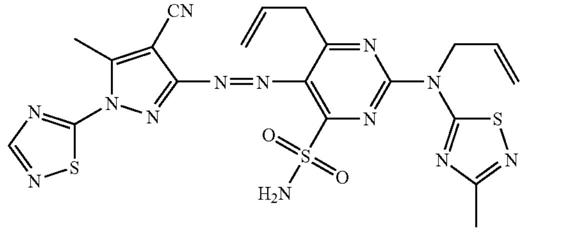
(87)
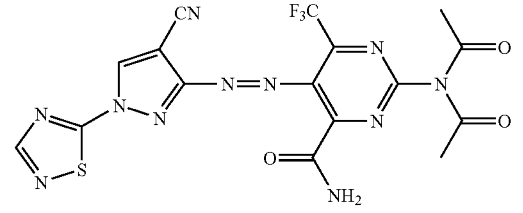
(88)
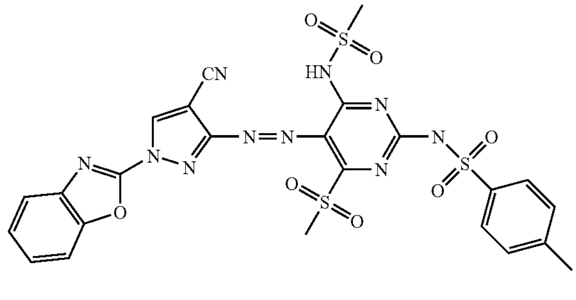
(89)
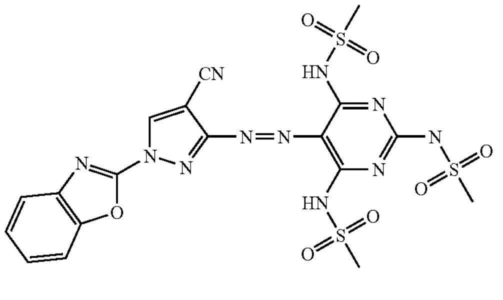

-continued
(90)
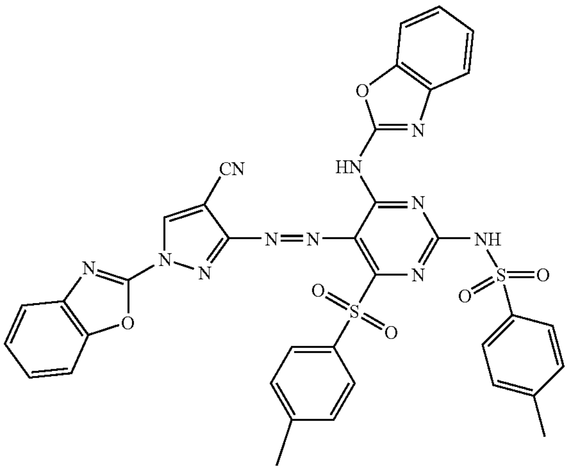
(91)
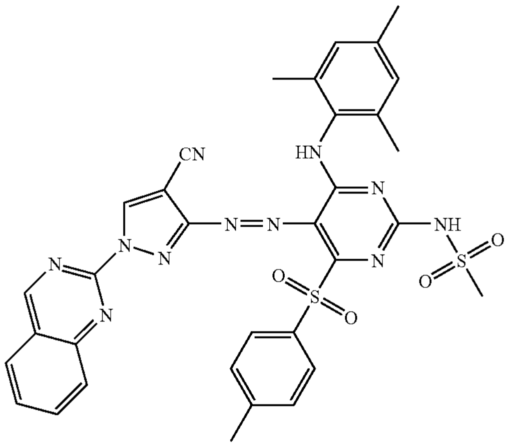
(92)
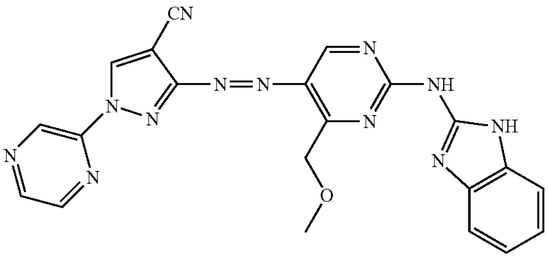
(93)
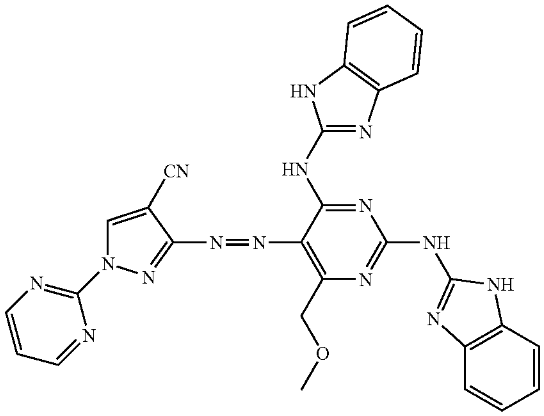
(94)
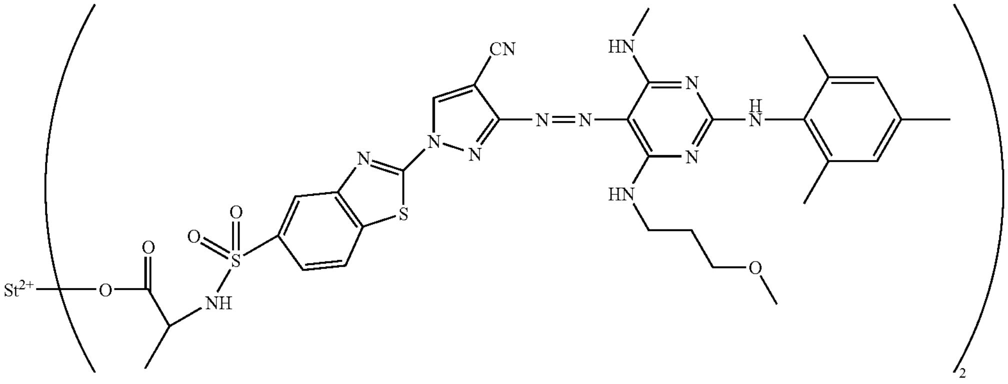

-continued
(95)
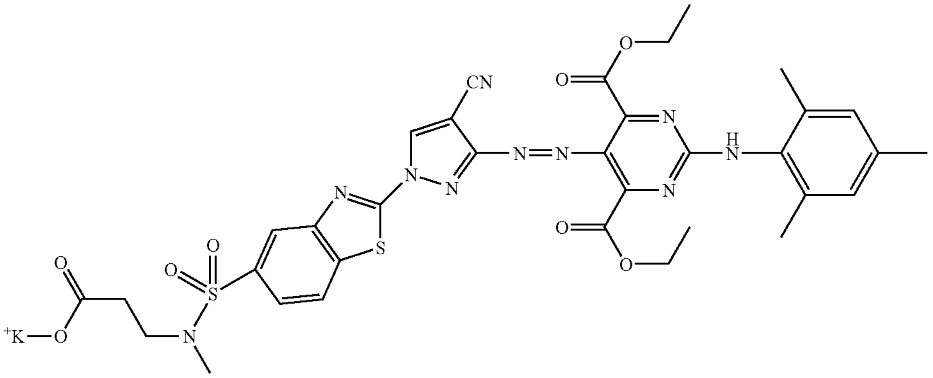
(96)
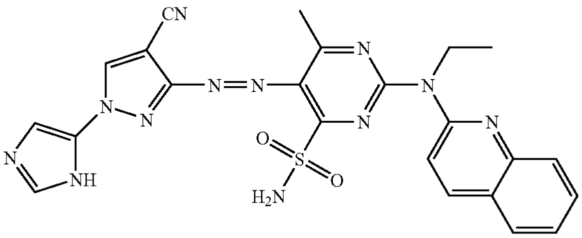
(97)
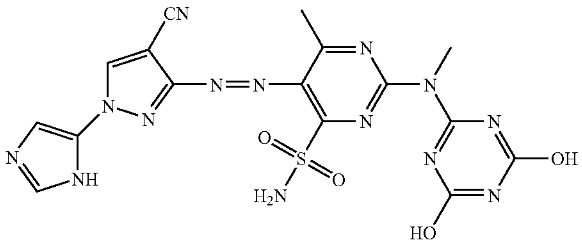
(98)
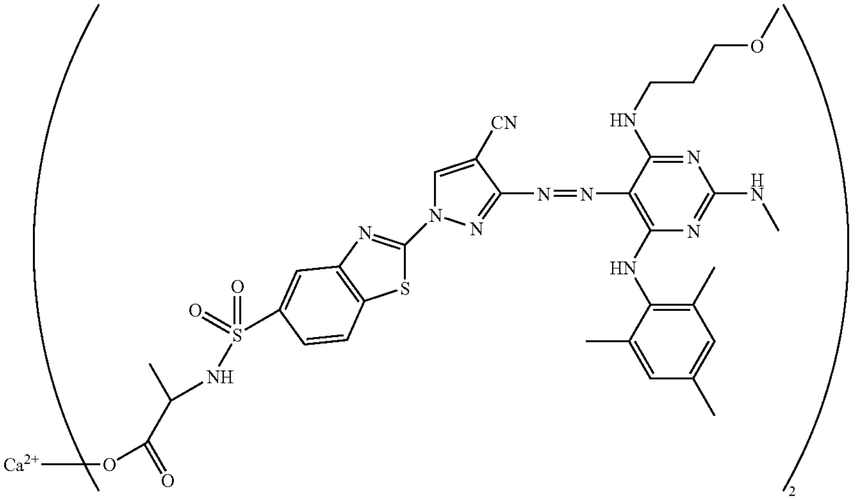
(99)
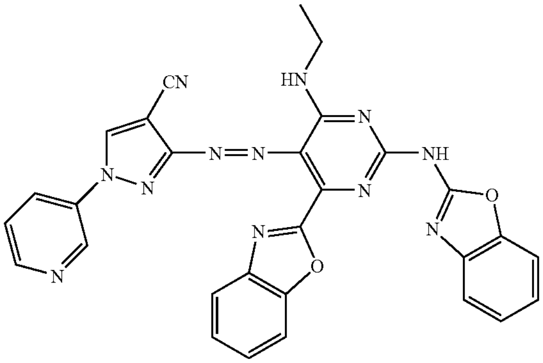
(100)
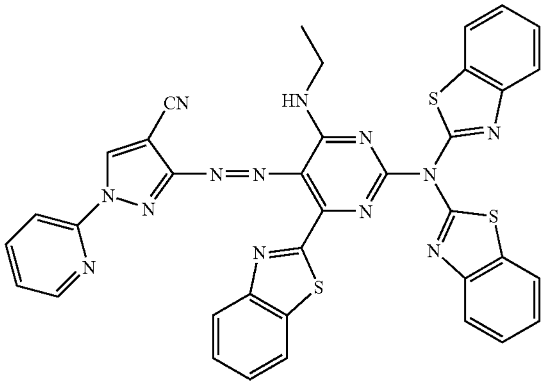

-continued
(101)
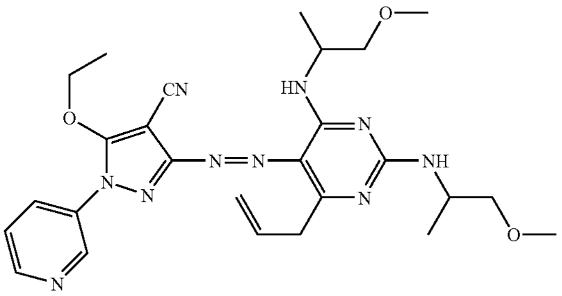
(102)
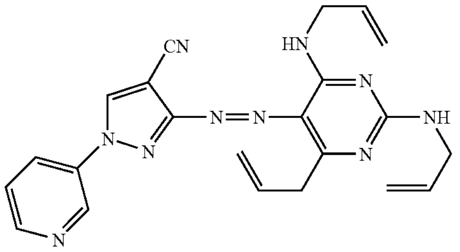
(103)
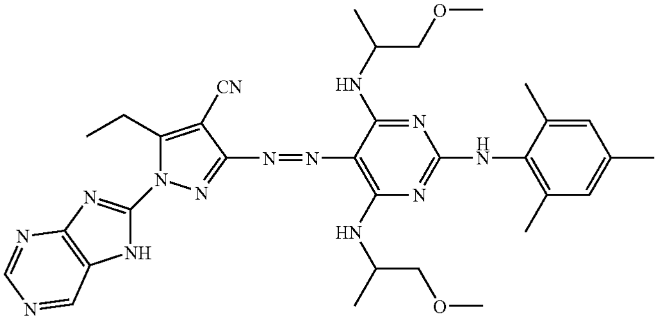
Further specific examples are listed up (exemplary compounds C-1 to C-59). In the invention, the dye is not limited to these examples.
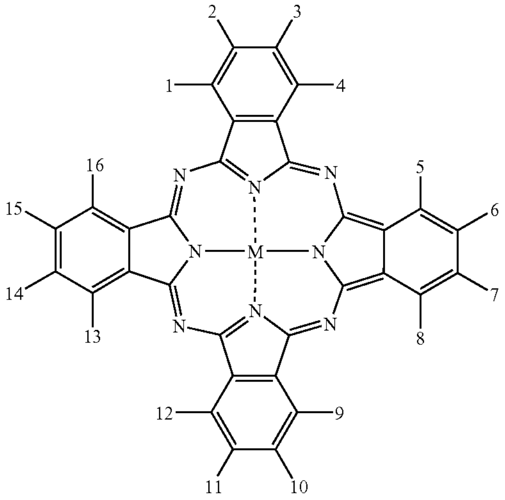
| Exemplary Compound | M | *1 | *2 |
|---|---|---|---|
| C-1 | Cu | 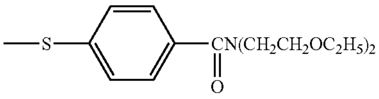 | H |
| C-2 | Cu | 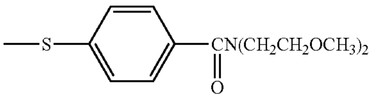 | H |
-continued
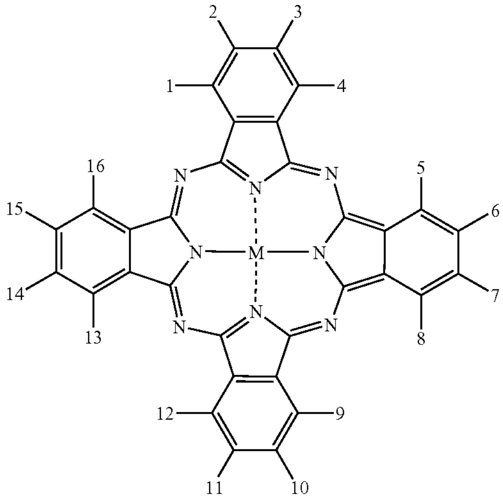
| Exemplary Compound | M | *1 | *2 |
|---|---|---|---|
| C-3 | Cu | 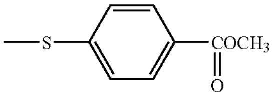 | H |
| C-4 | Cu | 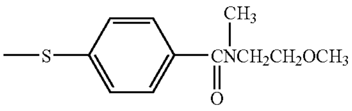 | H |

-continued

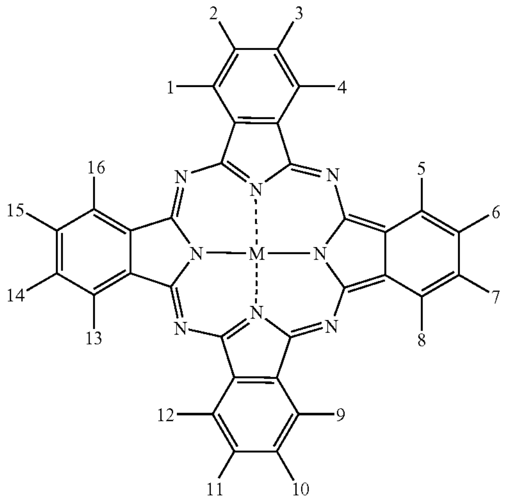

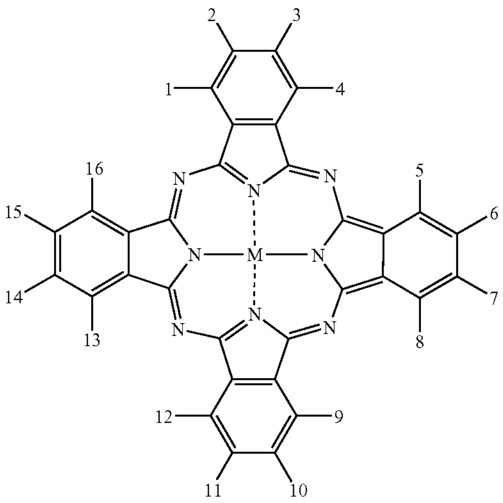

| Exemplary Compound | M | *1 | *2 |
| --- | --- | --- | --- |
| C-5 | Cu | 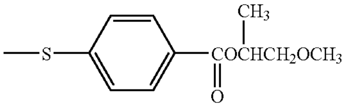 | H |
| C-6 | Cu | 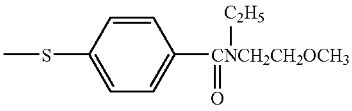 | H |
| C-7 | Cu | 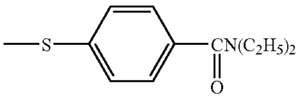 | H |
| C-8 | Cu | 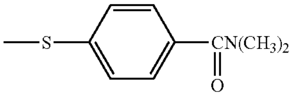 | H |

*1. The substituent at one of position 1 or 4, one of position 5 or 8, one of position 9 or 12, and one of position 13 or 16 (The substituent at the other one of each of the foregoing pairs of positions is H).
*2. The substituent at the other eight positions.

| Exemplary Compound | M | *1 | *2 |
| --- | --- | --- | --- |
| C-9 | Cu | 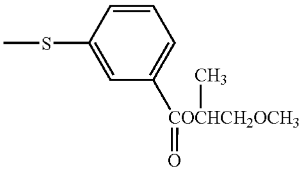 | H |
| C-10 | Cu | 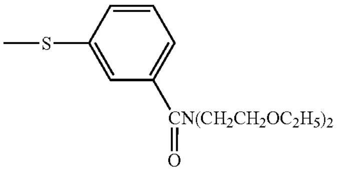 | H |
| C-11 | Cu | 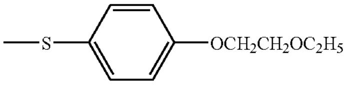 | H |
| C-12 | Cu | 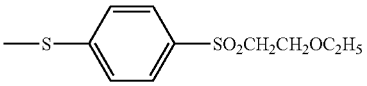 | *3 |
| C-13 | Cu | 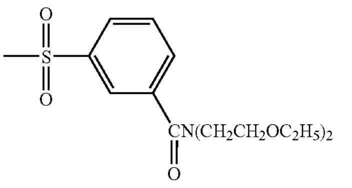 | H |

*1. The substituent at one of position 1 or 4, one of position 5 or 8, one of position 9 or 12, and one of position 13 or 16 (The substituent at the other one of each of the foregoing pairs of positions is H).
*2. The substituent at the other eight positions.
*3. The substituent at one of position 2 or 3, one of position 6 or 7, one of position 10 or 11, and one of position 14 or 15 is $CH_3$, and the substituent at the other one of each of the foregoing pairs of positions is H.

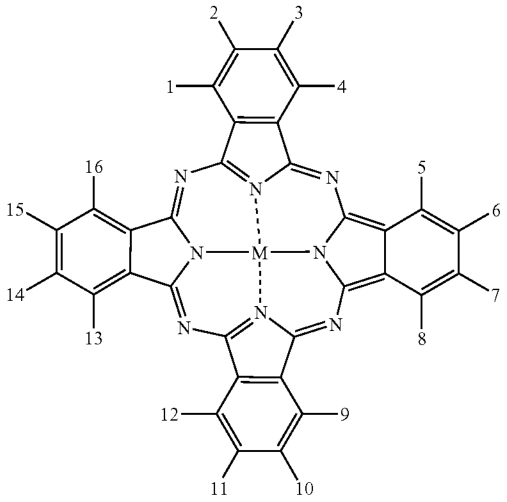

| Exemplary Compound | M | *1 | *2 |
|---|---|---|---|
| C-14 | Cu | 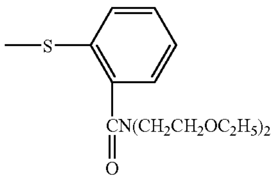 | H |
| C-15 | Cu | 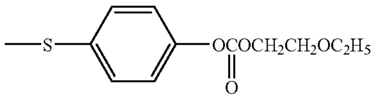 | *3 |
| C-16 | Cu | 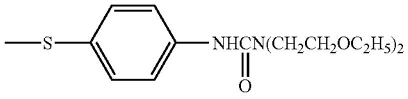 | H |
| C-17 | Cu | 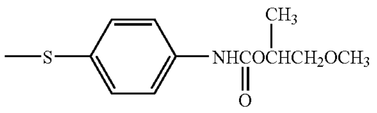 | H |
| C-18 | Cu | 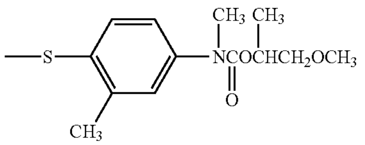 | H |
| C-19 | Cu | 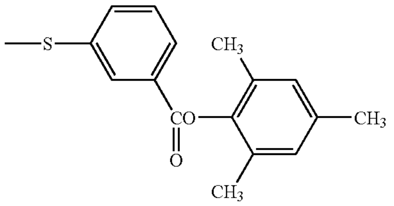 | H |

*1 The substituent at one of position 1 or 4, one of position 5 or 8, one of position 9 or 12, and one of position 13 or 16 (The substituent at the other one of each of the foregoing pairs of positions is H).
*2 The substituent at the other eight positions.
*3 The substituent at one of position 2 or 3, one of position 6 or 7, one of position 10 or 11, and one of position 14 or 15 is $CH_3$, and the substituent at the other one of each of the foregoing pairs of positions is H.

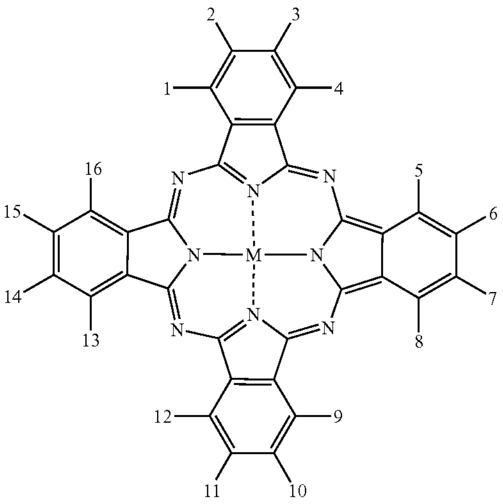
| Exemplary Compound | M | *1 | *2 |
|---|---|---|---|
| C-20 | Cu | 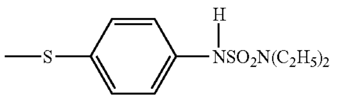 | H |
| C-21 | Cu | 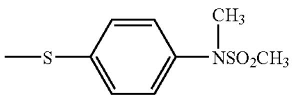 | H |
| C-22 | Cu | 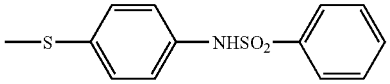 | H |
| C-23 | Cu | 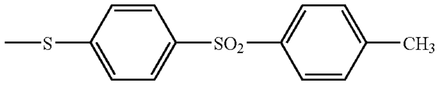 | H |
| C-24 | Cu | 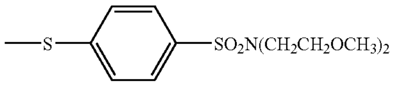 | H |
| C-25 | Cu | 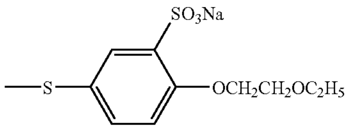 | H |
| C-26 | V=O | 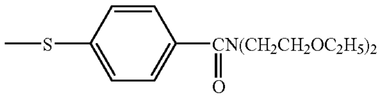 | H |
| C-27 | Co | 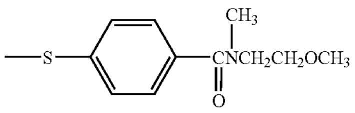 | H |
*1. The substituent at one of position 1 or 4, one of position 5 or 8, one of position 9 or 12, and one of position 13 or 16 (The substituent at the other one of each of the foregoing pairs of positions is H).
*2. The substituent at the other eight positions.

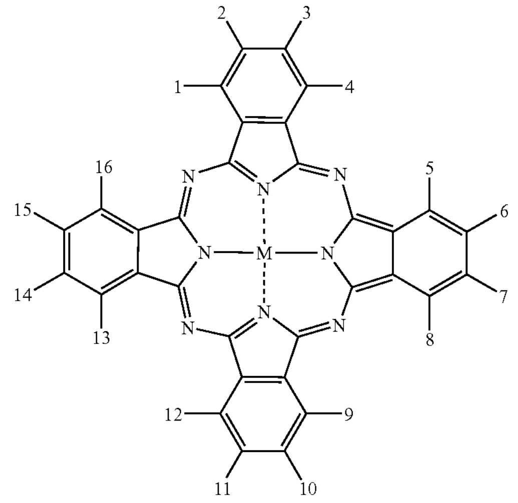
| Exemplary Compound | M | *1 | *2 |
|---|---|---|---|
| C-28 | Co | 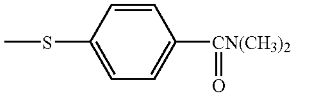 | H |
| C-29 | Zn | 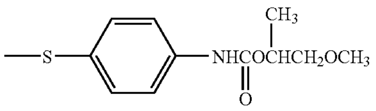 | H |
| C-30 | V═O | 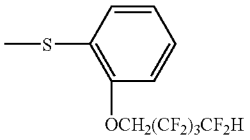 | H |
| C-31 | Cu | 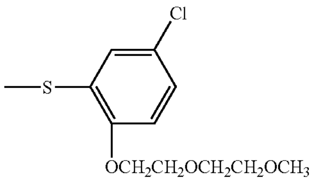 | H |
| C-32 | Cu | 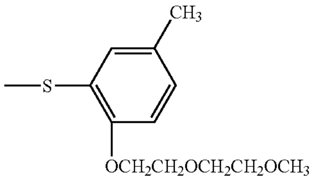 | H |
*1. The substituent at one of position 1 or 4, one of position 5 or 8, one of position 9 or 12, and one of position 13 or 16 (The substituent at the other one of each of the foregoing pairs of positions is H).
*2. The substituent at the other eight positions.

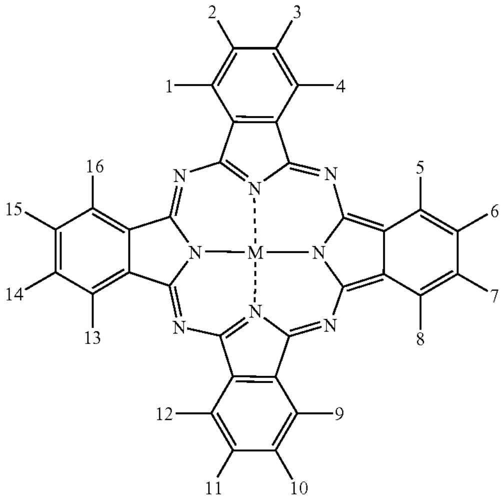

| Exemplary Compound | M | *1 | *2 |
|---|---|---|---|
| C-33 | Cu | 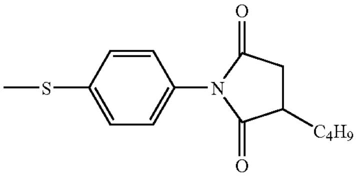 | H |
| C-34 | Cu | 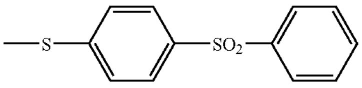 | H |
| C-35 | Cu | 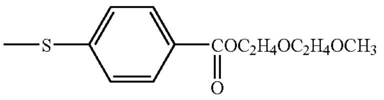 | H |

*1. The substituent at one of position 1 or 4, one of position 5 or 8, one of position 9 or 12, and one of position 13 or 16 (The substituent at the other one of each of the foregoing pairs of positions is H).

*2. The substituent at the other eight positions.

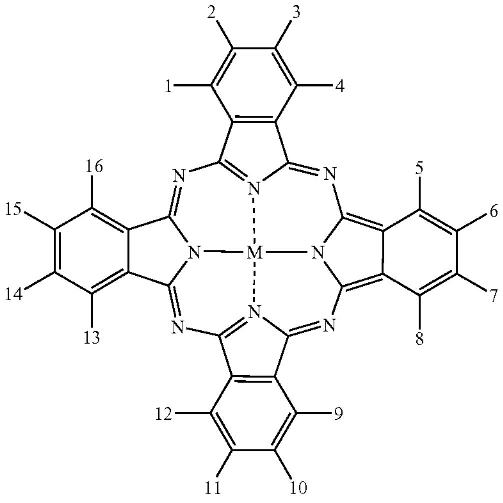

| Exemplary Compound | M | *4 | *5 |
|---|---|---|---|
| C-41 | Cu | 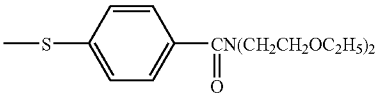 | H |
| C-42 | Cu | 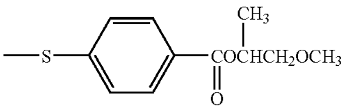 | H |
| C-43 | Cu | 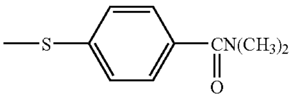 | H |
| C-44 | Cu | 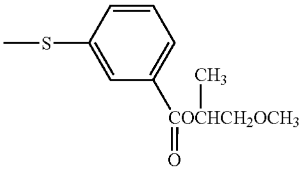 | H |
| C-45 | Co | 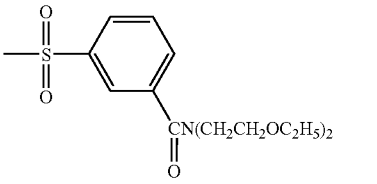 | H |

*4. The substituent at one of position 2 or 3, one of position 6 or 7, one of position 10 or 11, and one of position 14 or 15 (The substituent at the other one of each of the foregoing pairs of positions is H).

*5 The substituent at the other eight positions.

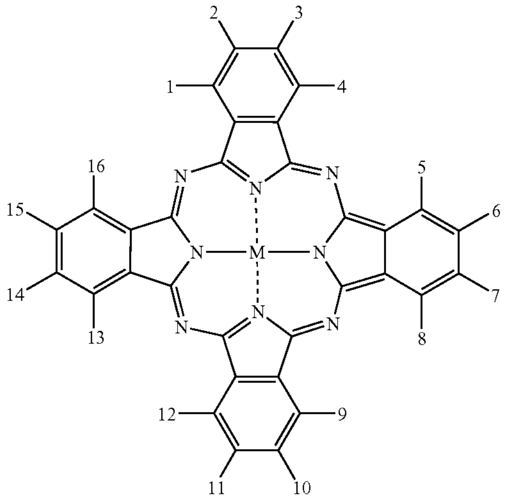

| Exemplary Compound | M | *4 | *5 |
|---|---|---|---|
| C-46 | Zn | 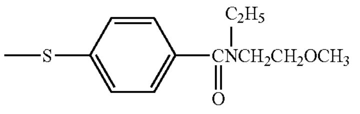 | H |
| C-47 | V═O | 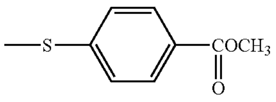 | H |
| C-48 | Cu | 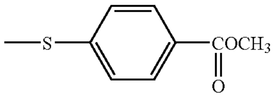 | *6 |
| C-49 | Cu | 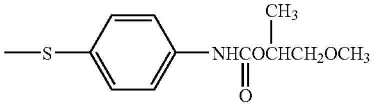 | H |

*4. The substituent at one of position 2 or 3, one of position 6 or 7, one of position 10 or 11, and one of position 14 or 15 (The substituent at the other one of each of the foregoing pairs of positions is H).

*5. The substituent at the other eight positions.

*6. The substituent at one of position 1 or 4, one of position 5 or 8, one of position 9 or 12, and one of position 13 or 16 is $CH_3$, and the substituent at the other one of each of the foregoing pairs of positions is H.

-continued
C-50
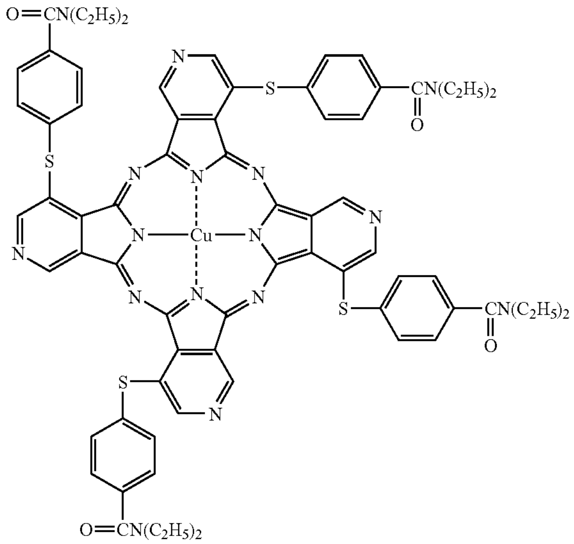
C-52
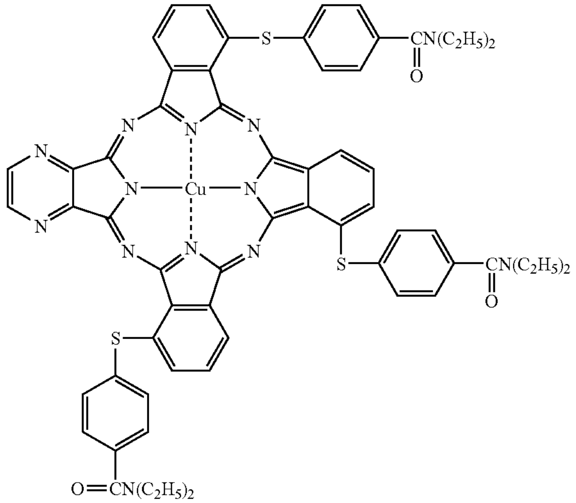
C-51
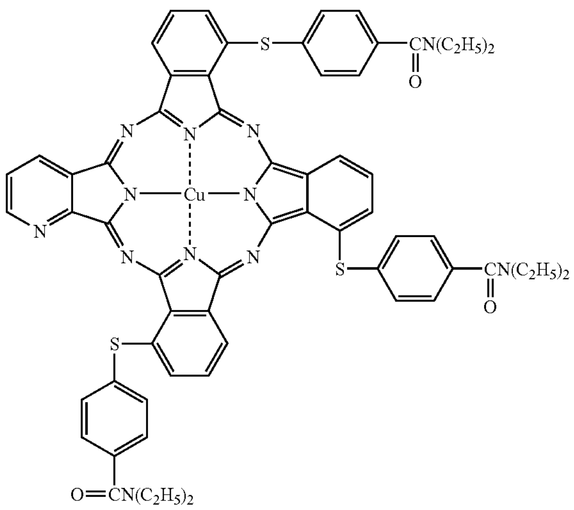
C-53
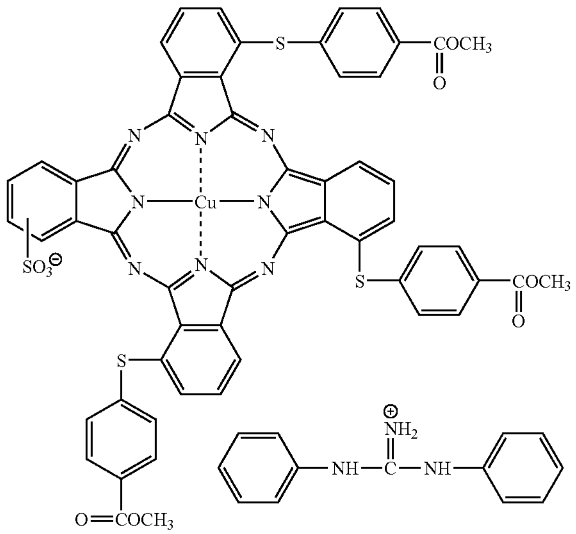

-continued
C-54
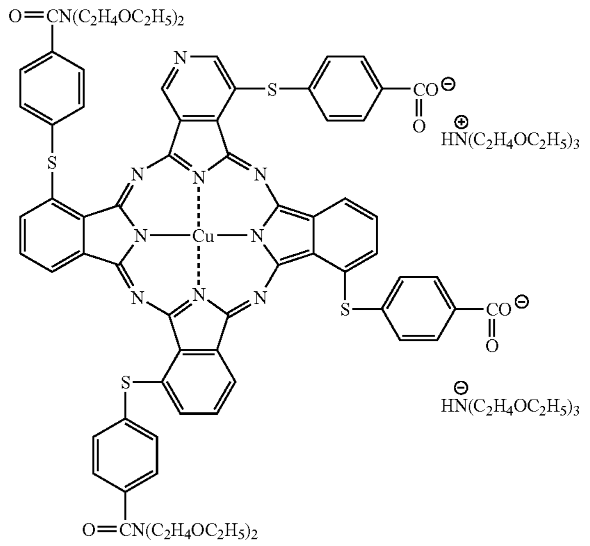
C-55
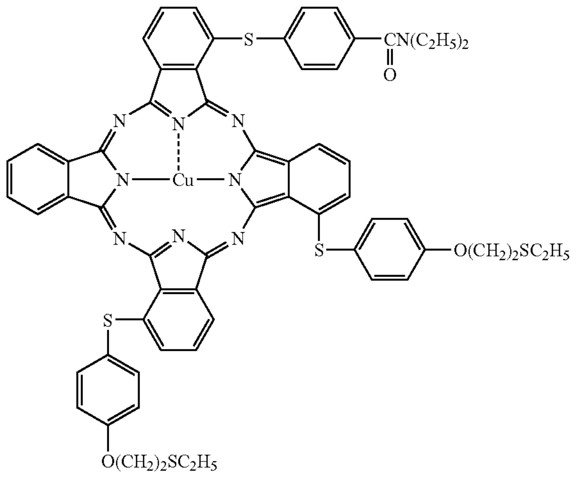
C-56
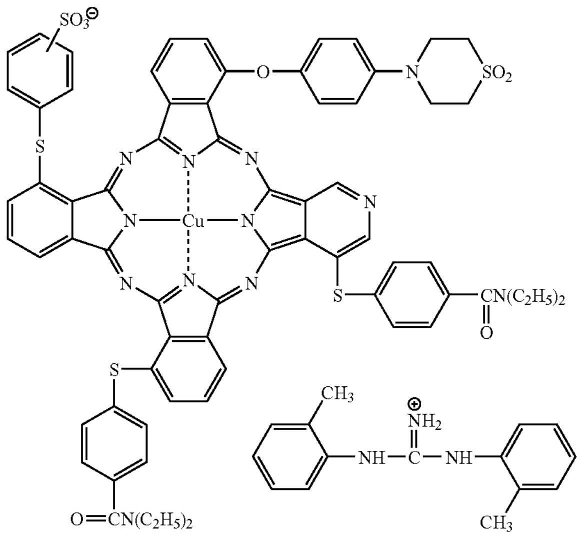
-continued
C-57
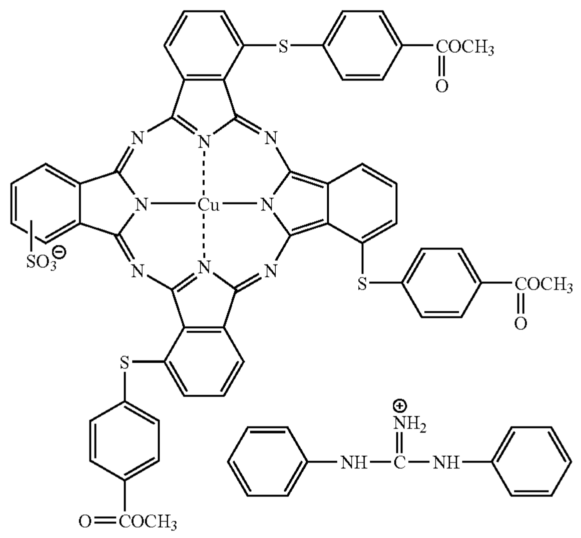
C-58
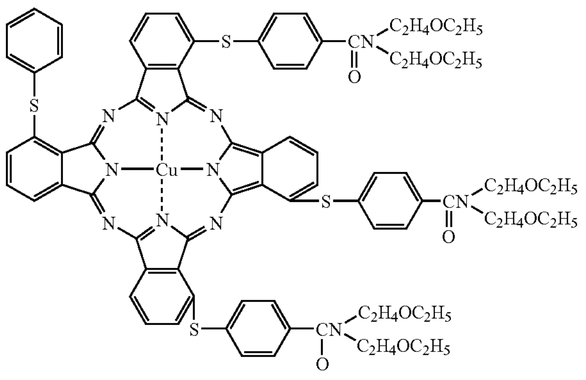
C-59
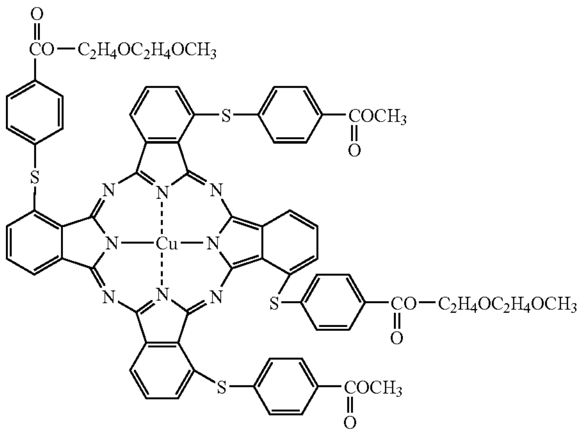
Further specific examples are listed below (specific examples 1 to 157). In the invention, the dye is not limited to these examples.

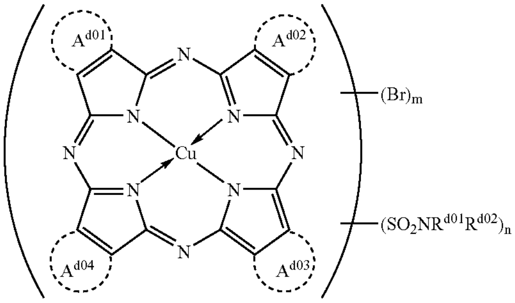
(Ring $A^{d01}$, ring $A^{d02}$, ring $A^{d03}$, and ring $A^{d04}$ are each independently a benzene ring or a pyridine ring.)
| No. | Number of 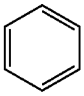 | Number of 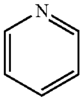 | m | n | $R^{d01}$ | $R^{d02}$ |
|---|---|---|---|---|---|---|
| 1 | 3 | 1 | 1 | 1 | H | $—C_2H_4OC_2H_5$ |
| 2 | 3 | 1 | 2 | 2 | H | $—C_2H_4OC_2H_5$ |
| 3 | 3 | 1 | 3 | 3 | H | $—C_2H_4OC_2H_5$ |
| 4 | 3 | 1 | 1 | 4 | H | $—C_2H_4OC_2H_5$ |
| 5 | 3 | 1 | 1 | 1 | $—C_2H_4OC_2H_5$ | $—C_2H_4OC_2H_5$ |
| 6 | 3 | 1 | 1 | 1 | H | $—C_3H_6OC_4H_9$ |
| 7 | 3 | 1 | 1 | 2 | H | $—C_3H_6OC_4H_9$ |
| 8 | 3 | 1 | 1 | 3 | H | $—C_3H_6OC_4H_9$ |
| 9 | 3 | 1 | 1 | 4 | H | $—C_3H_6OC_4H_9$ |
| 10 | 3 | 1 | 1 | 1 | $—C_2H_4OCH_3$ | $—C_2H_4OCH_3$ |
| 11 | 3 | 1 | 1 | 2 | $—C_2H_4OCH_3$ | $—C_2H_4OCH_3$ |
| 12 | 3 | 1 | 1 | 3 | $—C_2H_4OCH_3$ | $—C_2H_4OCH_3$ |
| 13 | 3 | 1 | 1 | 4 | $—C_2H_4OCH_3$ | $—C_2H_4OCH_3$ |
| 14 | 3 | 1 | 1 | 2 | $—C_4H_9$ | $—C_4H_9$ |
| 15 | 3 | 1 | 1 | 1 | H | 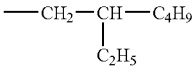 |
| 16 | 3 | 1 | 1 | 2 | H | 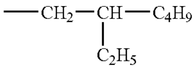 |
| 17 | 3 | 1 | 1 | 3 | H | 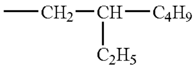 |
| 18 | 3 | 1 | 1 | 4 | H | 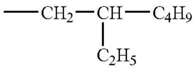 |
| 19 | 3 | 1 | 1 | 1 | H | 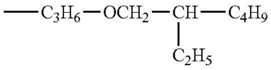 |
| 20 | 3 | 1 | 1 | 2 | H | 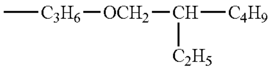 |
| 21 | 3 | 1 | 1 | 3 | H | 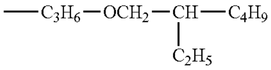 |

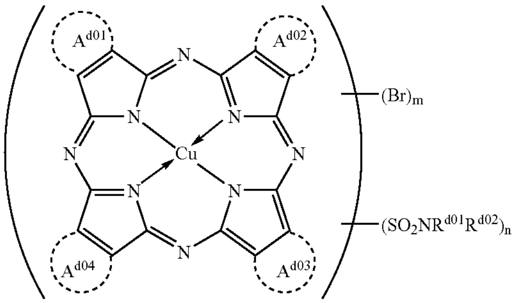

(Ring $A^{d01}$, ring $A^{d02}$, ring $A^{d03}$, and ring $A^{d04}$ are each independently a benzene ring or a pyridine ring.)

| No. | Number of 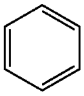 | Number of 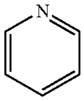 | m | n | $R^{d01}$ | $R^{d02}$ |
|---|---|---|---|---|---|---|
| 22 | 3 | 1 | 4 | 2 | H | $—C_3H_6—OCH_2—CH—C_4H_9$<br>\|<br>$C_2H_5$ |
| 23 | 3 | 1 | 5 | 2 | H | $—C_2H_4OC_2H_4OC_2H_5$ |
| 24 | 3 | 1 | 6 | 1 | $—C_2H_5$ | $—C_2H_4OC_2H_5$ |
| 25 | 3 | 1 | 8 | 1 | $—i\text{-}C_3H_7$ | 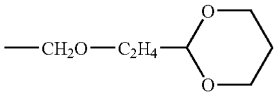 |
| 26 | 3 | 1 | 3 | 2 | H | $—CH—CH_2OCH_3$<br>\|<br>$C_2H_5$ |
| 27 | 3 | 1 | 1 | 1 | H | $—CH—CH_2OC_2H_4OC_2H_5$<br>\|<br>$C_2H_5$ |
| 28 | 3 | 1 | 1 | 2 | H | $—CH—CH_2OC_2H_4OC_2H_5$<br>\|<br>$C_2H_5$ |
| 29 | 3 | 1 | 2 | 2 | H | $—CH—CH_2OC_2H_4OC_2H_5$<br>\|<br>$C_2H_5$ |
| 30 | 3 | 1 | 3 | 2 | H | $—CH—CH_2OC_2H_4OC_2H_5$<br>\|<br>$C_2H_5$ |
| 31 | 3 | 1 | 1 | 1 | H | $—CH—COOCH_3$<br>\|<br>$i\text{-}C_3H_7$ |
| 32 | 3 | 1 | 1 | 2 | H | $—CH—COOCH_3$<br>\|<br>$i\text{-}C_3H_7$ |
| 33 | 3 | 1 | 1 | 2 | H | $—CH—COOCH_3$<br>\|<br>$i\text{-}C_3H_7$ |
| 34 | 3 | 1 | 1 | 1 | H | $—CH—COOCH_3$<br>\|<br>$i\text{-}C_3H_7$ |

-continued

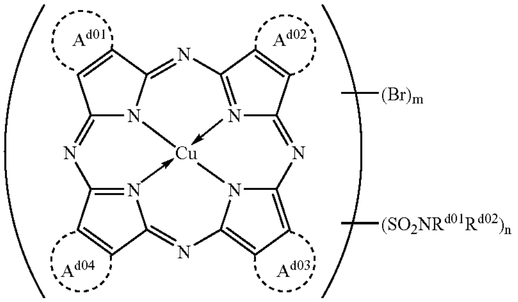

(Ring $A^{d01}$, ring $A^{d02}$, ring $A^{d03}$, and ring $A^{d04}$ are each independently a benzene ring or a pyridine ring.)

| No. | Number of 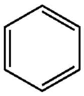 | Number of 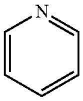 | m | n | $R^{d01}$ | $R^{d02}$ |
|---|---|---|---|---|---|---|
| 35 | 3 | 1 | 3 | 2 | —n-$C_8H_{17}$ | 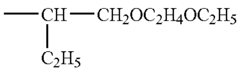 |
| 36 | 3 | 1 | 4 | 2 | H | 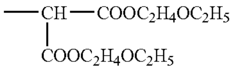 |
| 37 | 3 | 1 | 1 | 1 | —$C_2H_4OC_2H_4OC_2H_5$ | —$C_2H_4OC_2H_4OC_2H_5$ |
| 38 | 2 | 2 | 1 | 1 | H | —$C_2H_4OC_2H_5$ |

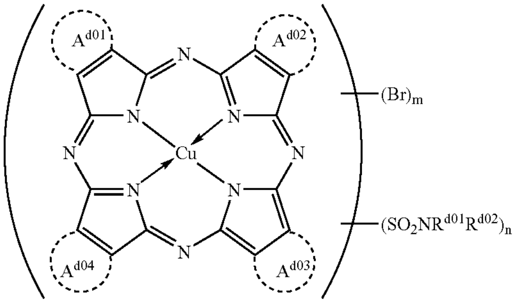

(Ring $A^{d01}$, ring $A^{d02}$, ring $A^{d03}$, and ring $A^{d04}$ are each independently a benzene ring or a pyridine ring.)

| No. | Number of 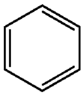 | Number of 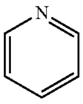 | m | n | $R^{d01}$ | $R^{d02}$ |
|---|---|---|---|---|---|---|
| 39 | 2 | 2 | 1 | 3 | H | —$C_2H_4OC_2H_5$ |
| 40 | 2 | 2 | 1 | 3 | H | —$C_2H_4OC_2H_5$ |
| 41 | 2 | 2 | 1 | 4 | H | —$C_2H_4OC_2H_5$ |
| 42 | 2 | 2 | 1 | 2 | —$C_2H_4OC_2H_5$ | —$C_2H_4OC_2H_5$ |
| 43 | 2 | 2 | 1 | 1 | H | —$C_3H_6OC_4H_9$ |
| 44 | 2 | 2 | 1 | 2 | H | —$C_3H_6OC_4H_9$ |
| 45 | 2 | 2 | 1 | 3 | H | —$C_3H_6OC_4H_9$ |
| 46 | 2 | 2 | 1 | 4 | H | —$C_3H_6OC_4H_9$ |
| 47 | 2 | 2 | 1 | 1 | —$C_2H_4OCH_3$ | —$C_2H_4OCH_3$ |
| 48 | 2 | 2 | 1 | 2 | —$C_2H_4OCH_3$ | —$C_2H_4OCH_3$ |
| 49 | 2 | 2 | 1 | 3 | —$C_2H_4OCH_3$ | —$C_2H_4OCH_3$ |

-continued
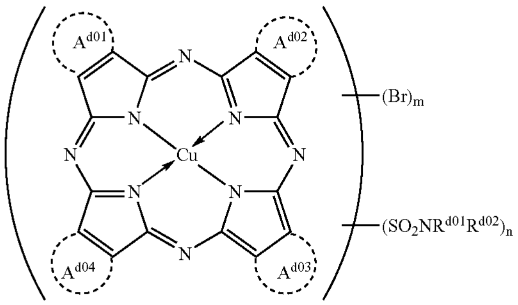
(Ring $A^{d01}$, ring $A^{d02}$, ring $A^{d03}$, and ring $A^{d04}$ are each independently a benzene ring or a pyridine ring.)
| No. | Number of 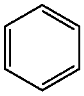 | Number of 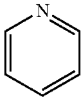 | m | n | $R^{d01}$ | $R^{d02}$ |
|---|---|---|---|---|---|---|
| 50 | 2 | 2 | 1 | 4 | $—C_2H_4OCH_3$ | $—C_2H_4OCH_3$ |
| 51 | 2 | 2 | 1 | 3 | $—C_4H_9$ | $—C_4H_9$ |
| 52 | 2 | 2 | 1 | 1 | H | 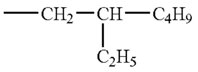 |
| 53 | 2 | 2 | 1 | 2 | H | 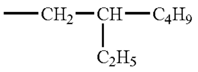 |
| 54 | 2 | 2 | 1 | 3 | H | 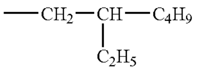 |
| 55 | 2 | 2 | 1 | 4 | H | 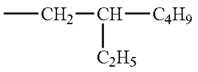 |
| 56 | 2 | 2 | 1 | 1 | H | 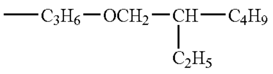 |
| 57 | 2 | 2 | 1 | 2 | H | 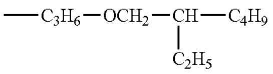 |
| 58 | 2 | 2 | 1 | 3 | H | 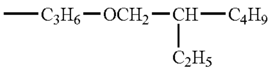 |
| 59 | 2 | 2 | 1 | 4 | H | 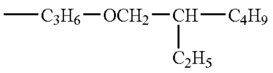 |
| 60 | 2 | 2 | 1 | 4 | H | $—C_2H_4OC_2H_4OC_2H_5$ |

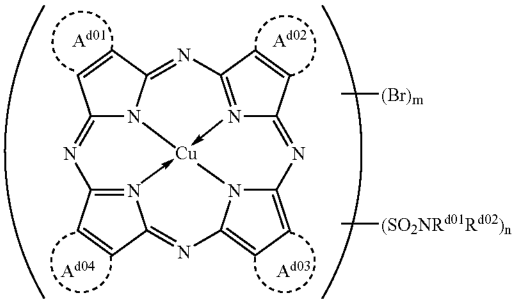
(Ring $A^{d01}$, ring $A^{d02}$, ring $A^{d03}$, and ring $A^{d04}$ are each independently a benzene ring or a pyridine ring.)
| No. | Number of 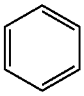 | Number of 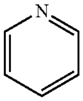 | m | n | $R^{d01}$ | $R^{d02}$ |
|---|---|---|---|---|---|---|
| 61 | 2 | 2 | 1 | 1 | $-C_2H_5$ | $-C_2H_4OC_2H_5$ |
| 62 | 2 | 2 | 2 | 2 | $-i-C_3H_7$ | 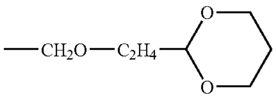 |
| 63 | 2 | 2 | 3 | 3 | H | 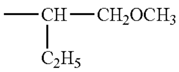 |
| 64 | 2 | 2 | 1 | 1 | H | 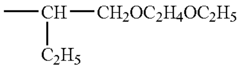 |
| 65 | 2 | 2 | 1 | 2 | H | 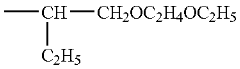 |
| 66 | 2 | 2 | 3 | 3 | H | 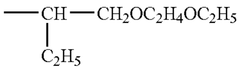 |
| 67 | 2 | 2 | 1 | 4 | H | 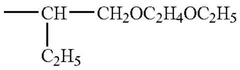 |
| 68 | 2 | 2 | 1 | 1 | H | 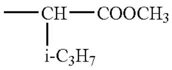 |
| 69 | 2 | 2 | 2 | 2 | H | 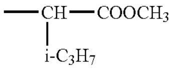 |
| 70 | 2 | 2 | 3 | 3 | H | 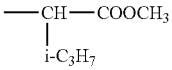 |
| 71 | 2 | 2 | 1 | 4 | H | 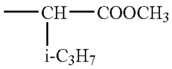 |
| 72 | 2 | 2 | 1 | 4 | $-n-C_8H_{17}$ | 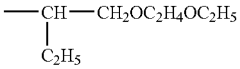 |
| 73 | 2 | 2 | 1 | 1 | H | 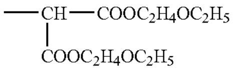 |

-continued

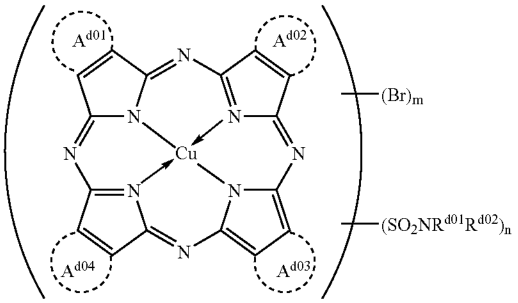

(Ring $A^{d01}$, ring $A^{d02}$, ring $A^{d03}$, and ring $A^{d04}$ are each independently a benzene ring or a pyridine ring.)

| No. | Number of 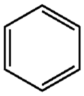 | Number of 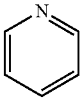 | m | n | $R^{d01}$ | $R^{d02}$ |
|---|---|---|---|---|---|---|
| 74 | 2 | 2 | 2 | 2 | $—C_2H_4OC_2H_4OC_2H_5$ | $—C_2H_4OC_2H_4OC_2H_5$ |
| 75 | 1 | 3 | 1 | 1 | H | $—C_2H_4OC_2H_5$ |
| 76 | 1 | 3 | 2 | 2 | H | $—C_2H_4OC_2H_5$ |

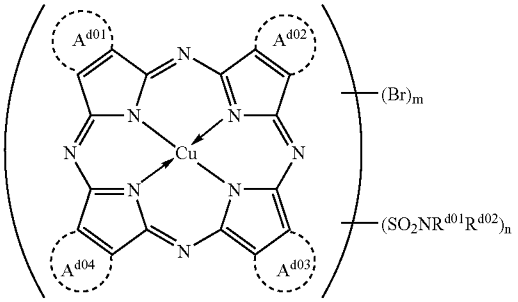

(Ring $A^{d01}$, ring $A^{d02}$, ring $A^{d03}$, and ring $A^{d04}$ are each independently a benzene ring or a pyridine ring.)

| No. | Number of 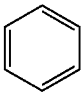 | Number of 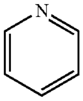 | m | n | $R^{d01}$ | $R^{d02}$ |
|---|---|---|---|---|---|---|
| 77 | 1 | 3 | 1 | 3 | H | $—C_2H_4OC_2H_5$ |
| 78 | 1 | 3 | 1 | 4 | H | $—C_2H_4OC_2H_5$ |
| 79 | 1 | 3 | 1 | 3 | $—C_2H_4OC_2H_5$ | $—C_2H_4OC_2H_5$ |
| 80 | 1 | 3 | 1 | 1 | H | $—C_3H_6OC_4H_9$ |
| 81 | 1 | 3 | 1 | 2 | H | $—C_3H_6OC_4H_9$ |
| 82 | 1 | 3 | 1 | 3 | H | $—C_3H_6OC_4H_9$ |
| 83 | 1 | 3 | 1 | 4 | H | $—C_3H_6OC_4H_9$ |
| 84 | 1 | 3 | 1 | 1 | $—C_2H_4OCH_3$ | $—C_2H_4OCH_3$ |
| 85 | 1 | 3 | 1 | 2 | $—C_2H_4OCH_3$ | $—C_2H_4OCH_3$ |
| 86 | 1 | 3 | 1 | 3 | $—C_2H_4OCH_3$ | $—C_2H_4OCH_3$ |
| 87 | 1 | 3 | 1 | 4 | $—C_2H_4OCH_3$ | $—C_2H_4OCH_3$ |
| 88 | 1 | 3 | 1 | 4 | $—C_4H_9$ | $—C_4H_9$ |
| 89 | 1 | 3 | 1 | 1 | H | 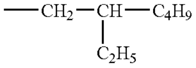 |
| 90 | 1 | 3 | 1 | 2 | H | 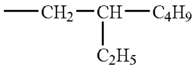 |

-continued
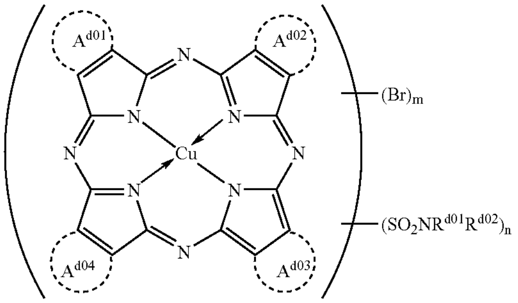
(Ring $A^{d01}$, ring $A^{d02}$, ring $A^{d03}$, and ring $A^{d04}$ are each independently a benzene ring or a pyridine ring.)
| No. | Number of 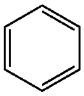 | Number of 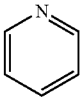 | m | n | $R^{d01}$ | $R^{d02}$ |
|---|---|---|---|---|---|---|
| 91 | 1 | 3 | 1 | 3 | H | 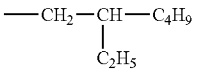 |
| 92 | 1 | 3 | 1 | 4 | H | 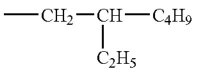 |
| 93 | 1 | 3 | 1 | 1 | H | 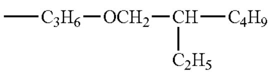 |
| 94 | 1 | 3 | 1 | 2 | H | 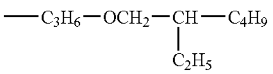 |
| 95 | 1 | 3 | 1 | 3 | H | 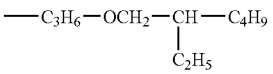 |
| 96 | 1 | 3 | 1 | 4 | H | 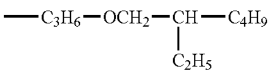 |
| 97 | 1 | 3 | 1 | 1 | H | $—C_2H_4OC_2H_4OC_2H_5$ |
| 98 | 1 | 3 | 1 | 2 | $—C_2H_5$ | $—C_2H_4OC_2H_5$ |

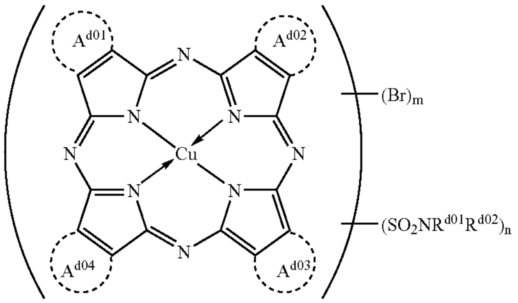
(Ring $A^{d01}$, ring $A^{d02}$, ring $A^{d03}$, and ring $A^{d04}$ are each independently a benzene ring or a pyridine ring.)
| No. | Number of 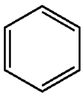 | Number of 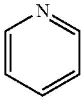 | m | n | $R^{d01}$ | $R^{d02}$ |
|---|---|---|---|---|---|---|
| 99 | 1 | 3 | 3 | 3 | $—i\text{-}C_3H_7$ | 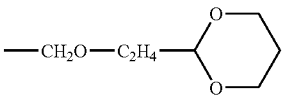 |
| 100 | 1 | 3 | 1 | 4 | H | 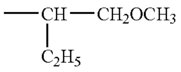 |
| 101 | 1 | 3 | 1 | 1 | H | 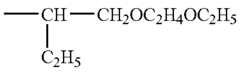 |
| 102 | 1 | 3 | 4 | 2 | H | 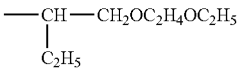 |
| 103 | 1 | 3 | 4 | 3 | H | 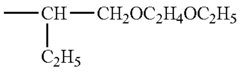 |
| 104 | 1 | 3 | 4 | 3 | H | 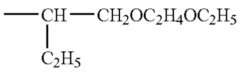 |
| 105 | 1 | 3 | 1 | 1 | H | $—CH_2—C_2H_4COCH_3$ |
| 106 | 1 | 3 | 2 | 2 | H | $—CH_2—C_2H_4COCH_3$ |
| 107 | 1 | 3 | 3 | 3 | H | $—CH_2—C_2H_4COC_3H_7$ |
| 108 | 1 | 3 | 1 | 4 | H | $—CH_2—C_2H_4COC_3H_7$ |
| 109 | 1 | 3 | 1 | 1 | $—n\text{-}C_8H_{17}$ | 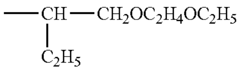 |
| 110 | 1 | 3 | 2 | 2 | H | 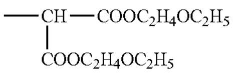 |
| 111 | 1 | 3 | 1 | 3 | $—C_2H_4OC_2H_4OC_2H_5$ | $—C_2H_4OC_2H_4OC_2H_5$ |
| 112 | 0 | 4 | 1 | 1 | H | $—C_2H_4OC_2H_5$ |
| 113 | 0 | 4 | 1 | 2 | H | $—C_2H_4OC_2H_5$ |
| 114 | 0 | 4 | 1 | 3 | H | $—C_2H_4OC_2H_5$ |
| 115 | 0 | 4 | 1 | 4 | H | $—C_2H_4OC_2H_5$ |
| 116 | 0 | 4 | 1 | 4 | $—C_2H_4OC_2H_5$ | $—C_2H_4OC_2H_5$ |
| 117 | 0 | 4 | 1 | 1 | H | $—C_3H_6OC_4H_9$ |
| 118 | 0 | 4 | 1 | 2 | H | $—C_3H_6OC_4H_9$ |
| 119 | 0 | 4 | 1 | 3 | H | $—C_3H_6OC_4H_9$ |
| 120 | 0 | 4 | 1 | 4 | H | $—C_3H_6OC_4H_9$ |
| 121 | 0 | 4 | 1 | 1 | $—C_2H_4OCH_3$ | $—C_2H_4OCH_3$ |

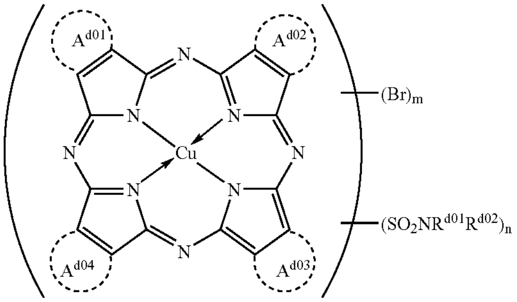
(Ring $A^{d01}$, ring $A^{d02}$, ring $A^{d03}$, and ring $A^{d04}$ are each independently a benzene ring or a pyridine ring.)
| No. | Number of 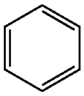 | Number of 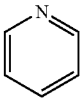 | m | n | $R^{d01}$ | $R^{d02}$ |
|---|---|---|---|---|---|---|
| 122 | 0 | 4 | 1 | 2 | $—C_2H_4OCH_3$ | $—C_2H_4OCH_3$ |
| 123 | 0 | 4 | 1 | 3 | $—C_2H_4OCH_3$ | $—C_2H_4OCH_3$ |
| 124 | 0 | 4 | 1 | 4 | $—C_2H_4OCH_3$ | $—C_2H_4OCH_3$ |
| 125 | 0 | 4 | 1 | 1 | $—C_4H_9$ | $—C_4H_9$ |
| 126 | 0 | 4 | 1 | 1 | H | 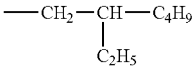 |
| 127 | 0 | 4 | 1 | 2 | H | 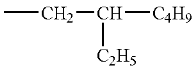 |
| 128 | 0 | 4 | 1 | 3 | H | 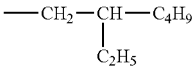 |
| 129 | 0 | 4 | 1 | 4 | H | 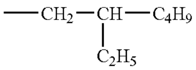 |
| 130 | 0 | 4 | 1 | 1 | H | $—CHCOCH_3$ |
| 131 | 0 | 4 | 1 | 2 | H | $—CHCOCH_3$ |
| 132 | 0 | 4 | 1 | 3 | H | $—CHCOOC_3H_7$ |
| 133 | 0 | 4 | 1 | 4 | H | $—CHCOOC_3H_7$ |
| 134 | 0 | 4 | 1 | 2 | H | $—C_2H_4OC_2H_4OC_2H_5$ |
| 135 | 0 | 4 | 1 | 3 | $—C_2H_5$ | $—C_2H_4OC_2H_5$ |
| 136 | 0 | 4 | 1 | 4 | $—i\text{-}C_3H_7$ | 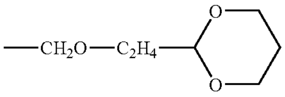 |
| 137 | 0 | 4 | 1 | 1 | H | 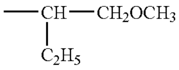 |
| 138 | 0 | 4 | 1 | 1 | H | 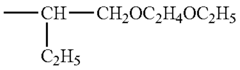 |
| 139 | 0 | 4 | 1 | 2 | H | 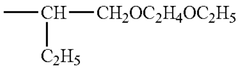 |
| 140 | 0 | 4 | 1 | 3 | H | 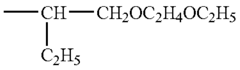 |

-continued
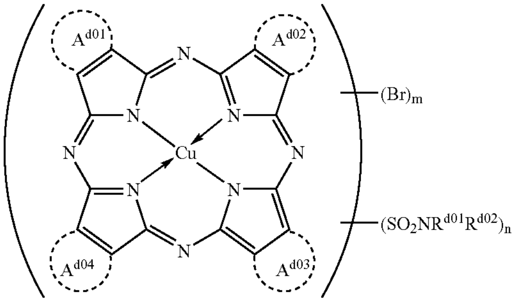
(Ring $A^{d01}$, ring $A^{d02}$, ring $A^{d03}$, and ring $A^{d04}$ are each independently a benzene ring or a pyridine ring.)
| No. | Number of 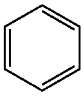 | Number of 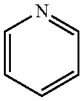 | m | n | $R^{d01}$ | $R^{d02}$ |
|---|---|---|---|---|---|---|
| 141 | 0 | 4 | 1 | 4 | H | 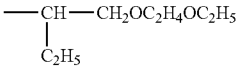 |
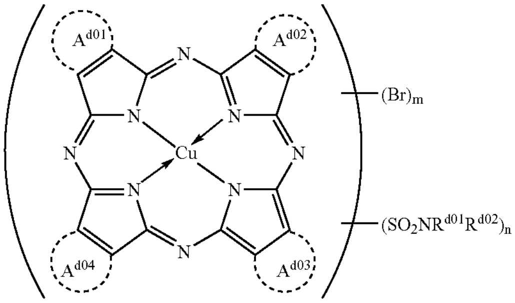
(Ring $A^{d01}$, ring $A^{d02}$, ring $A^{d03}$, and ring $A^{d04}$ are each independently a benzene ring or a pyridine ring.)
| No. | Number of 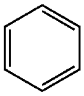 | Number of 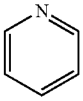 | m | n | $R^{d01}$ | $R^{d02}$ |
|---|---|---|---|---|---|---|
| 142 | 0 | 4 | 1 | 1 | H | 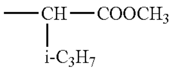 |
| 143 | 0 | 4 | 1 | 2 | H | 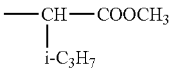 |
| 144 | 0 | 4 | 1 | 3 | H | 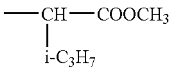 |
| 145 | 0 | 4 | 1 | 4 | H | 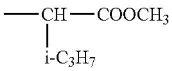 |
| 146 | 0 | 4 | 1 | 2 | —n-$C_8H_{17}$ | 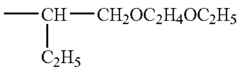 |

-continued
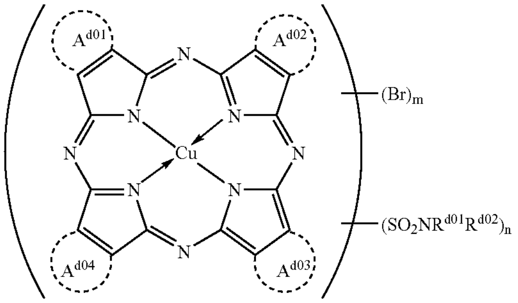
(Ring $A^{d01}$, ring $A^{d02}$, ring $A^{d03}$, and ring $A^{d04}$ are each independently a benzene ring or a pyridine ring.)
| No. | Number of 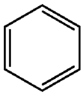 | Number of 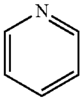 | m | n | $R^{d01}$ | $R^{d02}$ |
|---|---|---|---|---|---|---|
| 147 | 0 | 4 | 1 | 3 | H | 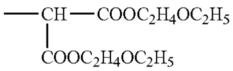 |
| 148 | 0 | 4 | 1 | 4 | $—C_2H_4OC_2H_4OC_2H_5$ | $—C_2H_4OC_2H_4OC_2H_5$ |
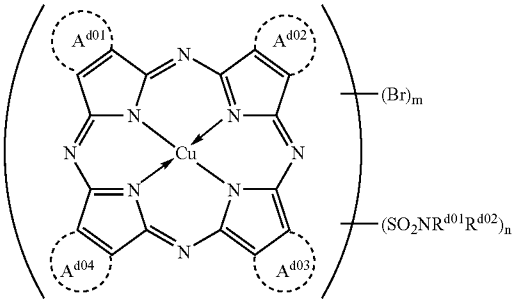
(Ring $A^{d01}$, ring $A^{d02}$, ring $A^{d03}$, and ring $A^{d04}$ are each independently a benzene ring or a pyridine ring.)
| No. | Number of 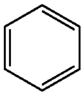 | Number of 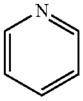 | m | n | $R^{d01}$ | $R^{d02}$ |
|---|---|---|---|---|---|---|
| 149 | 3 | 1 | 1 | 4 | $—C_{10}H_{21}$ | H |
| 150 | 3 | 1 | 1 | 3 | $—C_{12}H_{25}$ | $—C_{12}H_{25}$ |
| 151 | 3 | 1 | 1 | 4 | $—C_{12}H_{25}$ | $—C_2H_4OC_2H_5$ |
| 152 | 3 | 1 | 1 | 1 | 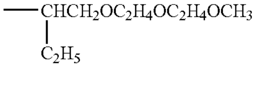 | H |
| 153 | 3 | 1 | 1 | 3 | 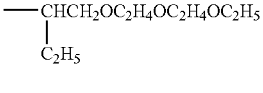 | $—C_2H_5$ |
| 154 | 3 | 1 | 1 | 1 | 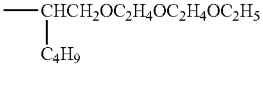 | H |

-continued
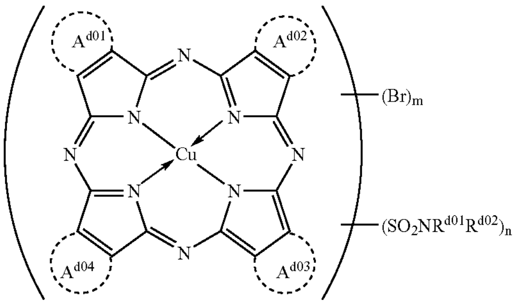
(Ring $A^{d01}$, ring $A^{d02}$, ring $A^{d03}$, and ring $A^{d04}$ are each independently a benzene ring or a pyridine ring.)
| No. | Number of 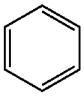 | Number of 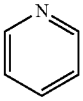 | m | n | $R^{d01}$ | $R^{d02}$ |
|---|---|---|---|---|---|---|
| 155 | 3 | 1 | 1 | 1 | 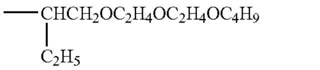 | H |
| 156 | 3 | 1 | 1 | 2 | 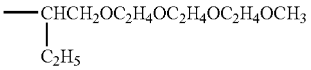 | H |
| 157 | 3 | 1 | 1 | 3 | 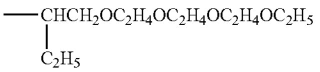 | H |
Further specific examples are listed below (exemplary colorants M-1 to M-84). In the invention, however, the dye is not limited to these examples.
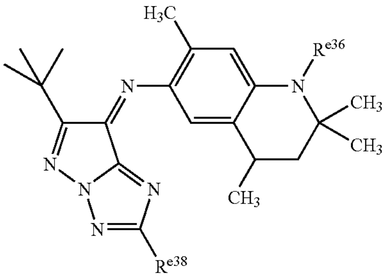
| No. | $R^{e38}$ | $R^{e36}$ |
|---|---|---|
| M-1 | 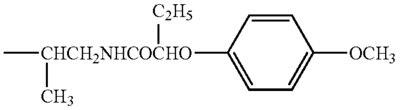 | $—CH_2CH_2CH_2OH$ |
| M-2 | 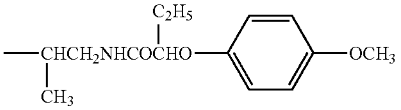 | $—CH_2CH_2OH$ |

-continued
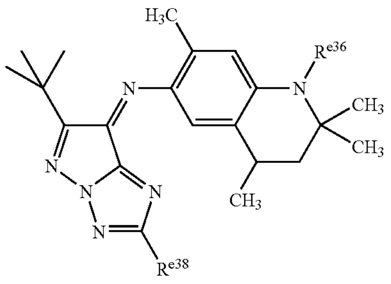
| No. | $R^{e38}$ | $R^{e36}$ |
|---|---|---|
| M-3 | 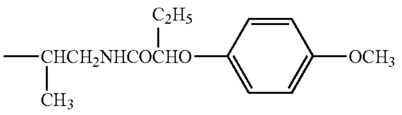 | $—CH_2COOC_2H_5$ |
| M-4 | 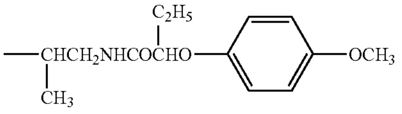 | $—CH_2CH_2CH_2COOH$ |
| M-5 | 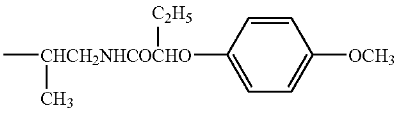 | $—C_3H_7$(iso) |
| M-6 | 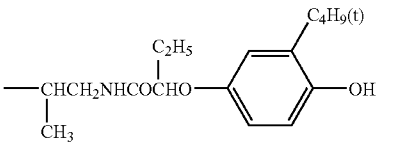 | $—CH_2CH(C_2H_5)C_4H_9$ |
| M-7 | 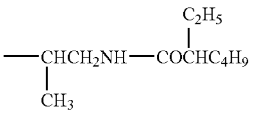 | $—CH_2CH_2NHSO_2CH_3$ |
| M-8 | 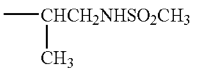 | $—CH_2CH_2CH_2COOH$ |
| M-9 | 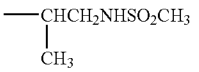 | $—CH_2CH_2CH_2CH_2COOH$ |
| M-10 | 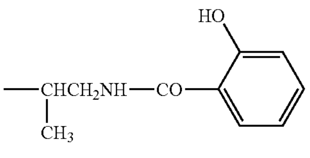 | $—CH_2CH_2CH_2OH$ |
| M-11 | 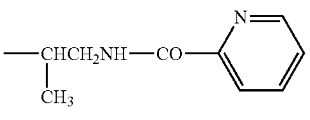 | $—CH_2CH_2CH_2OH$ |

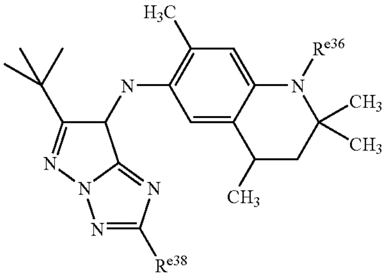
| No. | $R^{e38}$ | $R^{e36}$ |
|---|---|---|
| M-11 | 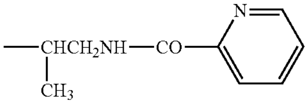 | $—CH_2CH_2CH_2OH$ |
| M-12 | 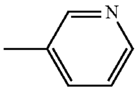 | $—CH_2CH_2CH_2OH$ |
| M-13 | 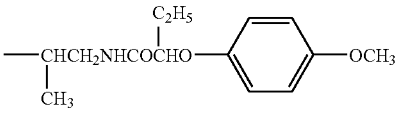 | 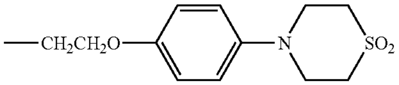 |
| M-14 | 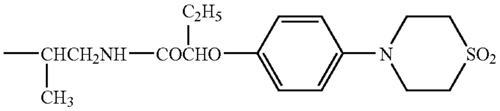 | 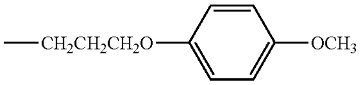 |
| M-15 | 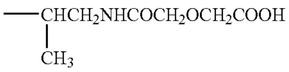 | $—CH_2CH(C_2H_5)C_4H_9$ |
| M-16 | 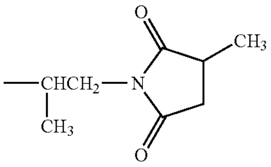 | $—CH_2CH(C_2H_5)C_4H_9$ |
| M-17 | 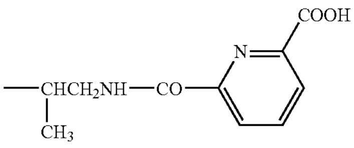 | $—C_8H_{17}$ |
| M-18 | 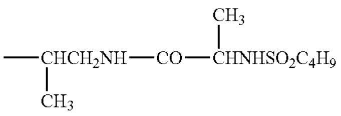 | $—C_8H_{17}$ |

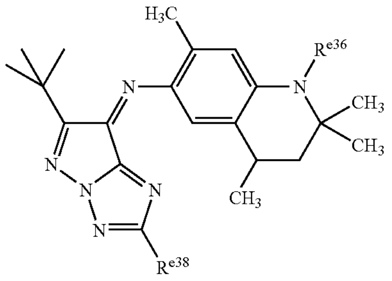
| No. | $R^{e38}$ | $R^{e36}$ |
| --- | --- | --- |
| M-19 | 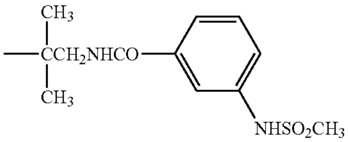 | $—CH_2CH_2CH_2OH$ |
| M-20 | 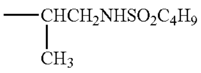 | $—CH_2CH_2CH_2OH$ |
| M-21 | 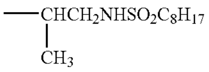 | $—CH_2CH_2CH_2OH$ |
| M-22 | 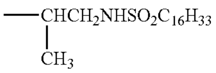 | $—C_2H_5$ |
| M-23 | 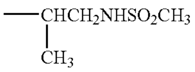 | 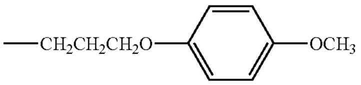 |
| M-24 | 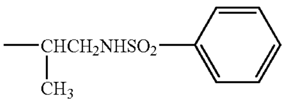 | 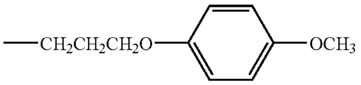 |
| M-25 | 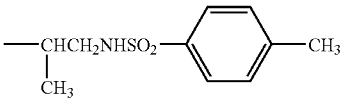 | $—CH_2CH_2CH_2OH$ |
| M-26 | 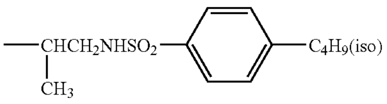 | $—CH_2CH_2CH_2OH$ |
| M-27 | 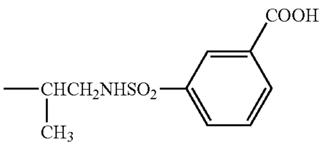 | $—C_8H_{17}$ |

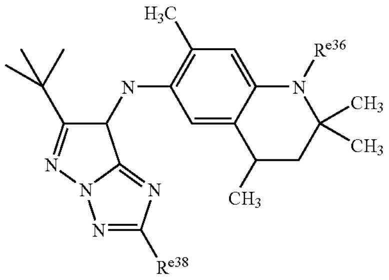
| No. | $R^{e38}$ | $R^{e36}$ |
|---|---|---|
| M-28 | 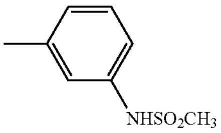 | $—CH_2CH(C_2H_5)C_4H_9$ |
| M-29 | 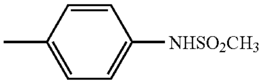 | $—CH_2CH(C_2H_5)C_4H_9$ |
| M-30 | 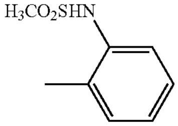 | $—C_{12}H_{25}$ |
| M-31 | 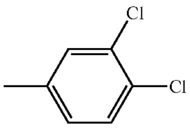 | $—C_{12}H_{25}$ |
-continued
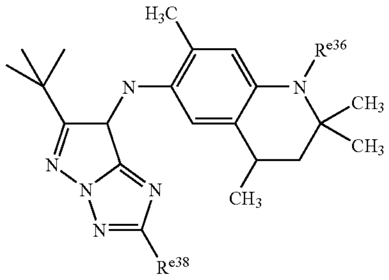
| No. | $R^{e38}$ | $R^{e36}$ |
|---|---|---|
| M-32 | 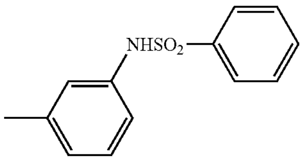 | $—CH_2CH_2OH$ |
| M-33 | 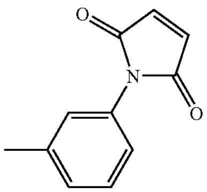 | $—CH_2CH_2OH$ |
| M-34 | 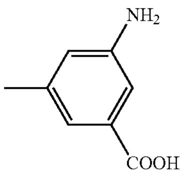 | $—CH_2CH(C_2H_5)C_4H_9$ |
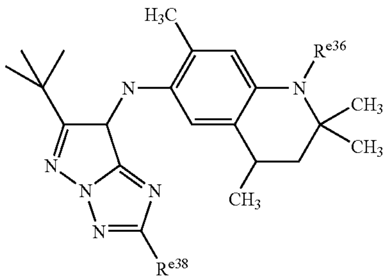
| No. | $R^{e38}$ | $R^{e36}$ |
|---|---|---|
| M-35 | 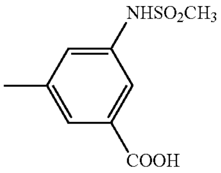 | 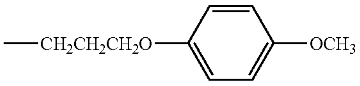 |

-continued
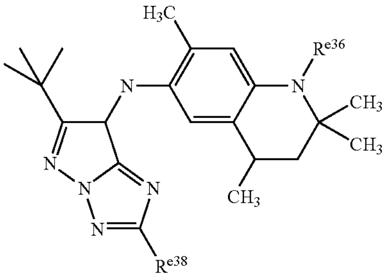
| No. | $R^{e38}$ | $R^{e36}$ |
|---|---|---|
| M-36 | 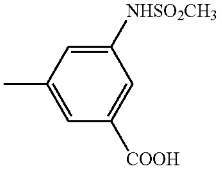 | 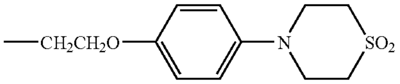 |
| M-37 | 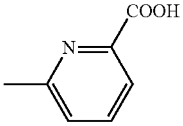 | 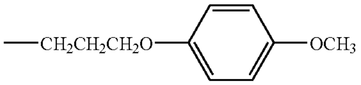 |
| M-38 | $-CF_3$ | 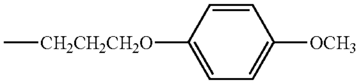 |
| M-39 | $-C_7F_{15}$ | 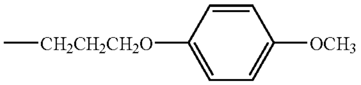 |
| M-40 | 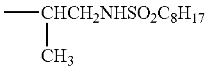 | $-CH_2CH_2SO_2CH_3$ |
| M-41 | 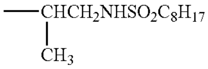 | $-CH_2CH_2SC_4H_9$ |
| M-42 | 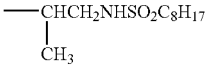 | $-CH_2CH_2OCH_2CH_2OCH_3$ |
M-43
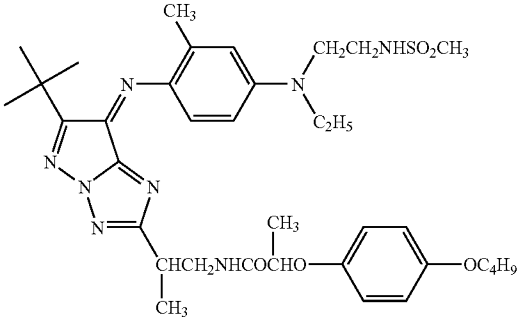
M-44
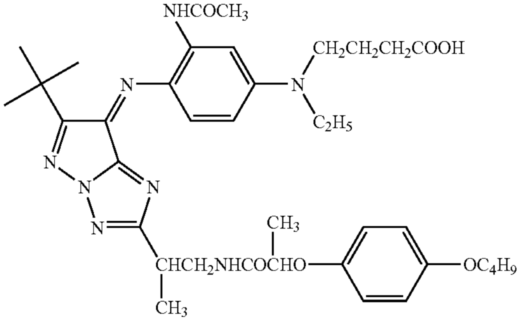

-continued
M-45
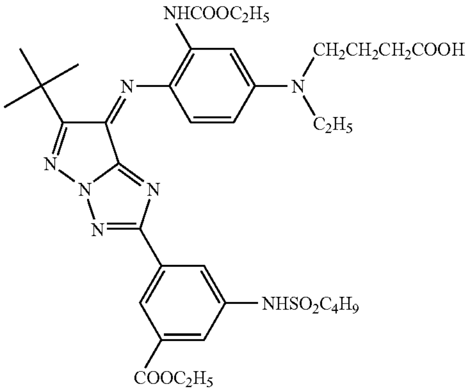
M-46
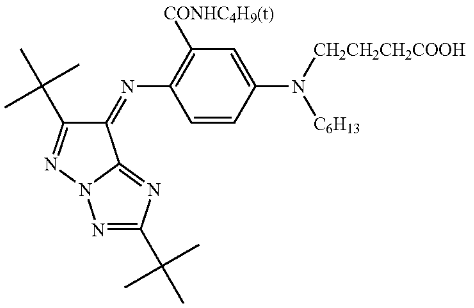
M-47
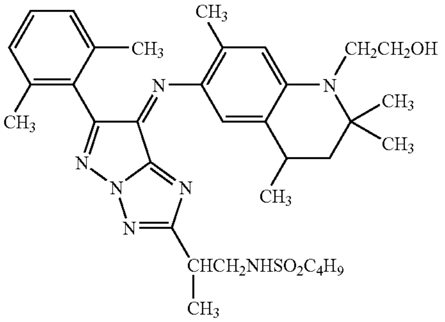
M-48
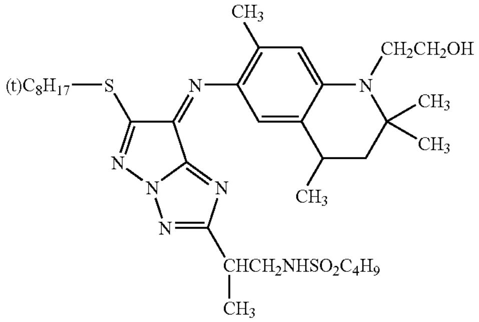
M-49
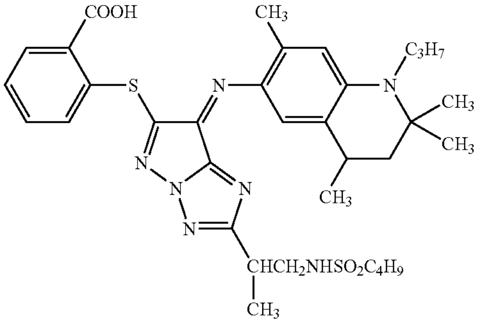
M-50
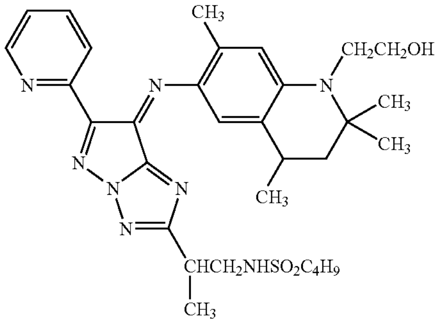
M-51
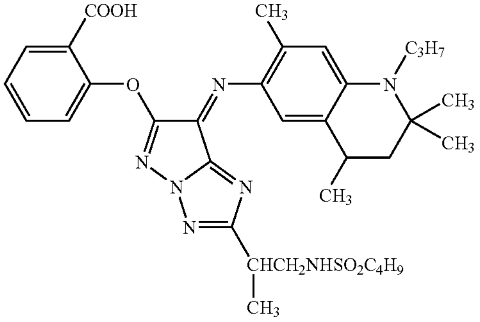
M-52
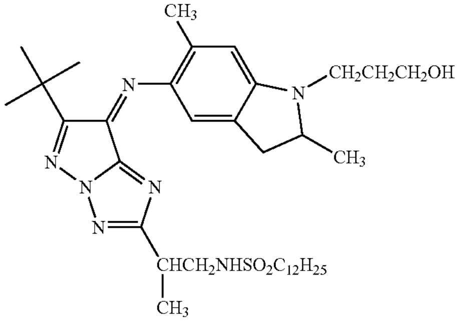

-continued
M-53
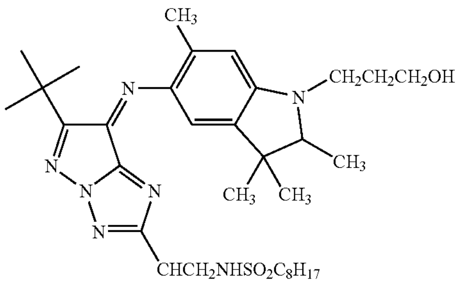
M-54
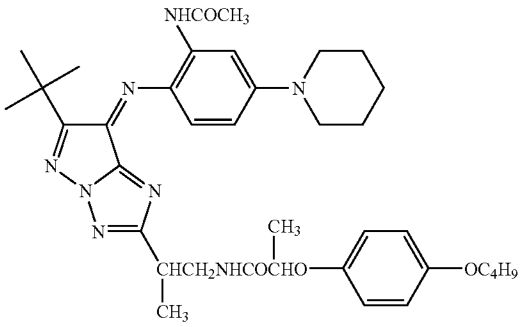
M-55
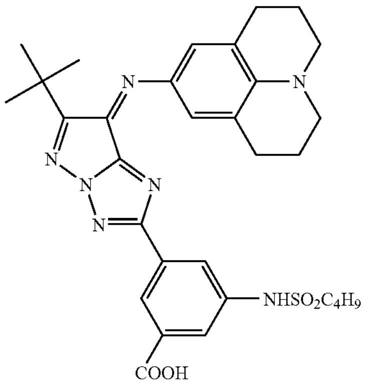
M-56
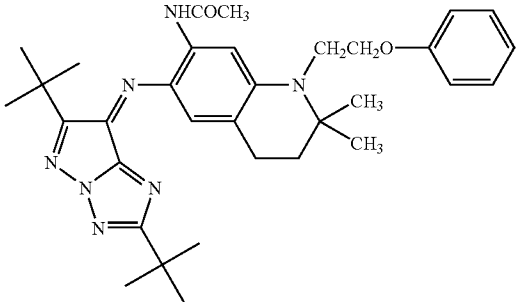
M-57
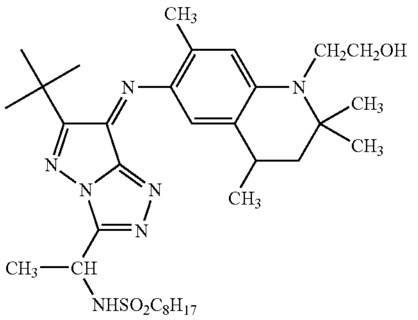
M-58
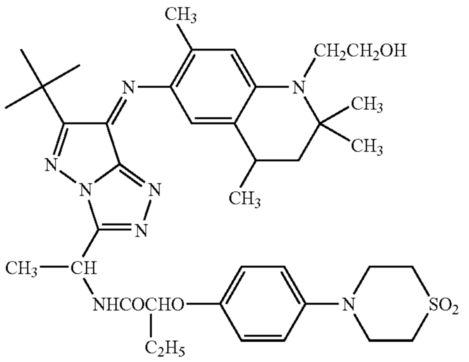
M-59
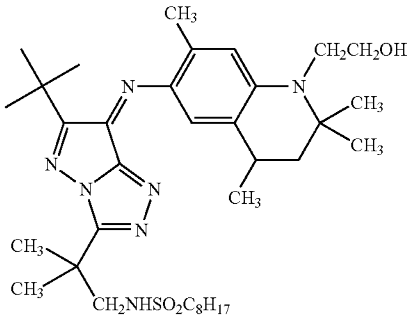
M-60
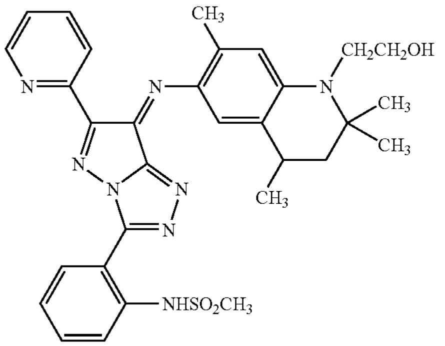

-continued
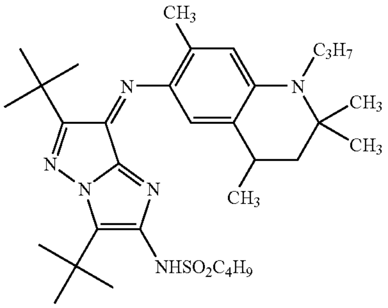
M-61
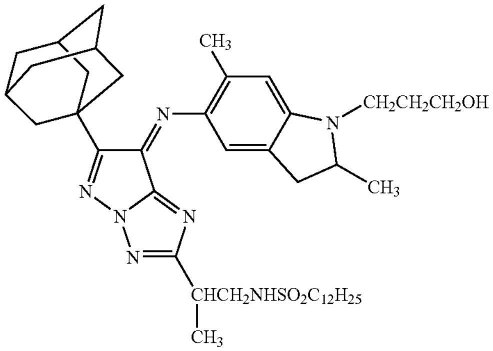
M-62
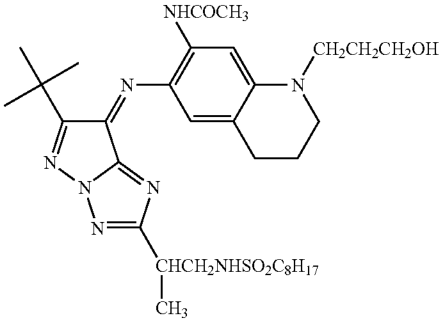
M-63
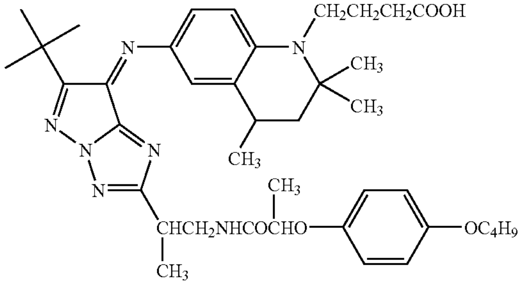
M-64
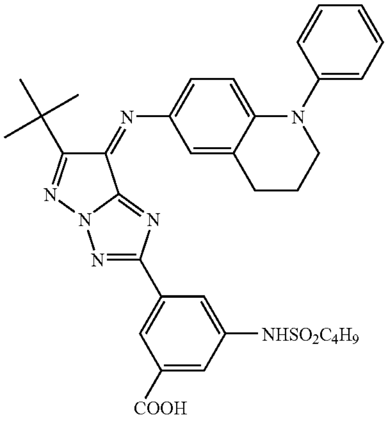
M-65
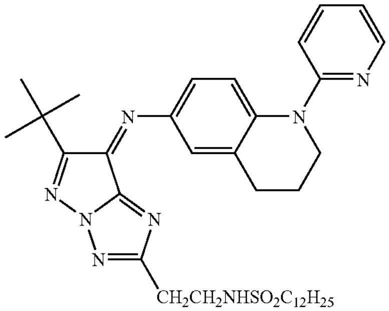
M-66
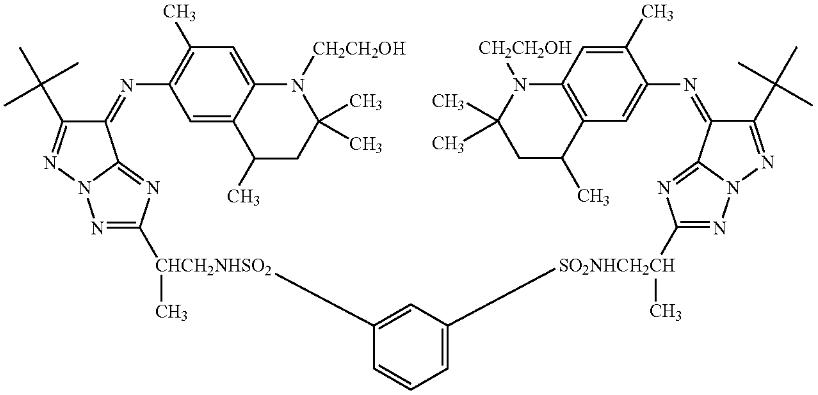
M-67

-continued
M-68
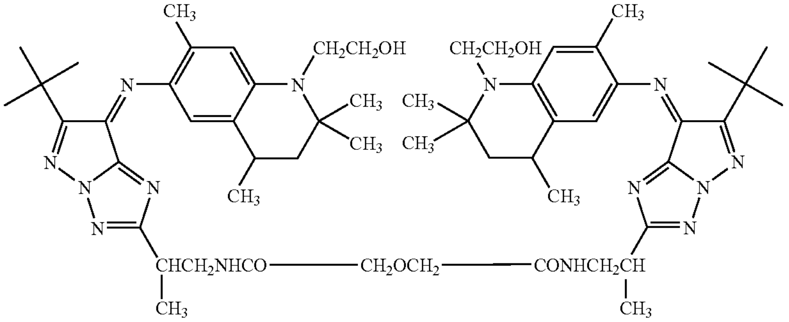
M-69
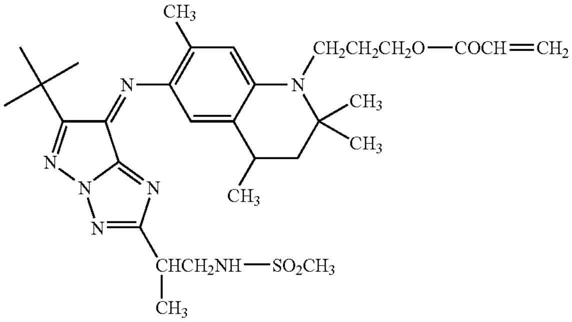
M-70
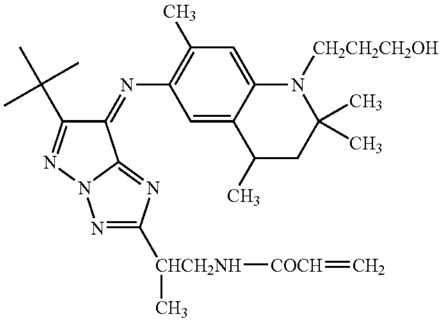
M-71
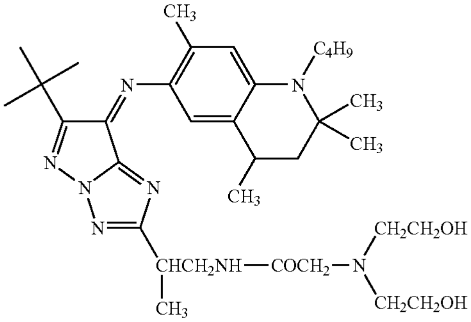
M-72
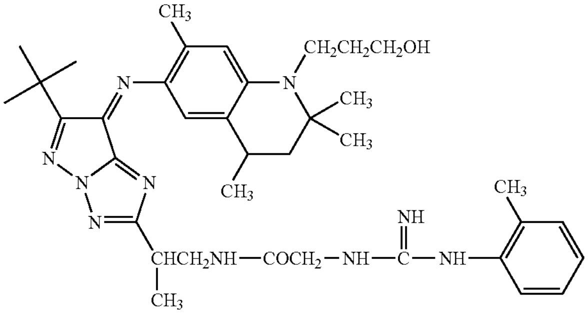
M-73
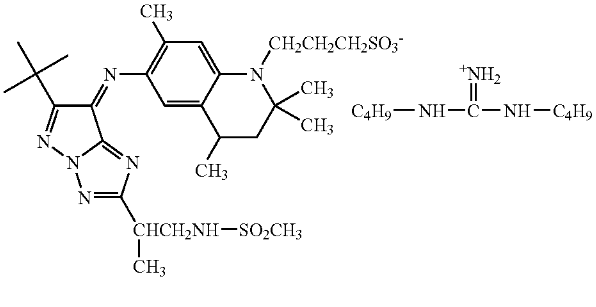
M-74
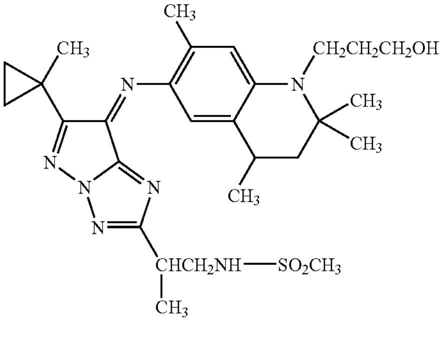

-continued
M-75
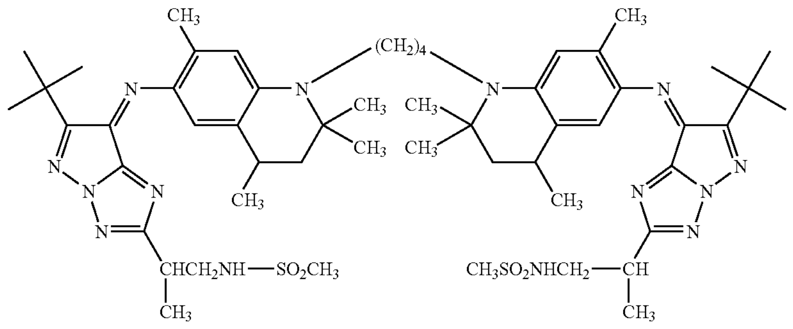
M-76
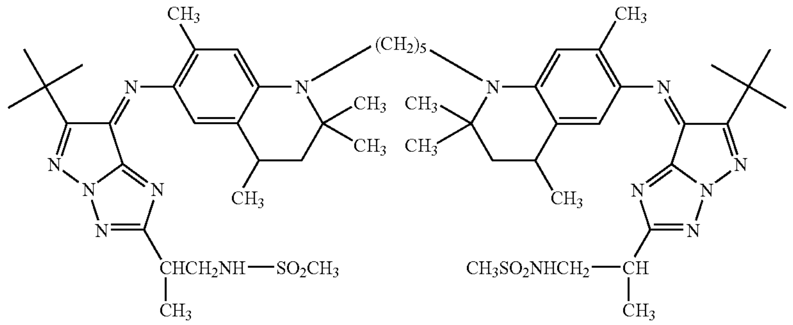
M-77
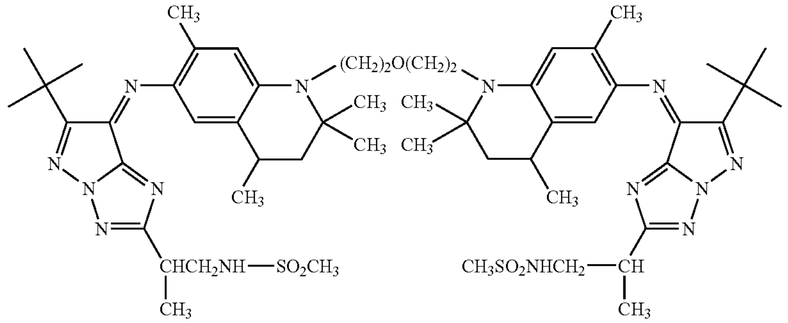
M-78
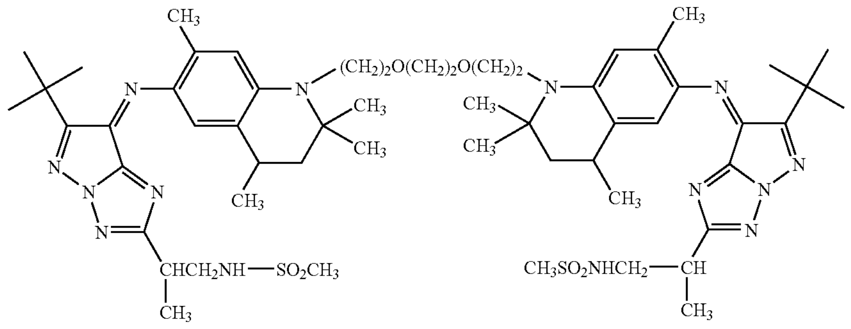

-continued
M-79
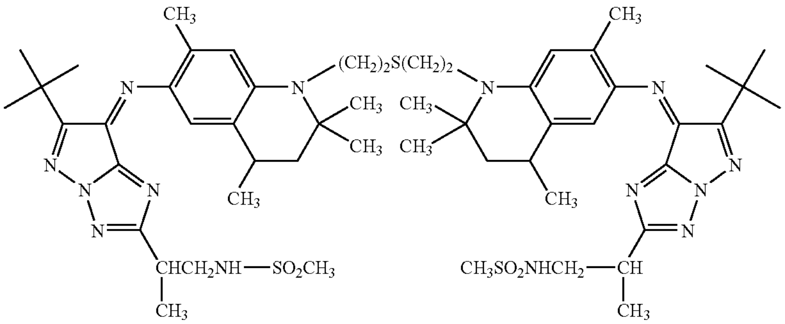
M-80
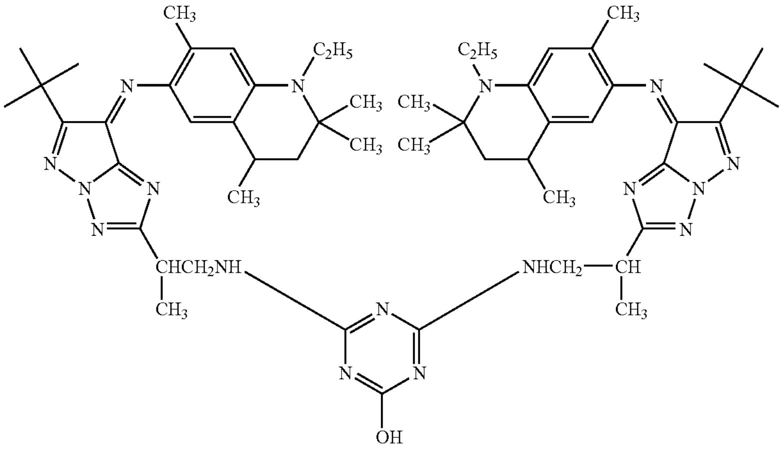
-continued
| 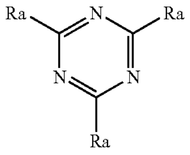 | 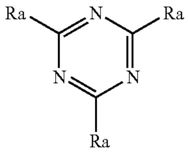 |
|---|---|
| M-81 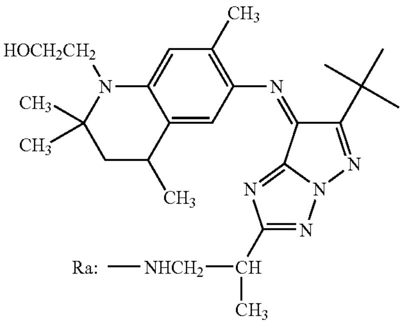 | M-82 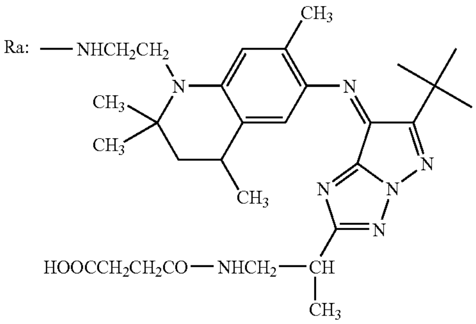 |

M-83

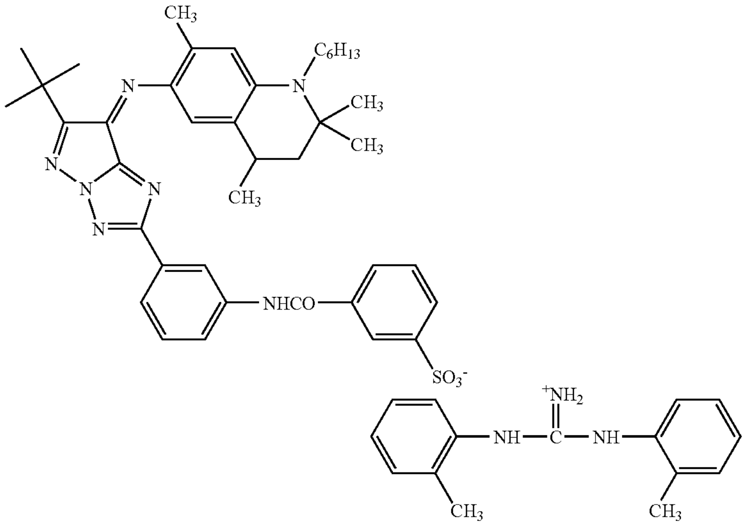

M-84

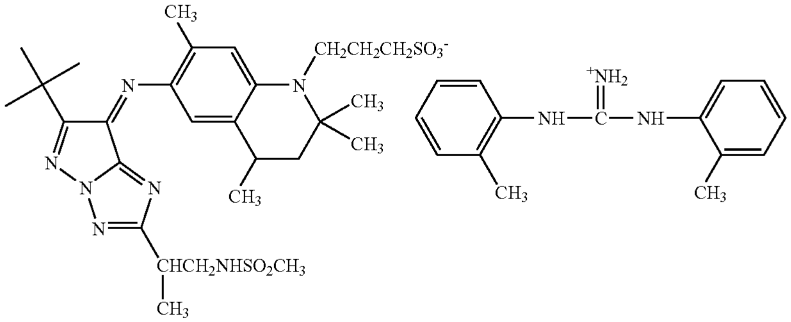

Examples of the colorant that can be used in the invention include, besides the above-mentioned dyes, various conventionally-known pigments, and (insulating) carbon black. In an embodiment, only one such other colorant is used. In another embodiment, a mixture of two or more such other colorants is used.

The pigments that can be used in the invention may be selected from various conventionally-known inorganic pigments or organic pigments. No matter the pigment is inorganic or organic, it preferably has a high transmittance. Use of a finer pigment is advantageous in this respect. However, in consideration of ease of handling, the average particle diameter of the pigments is preferably from 0.01 to 0.1 μm, more preferably from 0.01 to 0.05 μm. Examples of the inorganic pigments include metal compounds such as metal oxides and metal complexes. Specific examples thereof include metal oxides of iron, cobalt, aluminum, cadmium, lead, copper, titanium, magnesium, chromium, zinc, and antimony, and complex oxides of the metals.

Examples of the organic pigments include:

C.I. Pigment Yellow 11, 24, 31, 53, 83, 93, 99, 108, 109, 110, 138, 139, 147, 150, 151, 154, 155, 167, 180, 185, and 199;

C.I. Pigment Orange 36, 38, 43, and 71;

C.I. Pigment Red 81, 105, 122, 149, 150, 155, 171, 175, 176, 177, 209, 220, 224, 242, 254, 255, 264, and 270;

C.I. Pigment Violet 19, 23, 32, and 39;

C.I. Pigment Blue 1, 2, 15, 15:1, 15:3, 15:6, 16, 22, 60, and 66;

C.I. Pigment Green 7, 36, and 37;

C.I. Pigment Brown 25, and 28; and

C.I. Pigment Black 1 and 7.

In the invention, a pigment having, in the structural formula thereof, a basic N atom can be particularly preferably used. The pigment having a basic nitrogen atom exhibits a good dispersibility in the photopolymerizable composition. The reason therefor has not been sufficiently made clear. It is however presumed that the good dispersibility may derive from good affinity between the photosensitive polymerizable component and the pigment.

Of the above-mentioned various pigments, the following pigments can be cited as examples of pigments that can be preferably used in the invention However, preferable examples are not limited thereto.

C.I. Pigment Yellow 11, 24, 108, 109, 110, 138, 139, 150, 151, 154, 167, 180, and 185;

C.I. Pigment Orange 36 and 71;

C.I. Pigment Red 122, 150, 171, 175, 177, 209, 224, 242, 254, 255, and 264;

C.I. Pigment Violet 19, 23, and 32;

C.I. Pigment Blue 15:1, 15:3, 15:6, 16, 22, 60, and 66; and

C.I. Pigment Black 1 and 7.

In an embodiment, only one organic pigment is used. In another embodiment, a combination of organic pigments is used to improve color purity. Examples are described in the following. As a red pigment, usable pigments include the following: an anthraquinone pigment, a perylene pigment, and a diketopyrrolopyrrole pigment; and a mixture of at least one of the foregoing pigments and a disazo yellow pigment, an isoindoline yellow pigment, a quinophthalone yellow pigment, or a perylene red pigment. The anthraquinone pigment is, for example, C.I. Pigment Red 177; the perylene pigment is, for example, C.I. Pigment Red 155 or C.I. Pigment Red 224; and the diketopyrrolopyrrole pigment is, for example, C.I. Pigment Red 254. From the viewpoint of color reproducibility, a mixture of the red pigment with C.I. Pigment Yellow 83 or C.I. Pigment Yellow 139 is advantageous. The ratio by mass of the red pigment to the yellow pigment is preferably from 100:5 to 100:50. If the ratio is 100:4 or less, the light transmittance at a wavelength of from 400 to 500 nm cannot be restrained so that the color purity cannot be heightened. If the ratio is 100:51 or more, the main wavelength is shorter so that the color tone largely deviates from an NTSC target color tone. The ratio is optimally from 100:10 to 100:30. When two or more of the red pigments are combined with each other, the proportions of the respective red pigments are adjusted in accordance with the chromaticity thereof.

The green pigment that can be used may be a halogenated phthalocyanine pigment alone, or a mixture of a halogenated phthalocyanine pigment and a yellow pigment selected from a disazo yellow pigment, quinophthalone yellow pigment, azomethine yellow pigment or isoindoline yellow pigment. Preferable one is, for example, a mixture of C.I. Pigment Green 7, 36 or 37 and C.I. Pigment Yellow 83, 138, 139, 150, 180 or 185. The ratio by mass of the green pigment to the yellow pigment is preferably from 100:5 to 100:150. If the ratio is less than 100:5, the light transmittance at a wavelength of from 400 to 450 nm cannot be restrained so that the color purity cannot be heightened. If the ratio is more than 100:150, the main wavelength is longer so that the color tone largely deviates from an NTSC target color tone. The ratio is more preferably from 100:30 to 100:120.

The blue pigment that can be used may a phthalocyanine pigment alone, or a mixture of a phthalocyanine pigment and a dioxazine violet pigment. Preferable one is, for example, a mixture of C.I. Pigment Blue 15:6 and C.I. Pigment Violet 23. The ratio by mass of the blue pigment to the violet pigment is preferably from 100:0 to 100:30, more preferably less than 100:10.

A pigment-containing photosensitive resin superior in dispersibility and dispersion stability can be obtained by using a powdery processed pigment wherein any one of the above-mentioned pigments is finely dispersed in an acrylic resin, a maleic acid resin, a vinyl chloride-vinyl acetate copolymer, an ethylcellolose resin or the like.

Carbon, titanium carbon, iron oxide, or titanium oxide, or a mixture of two or more of such pigments is used as a pigment for a black matrix. A combination of carbon with titanium carbon is preferable. The ratio by mass of carbon to titanium carbon is preferably from 100:0 to 100:60.

The content by percentage of the colorant in the photopolymerizable composition according to the invention is preferably from 1 to 85% by mass with respect to all the solids in the composition, more preferably from 5 to 80% by mass.

If the content of the colorant is less than 1% by mass, the composition does not satisfy a desired color tone so that the composition may not function as a color filter or ink. If the content is more than 85% by mass, the optical absorbance decreases so that the sensitivity may decline.

(D) Colorant Dispersing Agent

When a pigment is used as the colorant in the composition according to the invention, it is preferable to use a dispersing agent for the colorant in order to disperse the above-mentioned organic pigment or carbon black.

As the dispersing agent, a coating resin described below is used. Besides, a dispersing agent that will be described later can be used together.

Examples of the coating resin include:

1) Polyolefin polymer polyethylene, polypropylene, polyisobutylene etc.

2) Diene polymer polybutadiene, polyisoprene etc.

3) Polymer having a conjugated polyene structure polyacetylene polymers, polyphenylene polymers etc.

4) Vinyl polymer polyvinyl chloride, polystyrene, polyvinyl acetate, polyvinyl alcohol, poly(meth)acrylic acid, poly(meth)acrylate, polyacrylamide, polyacrylonitrile, polyvinylphenol etc.

5) Polyether polyphenylene ether, polyoxirane, polyoxetane, polytetrahydrofuran, polyetherketone, polyetheretherketone, polyacetal etc.

6) Phenolic resin novolak resin, resol resin etc.

7) Polyester polyethylene terephthalate, polyphenolphthalein terephthalate, polycarbonate, alkyd resin, unsaturated polyester resin etc.

8) Polyamide nylon-6, nylon 66, water-soluble nylon, polyphenyleneamide etc.

9) Polypeptide gelatin, casein etc.

10) Epoxy resin and modified product thereof novolak epoxy resin, bisphenol epoxy resin, novolak epoxy acrylate, modified products thereof obtained by using an anhydride, etc.

11) Others polyurethane, polyimide, melamine resin, urea resin, polyimidazole, polyoxazole, polypyrrol, polyaniline, polysulfide, polysulfone, cellulose, etc.

More specifically, an acrylic resin containing a carboxyl group is, for example, a polymer obtained by copolymerizing one or more monomers having a carboxyl group—such as (meth)acrylic acid, maleic acid (anhydride), crotonic acid, itaconic acid, or fumaric acid—and one or more other copolymerizable components such as styrene, α-methylstyrene, methyl (meth)acrylate, ethyl (meth)acrylate, propyl (meth) acrylate, isopropyl (meth)acrylate, butyl (meth)acrylate, vinyl acetate, acrylonitrile, (meth)acrylamide, glycidyl (meth)acrylate, allyl glycidyl ether, glycidyl ethylacrylate, crotonic glycidyl ether, (meth)acrylic chloride, benzyl (meth) acrylate, hydroxyethyl (meth)acrylate, N-methylolacrylamide, N,N-dimethylacrylamide, N-methacryloylmorpholine, N,N-dimethylaminoethyl (meth)acrylate, or N,N-dimethylaminoethylacrylamide. Preferable one is, for example, an acrylic resin containing, as its constituent monomer, at least (meth)acrylic acid or (meth)acrylic alkyl ester. More preferable one is, for example, an acrylic resin containing (meth) acrylic acid and styrene.

These resins may have an ethylenic double bond in a side chain thereof. The presence of the double bond in the side chain is preferable since the presence of the double bond increases photo-curability whereby the resolution and adhesiveness can be further improved.

The method for introducing the ethylenic double bond is, for example, a method described in, e.g., JP-B No. 50-34443 or 50-34444.

A specific example thereof is a method of allowing a carboxyl or hydroxyl group to react with a glycidyl group, a compound having an epoxycyclohexyl group and a (meth)

acryloyl group, acrylic chloride, or the like. A resin having in its side chain a polymerizable group can be obtained by allowing such a compound as glycidyl (meth)acrylate, allyl glycidyl ether, glycidyl α-ethylacrylate, crotonyl glycidyl ether, (iso)crotonic glycidyl ether, (3,4-epoxycyclohexyl) methyl (meth)acrylate, (meth)acrylic chloride, or (meth)allyl chloride to react with a resin having a carboxyl or hydroxyl group.

Particularly preferable one is a resin obtained by allowing (3,4-epoxycyclohexyl)methyl (meth)acrylate to react with a resin having a carboxyl or hydroxyl group.

Furthermore, a polymer obtained by copolymerizing at least a monomer represented by the following general formula (X) with a monomer having at least an acidic group (examples of the monomer including the above-mentioned copolymerizable components) is also usable.

(X)

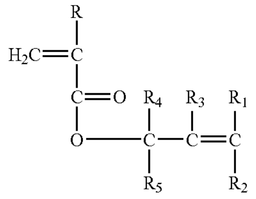

In the formula, R represents a hydrogen atom or a methyl group, $R_1$ to $R_5$ are each independently a group selected from a hydrogen atom, a halogen atom, a cyano group, an alkyl group, or an aryl group.

Specific examples of the halogen atom include Cl, Br and I. The alkyl group may be linear, branched or cyclic, and examples thereof include methyl, n-propyl, iso-propyl, and tert-butyl groups. The alkyl group is preferably an alkyl group having 1 to 7 carbon atoms. Examples of the aryl group include phenyl, furyl and naphthyl groups.

Resins descried below can also be used as the coating resin.

Preferable ones include linear organic high polymers which are soluble in an organic solvent and can be developed with a weakly alkaline solution. Of these linear organic high polymers, a polymer having, in its resin side chain or main chain, an acidic group such as a carboxyl group or a phenolic hydroxyl group is more preferable from the viewpoint of the prevention of environmental pollution since the polymer can be developed with an alkali. A resin having carboxyl groups, for example, acrylic acid (co) polymer, styrene/maleic anhydride resin, or an anhydride-modified product of novolak epoxy acrylate is particularly preferable since the resin has a high developability with an alkali developer. Examples of the polymer having in its side chain a carboxylic acid include methacrylic acid copolymer, acrylic acid copolymer, itaconic acid copolymer, crotonic acid copolymer, maleic acid copolymer, and partially-esterified maleic acid copolymer as described in, for example, JP-A Nos. 59-44615, 59-53836 and 59-71048, and JP-B Nos. 54-34327, 58-12577 and 54-25957; and acidic cellulose derivatives having in their side chains a carboxylic acid. Besides, a product wherein an acid anhydride is added to a polymer having hydroxyl groups is also useful. Of these compounds, preferable ones also include a benzyl (meth)acrylate-(meth)acrylic acid copolymer and a multicomponent copolymer of benzyl (meth)acrylate, (meth) acrylic acid, and one or more other monomers.

Besides, 2-hydroxyethyl methacrylate, polyvinylpyrrolidone, polyethylene oxide, polyvinyl alcohol or the like is also useful as a water-soluble polymer. In order to improve the strength of the cured film high, alcohol-soluble nylon, or a polyether made from 2,2-bis-(4-hydroxyphenyl)-propane and epichlorohydrin may be used. The amount of these polymers to be added may be arbitrary.

Furthermore, epoxy resins as described below can also be used.

1. Glycidylamine type epoxy resins
2. Triphenylglycidylmethane type epoxy resins
3. Tetraphenylglycidylmethane type epoxy resins
4. Aminophenol type epoxy resins
5. Diamidediphenylmethane type epoxy resins
6. Phenol novolak type epoxy resins
7. Ortho-cresol epoxy resins
8. Bisphenol A novolak type epoxy resins Of the above-mentioned examples, a copolymer made from (meth)acrylic acid and a (meth)acrylic ester is preferable since the copolymer design allows selection from various monomers and thus the solubility and acid value can be controlled.

The weight-average molecular weight Mw (mass-average molecular weight) of the coating resin as measured by gel permeation chromatography (GPC) is preferably from 1,000 to 300,000, more preferably from 3,000 to 150,000. When the molecular weight is set to 300,000 or less, satisfactory developability can be obtained.

Examples of the dispersing agent that can be used include known dispersing resins such as ANTI-TERRA-U and DISPERBYK-160, 161, 162 or 163 manufactured by BYK Co.; SOLSPERS 20000, 24000GR, 26000 or 28000 manufactured by Zeneca Co.; DA-703-50, NDC-8194L, NDC-8203L, NDC-8257L or KS-860 manufactured by Kusumoto Chemicals Ltd.; HOMOGENAL L-18, L-1820, L-95 or L-100 manufactured by Kao Corp.; VP5000 manufactured by Nippon Paint Co., Ltd.; E5703P manufactured by Goodrich Co.; VAGH manufactured by Union Carbide Co.; UR8200 manufactured by Toyobo Co., Ltd.; and MR113 manufactured by Nippon Zeon Co., Ltd. Other examples include phthalocyanine derivatives (trade name: EFKA-745) manufactured by EFKA Co., SOLSPERS 5000 manufactured by Zeneca Co., organosiloxane polymer KP341 manufactured by Shin-Etsu Chemical Co., Ltd., and (meth)acrylic acid based (co)polymers (trade name: POLYFLOW No. 75, 90 or 95) manufactured by Kyoei Chemical Co., Ltd. Further examples include cationic surfactants such as W001 manufactured by Yusho Co Ltd; nonionic surfactants such as polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol disearate and sorbitan aliphatic acid esters; anionic surfactants such as W004, W005, and W017 manufactured by Yusho Co Ltd.; polymeric dispersing agents such as EFKA-46, EFKA-47, EFKA-47EA, EFKA POLYMER 100, EFKA POLYMER 400, EFKA POLYMER 401 and EFKA POLYMER 450 manufactured by Morishita & Co., Ltd., and DISPERSE AID 6, DISPERSE AID 8, DISPERSE AID 15 and DISPERSE AID 9100 manufactured by San Nopco, Ltd.; various SOLSPERS dispersing agents, such as SOLSPERS 3000, 5000, 9000, 12000, 13240, 13940, 17000, 24000, 26000 or 28000, manufactured by Zeneca Co.; and ADECA PLURONIC L31, F38, L42, L44, L61, L64, F68, L72, P95, F77, P84, F87, P94, L101, P103, F108, L121 or P-123 manufactured by Asahi Denka Kogyo K.K., and ISONET S-20 manufactured by Sanyo Chemicals Co., Ltd.

Only one coating resin may be used, or a combination of two or more coating resins may be used. Only one dispersing agent may be used, or a combination of two or more dispersing agents may be used.

When the photopolymerizable composition according to the invention is a colorant-containing negative-type photocurable composition, the content by percentage of the colorant dispersing agent in the composition is preferably from 1 to 90% by mass with respect to all the solids in the composition, more preferably from 3 to 80% by mass.

If the content of the colorant dispersing agent is less than 1% by mass, the dispersion uniformity of the pigment may be insufficient. If the content is more than 90% by mass, curability of the composition at photopolymerization may be lowered.

(B) Radical Polymerizable Monomer

The photopolymerizable composition according to the invention contains at least one species of a radical polymerizable monomer. The radical polymerizable monomer is preferably a compound having at least one addition-polymerizable ethylenical unsaturated double bond and having a boiling point of 100° C. or higher under normal pressure.

Examples thereof include: monofunctional acrylates and methacrylates, such as polyethylene glycol mono(meth)acrylate, polypropylene glycol mono(meth)acrylate and phenoxyethyl (meth)acrylate; and polyfunctional acrylates or methacrylates such as polyethylene glycol di(meth)acrylate, trimethylolethane tri(meth)acrylate, neopentyl glycol di(meth)acrylate, pentaerythritol tri(meth)acrylate, pentaerythritol tetra(meth)acrylate, dipentaerythritol penta (meth)acrylate, dipentaerythritol hexa(meth)acrylate, hexanediol di(meth)acrylate, trimethylolpropane tri(acryloyloxypropyl) ether, tri(acryloyloxyethyl)isocyanurate, a product obtained by adding ethylene oxide or propylene oxide to a polyfunctional alcohol such as glycerin or trimethylolethane and then subjecting the obtained adduct to (meth)acrylation, urethane acrylates as described JP-B Nos. 48-41708 and 50-6034, and JP-A No. 51-37193, polyester acrylates described in JP-A No. 48-64183, and JP-B Nos. 49-43191 and 52-30490, epoxy acrylates, which are products of reaction between an epoxy resin and (meth)acrylic acid, and mixtures thereof. Other examples include compounds described as photocurable monomers and oligomers in Journal of the Adhesion Society of Japan, Vol. 20, No. 7, pp. 300-308.

Besides those described above, there can be preferably used radical polymerizable monomers containing a carboxyl group, as illustrated by the following general formula (V-1) or (V-2), wherein, in formulae (V-1) and (V-2), when T or G is an oxyalkylene group, the carbon atom at a terminal thereof is bonded to R, X or W.

(V-1)

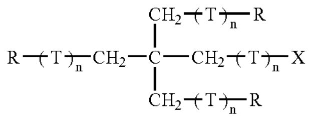

(V-2)

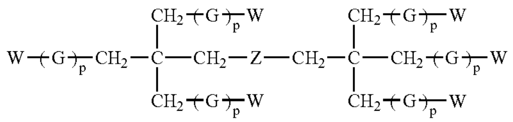

R: 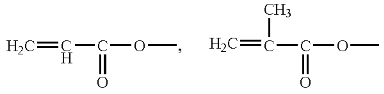

X: 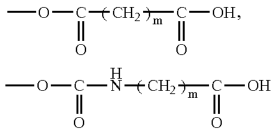

T: 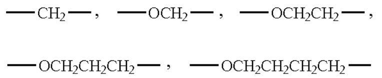

Z: 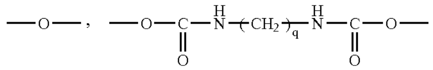

G: 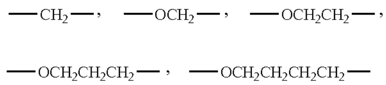

In the general formula (V-1), n is from 0 to 14, and m is from 1 to 8. In the general formula (V-2), W is R or X having the same meaning as in the general formula (V-1). Out of the six Ws, three or more Ws are Rs. "p" is from 0 to 14, and "q" is from 1 to 8. Plural Rs in one molecule may be the same as each other or different from each other. When there are plural Xs in one molecule, they may be the same as each other or different from each other. When there are plural Ts in one molecule, they may be the same as each other or different from each other. Plural Gs in one molecule may be the same as each other or different from each other.

Out of the radical monomers represented by the general formula (V-1) or (V-2), the following specific examples (exemplary compounds M-1 to M-12) are preferable, and the exemplary compounds M-2, M-3 and M-5 are more preferable.

(M-1)

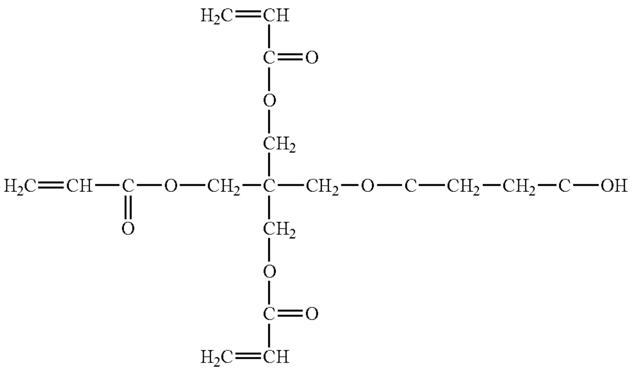

-continued
(M-2)
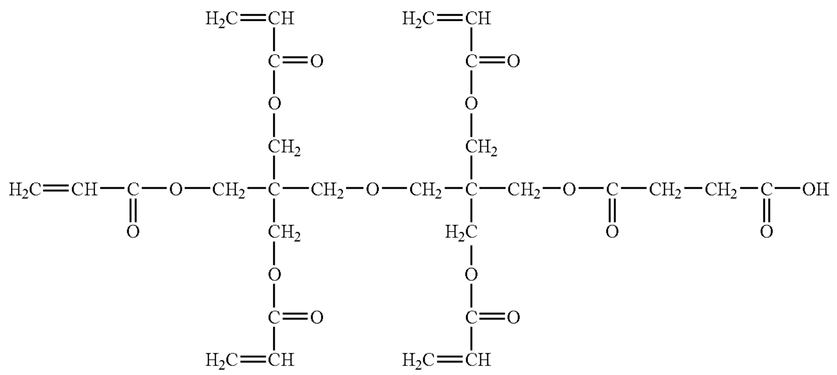
(M-3)
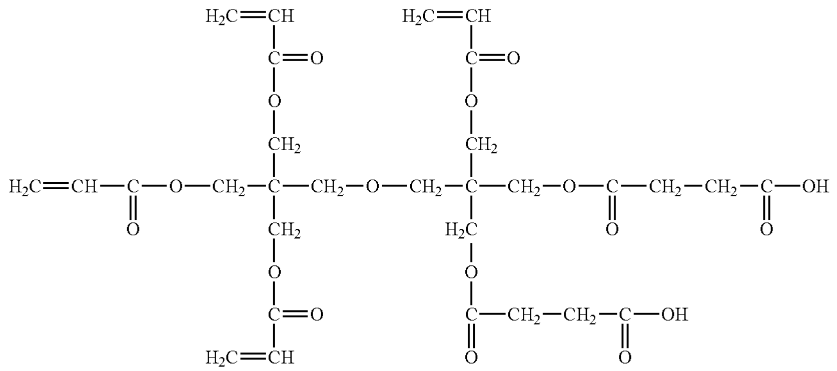
(M-4)
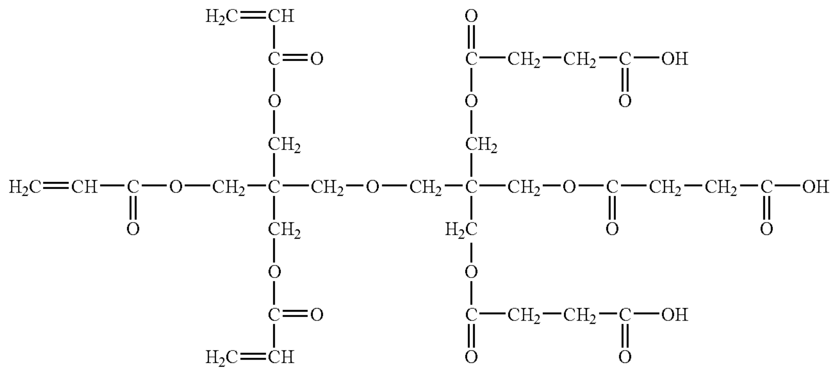
(M-5)
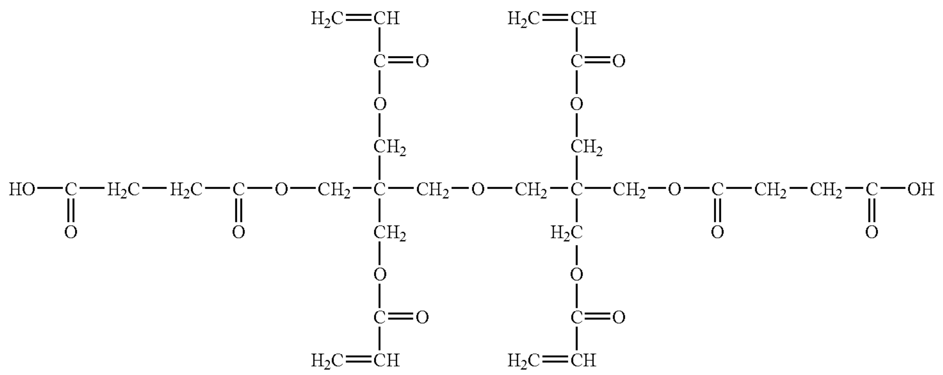

-continued
(M-6)
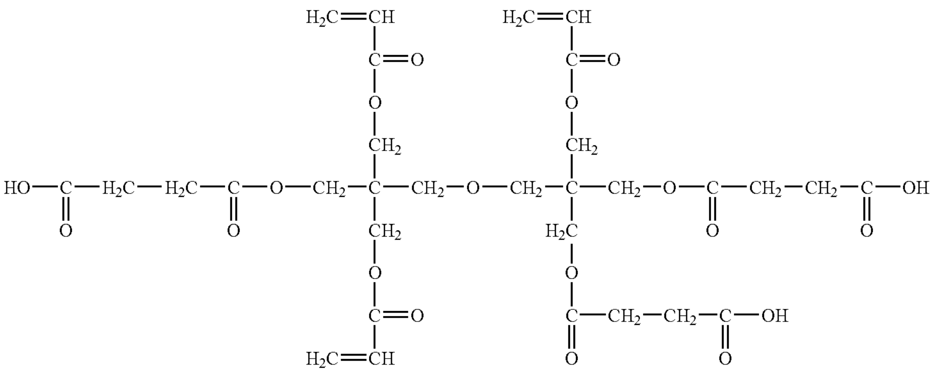
(M-7)
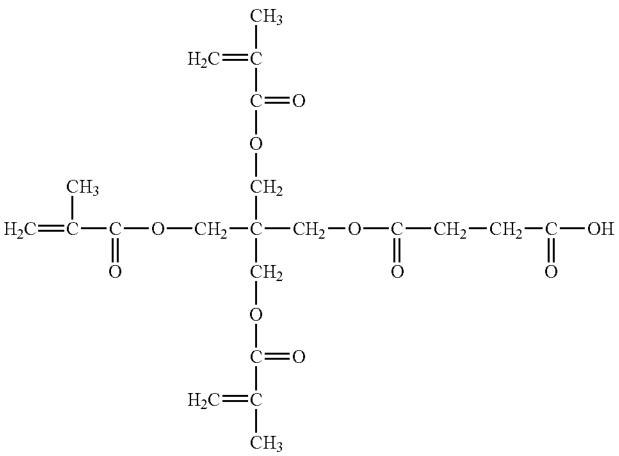
(M-8)
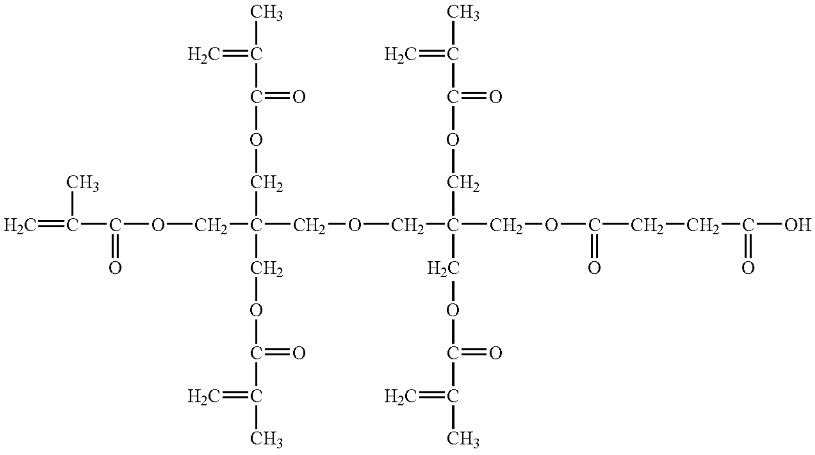

-continued
(M-9)
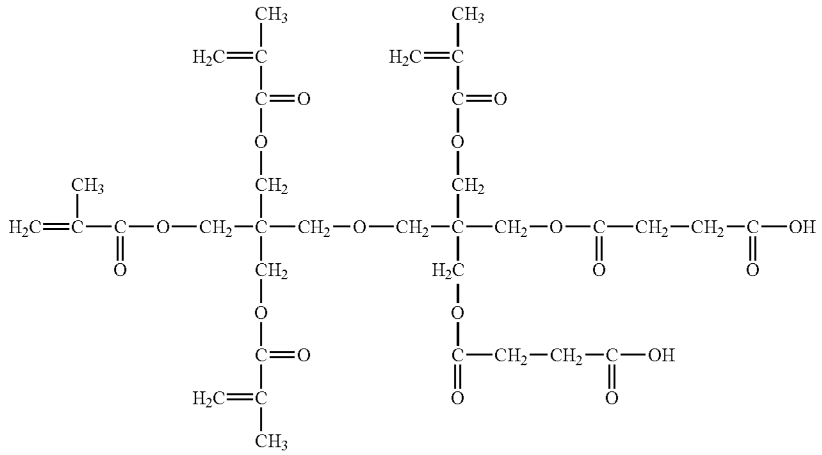
(M-10)
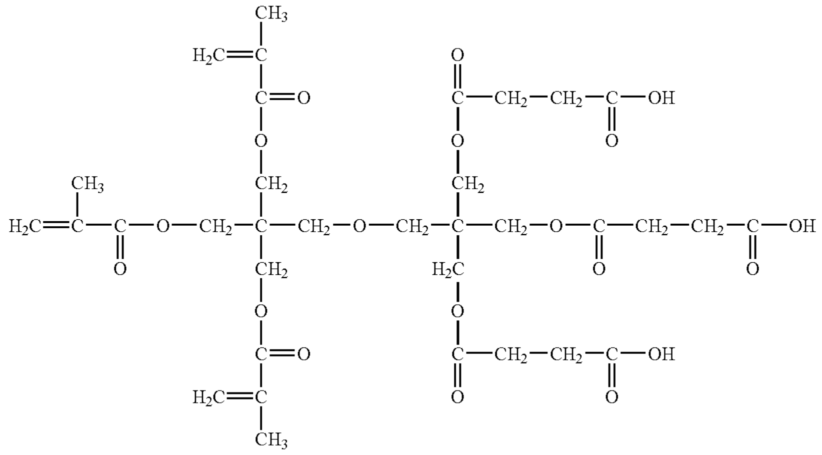
(M-11)
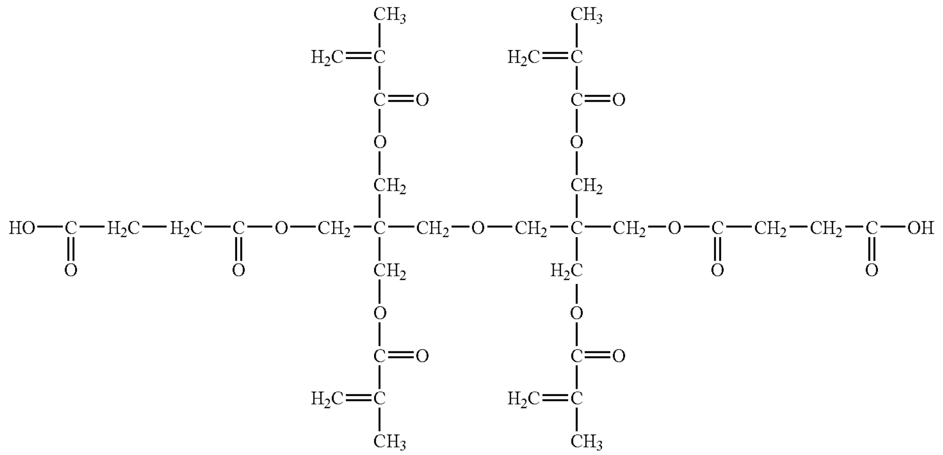

-continued (M-12)

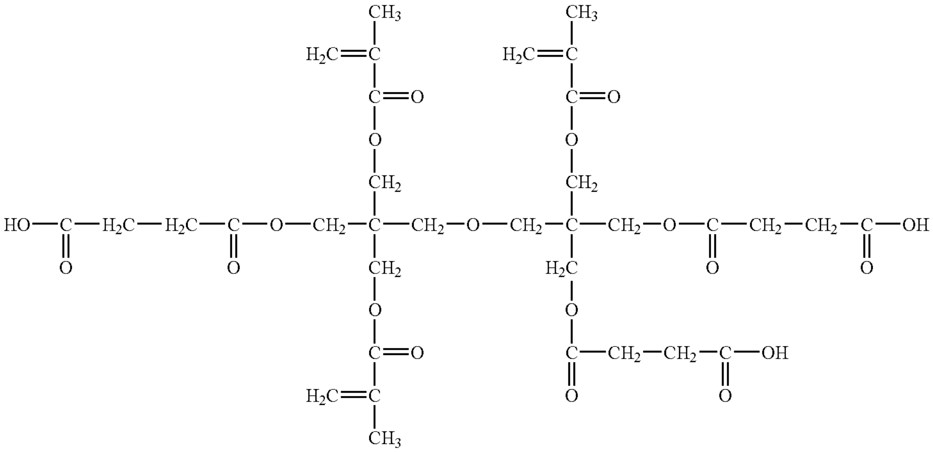

The solid content by percentage of the radical polymerizable monomer in the photopolymerizable composition is preferably 3% or more by mass with respect to all the solids in the composition, more preferably 5% or more by mass, and most preferably 7% or more by mass.

(E) Alkali-Soluble Resin (Binder)

The photopolymerizable composition according to the invention may further contain an alkali-soluble resin (binder). Any other resin can be appropriately used as long as the advantageous effects of the invention are not impaired.

The alkali-soluble resin (hereinafter referred to as alkali-soluble binder) will be described hereinafter.

The alkali-soluble binder is not particularly limited as long as the binder is alkali-soluble, and is preferably selected from the viewpoint of heat resistance, developability, availability, and others.

The alkali-soluble binder is preferably a linear organic high polymer which is soluble in an organic solvent and is developable in a weakly alkaline aqueous solution. Examples of the linear organic high polymer include polymers having, in a side chain thereof, a carboxylic acid whose examples include methacrylic acid copolymer, acrylic acid copolymer, itaconic acid copolymer, crotonic acid copolymer, maleic acid copolymer or partially-esterified maleic acid copolymer as described in, for example, JP-A Nos. 59-44615, 59-53836 and 59-71048, and JP-B Nos. 54-34327, 58-12577 and 54-25957. Acidic cellulose derivatives having, in a side chain thereof, a carboxylic acid are also useful.

Besides the above, the following are also useful: a product obtained by adding an acid anhydride to a polymer having a hydroxyl group; polyhydroxystyrene resins; polysiloxane resins; poly(2-hydroxyethyl(meth)acrylate); polyvinyl pyrrolidone; polyethylene oxide; and polyvinyl alcohol.

A monomer having hydrophilicity may be copolymerized with the binder. Examples of the monomer include alkoxyalkyl (meth)acrylate, hydroxyalkyl (meth)acrylate, glycerol (meth)acrylate, (meth)acrylamide, N-methylolacrylamide, secondary or tertiary alkylacrylamide, dialkylaminoalkyl (meth)acrylate, morpholine (meth)acrylate, N-vinylpyrrolidone, N-vinylcaprolactam, vinylimidazole, vinyltriazole, methyl (meth)acrylate, ethyl (meth)acrylate, branched or linear propyl (meth)acrylate, branched or linear butyl (meth) acrylate, and phenoxyhydroxypropyl (meth)acrylate.

As the monomer having hydrophilicity, monomers containing a tetrahydrofurfuryl group, phosphoric acid moiety, phosphoric acid ester moiety, quaternary ammonium salt moiety, ethyleneoxy chain, propyleneoxy chain, sulfonic acid group or salt thereof, morpholinoethyl group, or the like, are useful.

The binder may have a polymerizable group in a side chain from the viewpoint of improving the crosslinking efficiency. Thus, polymers containing, in a side chain thereof, an allyl group, a (meth)acrylic group, an allyloxyalkyl group or the like are useful. Examples of such polymers containing a polymerizable group are described below. However, the alkali-soluble polymers are not limited to these examples, and any polymer may be used as long as the polymer contains an alkali-soluble group such as a COOH, OH or ammonium group, and a carbon-carbon unsaturated bond.

Specifically, the following can be used: a compound obtained by allowing a compound having an epoxy ring, which is reactive with an OH group, and a carbon-carbon unsaturated bond (such as glycidyl acrylate) to react with a copolymer made from a compound having a OH group (such as 2-hydroxyethyl acrylate), a compound having a COOH group (such as methacrylic acid), and a monomer copolymerizable therewith (such as an acrylic or vinyl monomer).

As the portion having reactivity to a OH group, an acid anhydride, an isocyanate group, an acryloyl group may be used instead of the epoxy ring, and compounds having such a portion are also usable. There can also be used a reaction product obtained by allowing a saturated or unsaturated polybasic acid anhydride to react with a compound obtained by allowing an unsaturated carboxylic acid such as acrylic acid to react with a compound having an epoxy ring, which is described in JP-A Nos. 6-102669 and 6-1938.

Examples of the compound having both of an alkali-soluble group, such as a COOH group, and a carbon-carbon unsaturated group include: DIANAL NR series (manufactured by Mitsubishi Rayon Co., Ltd.); COOH-containing polyurethane acrylic oligomer, PHOTOMER 6173 (manufactured by Diamond Shamrock Co., Ltd.); VISCOAT R-264 and KS RESIST 106 (both of which are manufactured by Osaka Organic Chemical Industry Co., Ltd.); CYCLOMER P series and PRAKCEL CF series (both of which are manufactured by Daicel Chemical Industries, Ltd.); and EBECRY 13800 (manufactured by Daicel-UCB Co., Ltd.).

When the photopolymerizable composition contains the alkali-soluble resin (binder), the content by percentage of the resin is usually from 0.5 to 90% by mass of all the solids in the composition.

(F) Organic Solvent

When the photopolymerizable composition according to the invention is prepared, an organic solvent (referred to as "solvent" in the present specification) can be used in general. Basically, the solvent is not particularly limited as long as the solvent provides satisfactory solubility of the individual components and coatability of the photopolymerizable composition. The solvent is preferably selected in consideration of coatability, safety, and the solubility of the photopolymerization initiator, photosensitizer, colorant (in particular, dye), colorant dispersing agent, radical polymerizable monomer and alkali-soluble resin (binder) to be used.

Examples of the organic solvent include esters, for example, alkyl esters such as ethyl acetate, n-butyl acetate, isobutyl acetate, amyl formate, isoamyl acetate, butyl propionate, isopropyl butyrate, ethyl butyrate, butyl butyrate, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate and ethyl ethoxyacetate, alkyl 3-oxypropionates such as methyl 3-oxypropionate and ethyl 3-oxypropionate, (e.g., methyl 3-methoxypropionate, ethyl 3-methoxypropionate, methyl 3-ethoxypropionate and ethyl 3-ethoxypropionate), alkyl 2-oxypropionates such as methyl 2-oxypropionate, ethyl 2-oxypropionate and propyl 2-oxypropionate (e.g., methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate and ethyl 2-ethoxy-2-methylpropionate), methyl pyruvate, ethyl pyruvate, propyl pyruvate, methyl acetoacetate, ethyl acetoacetate, methyl 2-oxobutanoate, and ethyl 2-oxobutanoate;

ethers, for example, diethylene glycol dimethyl ether, tetrahydrofuran, ethylene glycol monomethyl ether, ethylene glycol monoethyl ether, methylcellosolve acetate, ethylcellosolve acetate, diethylene glycol monomethyl ether, diethylene glycol monoethyl ether, diethylene glycol monobutyl ether, propylene glycol methyl ether, propylene glycol methyl ether acetate, propylene glycol ethyl ether acetate, and propylene glycol propyl ether acetate;

ketones, for example, methyl ethyl ketone, cyclohexane, 2-heptanone, and 3-heptanone; and aromatic hydrocarbons such as toluene and xylene.

Of these, preferable ones include methyl 3-ethoxypropionate, ethyl 3-ethoxypropionate, ethylcellosolve acetate, ethyl lactate, diethylene glycol dimethyl ether, butyl acetate, methyl 3-methoxypropionate, 2-heptanone, cyclohexanone, cyclopentanone, ethylcarbitol acetate, butylcarbitol acetate, propylene glycol methyl ether, and propylene glycol methyl ether acetate.

The solvent is preferably one selected from cyclohexanone, ethyl lactate, propylene glycol monomethyl ether acetate, propylene glycol monomethyl ether and ethyl 3-ethoxypropionate, or a mixture of two or more selected therefrom, in view of the solubility of the individual components and coatability. The solvent is more preferably one selected from ethyl lactate, propylene glycol monomethyl ether acetate and ethyl 3-ethoxypropionate, or a mixture of two or more selected therefrom, in the point of precipitation after dissolving the individual components and planarity and evenness of the coated face.

(G) Other Components

—Surfactant—

The composition according to the invention may further contain a surfactant. The surfactant may be any one of the aforementioned examples of the colorant dispersing agent.

As to other surfactants than the aforementioned colorant dispersing agent, the surfactants may be selected from known surfactants, such as known nonionic, cationic, or anionic surfactants, in accordance with the purpose or the like. For example, a fluorine-containing organic compound having a fluorine content of 3 to 40% by mass may be used. When such a compound is incorporated into the composition, the property of the composition as a coating solution can be further improved so that the uniformity in coating thickness can be improved and the amount of the coating solution can be reduced. In particular, the coatability onto a substrate may be improved. Thus, a coating layer having an even thickness can be obtained with a smaller amount of the coating solution.

The fluorine content in the fluorine-containing organic compound may be from 3 to 40% by mass, preferably from 5 to 30% by mass, even more preferably from 7 to 25% by mass.

If the fluorine content in the fluorine-containing organic compound is too low, the effects in the uniformity of the thickness of the coating layer and in the reduction in the coating solution cannot be sufficiently obtained. Conversely, if the content is too large, the solubility in the composition is insufficient in some cases.

Examples of the fluorine-containing compound include MEGAFAC F171, F172, F173, F177, F141, F142, F143, F144, R30 and F437 (manufactured by Dainippon Ink & Chemicals, Inc.); FLORARD FC430, FC431 and FC171 (manufactured by Sumitomo 3M Ltd.); and SURFLON S-382, SC-101, SC-103, SC-104, SC-105, SC 1068, SC-381, SC-383, S 393 and KH-40 (manufactured by Asahi Glass Co., Ltd.).

The incorporation of the fluorine-containing compound makes it possible to improve the fluidity of the composition as a coating solution. In this way, the interfacial tension between the coating solution and the substrate is lowered so that the wettability onto the substrate is improved. Thus, a coating layer having less unevenness in thickness can be obtained even if the film is a thin film having a thickness of several micrometers. In particular, the effects are remarkable in the case of slit coating since coating unevenness, thickness unevenness, or solution discontinuity on the coating surface easily occurs in the slit coating when the coating layer is thinner.

The amount of surfactant to be added is preferably from 0.001 to 2.0% by mass with respect to the entire coating solution, more preferably from 0.005 to 1.0% by mass.

—Crosslinking Agent—

In the invention, a highly cured film can be obtained by additionally using a crosslinking agent. The crosslinking agent will be described hereinafter.

The crosslinking agent which can be used in the invention is not particularly limited as long as the agent is capable of curing a film through crosslinking reaction. Examples thereof include (a) an epoxy resin; (b) a melamine compound, guanamine compound, glycoluril compound or urea compound having at least one substituent selected from a methylol group, an alkoxymethyl group or an acyloxymethyl group; and (c) a phenol compound, naphthol compound or hydroxyanthracene compound having at least one substituent selected from a methylol group, an alkoxymethyl group or an acycloxymethyl group. Preferable one is a polyfunctional epoxy resin.

The epoxy resin (a) may be any epoxy resin as long as the resin has an epoxy group and crosslinking property. Examples thereof include bivalent glycidyl-group-containing low molecular weight compounds such as bisphenol A diglycidyl ether, ethylene glycol diglycidyl ether, butanediol diglycidyl ether, hexanediol diglycidyl ether, dihydroxybiphenyl diglycidyl ether, diglycidyl ester phthalate, and N,N-diglycidylaniline; trivalent glycidyl-group-containing low molecular weight compounds such as trimethylolpropane triglycidyl ether, trimethylolphenol triglycidyl ether, and Tris P-PA triglycidyl ether; tetravalent glycidyl-group-containing low molecular weight compounds such as pentaerythritol tetraglycidyl ether, and tetramethylol bisphenol A tetraglycidyl ether; polyvalent glycidyl-group-containing low molecular weight compounds such as dipentaerythritol pentaglycidyl ether and dipentaerythritol hexaglycidyl ether; and glycidyl-group-containing macromolecular compounds such as polyglycidyl (meth)acrylate, a 1,2-epoxy-4-(2-oxiranyl)cyclohexane adduct of 2,2-bis(hydroxymethyl)-1-butanol.

The number of methylol, alkoxymethyl, and acyloxymethyl groups contained as substituent groups in the crosslinking agent (b) is from 2 to 6 when it is a melamine compound, and is from 2 to 4 when it is a glycoluril, guanamine, or urea compound, but is preferably from 5 to 6 when it is a melamine compound, and is preferably from 3 to 4 when it is a glycoluril, guanamine, or urea compound.

Hereinafter, the melamine compound, guanamine compound, glycoluril compound and urea compound described in item (b) above is collectively referred to as compounds of item (b) (methylol group-containing compounds, alkoxymethyl group-containing compounds, or acyloxymethyl group-containing compounds) in some cases.

The methylol group-containing compound of item (b) can be prepared by heating an alkoxymethyl group-containing compound of item (b) in alcohol in the presence of an acid catalyst such as hydrochloric acid, sulfuric acid, nitric acid, or methanesulfonic acid. The acyloxymethyl group-containing compound of item (b) can be prepared by mixing and stirring a methylol group-containing compound of item (b) with an acyl chloride in the presence of a basic catalyst.

Hereinafter, specific examples of the compounds of item (b) having substituents as described above will be listed.

Examples of the melamine compounds include hexamethylolmelamine, hexamethoxymethylmelamine, compounds obtained by methoxymethylating 1 to 5 methylol groups of hexamethylolmelamine and mixtures thereof, hexamethoxyethylmelamine, hexacyloxymethylmelamine, and compounds obtained by acyloxymethylating 1 to 5 methylol groups of hexamethylolmelamine and mixtures thereof.

Examples of the guanamine compounds include tetramethylolguanamine, tetramethoxymethylguanamine, compounds obtained by methoxymethylating 1 to 3 methylol groups of tetramethylolguanamine and mixtures thereof, tetramethoxyethylguanamine, tetraacyloxymethylguanamine, compounds obtained by acyloxymethylating 1 to 3 methylol groups of tetramethylolguanamine and mixtures thereof.

Examples of the glycoluril compounds include tetramethylol glycoluril, tetramethoxymethyl glycoluril, compounds obtained by methoxymethylating 1 to 3 methylol groups of tetramethylol glycoluril and mixtures thereof, and compounds obtained by acyloxymethylating 1 to 3 methylol groups of tetramethylol glycoluril and mixtures thereof.

Examples of the urea compounds include tetramethylolurea, tetramethoxymethylurea, compounds obtained by methoxymethylating 1 to 3 methylol groups of tetramethylolurea and mixtures thereof, and tetramethoxyethylurea.

Only one compound of item (b) may be used, or a plurality of compounds of item (b) may be used in combination.

The crosslinking agent (c), i.e., the phenol, naphthol, or hydroxyanthracene compound substituted by at least one group selected from methylol, alkoxymethyl, and acyloxymethyl groups, prevents intermixing with the topcoat photoresist and improves the strength of the film further by thermal crosslinking in a similar manner to the crosslinking agent (b) above.

Hereinafter, these compounds may be referred to collectively as compounds of item (c) (methylol group-containing compounds, alkoxymethyl group-containing compounds, and acyloxymethyl group-containing compounds).

The number of the methylol, acyloxymethyl, and alkoxymethyl groups contained in the crosslinking agent (c) is at least two per molecule, and compounds having a skeletal phenol compound substituted at all 2- and 4-sites are preferable, from the viewpoints of thermal crosslinking property and storage stability. In addition, the skeletal naphthol or hydroxyanthracene compound is also preferably a compound having substituents at all ortho- and para-positions relative to the OH group. The 3- or 5-position of the skeletal phenol compound may be unsubstituted or substituted.

In addition, in the skeletal naphthol compound, the positions other than ortho-positions relative to the OH group may be unsubstituted or substituted.

The methylol group-containing compound of item (c) can be prepared by using a compound having a hydrogen atom at the ortho- or para-positions (2- or 4-site) to the phenolic OH group as raw material and reacting it with formalin in the presence of a basic catalyst such as sodium hydroxide, potassium hydroxide, ammonia, or a tetraalkylammonium hydroxide.

The alkoxymethyl group-containing compound of item (c) can be prepared by heating a methylol group-containing compound of item (c) in alcohol in the presence of an acid catalyst such as hydrochloric acid, sulfuric acid, nitric acid, or methanesulfonic acid.

The acyloxymethyl group-containing compound of item (c) can be prepared by reacting the methylol group-containing compound of item (c) with an acyl chloride in the presence of a basic catalyst.

Examples of the skeletal compounds for the crosslinking agent (c) include phenol, naphthol, and hydroxyanthracene compounds having no substituent on the ortho- and para-positions relative to the phenolic OH group, and specific examples thereof for use include phenol, respective isomers of cresol, 2,3-xylenol, 2,5-xylenol, 3,4-xylenol, 3,5-xylenol, bisphenols such as bisphenol A, 4,4'-bishydroxybiphenyl, Tris P-PA (manufactured by Honshu Chemical Industry Co., Ltd.), naphthol, dihydroxynaphthalene, and 2,7-dihydroxyanthracene.

Specific examples of the crosslinking agent (c) include, as phenol or naphthol compounds, trimethylol phenol, tri(methoxymethyl)phenol, compounds obtained by methoxymethylating 1 or 2 methylol groups of trimethylol phenol, trimethylol-3-cresol, tri(methoxymethyl)-3-cresol, compounds obtained by methoxymethylating 1 or 2 methylol groups of trimethylol-3-cresol, dimethylol cresol such as 2,6-dimethylol-4-cresol, tetramethylol bisphenol A, tetramethoxymethylbisphenol A, compounds obtained by methoxymethylating 1 to 3 methylol groups of tetramethylol bisphenol A, tetramethylol-4,4'-bishydroxybiphenyl, tetramethoxymethyl-4,4'-bishydroxybiphenyl, Tris P-PA in form of hexamethylol, hexamethoxymethylated Tris P-PA, compounds obtained by methoxymethylating 1 to 5 methylol groups of hexamethylol body of Tris P-PA, and bishydroxymethylnaphthalenediol.

Further examples include hydroxyanthracene compounds such as 1,6-dihydroxymethyl-2,7-dihydroxyanthracene, and acyloxymethyl-containing compounds such as compounds obtained by acyloxymethylating some or all of the methylol groups of the above-mentioned methylol-containing compounds.

Preferable examples of those compounds include trimethylol phenol, bishydroxymethyl-p-cresol, tetramethylol bisphenol A, hexamethylol body of Tris P-PA (manufactured by Honshu Kagaku Kogyo Co., Ltd.), or phenol compounds obtained by substituting some or all of the methylol groups of these compounds with alkoxymethyl groups or with methylol group(s) and alkoxymethyl group(s).

Only one compound of item (c) may be used, or a plurality of compounds of item (c) may be used in combination.

The photopolymerizable composition according to the invention does not necessarily contain a crosslinking agent. The total content of the crosslinking agents (a) to (c), if used, in a colorant-containing negative curable composition may vary according to the raw materials used, but is preferably from 1 to 70 wt %, more preferably from 5 to 50 wt %, with respect the total solid matters (by mass) in the composition.

—Various Additives—

The colorant-containing negative curable composition according to the invention may contain, as needed, various additives such as fillers, polymeric compounds other than those described above, surfactants other than those described above, adhesion accelerators, antioxidants, ultraviolet absorbents, aggregation inhibitors, transition metal complex, and others.

Specific examples of the various additives include: fillers such as glass and alumina; polymeric compounds other than binder resin such as polyvinylalcohol, polyacrylic acid, polyethylene glycol monoalkylethers, and polyfluoroalkyl acrylates; surfactants such as nonionic, cationic, and anionic surfactants; adhesion accelerators such as vinyltrimethoxysilane, vinyltriethoxysilane, vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane, and 3-mercaptopropyltrimethoxysilane; antioxidants such as 2,2-thiobis(4-methyl-6-t-butylphenol) and 2,6-di-t-butylphenol; ultraviolet absorbents such as 2-(3-t-butyl-5-methyl-2-hydroxyphenyl)-5-chlorobenzotriazole and alkoxybenzophenones; and aggregation inhibitors such as sodium polyacrylate.

The photopolymerizable composition according to the invention may contain a transition metal complex wherein the largest value of the molar absorption coefficient E is smaller than the molar absorption coefficient ε of the above-mentioned organic solvent soluble dye in a visible ray wavelength range. This transition metal complex is a complex wherein one or more negative, neutral or positive unidentate ligand or polydentate ligand are coordinated to a central transition metal atom or transition metal ion, and is effective for an improvement in light resistance of the colorant-containing photopolymerizable composition according to the invention and a color filter using this.

The transition metal complex is preferably a complex wherein the largest value of the molar absorption coefficient ε is 0 to 8000 in a visible ray wavelength range (of 380 to 780 nm) from the viewpoint of color vividness. The largest value of the molar absorption coefficient ε of the transition metal complex in the aforementioned wavelength range is more preferably from 0 to 6000, more preferably from 0 to 3000.

Examples of the transition metal or transition metal ion contained in the transition metal complex include scandium (Sc), titanium (Ti), vanadium (V), chromium (Cr), manganese (Mn), iron (Fe), cobalt (Co), nickel (Ni), copper (Co), yttrium (Y), zirconium (Zr), niobium (Nb), molybdenum (Mo), technetium (Tc), ruthenium (Ru), rhodium (Rh), palladium (Pd), silver (Ag), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), hafnium (Hf), tantalum (Ta), tungsten (W), rhenium (Re), osmium (Os), iridium (Ir), platinum (Pt), and gold (Au).

Preferable examples of the transition metal complex include a complex containing a transition metal which belongs to the first series (i.e., the fourth period in the long periodic table, the same applies hereinafter), that is, scandium (Sc), titanium (Ti), vanadium (V), chromium (Cr), manganese (Mn), iron (Fe), cobalt (Co), nickel (Ni), or copper (Co). Among these metals, the transition metal is preferably Mn, Fe, Co, Ni or Cu.

The maximum value of the molar absorption coefficient ε of the ligand itself contained in the transition metal complex is preferably from 0 to 3000 in the visible ray wavelength range, more preferably from 0 to 2000, even more preferably from 0 to 1000.

The molecular weight of any one of the ligands contained in the transition metal complex is preferably 20 or more but less than 300 from the viewpoint of light resistance and alkaline developability.

In order to improve the developability of the photopolymerizable composition according to the invention by increasing the alkali-solubility of an uncured portion, an organic carboxylic acid, preferably a low molecular weight organic carboxylic acid having a molecular weight of 1000 or less, can be incorporated into the composition.

Specific examples thereof include aliphatic monocarboxylic acids such as formic acid, acetic acid, propionic acid, butyric acid, valeric acid, pivalic acid, caproic acid, diethylacetic acid, enanthic acid, and caprylic acid; aliphatic dicarboxylic acids such as oxalic acid, malonic acid, succinic acid, glutaric acid, adipic acid, pimelic acid, suberic acid, azelaic acid, sebacic acid, brasylic acid, methylmalonic acid, ethylmalonic acid, dimethylmalonic acid, methylsuccinic acid, tetramethylsuccinic acid, and citraconic acid; aliphatic tricarboxylic acids such as tricarballylic acid, aconitic acid, and camphoronic acid; aromatic monocarboxylic acids such as benzoic acid, toluic acid, cuminic acid, hemellitic acid, and mesitylenic acid; aromatic polycarboxylic acids such as phthalic acid, isophthalic acid, terephthalic acid, trimellitic acid, trimesic acid, mellophanic acid, and pyromellitic acid; and other carboxylic acids such as phenylacetic acid, hydroatropic acid, hydrosuccinic acid, mandelic acid, phenylsuccinic acid, atropic acid, cinnamic acid, methyl cinnamate, benzyl cirmamate, cinnamylidene acetic acid, coumaric acid, and umbellic acid.

Other specific examples include those having a carboxyl group among the compounds described as examples of the component (D).

Besides the above components, it is preferable to add a thermal polymerization inhibitor to the composition according to the invention. Useful examples thereof include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and 2-mercaptobenzoimidazole.

The photopolymerizable composition according to the invention can be used for various purposes. For example, the photopolymerizable composition according to the invention can be used as a printing ink such as a screen printing ink, offset printing ink or flexographic printing ink, as a transparent finishing agent, as a white or color finishing agent for wood or metal, as a powdery coating material (in particular, a coating material for paper, wood, metal or plastics), as a marking agent for a building or road; or for a photographic copying process or image recording process. The composition can also used as a holographic recording material, as a sunlight curable coating material for producing a printing plate precursor developable with organic solvent or aqueous alkali or for producing a screen printing mask, a filling composition for dentistry, an adhesive agent, a pressure-sensitive adhesive agent, a laminating resin, an etching resist, solder resist, electroplating resist or permanent resist for both of liquid and dry thin films, or an optically-formable dielectric for printed circuit boards or electronic circuits; or for various displays. The composition can be used also for the formation of a structure in the process of producing a plasma display panel or an electroluminescent display device, for the production of a color filter (as described in, for example, U.S. Pat. Nos. 5,853,446 and 5,840,465, European Patent Nos. 863, 534 and 855,731, and JP-A Nos. 9-244,230, 10-62,980, 8-171,863, 5-271,576 and 5-67,405), for the production of an optical switch, an optical lattice (interference lattice), or an optical circuit, for the production of a three-dimensional article by mass curing (UV curing by use of a transparent molding die) or stereo-lithography (as described in, for example, U.S. Pat. No. 4,575,330), for the production of a composite material (such as a styrene-based polyester which may contain glass fiber and/or some other fiber, and a different auxiliary if desired) or other thick-layer composition. The composition according to the invention can be also used as a resist for the coating or sealing of an electronic member or an integrated circuit, or a coating material for producing an optical fiber or an optical lens (for example, a contact lens or a Fresnel lens). The composition according to the invention is also suitable for producing medical instruments, subsidiary measures, or implants. Furthermore, the composition according to the invention is suitable for producing gel having thermotropic property, as described in German Patent No. 19,700, 064 and European Patent No. 678,534.

Further, the novel photoinitiator disclosed herein may be used as an initiator for emulsion polymerization, pearl polymerization or suspension polymerization, as a polymerization initiator for fixing a regular state of a monomer or oligomer of liquid crystal, or as an initiator for fixing and bonding a dye onto an organic material.

In particular, the composition can be preferably used for forming colored pixels of a color filter used in a liquid crystal display (LCD) or a solid imaging element (such as a CCD or CMOS), or for forming colored pixels of a color filter for electroluminescence, or for producing a printing ink, inkjet ink or UV ink, or a paint.

<<Photopolymerizing Method>>

The photopolymerizing method according to the invention includes irradiating the photopolymerizable composition with an electromagnetic radiation having a wavelength in the range of 150 to 600 nm, an electron beam or an X-ray, thereby polymerizing the radical polymerizable monomer contained in the composition.

Upon irradiation with the electromagnetic radiation, electron beam or X-ray, photopolymerization reaction of the radical polymerizable monomer contained in the photopolymerizable composition initiates by the action of the photopolymerization initiator, whereby the photopolymerizable composition is cured to form a film of the composition.

<<Process for Producing the Photopolymerizable Composition According to the Invention and Method of Using the Composition when the Composition Contains a Pigment as a Colorant>>

In the following, a process for producing the photopolymerizable composition according to the invention and a method of using the composition in the case where the composition contains a pigment as a colorant are explained.

The composition can be prepared through a mixing and dispersing step of adding the photopolymerization initiator, radical-polymerizable monomer, colorant, colorant dispersing agent and optional other additives to a solvent, and then mixing and dispersing these components in the solvent by use of various mixers and/or dispersers.

The mixing and dispersing step is preferably a step including kneading and dispersing and subsequent finely-dispersing treatment. The kneading and dispersing may be omitted.

The production process is preferably a process including conducting kneading and dispersing treatment of dispersing the colorant into the resin component by kneading to set the viscosity after the kneading and dispersing treatment to a relatively high viscosity of 10,000 mPa·s or more, desirably 100,000 mPa·s or more; adding a solvent thereto; conducting finely-dispersing treatment to set the viscosity after the finely-dispersing treatment to a relatively low viscosity of 1,000 mPa·s or less, desirably 100 mPa·s or less; adding a high boiling point solvent or the like thereto; and stirring the resultant mixture to mix the components.

The machine used in the kneading and dispersing treatment may be a two-roll machine, a three-roll machine, a ball mill, a tron mill, a disper, a kneader, a co-kneader, a homogenizer, a blender, a monoaxial or biaxial extruder, or the like. The dispersing is performed under strong shearing force. Next, the solvent is added thereto, and the composition is subjected to finely-dispersing treatment with beads having a grain size of 0.1 to 1 mm and made of glass, zirconia or the like by using, typically, a vertical or horizontal sand grinder, a pin mill, a slit mill, an ultrasonic disperser or the like. The mixing and dispersing treatment may be omitted. In this case, the pigment, the dispersing agent or surfactant, and the acrylic copolymer in the invention are dispersed into a solvent with beads.

Details of kneading and dispersing are described in T. C. Patton, “Paint Flow and Pigment Dispersion”, published by John Wiley and Sons Co. in 1964. The method disclosed therein may be used.

<<Color Filter and Process for Producing the Same>>

In the following, the color filter according to the invention is described in detail by reference to a process for producing the same.

The process for producing the color filter according to the invention is a process for producing the color filter by use of the above-mentioned photopolymerizable composition according to the invention. Specifically, an image forming step (and an optional curing step) are repeated for the respective desired hues, whereby a color filter having the desired hues can be produced.

The composition according to the invention is applied to a substrate by a coating method such as slit coating, inkjet method, spin coating, cast coating, roll coating, or screen printing so as to form a coating layer of the colored resin composition. In this process, the composition according to the invention may be applied directly onto the substrate, or may be applied onto the top of one or more other layers provided on the substrate The film is exposed to radiation to cure only the light-radiated portion of the coating layer. The exposure radiation is optionally patterned by using a predetermined mask pattern. The coating layer is subjected to developing treatment with a developer, thereby forming a negative colored pattern (an image forming step). If necessary, a curing step of curing the formed colored pattern by heating and/or exposure to radiation may be conducted. This image forming step (and the optional curing step) are repeated for the respective desired hues, whereby a color filter having the desired hues can be produced. The radiation used in this process is preferably a ultraviolet light such as the g-line, the h-line, or the i-line.

Examples of the substrate include non-alkali glass, sodium glass, PYREX (registered trade name) glass and quartz glass substrates for liquid crystal display elements or the like; a product wherein a transparent electroconductive film is deposited on any one of these substrates; photoelectric converting substrates for solid imaging elements or the like, such as a silicon substrate; complementary metal oxide semiconductor (CMOS) substrates; and plastic substrates. It is preferable that the plastic substrates have, on a surface thereof, a gas barrier layer and/or a solvent resistant layer. A plastic stripe for separating individual pixels may be formed on the above described substrates. If necessary, an undercoat layer may be provided on the substrate as necessary, so as to improve adhesion between the substrate and the layers above the undercoat layer, so as to prevent diffusion of substances, or so as to improve planarity of the surface of the substrate.

The drying (pre-baking) of the coating layer made of the composition according to the invention and applied on the substrate can be performed by use of a hot plate, an oven or the like at a temperature of 50 to 140° C. for 10 to 300 seconds.

The thickness of the (dried) coating layer made of the composition according to the invention is generally from 0.3 to 5.0 μm, desirably from 0.5 to 3.5 μm, more desirably from 0.7 to 2.5 μm.

The developer may be any developer as long as the developer dissolves non-cured portions of the photopolymerizable composition of the invention but does not dissolve cured portions. Specifically, a combination of various organic solvents, or an aqueous alkaline solution can be used. Examples of the organic solvents include those cited in the explanation of the organic solvent used for the preparation of the photopolymerizable composition according to the invention.

A preferable example of the aqueous alkaline solution is an aqueous alkaline solution wherein an alkaline compound is dissolved in water to give a concentration of 0.001 to 10% by mass, preferably 0.01 to 1% by mass. Example of the alkaline compound include sodium hydroxide, potassium hydroxide, sodium carbonate, sodium silicate, sodium metasilicate, ammonia water, ethylamine, diethylamine, dimethylethanolamine, tetramethylammonium hydroxide, tetraethylammonium hydroxide, choline, pyrrole, piperidine, and 1,8-diazabicyclo-[5.4.0]-7-undecene. When such a developer made of an aqueous alkaline solution is used, washing (rinsing) with water is generally conducted after development.

The post-baking of the coating layer, which is optionally conducted after development, is a heating treatment for completing the curing of the coating layer. The temperature for the heating is usually from about 200 to about 220° C. (hard baking).

This post-baking treatment can be performed in a continuous manner or a batch manner by heating the developed coating layer with a heating device such as a hot plate, a convection oven (hot wind circulating drier), or a high-frequency heater under the condition described above.

The color filter according to the invention is produced by use of the photopolymerizable composition according to the invention, and is preferably produced by providing, onto a support, colored areas in two or more colors (for example, colored areas in three colors of red (R), green (G) and blue (B)) in a desired pattern form (for example, a stripe form, a lattice form, a delta arrangement form). The color filter according to the invention can be most preferably produced by the color filter production process according to the invention. Thus, color filters can be produced with high productivity.

The color filter according to the invention can be used in a liquid crystal display (LCD), or a solid imaging element (such as a CCD or a CMOS).

As the use of the composition according to the invention, use in a color filter has mainly been described. However, the composition can be naturally used to form a black matrix disposed between pixels of a color filter. The black matrix can be formed by adding a black colorant such as carbon black or titanium black into the composition according to the invention, exposing the resultant composition to radiation, developing the resultant film with alkali, and then post-baking the film to promote the curing of the film.

Exemplary embodiments of the invention are described below:

<1> A compound represented by the following formula (I):

Formula (I)

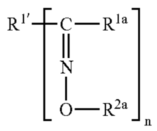

wherein, in formula (I), $R^{1'}$ represents a substituent containing an aromatic ring or heteroaromatic ring; $R^{1'}$ represents an alkyl group having at least one substituent selected from the following group A; $R^{2a}$ represents an alkanoyl group, an alkenoyl group, an aryloyl group, an alkoxycarbonyl group, an aryloxycarbonyl group, a heterocyclic oxycarbonyl group, a heteroaryloxycarbonyl group, an alkylthiocarbonyl group, an arylthiocarbonyl group, a heterocyclic thiocarbonyl group, a heteroarylthiocarbonyl group, or —CO—CO-Rd wherein Rd represents an aromatic or heteroaromatic group which may have a substituent; and n represents an integer of 1 to 6;

Group (A): a cyano group, an alkenyl group, an alkynyl group, —NArAr', —SAr, —COOH, —CONRaRb, —NRa—CO—Rb, —O—CO—NRaRb, —NRa—CO—ORb, —NRa—CO—NRaRb, —SO-Rc, —$SO_2$-Rc, —O—$SO_2$-Rc, —$SO_2$—NRaRb, —NRa—$SO_2$—Ra, —CO—NRa—CORb, —CO—NRa—$SO_2$—Rb, —$SO_2$—NRa—CO—Rb, —$SO_2$—NRa—$SO_2$-Rc, —$Si(Ra)_l(ORb)_m$, and a heterocyclic group, wherein, in group (A), Ar and Ar' each independently represent an aromatic ring or heteroaromatic ring which may have a substituent; Ra and Rb each independently represent a hydrogen atom, or an alkyl, aromatic or heteroaromatic group which may have a substituent; Rc represents an alkyl, aromatic or heteroaromatic group which may have a substituent; and l and m each independently represents an integer of 0 to 3 provided that l and m satisfy the relationship: l+m=3.

<2> The compound of <1>, wherein $R^{1a}$ represents an alkyl group having —SAr.

<3> The compound of <1>, wherein $R^{2a}$ represents an alkanoyl group.

<4> The compound of <1>, wherein the compound is represented by the following formula (A):

(A)

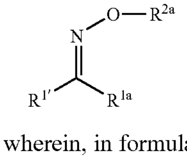

wherein, in formula (A), $R^{1'}$, $R^{1a}$, and $R^{2a}$ have the same definition as in the formula (I).

<5> The compound of <1>, wherein the compound is represented by the following formula (B):

(B)

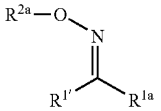

wherein, in formula (B), $R^{1'}$, $R^{1a}$, and $R^{2a}$ have the same definition as in the formula (I).

<6>. A photopolymerizable composition comprising a photopolymerization initiator represented by the above formula (I) and a radical polymerizable monomer:

<7> The photopolymerizable composition of <6>, wherein $R^{1a}$ represents an alkyl group having —SAr.

<8> The photopolymerizable composition of <6>, wherein $R^{2a}$ represents an alkanoyl group.

<9> The photopolymerizable composition of <6>, further comprising a colorant.

<10> The photopolymerizable composition of <6>, further comprising a colorant dispersing agent.

<11> A color filter wherein the color filter is made from the photopolymerizable composition of <6>.

<12> A process for producing a color filter comprising:

applying the photopolymerizable composition of <6> onto a support;

exposing the composition to radiation through a mask; and developing the composition to form a pattern, so as to form a color filter.

EXAMPLES

Hereinafter, the present invention will be described in detail by reference to Examples; however, the Examples should not be construed as limiting the invention. Unless otherwise specified, the word "part(s)" represent "part(s) by mass".

Example 1

<Synthesis of a Compound (1)>

Into a 200 mL three-neck flask were added 18.63 g (0.1 mol) of phenylsulfide, 75 mL of carbon disulfide, and 14.24 g (0.1 mol) of 4-chlorobutyryl chloride, and the resultant mixture was cooled to 0° C. while the air inside the flask was substituted with nitrogen. Thereafter, 13.47 g (0.1 mol) of aluminum (III) chloride was gradually added thereto. After completion of the addition, the solution was stirred at room temperature for 2 hours. The reaction solution was poured into 100 mL of a 0.5 N solution of hydrochloric acid aqueous solution, and extraction with ethyl acetate was conducted. The ethyl acetate layer was successively washed with a saturated aqueous solution of sodium hydrogencarbonate and a saturated aqueous solution of sodium chloride. Magnesium sulfate was added thereto for dehydration. Magnesium sulfate was filtrated off, and the solution was concentrated with an evaporator. Thereafter, purification was conducted by silica gel column chromatography to yield 22.45 g of a compound (1) (yield: 77%).

Compound (1)

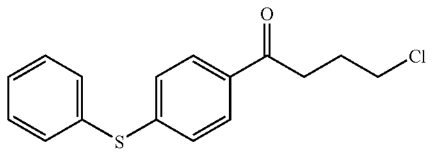

<Synthesis of a Compound (2)>

Into a 300 mL three-neck flask were added 10.95 g (0.0757 mol) of 4-chlorothiophenol, 30 mL of tetrahydrofuran (THF), 20 mL of distilled water, 3.03 g (0.0757 mol) of sodium hydroxide, and 1.26 g (0.0076 mol) of potassium iodide, and the solution was stirred at room temperature.

A solution of 22 g (0.0757 mol) of the compound (1) synthesized as described above in 20 mL of THF was added thereto dropwise over 30 minutes. After completion of the addition, the reaction solution was heated at 80° C., and stirred for 4 hours. Thereafter, the solution was naturally cooled to room temperature, and extraction with ethyl acetate was conducted. Washing with a saturated aqueous solution of sodium chloride, and addition of magnesium sulfate for dehydration was conducted. Magnesium sulfate was filtrated off, and the solution was concentrated with an evaporator. Thereafter, purification by silica gel column chromatography was conducted to yield 18.12 g of a compound (2) (yield: 60%).

Compound (2)

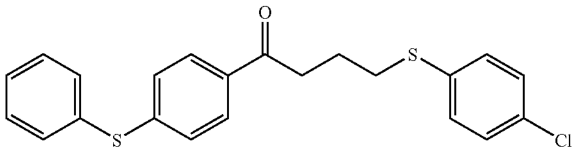

<Synthesis of a Compound (3)>

Into a 100 mL three-neck flask were added 15 mL of methanol, and 1.53 g (0.028 mol) of sodium methoxide, and the air inside the system was substituted with nitrogen. The reaction solution was cooled to 0° C., and then a solution of 10.69 g (0.0268 mol) of the compound (2) synthesized as described above in 20 mL of THF was added thereto dropwise over 30 minutes.

After completion of the addition, the solution was stirred at room temperature for 2 hours. While the temperature of the reaction solution was maintained at 10° C. by using a thermostat, a solution of 3.31 g (0.028 mol) of isopentyl nitrite in 10 mL of THF was dropwise added to the mixture solution over 30 minutes. After completion of the addition, the reaction solution was further stirred at room temperature for 2 hours, and then poured into a solution of 100 mL of distilled water and 3.0 mL of acetic acid which had been cooled to 0° C.

Thereafter, extraction with ethyl acetate was conducted, followed by washing with a saturated aqueous solution of sodium chloride. Magnesium sulfate was added thereto for dehydration. Magnesium sulfate was filtrated off, and the solution was concentrated with an evaporator. Thereafter, purification by silica gel column chromatography was conducted to yield 7.11 g of a compound (3) (yield: 62%).

Compound (3)

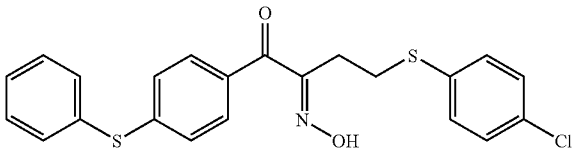

<Synthesis of a Compound (I-1) According to the Invention>

Into a 100 mL three-neck flask were added 6.51 g (0.0152 mol) of the compound (3) synthesized as described above, and 20 mL of THF. While the air inside the system was substituted with nitrogen, the reaction solution was cooled to 0° C. while stirred.

A solution of 2.18 g (0.028 mol) of pyridine in 5 mL of THF and a solution of 1.97 g (0.025 mol) of acetyl chloride in 5 mL of THF were dropwise added thereto simultaneously but separately. The dropwise addition was continued over 15 minutes, and then the solution was further stirred at room temperature for 3 hours.

Thereafter, the reaction solution was poured into 200 mL of distilled water. Extraction with ethyl acetate was conducted, followed by washing with a saturated aqueous solution of sodium chloride and addition of magnesium sulfate for dehydration. Magnesium sulfate was filtrated off, and the solution was concentrated with an evaporator. Thereafter, purification by silica gel column chromatography was conducted to yield 6.79 g of a compound (I-1) (photopolymerization initiator) according to the invention (yield: 95%). The chemical structure thereof was confirmed by the following analytical results.

The resultant compound (photopolymerization initiator) (I-1) was identified by $^1$H-NMR. The $^1$H-NMR spectrum of the resultant oxime derivative (photopolymerization initiator) (I-1) is shown below.

(Acetone-d6: internal standard TMS) δ [ppm]: 8.05 (d, 2H), 7.59 (m, 2H), 7.52 (m. 3H), 7.39 (m, 4H), 7.25 (d, 2H), 3.31 (t, 2H), 3.13 (t, 2H), 2.19 (s, 3H)

Compound (1-1) according to the invention

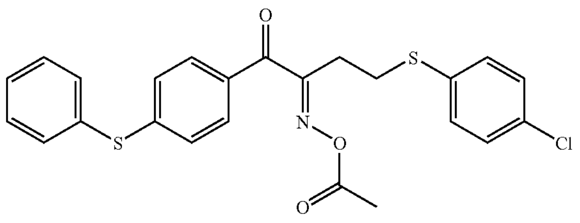

Other oxime derivatives according to the invention can also be synthesized in a similar manner.

Examples 2-6 and Comparative Example 1

1) Preparation of a Resist Solution

The following compounds were mixed, and the solid components were dissolved to form a resist solution:

Propylene glycol monomethyl ether acetate (PGMEA): 19.20 parts

Ethyl lactate: 36.67 parts

Resin (binder) [a 41% solution of benzyl methacrylate/methacrylic acid/2-hydroxyethyl methacrylate copolymer (molar ratio=60/20/20, and weight-average molecular weight=15000) in PGMEA]: 30.51 parts Dipentaerythritol hexaacrylate (photopolymerizable compound): 12.20 parts Polymerization inhibitor (p-methoxyphenol): 0.0061 part Fluorine-containing surfactant (trade name: F-475, manufactured by Dainippon Ink & Chemicals, Inc.): 0.83 part Trihalomethyltriazine-based photopolymerization initiator (trade name: TAZ-107, manufactured by Midori Kagaku Co., Ltd.): 0.586 part 2) Preparation of Glass Substrate Having Undercoat Layer A 6-inch silicon wafer was heated in an oven at 200° C. for 30 minutes or longer. Next, the above-mentioned resist solution was applied onto the silicon wafer to give a dry thickness of 2 μm. Furthermore, the silicon wafer was heated and dried in the oven at 220° C. for 1 hour to form an undercoat layer. In this way, a silicon wafer substrate having the undercoat layer was obtained.

3) Preparation (1) of Photopolymerizable Composition Containing Colorant (Dye)

Raw materials shown in Table 1 were dissolved into a mixed solution of propylene glycol monomethyl ether acetate/ethyl lactate (6/4) to give a solid concentration of 20% by mass, thereby preparing photopolymerizable compositions N-1 to N-5 containing a colorant (dye).

4) Exposure and Development of the Photopolymerizable Composition Containing a Colorant (Dye) (Image Forming Step)

A filter was used to filtrate the photopolymerizable compositions N-1 to N-5 containing a colorant (dye) prepared in item 3) above. Then, the silicon wafers obtained in item 2) above were coated with the photopolymerizable composition by using a spin coater to give a film thickness of 0.8 μm. The coated wafers were subjected to heating treatment (pre-baking) at 100° C. for 120 seconds.

The coating layer obtained as described above was irradiated with radiation having a wavelength of 365 nm emitted from an i-line reduced projection exposure device through a mask having a line width of 2 μm while changing the exposure amount in increment of 100 mJ. After irradiation, development was conducted with a developer that was a 60% CD-2000 developer manufactured by Fuji Photo Film Electronic Materials Co., Ltd. at 23° C. for 60 seconds. Next, rinsing with flowing water was conducted for 20 seconds, followed by spray drying, so that a colored filter film (color filter) was obtained. The formation of image was checked by a usual method through optical microscopic and SEM photographic observation.

5) Evaluation

The photopolymerizable compositions N-1 to N-5 and NH-1 prepared in the Examples and Comparative Example containing a colorant (dye), and the color filters were evaluated with respect to the state of the coating layer and the sensitivity by methods described below. The evaluation results are shown in Table 1.

1. Evaluation of State of the Coating Layer Based on Presence or Absence of Precipitate Each of the coating layers obtained in the item 4), which underwent the coating and the thermal treatment, was observed 24 hours after the thermal treatment. Grade "B" was given when a precipitation component was observed, and grade "A" was given when no precipitation component was observed.

2. Evaluation of Sensitivity

In the 2-μm width pattern obtained as described above, an adequate exposure amount (sensitivity) was assumed to be the exposure quantity at which the ratio between the width of dots and that of spaces is 1/1. A relative sensitivity was then calculated form according to the following equation:

Relative sensitivity=(sensitivity of the composition *N*-1,*N*-2,*N*-3,*N*-4 or *N*-5)/(sensitivity of the composition *NH*-1)

A smaller relative sensitivity indicates better performance.

TABLE 1

| | Composition No. | Photopolymerization initiator | Colorants | | Radical polymerizable monomer | Precipitation after coating | Sensitivity (relative value) |
|---|---|---|---|---|---|---|---|
| Example 2 | N-1 | I-1 (13) | A1-5 (39) | A2-2 (17) | C-1 (31) | A | 0.65 |
| Example 3 | N-2 | I-1 (14) | A3-6 (23) | A4-1 (31) | C-1 (32) | A | 0.54 |
| Example 4 | N-3 | I-1 (15.5) | A5-10 (32) | A6-6 (15.5) | C-1 (37) | A | 0.52 |
| Example 5 | N-4 | I-2 (13) | A1-5 (39) | A2-2 (17) | C-1 (31) | A | 0.55 |
| Example 6 | N-5 | I-3 (14) | A3-6 (23) | A4-1 (31) | C-1 (32) | A | 0.45 |
| Comparative Example 1 | NH-1 | IH-1 (13) | A1-5 (39) | A2-2 (17) | C-1 (31) | B | 1 |

(Each of the numerical values inside the parentheses in the table represent the proportion (unit: parts by mass) of the component based on the total solids of the composition.)

I-1 to I-3: photopolymerization initiators according to the invention (shown below)

IH-1: IRGACURE OXE 01 (manufactured by Ciba Specialty Chemicals Ltd., shown below)

C-1: mixture of the above-mentioned exemplary compound (M-2) as a radical polymerizable monomer and dipentaerythritol hexaacrylate (ratio by mass=3:7)

I-1

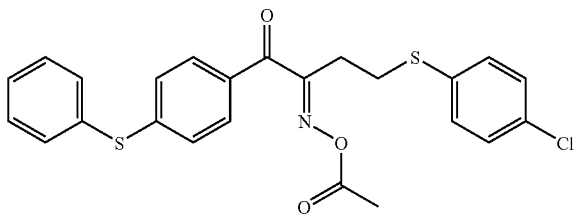

IH-1

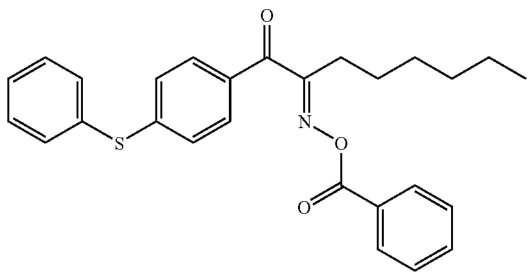

I-2

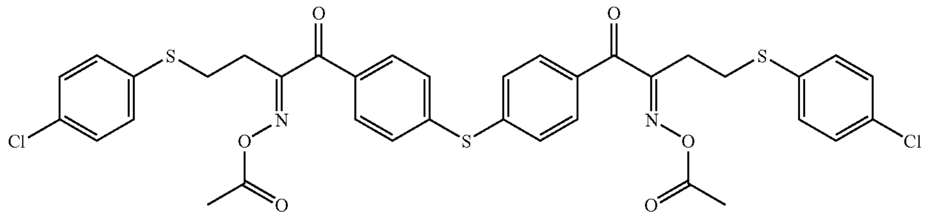

-continued
I-3
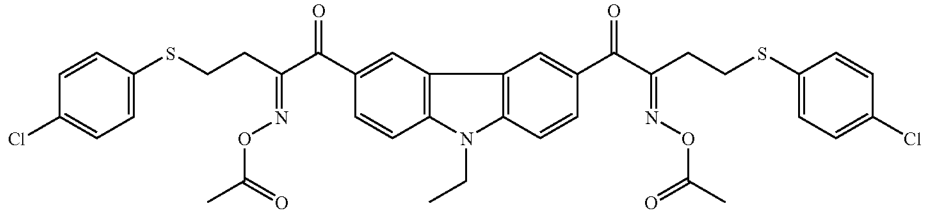
Colorants: the compounds mentioned in Table 1 are as follows:
(A1-5)
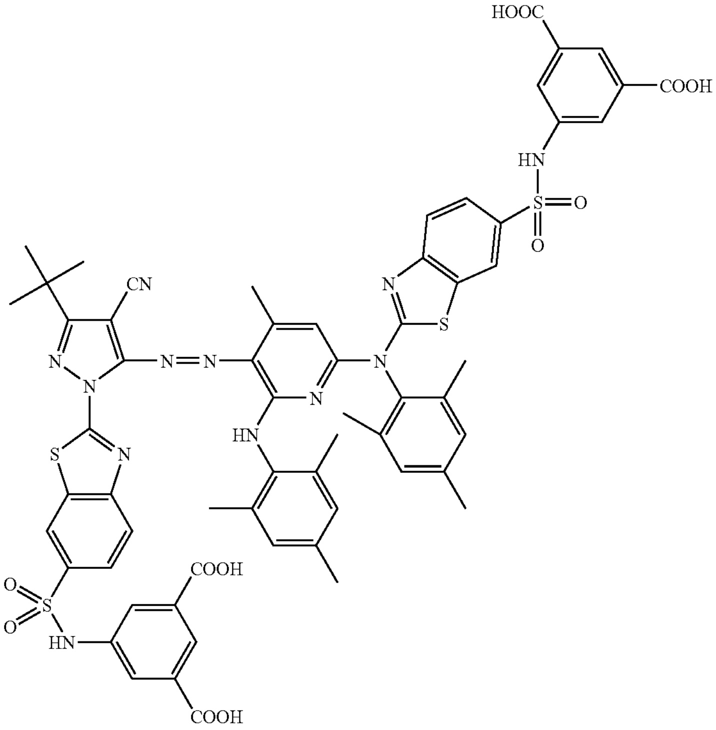
(A2-2)
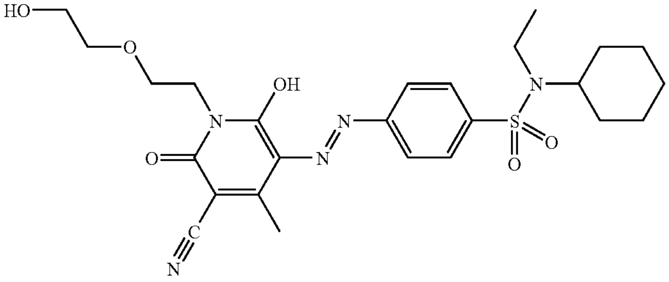
(2)

-continued
(A3-6)
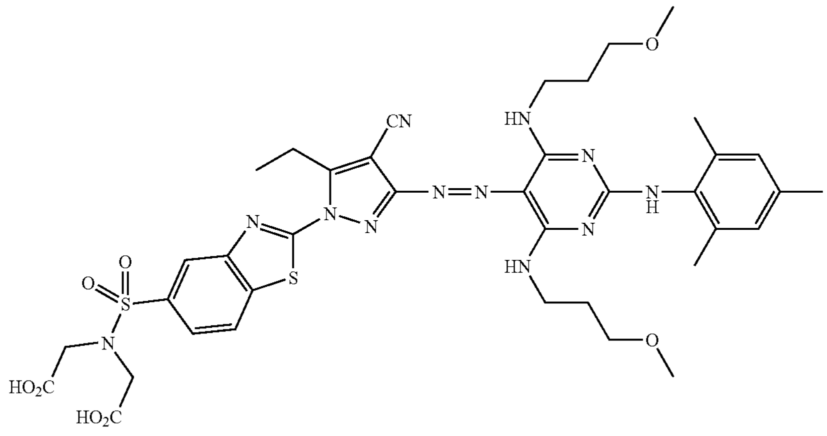
A6-6
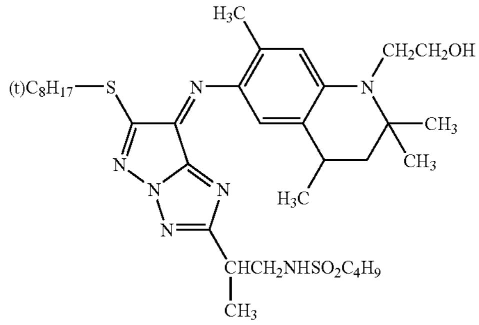
As the colorant A4-1, a compound synthesized according to the following scheme was used.
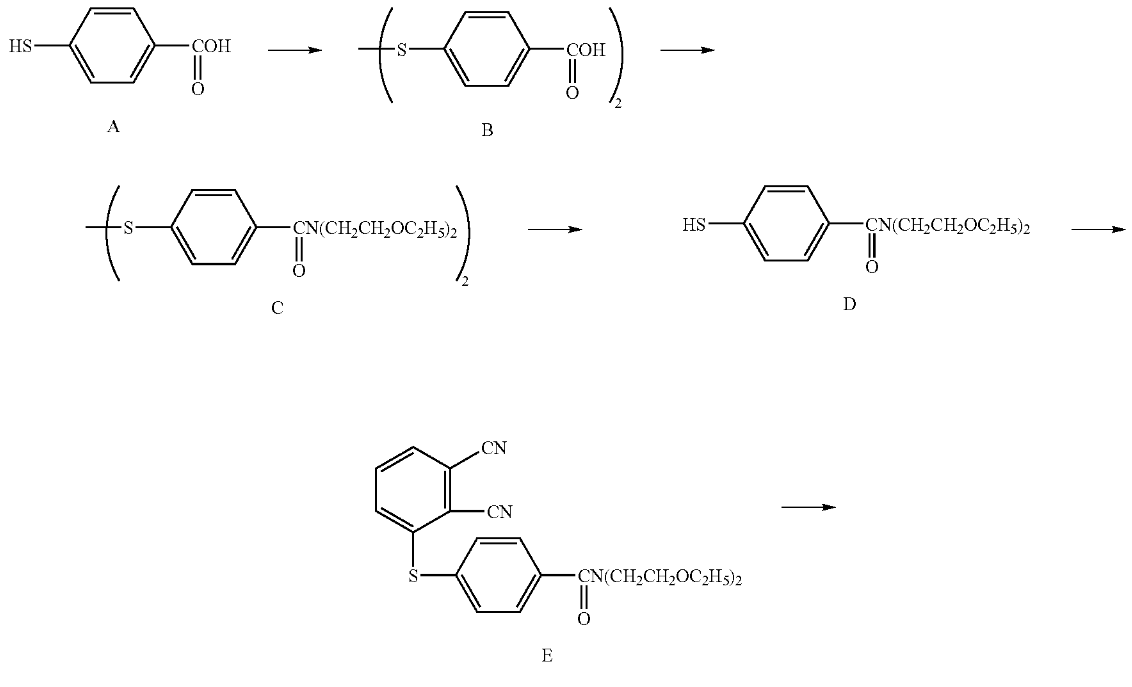
A B C D E -continued

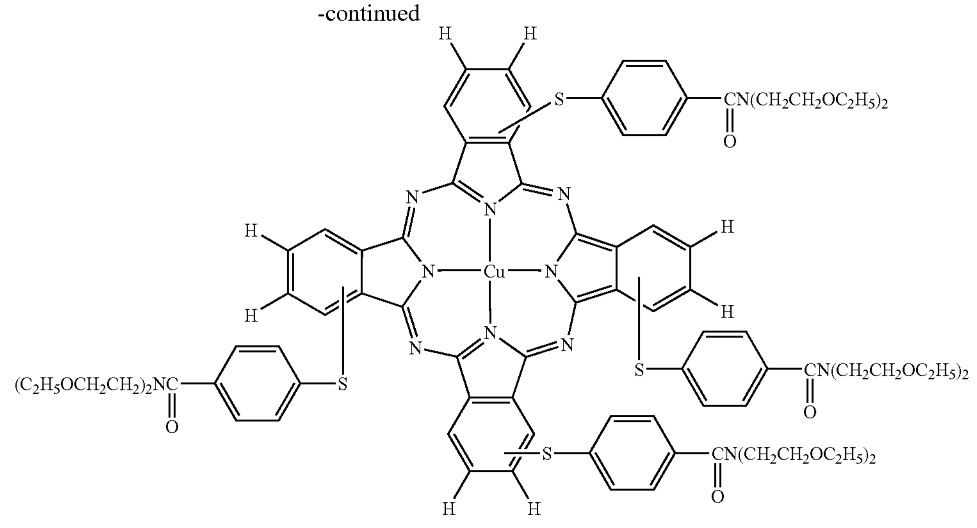

C-1

<Synthesis of an Intermediate Product B>

25.0 g (0.162 mol) of the compound A was dissolved in a mixed solvent of 100 mL of methanol and 23 mL of triethylamine. The resultant solution was cooled to 5° C., and 9 mL of a 30% hydrogen peroxide aqueous solution was dropwise added thereto while the solution of the compound A was stirred and the internal temperature was maintained at or under 25° C. After the dropwise addition, the reaction solution was further stirred at 25° C. for 30 minutes, and then cooled to 5° C. again. While the solution was stirred, 15 mL of concentrated hydrochloric acid was dropwise added thereto. Thereafter, 200 mL of water was further added thereto, and the resultant solution was stirred at 25° C. for 1 hour. The precipitated crystal was filtrated, washed sufficiently with water, and dried to yield 24.7 g of the intermediate product B as a white crystal (yield: 99.5%).

<Synthesis of Intermediate Products C, D and E>

Subsequently, 100 mL of toluene and 0.25 mL of dimethylacetoamide were added to 17.5 g (0.114 mol) of the intermediate product B obtained as described above. Under reflux, 25 mL of thionyl chloride was dropwise added thereto over 10 minutes. The solution was further heated and refluxed for 1 hour, and then concentrated under reduced pressure to yield a viscous liquid. Separately, 10 mL of dimethylacetoamide and 100 mL of acetonitrile were added to 38.0 g (0.235 mol) of diethoxyethylamine. To the mixed solution which was stirred at 10° C., the viscosity liquid was dropwise added over 15 minutes while the temperature was maintained at or under 15° C. The resultant solution was stirred for another 30 minutes, and then was poured into a mixed solution of 100 mL of water and 100 mL of ethyl acetate. The ethyl acetate phase was separated, and washed two times with 100 mL of water. The ethyl acetate phase was dried by using magnesium sulfate. Thereafter, ethyl acetate was distilled off under reduced pressure to yield the intermediate product C as a light yellow viscosity liquid.

Next, 50 mL of water, 200 mL of ethanol and 12 g of zinc powder were added to this intermediate product C. Under heat and reflux, a solution was dropwise added thereto over 20 minutes, the added solution containing 10 mL of sulfuric acid diluted with 40 mL of water. The resultant solution was further heated and stirred for 30 minutes, and then cooled. Insoluble matters were filtrated off therefrom. To the resultant solution, 50 mL of a saturated sodium chloride aqueous solution and 100 mL of ethyl acetate were added to separate the solution into two phases. The ethyl acetate phase was washed with 100 mL of water 2 times. The ethyl acetate phase was dried by using magnesium sulfate. Ethyl acetate was distilled off under reduced pressure to yield the intermediate product D as a light yellow viscous liquid.

Next, 70 mL of dimethylacetoamide and 15 g (0.108 mol) of potassium carbonate were added to this intermediate product D in a nitrogen atmosphere while the solution was stirred. While the resultant solution was stirred at 20° C. and the liquid temperature is maintained at 25° C. or lower, 19.7 g (0.113 mol) of 3-nitrophthalonitrile was gradually added thereto. The resultant solution was further stirred for 30 minutes, and poured into 300 mL of water under stirring. The crystal obtained was filtrated, and then the crystal was sufficiently washed with water. The resultant crystal was recrystallized with 70 mL of methanol, and the precipitated crystal was washed with 30 mL of cold methanol and dried to yield 35.0 g of the intermediate product E as a white crystal (yield: 72.6 g).

<Synthesis of a Colorant A4-1>

Next, 150 mL of butanol, 6.7 g (0.070 mol) of ammonium carbonate and 4.7 g (0.035 mol) of copper chloride were added to 34.4 (0.081 mol) of the intermediate product E, and the resultant solution was heated and stirred for 7 hours. Thereafter, butanol was distilled off under reduced pressure. The resultant solid was purified by silica gel chromatography to yield 25 g of powder of a colorant A4-1 (yield: 72.7%). The maximum absorption wavelength (λmax) and the molar absorption coefficient (ε) of the resultant dye in ethyl acetate were measured with a spectrophotometer (trade name: UV-2400PC, manufactured by Shimadzu Corp. As a result, the maximum absorption wavelength (λmax) was found to be 706.8 nm, and the molar absorption coefficient (ε) was found to be 55,600.

As the above-mentioned colorant A5-10, a compound synthesized as follows was used.

(1) 29.6 g of phthalic anhydride, 22.2 g of 4-bromophthalic anhydride, and 16.7 g of pyridine-2,3-dicarboxylic anhydride (ratio by mole: 2/1/1) were mixed. 144 g of urea, 9.9 g of cuprous chloride, 1.6 g of ammonium molybdate, and 400 mL of 1-chloronaphthalene were further added thereto. The mixture was heated, whereby a compound having a bromo-substituted tetraazaporphyrin skeleton was obtained.

(2) 13.1 g of the compound obtained in the above (1) was added to 2.5 g of chlorosulfonic acid. The temperature of the mixture was raised, and 10 g of thionyl chloride was dropwise added thereto. The mixture was cooled, and poured into water. The solid was collected by filtration, and 400 g of ice water was added to the solid. 2.80 g of bis(2-methoxyethyl) amine was dropwise added thereto. The resultant solid was collected by filtration, and dried to yield the following compound A5-10:

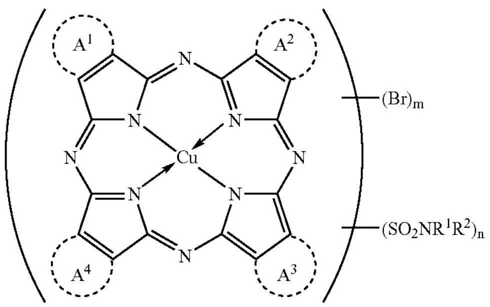

| Example No. | Number of 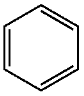 | Number of 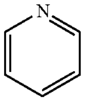 | m | n | $R^1$ | $R^2$ |
|---|---|---|---|---|---|---|
| A5-10 | 3 | 1 | 1 | 1 | $—C_2H_4OCH_3$ | $—C_2H_4OCH_3$ |

It can be understood from Table 1 that in Invention Examples, precipitation did not occur after coating and the sensitivity was satisfactory in comparison with Comparative Example 1. Thus, it is clear that the photopolymerizable composition according to the invention exhibits better performances.

According to the invention, a novel oxime derivative which is useful as a photopolymerization initiator and the like can be provided.

According to the invention, a photopolymerizable composition which exhibits a high sensitivity and may generate less solid precipitate after formation thereof can be provided.

When the composition is used to form, in particular, a color filter or a black matrix used in a liquid crystal display element (LCD) or a solid liquid crystal imaging element (such as a CCD or a CMOS), the composition has improved developer resistance after photopolymerization, in addition to the above-mentioned effects.

Moreover, according to the invention, a color filter can be provided which has excellent pattern, hue and resolution power by using the photopolymerizable composition.

Furthermore, according to the invention, there can be provided a color filter production process that uses the photopolymerizable composition and is capable of producing color filters with high productivity (or with improved cost performance).

All publications, patent applications, and technical standards mentioned in this specification are herein incorporated by reference to the same extent as if each individual publication, patent application, or technical standard was specifically and individually indicated to be incorporated by reference.

What is claimed is:

1. A compound represented by the following formula (I):

Formula (I)

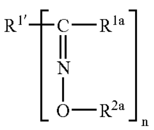

wherein, in formula (I), $R^{1'}$ represents a substituent containing an aromatic ring or heteroaromatic ring; Ria represents an alkyl group having a substituent —SAr wherein Ar represents an aromatic ring or heteroaromatic ring which may have a substituent; $R^{2a}$ represents an alkanoyl group, an alkenoyl group, an aryloyl group, an alkoxycarbonyl group, an aryloxycarbonyl group, a heterocyclic oxycarbonyl group, a heteroaryloxycarbonyl group, an alkyithiocarbonyl group, an arylthiocarbonyl group, a heterocyclic thiocarbonyl group, a heteroaryithiocarbonyl group, or —CO—CO-Rd wherein Rd represents an aromatic or heteroaromatic group which may have a substituent; and n represents an integer of 1 to 6.

2. The compound of claim 1, wherein $R^{2a}$ represents an alkanoyl group.

3. A photopolymerizable composition comprising a photopolymerization initiator represented by the following formula (I) and a radical polymerizable monomer:

Formula (I)

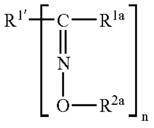

wherein, in formula (I), $R^{1'}$ represents a substituent containing an aromatic ring or heteroaromatic ring; $R^{1a}$ represents an alkyl group having a substituent —SAr wherein Ar represents an aromatic ring or heteroaromatic ring which may have a substituent; $R^{2a}$ represents an alkanoyl group, an alkenoyl group, an aryioyl group, an alkoxycarbonyl group, an aryloxycarbonyl group, a heterocyclic oxycarbonyl group, a heteroaryloxycarbonyl group, an alkyithiocarbonyl group, an aryithiocarbonyl group, a heterocyclic thiocarbonyl group, a heteroaryithiocarbonyl group, or —CO—CO-Rd wherein Rd represents an aromatic or heteroaromatic group which may have a substituent; and n represents an integer of 1 to 6.

4. The photopolymerizable composition of claim 3, wherein $R^{2a}$ represents an alkanoyl group.

5. The photopolymerizable composition of claim 3, further comprising a colorant.

6. The photopolymerizable composition of claim 3, further comprising a colorant dispersing agent.

7. A process for producing a color filter comprising:

applying the photopolymerizable composition of claim 3 onto a support;

exposing the composition to radiation through a mask; and developing the composition to form a pattern, so as to form a color filter.

* * * * *